(12) United States Patent
Gitman et al.

(10) Patent No.: US 11,969,864 B2
(45) Date of Patent: Apr. 30, 2024

(54) MULTI-TIER TORQUE ENHANCER DRIVER AND/OR RECEIVER AND METHOD OF USING SAME

(71) Applicant: ScalPal, LLC, Baltimore, MD (US)

(72) Inventors: Eliot Robert Gitman, Jerusalem (IL); Tuvia Gitman, Jerusalem (IL)

(73) Assignee: SCALPAL LLC, Wilmington, DE (US)

( * ) Notice: Subject to any disclaimer, the term of this patent is extended or adjusted under 35 U.S.C. 154(b) by 0 days.

(21) Appl. No.: 17/821,714

(22) Filed: Aug. 23, 2022

(65) Prior Publication Data

US 2022/0402105 A1 Dec. 22, 2022

Related U.S. Application Data

(63) Continuation-in-part of application No. 15/977,431, filed on May 11, 2018, now Pat. No. 11,458,071.

(Continued)

(51) Int. Cl.
 *B25B 23/10* (2006.01)
 *B25B 13/50* (2006.01)
 (Continued)

(52) U.S. Cl.
 CPC .......... *B25B 23/108* (2013.01); *A61B 17/888* (2013.01); *B25B 13/5091* (2013.01);
 (Continued)

(58) Field of Classification Search
 CPC . A61B 17/8615; A61B 17/888; B25B 23/108; B25B 15/005; B25B 15/007; F16B 23/0092
 See application file for complete search history.

(56) References Cited

U.S. PATENT DOCUMENTS

| 135,809 A | 2/1873 | Hubbard |
| 181,716 A | 8/1876 | Pickles |

(Continued)

FOREIGN PATENT DOCUMENTS

| CN | 2010/23742 Y | 2/2008 |
| DE | 296 06 408 U1 | 6/1996 |

(Continued)

OTHER PUBLICATIONS

FR-2945437-A1 machine translation (Year: 2010).*

(Continued)

*Primary Examiner* — Michael W Hotchkiss
(74) *Attorney, Agent, or Firm* — Smith, Gambrell & Russell, LLP

(57) ABSTRACT

A torque enhancing device that includes a torque contact body having one or more torque driver and/or recessed recipient torque contact surface configurations, inclusive of those in a multi-tier arrangement. The body having a Z-axis depth or thickness, and each of the torque contact surface configurations includes a pair of X-axis extending torque contact side walls that are spaced apart by L1 along a Y-axis, and a pair of Y-axis extending torque contact side walls that are spaced apart by L2 along the X-axis, with at least one of the one or more torque contact surface configurations having four concave contoured surface portions positioned between respective adjacent most ends of the X-axis extending torque contact side walls and the Y-axis extending torque contact side walls, and a length ratio L2/L1 is less than 1 as to provide a torque enhancement contact surface configuration. A method of driving such as insertion or removal of the recessed recipient such as in fastener form is included.

30 Claims, 65 Drawing Sheets

Related U.S. Application Data

(60) Provisional application No. 62/505,034, filed on May 11, 2017.

(51) Int. Cl.
  *B25B 15/00* (2006.01)
  *B25B 15/02* (2006.01)
  *B25B 21/00* (2006.01)
  *F16B 23/00* (2006.01)
  *F16B 37/16* (2006.01)
  *A61B 17/88* (2006.01)

(52) U.S. Cl.
  CPC ............. *B25B 15/005* (2013.01); *B25B 15/02* (2013.01); *B25B 21/00* (2013.01); *F16B 23/0023* (2013.01); *F16B 23/0061* (2013.01); *F16B 23/0092* (2013.01); *F16B 37/16* (2013.01)

(56) References Cited

U.S. PATENT DOCUMENTS

| | | | |
|---|---|---|---|
| 225,121 A | 3/1880 | Hackman et al. | |
| 244,379 A | 7/1881 | Coulter et al. | |
| 331,169 A | 11/1885 | Thomas | |
| 332,540 A | 12/1885 | Law | |
| 367,196 A | 7/1887 | Deblieux | |
| 779,751 A | 1/1905 | Waitt | |
| 975,285 A * | 11/1910 | Robertson | F16B 23/003 |
| | | | 411/403 |
| 1,289,450 A | 12/1918 | Holaday | |
| 1,320,259 A | 10/1919 | Martens | |
| 1,467,824 A | 9/1923 | Ahlers | |
| 1,632,227 A | 6/1927 | Halsey | |
| 1,764,990 A | 6/1930 | Schultz | |
| 1,773,146 A | 8/1930 | Kellogg | |
| 1,798,944 A | 3/1931 | Jackman | |
| 1,875,930 A | 9/1932 | Martin | |
| 1,919,728 A | 7/1933 | Kellogg | |
| 2,083,045 A | 6/1937 | Vaurs | |
| 2,116,775 A * | 5/1938 | Blackburn | B25B 15/005 |
| | | | 76/119 |
| 2,140,449 A * | 12/1938 | Brown | F16B 23/0007 |
| | | | 81/436 |
| 2,173,707 A * | 9/1939 | Brown | F16B 23/0092 |
| | | | 81/460 |
| 2,216,381 A | 10/1940 | West et al. | |
| 2,259,425 A | 10/1941 | Murphy | |
| 2,305,427 A | 12/1942 | Joachim | |
| 2,317,319 A * | 4/1943 | West | B25B 15/007 |
| | | | 81/438 |
| 2,335,205 A | 11/1943 | Zepp | |
| 2,361,814 A | 10/1944 | Berry | |
| 2,383,670 A | 8/1945 | Moss | |
| 2,397,238 A | 3/1946 | Brose | |
| 2,400,684 A * | 5/1946 | Clark | F16B 23/0092 |
| | | | 411/404 |
| 2,402,342 A | 6/1946 | Phillips | |
| 2,538,350 A | 1/1951 | Baule | |
| 2,639,622 A | 5/1953 | Ginder | |
| 2,742,939 A | 4/1956 | Larson | |
| 2,752,814 A | 7/1956 | Iaia | |
| 2,764,197 A * | 9/1956 | Torresen | B25B 15/005 |
| | | | 411/404 |
| 2,800,829 A * | 7/1957 | West | B25B 15/005 |
| | | | 411/404 |
| 2,930,424 A | 3/1960 | Van Buren, Jr. | |
| 3,086,414 A * | 4/1963 | Nardi | F16B 37/16 |
| | | | 81/176.1 |
| 3,123,120 A | 3/1964 | Grimm et al. | |
| 3,171,459 A | 3/1965 | Storch | |
| 3,175,454 A | 3/1965 | Morse | |
| 3,208,494 A | 9/1965 | Skidmore | |
| 3,242,775 A | 3/1966 | Hinkle | |
| 3,304,109 A | 2/1967 | Schuster | |
| 3,319,509 A | 5/1967 | Romeo | |
| 3,340,920 A | 9/1967 | Johnson | |
| 3,409,058 A | 11/1968 | La Pointe | |
| 3,412,772 A | 11/1968 | Meyfarth et al. | |
| 3,422,721 A | 1/1969 | Yonkers | |
| 3,463,209 A * | 8/1969 | Romain | B25B 15/004 |
| | | | 81/436 |
| 3,466,956 A | 9/1969 | Bowers | |
| 3,474,009 A | 10/1969 | Wang | |
| 3,584,531 A | 6/1971 | Greenleaf et al. | |
| 3,584,667 A | 6/1971 | Reiland | |
| 3,628,584 A | 12/1971 | Gutshall | |
| 3,675,694 A * | 7/1972 | Barlow | B25B 15/007 |
| | | | 81/460 |
| 3,695,324 A | 10/1972 | Gulistan | |
| 3,854,372 A | 12/1974 | Gutshall | |
| 3,856,066 A | 12/1974 | Reynolds | |
| 3,931,749 A | 1/1976 | Evans | |
| 3,985,170 A | 10/1976 | Iskra | |
| 4,027,572 A * | 6/1977 | Burge | B25B 13/485 |
| | | | 81/461 |
| 4,079,643 A * | 3/1978 | Evans | B25B 13/48 |
| | | | 81/439 |
| 4,084,478 A | 4/1978 | Simmons | |
| 4,089,357 A * | 5/1978 | Gill | F16B 23/0023 |
| | | | 411/404 |
| 4,202,244 A | 5/1980 | Gutshall | |
| 4,227,561 A | 10/1980 | Molina | |
| 4,246,811 A | 1/1981 | Bondhus et al. | |
| 4,291,737 A | 9/1981 | McMurray et al. | |
| 4,292,007 A | 9/1981 | Wagner | |
| 4,293,262 A | 10/1981 | Holmes | |
| 4,355,552 A | 10/1982 | Gutshall | |
| 4,378,187 A | 3/1983 | Fullerton | |
| 4,459,074 A | 7/1984 | Capuano | |
| 4,462,731 A | 7/1984 | Rovinsky et al. | |
| 4,512,220 A | 4/1985 | Barnhill, III et al. | |
| 4,569,259 A * | 2/1986 | Rubin | F16B 23/0061 |
| | | | 81/460 |
| 4,580,322 A | 4/1986 | Wright et al. | |
| 4,581,957 A | 4/1986 | Dossier | |
| 4,598,616 A | 7/1986 | Colvin | |
| 4,600,344 A | 7/1986 | Sutenbach et al. | |
| 4,646,594 A | 3/1987 | Tien | |
| 4,701,088 A | 10/1987 | Crull | |
| 4,712,957 A | 12/1987 | Edwards et al. | |
| 4,729,703 A | 3/1988 | Sato | |
| 4,882,957 A | 11/1989 | Wright et al. | |
| 4,895,484 A | 1/1990 | Wilcox | |
| 4,970,922 A | 11/1990 | Krivec | |
| 5,067,750 A | 11/1991 | Minneman | |
| 5,131,312 A | 7/1992 | Macor | |
| 5,139,380 A | 8/1992 | Reynolds | |
| 5,146,668 A | 9/1992 | Gulistan | |
| 5,214,987 A * | 6/1993 | Fenton, Sr. | B25B 15/005 |
| | | | 81/463 |
| 5,251,521 A | 10/1993 | Burda et al. | |
| 5,279,190 A | 1/1994 | Goss et al. | |
| 5,340,252 A | 8/1994 | Weddendorf | |
| 5,358,368 A * | 10/1994 | Conlan | F16B 23/0092 |
| | | | 411/410 |
| 5,364,212 A * | 11/1994 | Gill | F16B 23/0007 |
| | | | 411/404 |
| 5,370,021 A | 12/1994 | Shigematsu | |
| 5,378,101 A | 1/1995 | Olson et al. | |
| 5,386,749 A | 2/1995 | Kim | |
| 5,528,966 A * | 6/1996 | Coppejans | B25B 15/005 |
| | | | 81/439 |
| 5,553,983 A | 9/1996 | Shinjo | |
| 5,575,602 A | 11/1996 | Savage et al. | |
| 5,577,871 A | 11/1996 | Brugola | |
| 5,578,050 A | 11/1996 | Webb | |
| 5,674,036 A * | 10/1997 | Hsieh | F16B 23/0092 |
| | | | 411/410 |
| 5,674,037 A * | 10/1997 | Lu | F16B 23/0092 |
| | | | 411/404 |
| 5,709,356 A | 1/1998 | Avenet et al. | |

(56) References Cited

U.S. PATENT DOCUMENTS

| | | | |
|---|---|---|---|
| 5,762,457 A | 6/1998 | Lide | |
| 5,827,027 A | 10/1998 | Wakabayashi | |
| 5,868,049 A * | 2/1999 | Kanwal | F16B 23/0007 |
| | | | 81/460 |
| 5,873,290 A | 2/1999 | Chaconas | |
| 5,919,019 A | 7/1999 | Fischer | |
| 5,931,618 A | 8/1999 | Wallace et al. | |
| 6,032,556 A | 3/2000 | Hu | |
| D427,053 S | 6/2000 | Nelson | |
| 6,089,807 A | 7/2000 | Larsson | |
| 6,109,849 A | 8/2000 | Nagayama | |
| 6,128,983 A * | 10/2000 | Arnn | B25B 15/005 |
| | | | 81/436 |
| 6,129,493 A | 10/2000 | Leistner et al. | |
| 6,227,784 B1 | 5/2001 | Antoine et al. | |
| 6,238,372 B1 | 5/2001 | Zinger et al. | |
| 6,283,689 B1 | 9/2001 | Roytberg et al. | |
| 6,289,772 B1 | 9/2001 | Ying-Wen | |
| 6,293,745 B1 | 9/2001 | Lu | |
| 6,295,900 B1 | 10/2001 | Julicher et al. | |
| 6,314,840 B2 * | 11/2001 | Bozonnet | F16D 1/101 |
| | | | 81/436 |
| 6,321,625 B1 | 11/2001 | Fernandez | |
| 6,341,546 B1 | 1/2002 | Totsu | |
| 6,511,274 B1 | 1/2003 | Nagayama | |
| 6,572,316 B2 | 6/2003 | Toyooka | |
| 6,575,061 B2 | 6/2003 | Wagner | |
| 6,585,695 B1 | 7/2003 | Adair et al. | |
| 6,626,067 B1 | 9/2003 | Iwinski et al. | |
| 6,715,384 B1 | 4/2004 | Kozak | |
| 6,725,746 B1 | 4/2004 | Wright | |
| 6,755,748 B2 | 6/2004 | Brooks | |
| 6,761,089 B2 * | 7/2004 | Bergamo | B25B 27/18 |
| | | | 81/53.2 |
| 6,792,838 B2 * | 9/2004 | Brooks | B25B 15/008 |
| | | | 81/439 |
| 6,843,729 B2 * | 1/2005 | Hughes | B25B 15/005 |
| | | | 470/8 |
| 6,854,943 B2 | 2/2005 | Nagayama | |
| 6,889,580 B1 | 5/2005 | Tseng | |
| 6,890,139 B2 | 5/2005 | Hughes | |
| 6,904,833 B2 | 6/2005 | Wright | |
| 6,918,725 B2 | 7/2005 | Gauron | |
| 6,951,158 B1 | 10/2005 | Edland | |
| 6,988,432 B2 * | 1/2006 | Brooks | B25B 15/008 |
| | | | 411/407 |
| D514,405 S | 2/2006 | Chaconas | |
| 6,997,085 B2 | 2/2006 | Yamamoto | |
| 7,021,875 B2 | 4/2006 | Yake et al. | |
| 7,059,816 B2 | 6/2006 | Toosky | |
| 7,107,879 B1 | 9/2006 | Cheng | |
| 7,156,598 B2 | 1/2007 | Tibbenham et al. | |
| 7,228,764 B1 | 6/2007 | Macor | |
| 7,231,851 B2 | 6/2007 | Tuan-mu | |
| 7,255,522 B2 | 8/2007 | Dilling | |
| 7,322,265 B2 | 1/2008 | Chen | |
| 7,325,470 B2 * | 2/2008 | Kay | A61B 17/888 |
| | | | 606/279 |
| 7,340,983 B2 | 3/2008 | Ling et al. | |
| D568,731 S * | 5/2008 | Campbell | D8/387 |
| 7,373,709 B2 | 5/2008 | Fernando et al. | |
| 7,437,975 B1 | 10/2008 | De Anfrasio | |
| 7,438,513 B2 | 10/2008 | Craven et al. | |
| 7,452,361 B2 * | 11/2008 | Kreidler | B25B 15/007 |
| | | | 606/305 |
| 7,462,007 B2 | 12/2008 | Sullivan et al. | |
| 7,478,986 B2 | 1/2009 | Bushell et al. | |
| 7,568,872 B2 | 8/2009 | Schultz | |
| 7,628,772 B2 | 12/2009 | McConnell et al. | |
| 7,674,081 B2 | 3/2010 | Selle | |
| 7,730,812 B2 | 6/2010 | Edland | |
| 7,771,459 B2 * | 8/2010 | von Oepen | A61B 17/888 |
| | | | 606/301 |
| D624,796 S | 10/2010 | Taylor, Jr. | |
| 7,955,036 B2 | 6/2011 | Palm | |
| 7,988,683 B2 | 8/2011 | Adair et al. | |
| 8,065,940 B2 | 11/2011 | Wilson et al. | |
| 8,083,082 B2 | 12/2011 | Sasaki | |
| 8,206,071 B1 | 6/2012 | Johnson | |
| 8,210,786 B2 | 7/2012 | Okada et al. | |
| 8,257,004 B2 | 9/2012 | Smith | |
| 8,273,061 B2 | 9/2012 | McConnell et al. | |
| 8,342,061 B2 | 1/2013 | Super | |
| 8,347,761 B2 * | 1/2013 | Goss | F16B 23/003 |
| | | | 81/120 |
| 8,353,230 B2 | 1/2013 | Cole | |
| 8,506,578 B2 | 8/2013 | Smith | |
| 8,545,156 B2 | 10/2013 | Kageyama et al. | |
| 8,562,582 B2 | 10/2013 | Tuckwell et al. | |
| 8,640,575 B2 * | 2/2014 | Huang | B25B 15/008 |
| | | | 81/436 |
| 8,647,035 B2 | 2/2014 | Bakken et al. | |
| 8,696,275 B2 | 4/2014 | Wallace et al. | |
| 8,739,660 B2 | 6/2014 | Edland et al. | |
| 8,740,533 B2 | 6/2014 | Gaillard | |
| 8,745,825 B2 | 6/2014 | Gitman et al. | |
| 8,757,950 B2 * | 6/2014 | Ogawa | F16B 23/0061 |
| | | | 411/404 |
| 8,794,113 B2 | 8/2014 | Maury | |
| 8,850,662 B2 | 10/2014 | Gitman et al. | |
| 8,864,725 B2 | 10/2014 | Ranalletta et al. | |
| 8,944,736 B2 | 2/2015 | Figge et al. | |
| 8,955,417 B2 | 2/2015 | Stiebitz et al. | |
| 8,973,471 B2 | 3/2015 | Hsieh | |
| 9,039,673 B2 | 5/2015 | Weitzel et al. | |
| 9,044,843 B1 * | 6/2015 | Mokhtee | B25B 15/005 |
| D741,159 S | 10/2015 | Campbell | |
| 9,283,324 B2 | 3/2016 | Lev et al. | |
| 9,316,245 B2 | 4/2016 | Dvorak | |
| 9,422,965 B2 | 8/2016 | Campbell, II | |
| 9,522,457 B2 * | 12/2016 | Huang | B25B 23/105 |
| 9,587,688 B2 | 3/2017 | Zdeb et al. | |
| 9,624,962 B2 | 4/2017 | Unseld et al. | |
| 9,637,893 B2 | 5/2017 | Lin et al. | |
| 9,638,234 B2 * | 5/2017 | Campbell | B25B 15/004 |
| 9,651,078 B2 | 5/2017 | Santiago-Anadon | |
| 9,664,225 B2 | 5/2017 | Szczukowski et al. | |
| 9,687,968 B2 | 6/2017 | Doroslovac et al. | |
| D794,405 S | 8/2017 | Doroslovac et al. | |
| D798,682 S | 10/2017 | Doroslovac et al. | |
| 9,795,536 B2 | 10/2017 | Lev et al. | |
| 9,829,020 B2 | 11/2017 | Ortega Dona | |
| 9,839,580 B2 | 12/2017 | Lev et al. | |
| 9,840,002 B2 * | 12/2017 | Schon | B25B 23/0007 |
| 9,907,729 B2 | 3/2018 | Nord et al. | |
| 9,943,463 B2 | 4/2018 | Marks et al. | |
| 10,022,298 B2 | 7/2018 | Marici et al. | |
| D829,088 S | 9/2018 | Campbell, II | |
| 10,081,094 B2 * | 9/2018 | Doroslovac | B25B 23/105 |
| 10,197,088 B2 | 2/2019 | Dang | |
| 10,215,217 B2 | 2/2019 | Hess et al. | |
| 10,286,201 B2 | 5/2019 | McKinnon et al. | |
| 10,731,692 B2 * | 8/2020 | Goss | B21K 1/463 |
| 10,882,162 B2 | 1/2021 | Kukucka et al. | |
| 10,926,384 B2 * | 2/2021 | Norton | B21K 1/463 |
| 10,960,520 B2 | 3/2021 | Schulz | |
| 10,995,788 B2 | 5/2021 | Dilling | |
| 11,028,870 B2 | 6/2021 | Tomaszewski et al. | |
| 11,154,969 B2 | 10/2021 | Kukucka et al. | |
| 11,173,589 B2 | 11/2021 | Campbell, II | |
| 11,215,215 B2 | 1/2022 | Lukes | |
| 11,234,899 B2 | 2/2022 | Gitman et al. | |
| 11,337,892 B2 | 5/2022 | Gitman | |
| 11,413,730 B2 * | 8/2022 | Doroslovac | B25B 15/005 |
| 11,458,071 B2 | 10/2022 | Gitman et al. | |
| 11,554,467 B2 * | 1/2023 | Lin | B25B 15/008 |
| 11,572,914 B2 * | 2/2023 | Chen | F16B 23/0053 |
| 11,592,054 B1 | 2/2023 | Kemeny | |
| D980,707 S * | 3/2023 | Lee | D8/387 |
| 11,602,828 B2 * | 3/2023 | Kukucka | B25B 23/108 |
| 2002/0016595 A1 * | 2/2002 | Michelson | A61F 2/4455 |
| | | | 606/301 |
| 2002/0141847 A1 | 10/2002 | Oh et al. | |

(56) References Cited

U.S. PATENT DOCUMENTS

| | | | |
|---|---|---|---|
| 2004/0100097 A1 | 5/2004 | Fukano et al. | |
| 2005/0047891 A1* | 3/2005 | Toyooka | F16B 23/0023 411/403 |
| 2005/0126349 A1 | 6/2005 | Trank et al. | |
| 2005/0129488 A1 | 6/2005 | Weinstein et al. | |
| 2005/0137523 A1 | 6/2005 | Wyatt et al. | |
| 2005/0216015 A1* | 9/2005 | Kreidler | B25B 23/106 606/104 |
| 2005/0254921 A1 | 11/2005 | Leblanc | |
| 2006/0002781 A1 | 1/2006 | Mangapora | |
| 2006/0089601 A1 | 4/2006 | Dionigi | |
| 2006/0116644 A1 | 6/2006 | Norton | |
| 2006/0162505 A1 | 7/2006 | Choi et al. | |
| 2006/0233626 A1* | 10/2006 | Lin | F16B 23/0092 411/304 |
| 2007/0043379 A1* | 2/2007 | Sullivan | A61B 17/8615 606/104 |
| 2007/0060904 A1 | 3/2007 | Vedrine et al. | |
| 2007/0079894 A1 | 4/2007 | Kraus et al. | |
| 2007/0183865 A1 | 8/2007 | Severns | |
| 2007/0245863 A1 | 10/2007 | Edland | |
| 2008/0009789 A1 | 1/2008 | Zinger et al. | |
| 2008/0172024 A1 | 7/2008 | Yow | |
| 2008/0179353 A1 | 7/2008 | Maymon | |
| 2008/0249479 A1 | 10/2008 | Zinger et al. | |
| 2008/0287914 A1 | 11/2008 | Wyatt et al. | |
| 2009/0043282 A1 | 2/2009 | Hughes et al. | |
| 2009/0092462 A1 | 4/2009 | Pratt | |
| 2009/0220321 A1 | 9/2009 | Sakamura | |
| 2010/0030282 A1* | 2/2010 | Ciccone | A61B 17/1691 606/108 |
| 2010/0095487 A1 | 4/2010 | Gitman et al. | |
| 2010/0140431 A1 | 6/2010 | Van Horne | |
| 2010/0192344 A1 | 8/2010 | Zollmann | |
| 2010/0192736 A1* | 8/2010 | Burch | B25B 15/007 81/436 |
| 2011/0044784 A1 | 2/2011 | Da Fonseca et al. | |
| 2011/0172719 A1* | 7/2011 | Gorhan | A61B 17/8685 606/305 |
| 2011/0264037 A1 | 10/2011 | Foshee et al. | |
| 2011/0271800 A1* | 11/2011 | Lin | B25B 15/008 81/436 |
| 2011/0314768 A1 | 12/2011 | Johnson | |
| 2012/0155988 A1 | 6/2012 | Schumacher et al. | |
| 2012/0241332 A1 | 9/2012 | Crossman | |
| 2013/0030476 A1* | 1/2013 | Shimko | A61B 17/888 606/308 |
| 2013/0097848 A1 | 4/2013 | Inaba et al. | |
| 2013/0144248 A1 | 6/2013 | Putter et al. | |
| 2013/0213193 A1 | 8/2013 | Lukes | |
| 2013/0226100 A1 | 8/2013 | Lev | |
| 2013/0282019 A1* | 10/2013 | Bouliane | A61B 17/888 606/104 |
| 2014/0066945 A1* | 3/2014 | Humphreys | A61B 17/8615 606/104 |
| 2014/0217099 A1 | 8/2014 | Browne | |
| 2015/0104269 A1 | 4/2015 | Gillis et al. | |
| 2015/0265500 A1 | 9/2015 | Russo et al. | |
| 2016/0061246 A1 | 3/2016 | Campbell | |
| 2016/0167838 A1 | 6/2016 | Dong et al. | |
| 2016/0193722 A1* | 7/2016 | Cunningham | B25B 13/481 81/439 |
| 2017/0128948 A1 | 5/2017 | Anger | |
| 2017/0175798 A1 | 6/2017 | Arndt et al. | |
| 2017/0252905 A1 | 9/2017 | Doroslovac et al. | |
| 2017/0312897 A1* | 11/2017 | Doroslovac | B25B 15/008 |
| 2018/0003241 A1 | 1/2018 | Goss | |
| 2018/0106286 A1* | 4/2018 | Cone, III | F16B 23/0053 |
| 2018/0128301 A1 | 5/2018 | Rosén | |
| 2018/0156257 A1* | 6/2018 | Rühl | F16B 23/0007 |
| 2018/0280067 A1* | 10/2018 | Bjork | A61B 17/888 |
| 2018/0313395 A1 | 11/2018 | Rajewski et al. | |
| 2018/0347612 A1* | 12/2018 | Falkenstein | B25B 15/005 |
| 2020/0180123 A1 | 6/2020 | Lukes et al. | |
| 2020/0269398 A1 | 8/2020 | Donovan et al. | |
| 2021/0148395 A1 | 5/2021 | Kukucka et al. | |
| 2022/0192925 A1 | 6/2022 | Gitman et al. | |
| 2022/0281085 A1 | 9/2022 | Kukucka et al. | |
| 2023/0053731 A1 | 2/2023 | Gitman et al. | |

FOREIGN PATENT DOCUMENTS

| | | | |
|---|---|---|---|
| EP | 2278175 A2 * | 1/2011 | F16B 23/003 |
| FR | 2945437 A1 * | 11/2010 | A61B 17/8615 |
| GB | 1 032 144 | 6/1966 | |
| GB | 1 205 445 | 9/1970 | |
| GB | 1 360 644 | 7/1974 | |
| GB | 1 398 180 | 6/1975 | |
| GB | 2 141 803 | 1/1985 | |
| GB | 2 153 033 | 8/1985 | |
| GB | 2 271 738 | 4/1994 | |
| GB | 2 413 296 | 10/2005 | |
| KR | 101276303 B1 | 6/2013 | |
| RU | 2 160 396 C1 | 12/2000 | |
| WO | 2010/037250 A1 | 4/2010 | |
| WO | 2015/118521 A1 | 8/2015 | |
| WO | 2018/073153 A1 | 4/2018 | |
| WO | 2018/167321 A2 | 9/2018 | |

OTHER PUBLICATIONS

EP-2278175-A2 machine translation (Year: 2011).*
Engineer Edge, Ansi Inch Wing Nut Specification Chart. Mar. 2015 https://www.engineersedge.com/hardware/wing-nut-ansi-chart.htm Accessed Aug. 17, 2023 (2 pages).
U.S. Appl. No. 17/821,357, Gitman et al., filed Aug. 22, 2022.
Polyvinyl chloride, Wikipedia, Website, Accessed May 12, 2017, 19 pages, https://en.wikipedia.org/wiki/Polyvinyl_chloride.
Thermoplastic Elastomer, Wikipedia, Website, Accessed May 12, 2017, 4 pages, https://en.wikipedia.org/wiki/Thermoplastic_elasomer.
TPR: Thermpoplastic Rubber—S&E Specialty Polymers, Website, Accessed May 12, 2017, 2 pages, http://www.sespoly.com/products/tpr-thermoplastic-rubber/.
(1/4"-3/8"-1/2") Drive Finger Ratchet Head with Quick Release 72 Teethe Gears (GS-4343BH-BK). Accessed Oct. 20, 2021 (3 pages). https://www.alibaba.com/product-detail/-1-4-3-8-1_1700001046437.html.
TE-5003-9-3, Plastic Thumb Nut, set of 4. Accessed Oct. 20, 2021 (3 pages). https://tisch-env.com/product/te-5003-9-3-plastic-thumb-nut-set-of-4/.
(1/4"-3/8"-1/2") Drive Finger Ratchet Head CR-V Steel (GS-4343BE-BG). Accessed Oct. 22, 2021 (3 pages). https://golconda-source.en.alibaba.com/product/1700000997430-813579114/_1_4_3_8_1_2_DRIVE_FINGER_RATCHET_HEAD_CR_V_STEEL_GS_4343BE_BG_.html.
1/4"-3/8"-1/2") Drive Finger Ratchet Head with 72 Teeth Gears (GS-4343BB-BD) Accessed Oct. 22, 2021 (3 pages). https://golconda-source.en.alibaba.com/product/1700001028449-813579114/_1_4_3_8_1_2_DRIVE_FINGER_RATCHET_HEAD_WITH_72_TEETH_GEARS_GS_4343BB_BD_.html.
PAGOW 2pcs Power Wing Nut Driver Set, Wing Nut Drill Bit Socket Wrench Tool Set, 1/4" Hex Shank for Panel Nuts, Screws Eye, C Hook Bolt, Q-Hanger. https://www.amazon.com/PAGOW-2-Pack-Hurricane-Wing-Driver/dp/B075XBG8LB?th=1 Accessed Oct. 22, 2021 (8 pages).
Theengineeringtoolbox, Wrench Conversion Chart, May 9, 2017, p. 1 (Year:2017) 2 Pages.
Stanley Engineered Fastening. TORX Plus® Drive System. 16 pages. Accessed Apr. 25, 2023.https://pdf.directindustry.com/pdf/stanley-engineered-fastening/torx-plus/22234-645055.html.
OSG System Products. Qua Stix®. 6 pages. Accessed Apr. 25, 2023. https://www.j-osp.com/_userdata/pdf/neji/catalog/2-QuaStix.pdf.
Eccles, Bill. Self-loosening of threaded fasteners. Bolt Science. 2 pages. Accessed Apr. 25, 2023. https://www.boltscience.com/pages/self-loosening-of-threaded-fasteners.pdf.
Mountz. What is Torque? 6 pages. Accessed Apr. 25, 2023. https://www.mountztorque.com/What-is-Torque_3.

(56) References Cited

OTHER PUBLICATIONS

Eccles, Bill. The basics of bolted joints. Bolt Science. 2011. 2 pages. Accessed Apr. 25, 2023. https://www.boltscience.com/pages/the-basics-of-bolted-joints.pdf.
Eccles, Bill. The loosening of prevailing torque nuts. Bolt Science. 2009. 2 pages. Accessed Apr. 25, 2023. https://www.boltscience.com/pages/the-loosening-of-prevailing-torque-nuts.pdf.
APM HEXSEAL. Bolting failure analysis. 2015. 8 pages. Accessed Apr. 25, 2023. https://www.fastenerandfixing.com/application-technology/bolting-failure-analysis/.
HILTI. Fastening Technology Manual: Dynamic Design for Anchors. p. 43. Accessed Apr. 25, 2023. https://www.hilti.co.uk/medias/sys_master/documents/h81/h73/9484926484510/Dynamic-design-of-anchors-Brochure-ASSET-DOC-LOC-2521843.pdf.
Stanley Engineered Fastening. 2020 Selection and Configuration Guide. pp. 128-132. Accessed Apr. 25, 2023. https://www.stanleyengineeredfastening.com/-/media/Web/SEF/Resources/Docs/STANLEY-Assembly-Technologies/2020_STANLEY_Catalog_A4.pdf.
SPS Technologies Aerospace Fasteners Group. Preload Indicating Washers: Maximize bolted joint strength by controlling clamp force. 12 pages. Accessed Apr. 25, 2023. https://www.pccfasteners.com/assets/local/documents/product-literature/pli_brochure.pdf.
Wikipedia. Circular motion. 10 Pages. Accessed Apr. 26, 2023. https://en.wikipedia.org/wiki/Circular_motion#.
DeWalt Anchors and Fasteners. General Information: Wood-knocker®II+ and Pan-Knocker®II+. 13 pages. Accessed Apr. 25, 2023. https://anchors.dewalt.com/anchors/_documents/uploads/DWANF_WKII_PKII_TP_revJ.pdf?1682534413.
DeWalt Anchors and Fasteners. Cast-in-Place Concrete Inserts. Bang-it®+ and Wood-Knocker® II +. 8 pages. Accessed Apr. 25, 2023. https://anchors.dewalt.com/anchors/_documents/uploads/DWANF_WDKBANGR_BR_r01.pdf?1622227270.
The FreeDictionary. Torque. 10 pages. Accessed Apr. 25, 2023. https://encyclopedia.thefreedictionary.com/Torque.
The FreeDictionary. Dampening. 5 pages. Accessed Apr. 25, 2023. https://encyclopedia.thefreedictionary.com/dampening.
The FreeDictionary. Non-uniform circular motion. 9 pages. Accessed Apr. 25, 2023. https://encyclopedia.thefreedictionary.com/non-uniform+circular+motion.
Wikipedia. Torque. 11 pages. Accessed Apr. 25, 2023. https://en.wikipedia.org/wiki/Torque.
University of Guelph. Torque and Rotational Motion Tutorial. 8 pages. Accessed Apr. 25, 2023. https://www.physics.uoguelph.ca/torque-and-rotational-motion-tutorial.
Spencer, Kevin R., et al. Screw Head Design: An Experimental Study to Assess the Influence of Design on Performance. Journal of Oral and Maxillofacial Surgery. 2004. vol. 62. pp. 473-478. https://www.joms.org/article/S0278-2391(03)01270-9/fulltext.
Lin, Chen-Huei, et al. Improving socket design to prevent difficult removal of locking screws. Injury. 2018. vol. 49. pp. 585-592. https://www.sciencedirect.com/science/article/pii/S0020138318300561.
Borowski, Larry. Inspecting Combination Screw Drive Systems. Fastener World. 170. May/Jun. 2018. p. 302. Accessed Apr. 25, 2023. https://www.fastener-world.com/data/pdf_download/FW_170_E.pdf.
Bosch. Drilling and Fastening. p. 169. Accessed Apr. 25, 2023. https://www.scribd.com/document/444711224/bosch-20182019-catalog-drillingfastening-1-pdf#.
Torx Plus® drive system exclusives. p. 9. Accessed Apr. 25, 2023. https://www.yumpu.com/en/document/read/1355808/licensed-products-acument-global-technologies.
CELO Screws Technology. Catalogue V. 02. pp. 95, 99, 101 and 102. Accessed Apr. 25, 2023. https://www.celofixings.es/import/catalogue_celo_industry.pdf.
Böllhoff. Hexalobular / TORX®. Efficient Assembly. pp. 16. Accessed Apr. 25, 2023. https://eshop.boellhoff.de/out/media/pdf/prospekte/hexalobular-torx_8200_en.pdf.
SPS Technologies Aerospace Fasteners Group. SPS MP98T Fasteners. 4 pages. Accessed Apr. 25, 2023. https://www.pccfasteners.com/assets/local/documents/product-literature/SPS-MP98T-BrochureRev4.pdf.
Nitto Seiko. Co., Ltd. Tough Cross. 2 pages. Accessed Apr. 25, 2023. https://www.nittoseiko.co.jp/dcms_media/other/F-J-IE.pdf.
Würth. Tools & Shop Supplies. p. 5. Accessed Apr. 25, 2023. https://catalogs.wurthusa.com/WurthUSACatalog/Section8Tools/.
PROTO®. Aviation Hand Tools & Storage solutions. Torqueplus™ For Impact Sockets. p. 96. Accessed Apr. 25, 2023. https://www.protoindustrial.com/literatures/Brand/Proto/MKT-2870_ICPRAEROCAT_Proto%20Aviation%20Catalog.pdf.
Atlas Copco. Pocket Guide to Tightening Technique. 28 pages. Accessed Apr. 25, 2023. https://www.atlascopco.com/content/dam/atlas-copco/industrial-technique/general/documents/pocketguides/9833864801_L.pdf.
OSG System Products., Ltd. Excellent torque transmission No Cam-out design. 9 pages. Accessed Apr. 25, 2023. https://www.j-osp.com/en/neji/index.html.
The Difference Between Torque and Clamp. Video runtime of 8:11. Screenshots from Youtube. 6 pages. Accessed Apr. 26, 2023. https://www.youtube.com/watch?v=ZDDrtIL7SQ4.
Multifunctional Wedge-Lock Washers | Nord-Lock X-series™. Screenshot from Youtube. Video runtime of 8:18. Screenshot from Youtube. 1 page. Accessed Apr. 27, 2023. https://www.youtube.com/watch?v=cDlmbMV9ICU.
Non Final Office Action dated Aug. 16, 2023 for U.S. Appl. No. 17/821,357 (37 pages).
Notice of Allowance and Fees Due mailed Dec. 13, 2023 for U.S. Appl. No. 17/821,357 (14 pages).

\* cited by examiner

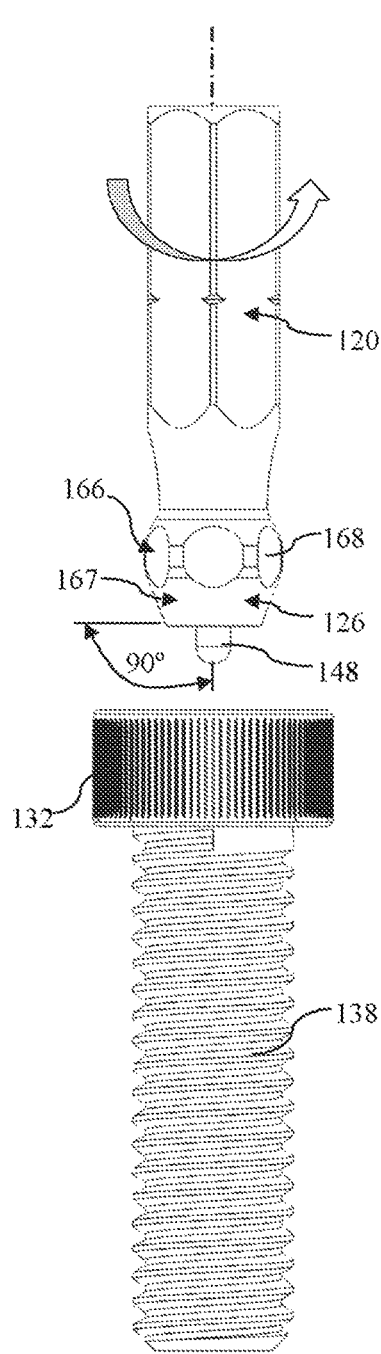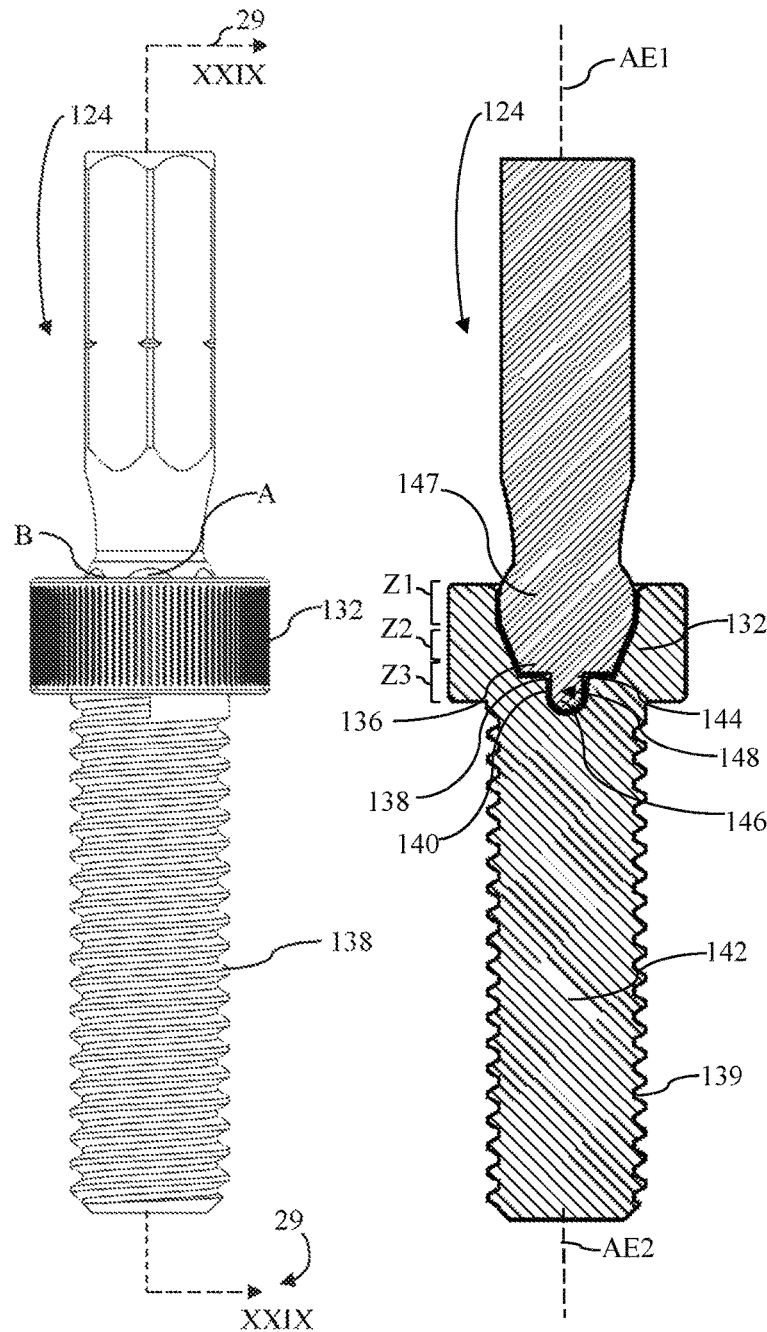
FIG. 27  FIG. 28  FIG. 29

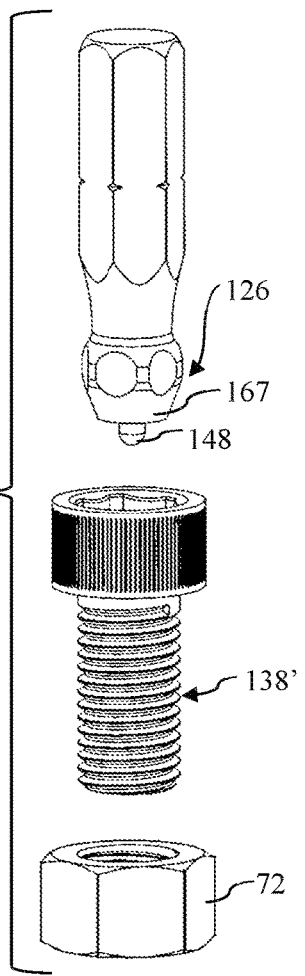
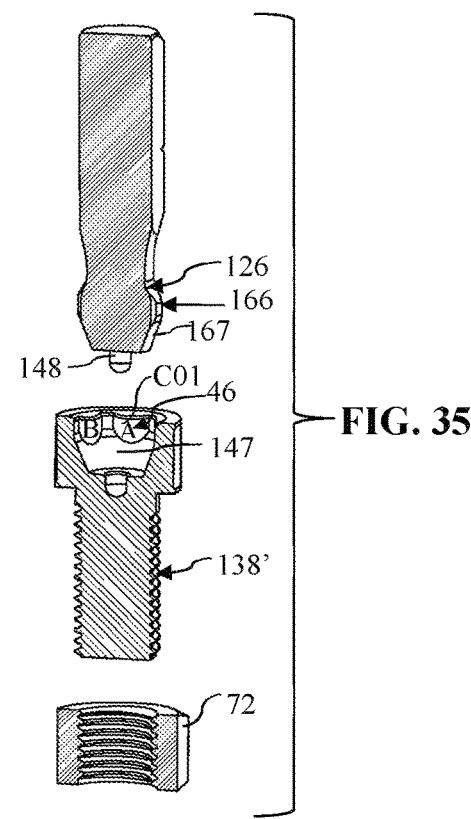
FIG. 34
FIG. 35

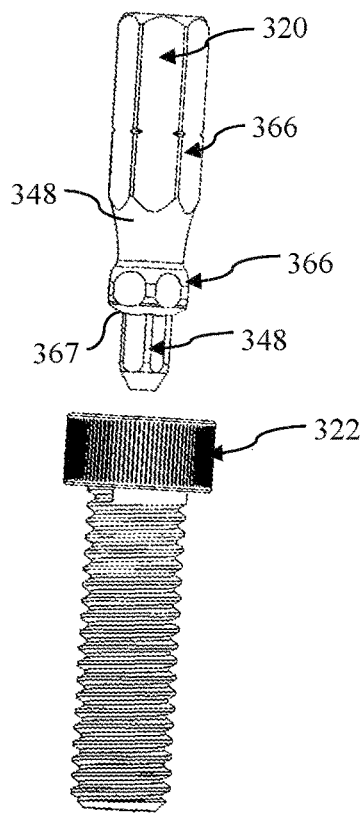
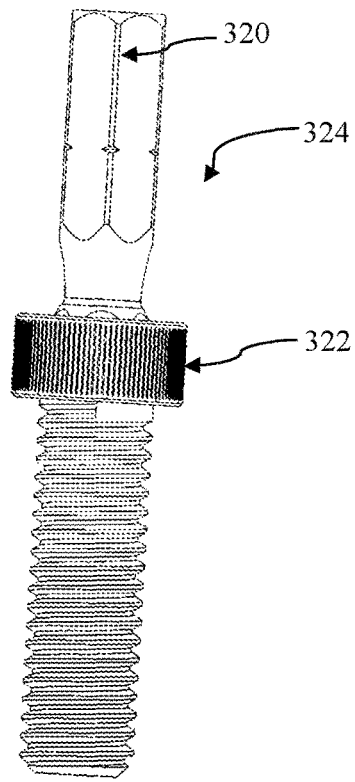
FIG. 44  FIG. 45
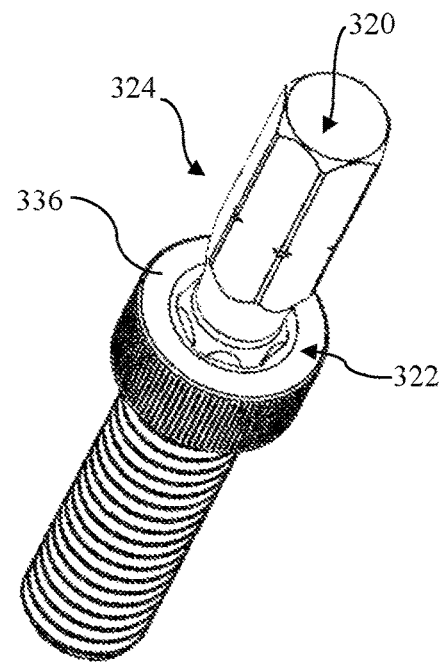
FIG. 46

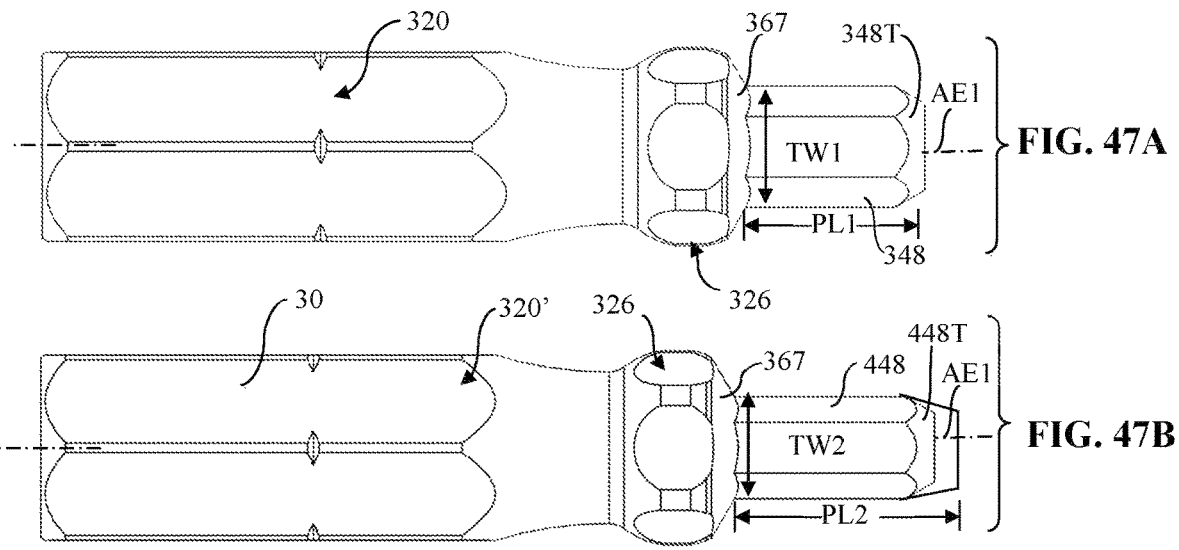
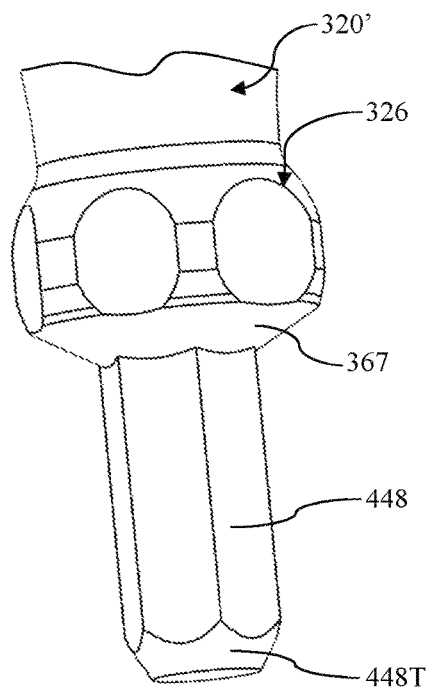
FIG. 48

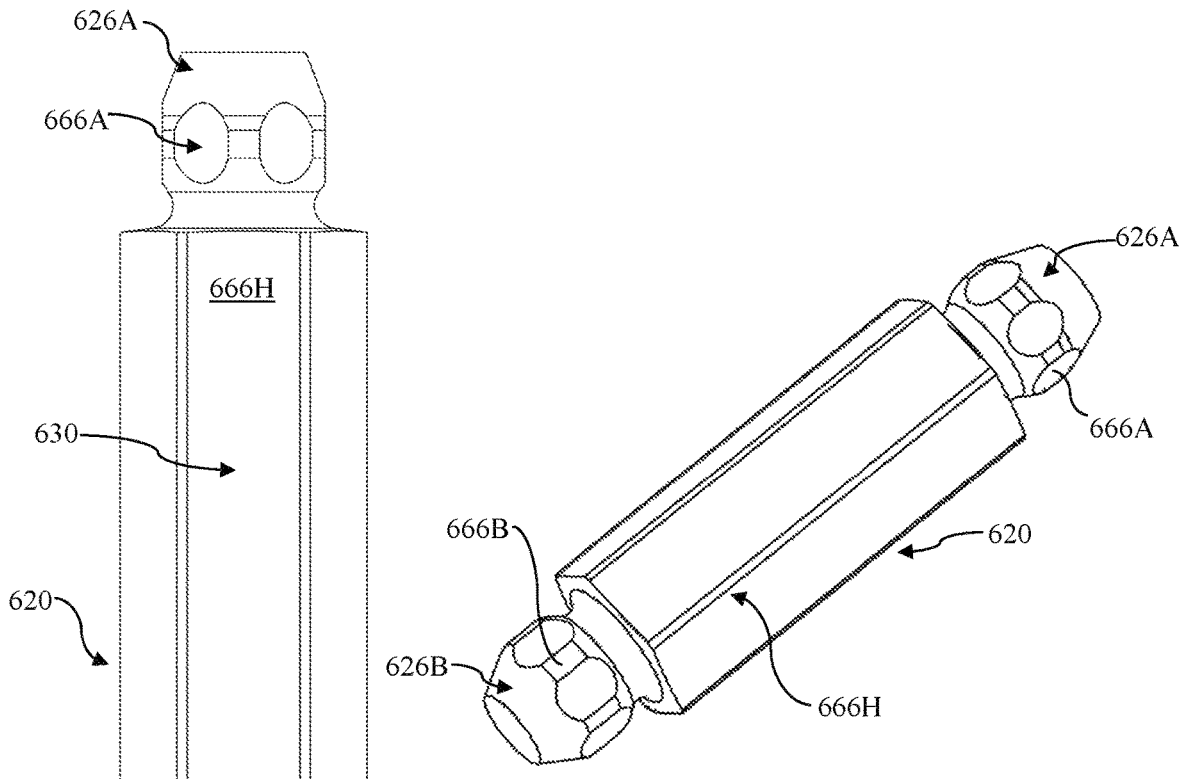
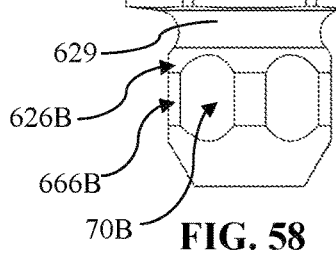
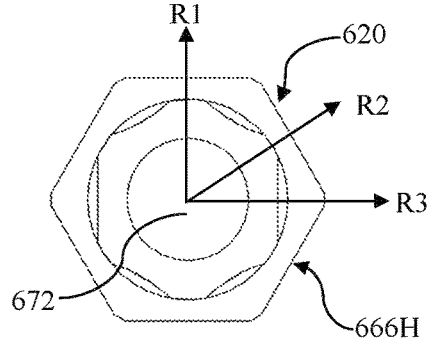
FIG. 58
FIG. 59
FIG. 60
FIG. 61

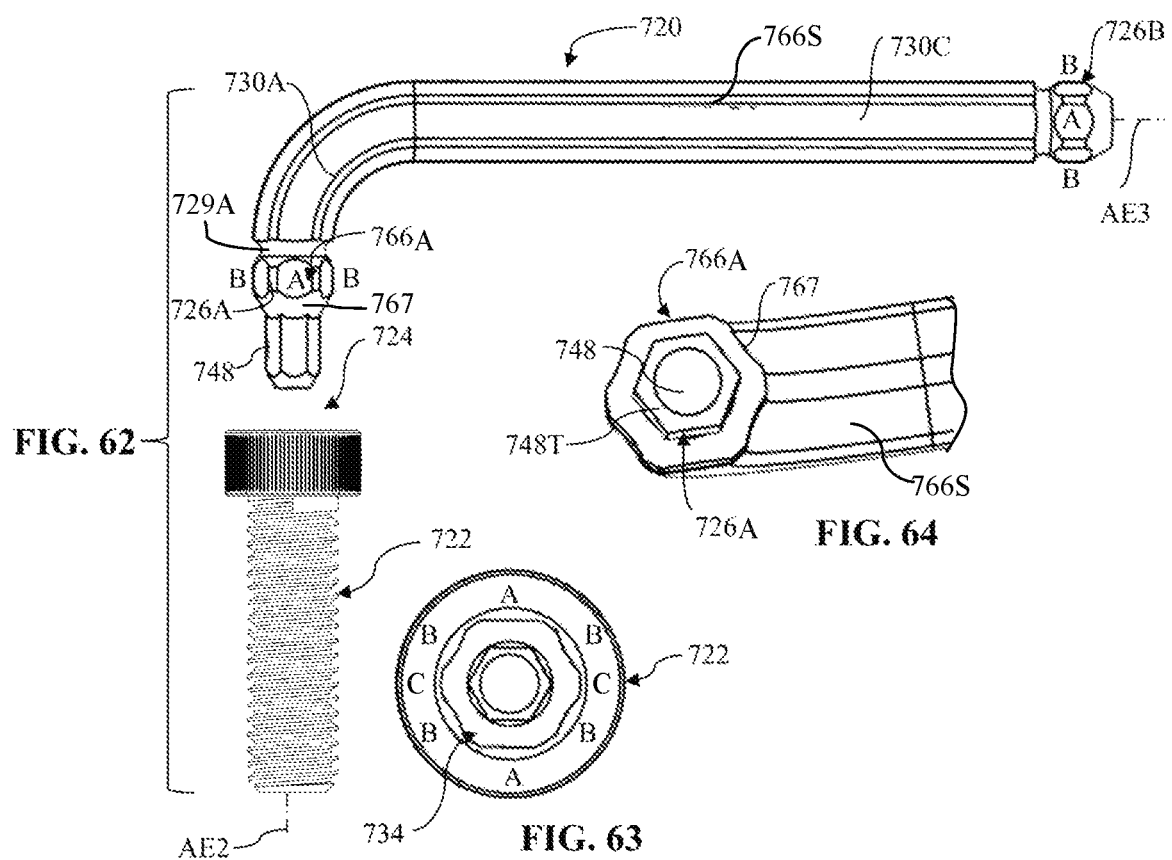
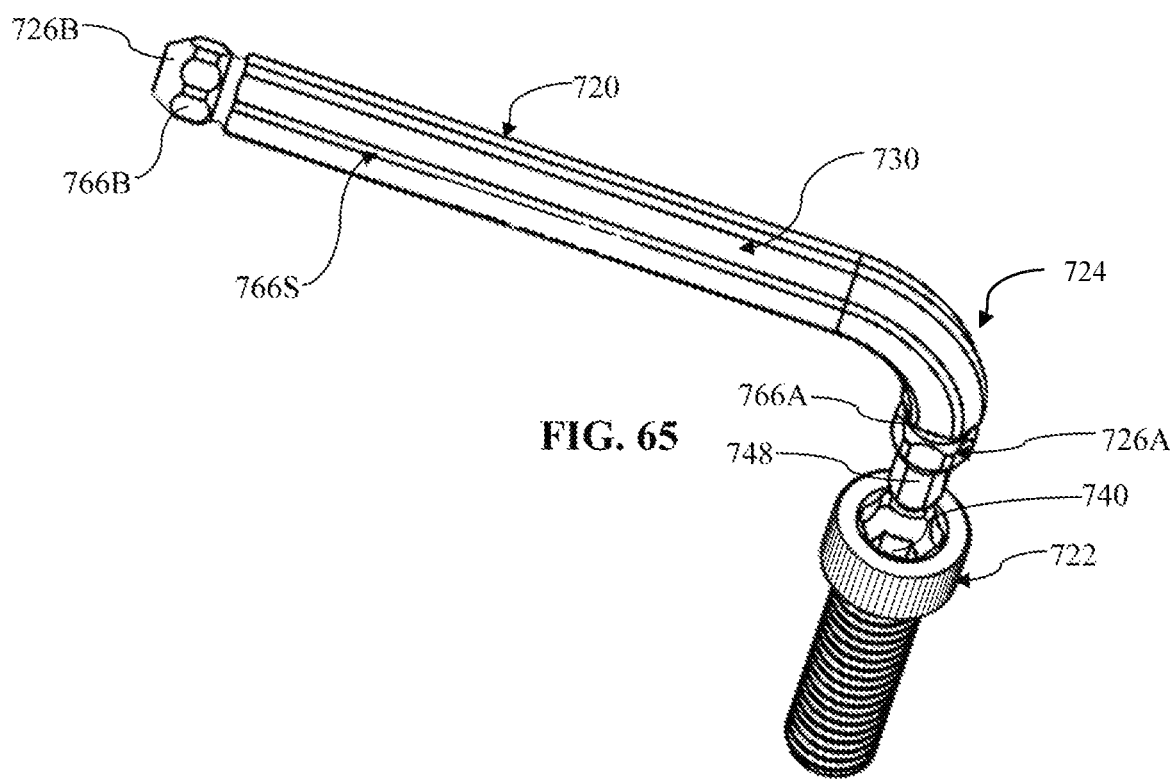

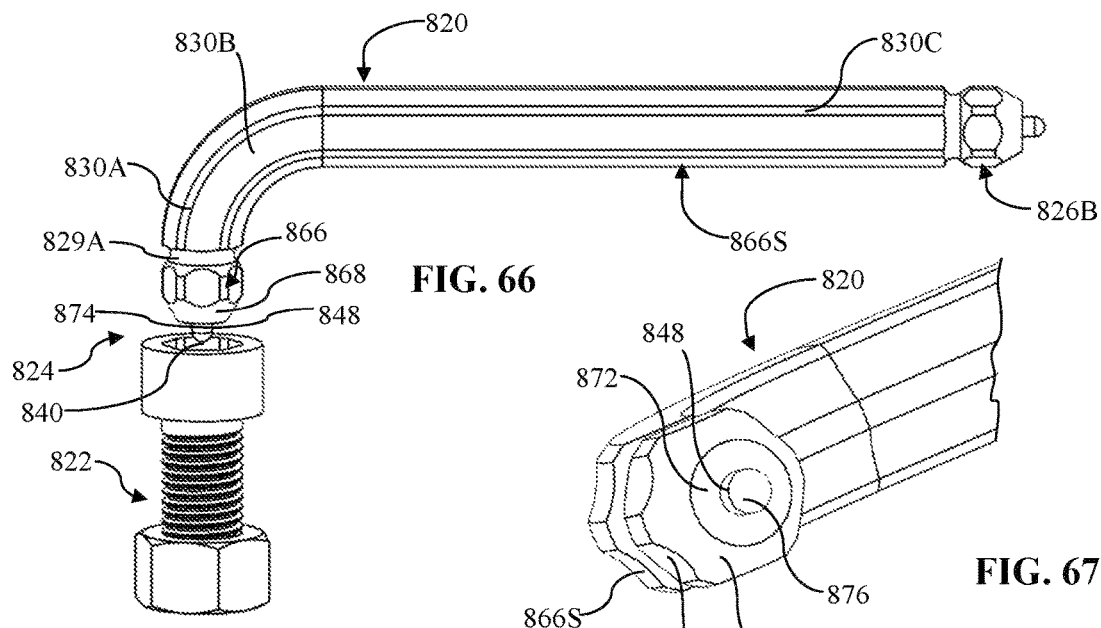
FIG. 66
FIG. 67
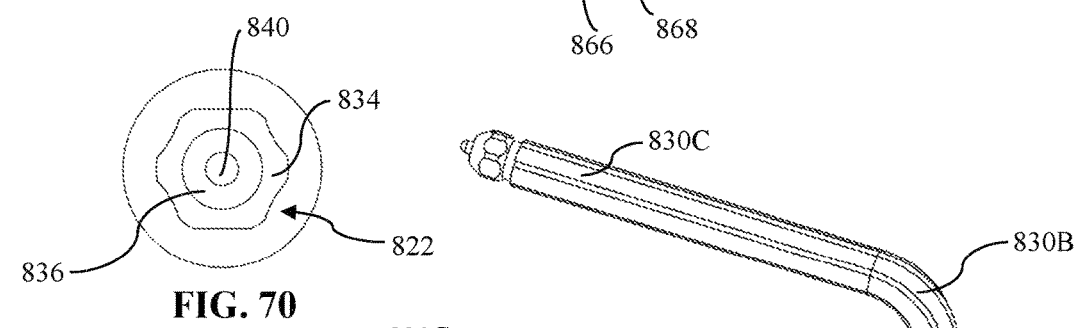
FIG. 70
FIG. 68
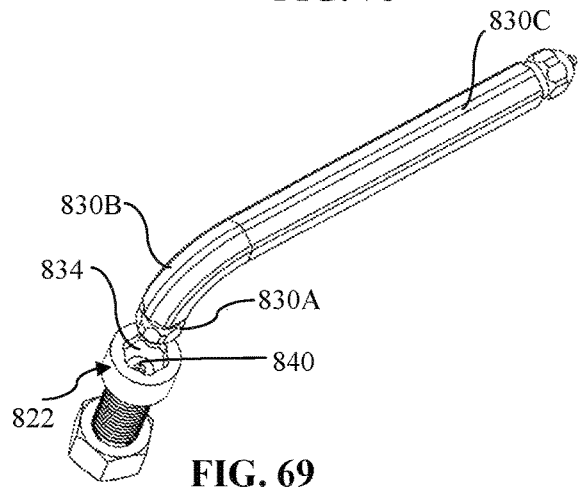
FIG. 69

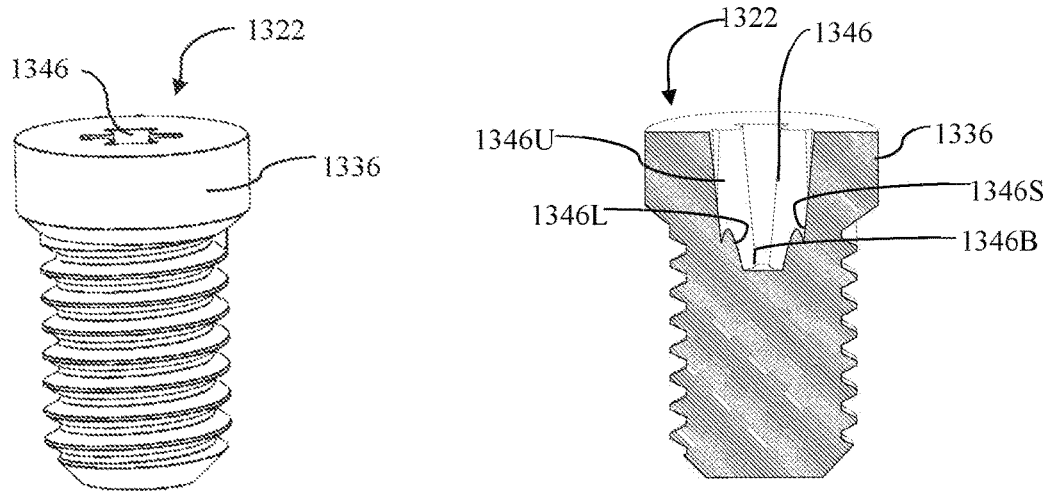
FIG. 97
FIG. 98
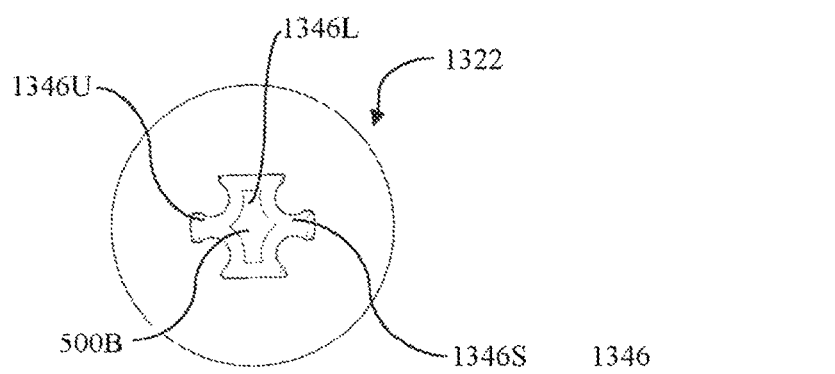
FIG. 99
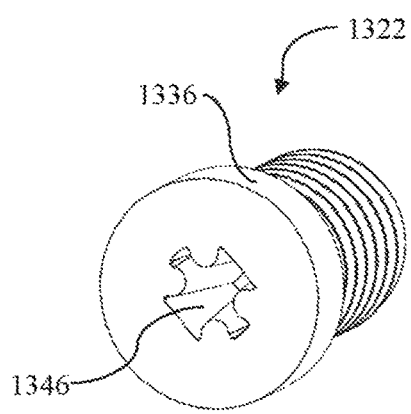
FIG. 100
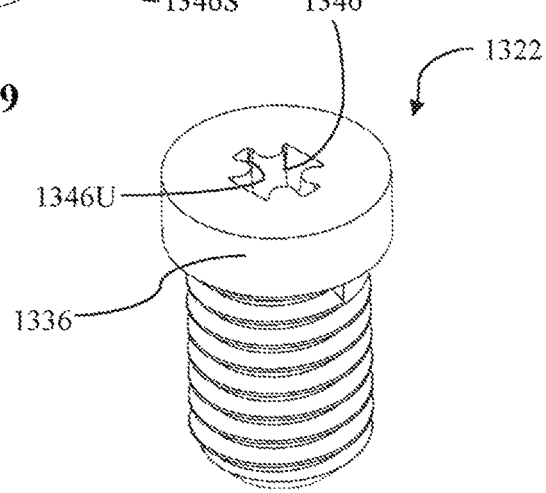
FIG. 101

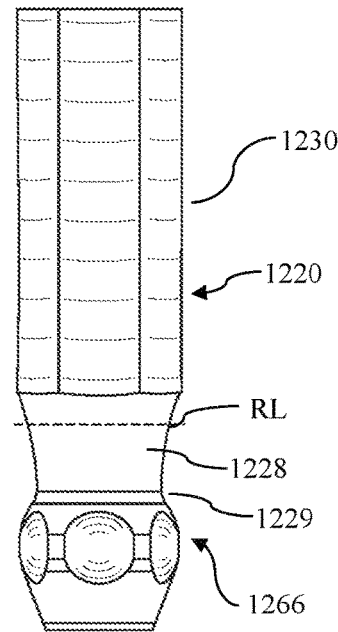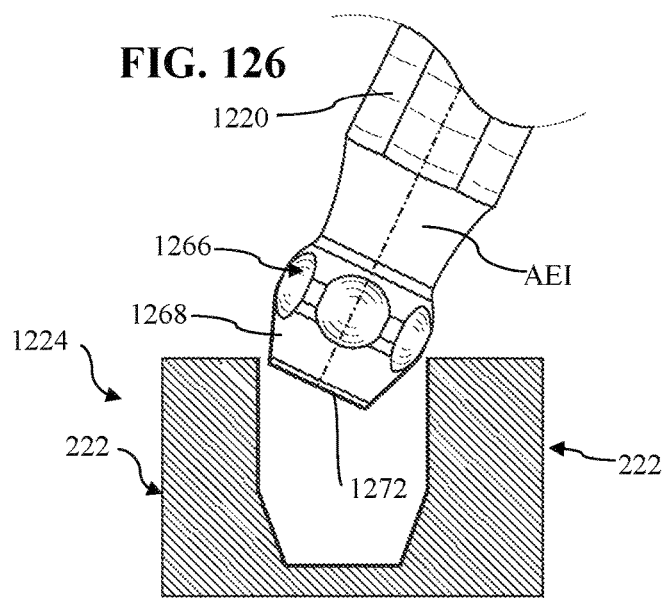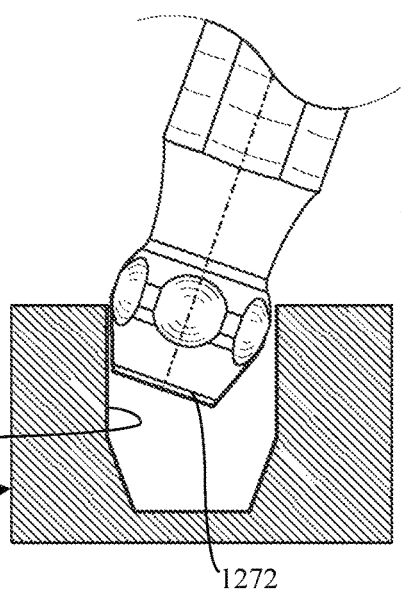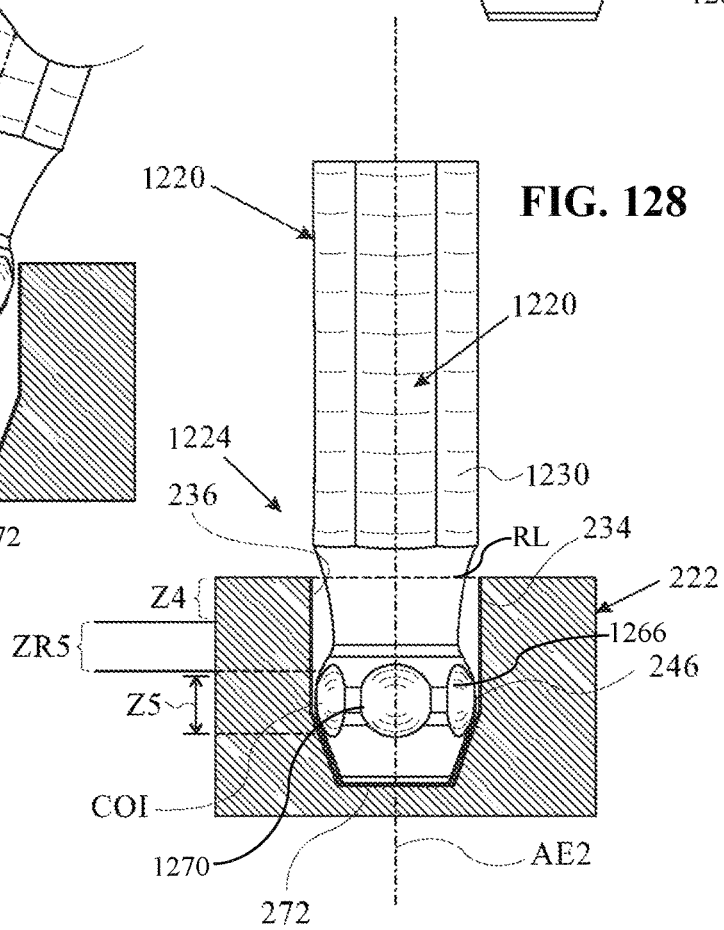

MULTI-TIER TORQUE ENHANCER DRIVER AND/OR RECEIVER AND METHOD OF USING SAME

CROSS REFERENCE TO RELATED APPLICATIONS

The present application is a Continuation-in-Part of U.S. Ser. No. 15/977,431 filed on May 11, 2018 which claims priority to U.S. Provisional Patent Application 62/505,034 filed May 11, 2017, and each of these two applications is incorporated herein by reference in their entirety.

FIELD OF THE INVENTION

The present application pertains to torque generation and receiving devices and methods of utilizing the same, with examples including hand and higher speed rotation devices that utilize the torque generation device of the present application, as in a rotated driver and/or torque recipient devices (e.g., fasteners). The rotation devices and/or torque recipient devices are well suited for use, for example, in tightening and extracting fasteners and/or the fasteners themselves, such as those found in medical and industrial settings, inclusive of micro-fasteners and much larger scaled fasteners.

BACKGROUND DISCUSSION

The relationship between a torque generator and a torque recipient, as in the relationship between a driver and a fastener's head (e.g., screw or bolt head) is a subject of immense study in the prior art. While there has been a great deal of study and activity in this field, there is still lacking in the prior art a driver/recipient relationship that is sufficiently able to avoid at least some of the multiple problems associated with such driver/recipient relationships.

For instance, there is found in the prior art the constant conflict between items such as: ease in insertion of the driver (within and/or about) relative to the recipient (which becomes even more difficult in a currently rotating driver being attempted for insertion); camming out (torque induced exiting of the driver once in a recipient recess); slippage—inclusive of slippage caused by a degradation in the original configuration of the driver and/or recipient recess or contaminates on surfaces of the same); chipping of contacting surfaces as in mismatched surfaces, lack of sufficient torque generation—which can be particularly pronounced on the extraction side due to (in addition to the normal clamped friction adhesion) one or more of corrosion, rusting, hydraulic fluid cohesion, cold welding, etc. Many of the above characteristics in the noted items can be interrelated as in the higher extraction level noted can be a precursor to slippage brought on by breaking or bending of contacting torque generation surfaces.

The issues of slippage and difficulty in extracting a fastener can arise in a variety of settings inclusive of industrial and medical settings. This includes micro-fasteners as in micro-screws such as those having a fastener with a head size of less than 6 mm (e.g., 5 mm or less, or 4 mm or less) and inclusive of 2 mm or less as in 0.25 to 1.6 mm. These micro-fasteners are used in a variety of specialties such as time pieces, optical instruments, electrical meters, measuring instruments, and in the medical field (e.g., orthopedic, oral and maxillofacial surgery). These fasteners introduce the potential for difficulty in removing due to location etc., if the driver/recipient relationship becomes degraded.

For instance, if such a fastener becomes stripped (internally or externally), it may lead to the inability or great difficulty in extracting due to the inability to readily drill out the degraded fastener. When used in the medical field, these type of fasteners can also be much more difficult to remove due to bone welding or the like over time.

As an additional example of difficulties faced with stripped fastener removal, there can be seen industrial fasteners, inclusive of those above the micro-screw size (e.g., 6 mm or up, as in to larger size (e.g. 11 cm) and even much larger sized fastener heads as in 50 cm or even more featured in shipyards, for example) subject to harsh environmental conditions, as in outdoor equipment (farm, marine, bridges, etc.) which are highly subjected to corrosive and rusting environments. These too can become readily stripped and/or not removable with the driving tool.

There is also a deficiency in the art in accommodating the different levels of torque that can exist under fastener usages, including the aforementioned different torque levels in the lower, initial fastener insertion mode and a subsequent higher, extraction mode torque level requirement. Additional scenarios where different torque level attributes are associated with a common fastener can be seen in the need for initial assembly versus final assembly settings, wherein there may not be fully clamped down a fastener under a first setting (e.g., to accommodate for a plurality of fasteners on a common component wherein there is a need for some adjustment flexibility until all fasteners are received in position before a full level torque application, or where there is an initial assembly at a factory or the like and a downstream recipient is to complete the final assembly inclusive of the full torque level predetermined for that fastener, environmental temperature differences wherein there is allowed for some expansion as during a heat treatment of an assembled product during initial manufacturing followed by a final assembly step, inherent relaxation of twisted components upon release of a driving force, etc.).

SUMMARY OF EXEMPLARY INVENTIVE FEATURES

Aspects of the invention include a male (or female; or both) driver component, a female (or male; or both) reception component, and a combination of these components, inclusive of wherein each of the female and male components have coordinated meshing geometries, with there being an enhanced torque generation relationship based on at least one of the components having the enhanced torque configuration described herein and in the parent application US Publ. No. US2018/0325776, having U.S. Ser. No. 15/977,431 filed on May 11, 2018 which claims priority to U.S. Provisional Patent Application 62/505,034 filed May 11, 2017, and each of these two applications are incorporated herein in their entirety.

Aspects of the present invention are inclusive of there being a driver and reception component relationship having (in addition to the above noted torque enhancement relationship) a good self-centering characteristic which, in preferred embodiments, provides for on-going rotation during insertion of the male component into the female component. Also, aspects of the present invention include a male/female relationship that achieves the noted torque enhancement (inclusive of enhanced surface and self-centering while still avoiding camming out of the engaged components, as well as avoidance of stripping one or the other or both of the engaged components during insertion (including RPM insertion) and during torque generation).

Aspects of the present invention include providing a geometrical configuration in the male driver component (and/or also in the female component in preferred embodiments of the invention) that provides for engagement of the fastening process, while not stopping the rotation or revolutions-per-minute "RPM" of the driver (hereafter "RPM engagement"). Under such a fastening engagement the geometries are preferably such that there is self-centering between the male and female components while avoiding stripping to an extent of degrading the ability to remove or install an engaged fastener head. The geometries involved under the present invention provide for added surface area at the point of impact (and associated enhanced torque levels) and a sufficiently corresponding receptive recess geometry, as to provide for relatively precise alignment, which is useful in many environments of use including, for example, uninterrupted production/assembly line demands. The geometries can also be under the present invention of a nature to facilitate an initial point of contact having slanted and/or gradual curving or the like, as to facilitate initial insertion impact followed by a desired torque enhancement meshing of contact (or potential contact) surfaces upon a desired degree of male/female meshing depth of penetration (e.g., at full depth Z-axis contact).

Aspects of the invention are also inclusive of providing coordinated geometries in the male driver component (also referenced as "bit" or "component A" below) and female reception component (or just "recess" or "component B" below) engagement relationship.

The bit and recess geometry relationship is also well suited for avoiding situations such as having component A and/or component B becoming stripped upon engagement or during usage. When this occurs in other geometric forms not of a present invention design, there can occur free spin between components, as when the corners of a hex driver or hex recess smooth out to the extent there is insufficient engagement to either install or remove the fastener or the like. Such free spin situations can present difficult situations in any setting, but particularly in industrial or medical scenarios, as it becomes extremely difficult, if not impossible in some settings, to extract or complete a desired engagement. The geometry(ies) of the present invention are well suited for avoiding such stripping issues. For instance, the longer length/shorter length relationship in the side wall positions of the torque enhancement bit and/or recess of the present invention is/are more adapt at providing greater surface area options that, despite wear or the like, still retain sufficing torque generation to achieve desired installation or retraction. In addition, because of this differential there is enabled additional options not available in prior art geometries, as in usage of a step down in size bit to function as a driver relative to the non-stepped down in size appropriately shaped recess, as well as usage of a present invention driver geometry on a prior art recess as in a hex-shaped recess in a fastener head. Further, in view of the enhanced torque generation, aspects of the invention include providing drivers of the present design with torque limits that initiate slip (e.g., a safety clutch initiation) when sensed torque levels reach a limit.

The bit and/or recess geometry(ies) of the present invention are also considered well suited for avoiding the problem of camming out, wherein centrifugal forces tend to lift the bit out of engagement (e.g., out of the recess). The enhanced torque and enlarged surface contact potential provided for the relative longer/shorter length sides of preferred torque enhancement bits and/or recesses are considered to help avoid such camming out while there is still enabled rapid insertion as the enlarged contact surface potential also helps avoid strict tolerance requirements as is required in some prior art geometries. Also, at play relative to the avoiding of camming out issues, is the nature of the corner recesses (both depth and configuration for example) with some corner configurations more suited for rapid insertion (higher RPM environments) and others less suited for such environments based on the nature of the corner recesses (e.g., deeper corner recesses facilitate harnessing of centrifugal forces, but may involve less rapid engagement potential).

Under aspects of the invention there is featured the noted longer/shorter length geometry but with a preference for a minimized differential in some embodiments (e.g., the contactable side walls of the present invention have opposing pairs of surface contact walls (preferably parallel or essentially parallel as in a slight curvature) that are spaced apart, respectively, by lengths L2 and L1, as to provide a ratio L2/L1 that is below 100% (with 100% representing a square, two set parallel, side relationship)). That is, for environments where, for instance, higher RPM operations are involved and with either or both of the bit and fastener having torque enhancement geometry, that geometry is preferably a torque enhancement rectangular shape, but one that is relatively close to the above noted "square" relationship, as in with L2/L1 being in a range of 75%≤X<100%; and more preferably 80%≤X<100%, as in 90%≤X≤98%. In this way the geometry is well suited for RPM at relatively high levels usage as in those associated with high RPM electrical drivers and air compressor driven mechanical drivers without detrimental wobble forces developing, with an added benefit in having the noted "close" to square relationship, is in the ability to use a driver of the present invention on a variety of prior art configurations as in hex-recessed fasteners. The noted contactable side wall L2/L1 differential also facilitates enhanced friction contact between the engaging driver and engaged torque recipient, which can enhance tightening levels and removal efficiency, particularly when considering that, in many fastener attachment situations, the friction levels involved (e.g., fastener head to contact surface friction, threading friction, etc.) are the largest forces involved and are of primary concern. The enhanced potential for rapid insertion, while still providing for good torque generation, also facilitates any follow up reinsertion of a driver, as upon torque driving return following release of built up strain generated during initial tightening. That is, joints have a tendency to reset after tightening. This means that after a short time, the clamping force in the joint is less than it was when the tightening stopped. For joints which include elastic components such as gaskets this relaxation can be even more considerable and a subsequent torque test may show that the torque is just a fraction of the intended specification. Relaxation is usually overcome by tightening in two stages. Under the present invention a pulse tool or impact wrench can also be a means for handling such relaxation without the need for reinsertion, as the pulsating drive allows relaxation of the joint between the pulses or impacts.

The bit and/or recess geometry(ies) configurations of the present invention are directed at providing a bit and/or recess that provides for stable engagement, is relatively easy to manufacture and maintain, and is difficult to damage in use (even when utilized, for example, in an industrial assembly line wherein the bit and/or recess geometry(ies) provide for continuous spinning of the driver in going from bit/recess engagement from one fastener (e.g., screws or bolts) to the next in an assembly line or similar situations where multiple fasteners are presented at a generally common location for treatment).

Aspects of the present invention are also inclusive of providing one torque force contact relation or tier between the bit and recess, but alternate embodiments are inclusive of more than one torque force contact relationship as in two torque force contacting relationships or tiers (inclusive of common plane (radially separated) two-tier embodiments and axially separated two-tier engagement configurations or a combination of both) with either a common or coordinated general geometrical configuration for each, or two different geometrical configurations for each of the two torque force contacting or meshing relationships. Such a two level torque force contact relationship in the component A (e.g., bit), and component B (e.g., the recess), or each of the two is particularly useful in better accommodating the difference in torque forces that can be experienced between installation and extraction of fasteners and the like. For instance, relative to a situation where, for example, the bit and recess each have corresponding two torque force contact relationships, one torque contact relationship or tier (as in one presenting less surface area contact) can be relied upon in an installation setting, while the other torque contact relationship or tier can be used in an extraction setting (e.g., where the torque levels required for extraction are higher as due to, for example, one or more of the following characteristics: corrosion, rusting, cold welding, hydraulic fluid cohesion, and other similar torque increasing generators). An additional example, would be where there is an initial low level tightening setting with the less torque generating tier or due to strain relaxation, followed by a subsequent, higher torque level tightening utilizing the higher level torque generating tier.

In the discussion below referencing "bit" and "recess", such terminology is also intended to be in reference to a more generic "component A" and "component B" absent an indication otherwise and where physically applicable (e.g., a gear and gear driver combination, etc.). An example of a two tier bit configuration featured under aspects of the invention is one where the bit has a thinner and more distally extending projection first torque surface geometry, and a second radially larger and more proximally located to the shaft (e.g., shank) support second torque surface geometry, as in a bulbous region from which the more distally extending projection extends away from. On the recess side in a corresponding two tier recess relationship, there is featured a thinner (less radially extending) recess section for receiving the thinner and more distally extending projection first torque surface geometry, and a less-thin (more radially extending, but preferably shallower) recess section that is configured to receive the second torque surface geometry, as in the noted bulbous region of the bit. The relative meshing relationship between the bit and recess section can feature the less-torque setting as involving not fully inserting the bit into the recess, but inserting, for example, a radially thinner bit section sufficiently into a radially thinner recess section to provide for the relative meshing of those two sections (but not the bulbous portion of the bit which remains non-engaged with its larger radial recess counter-part). The higher torque setting involves, in some embodiments, the full insertion of the thinner bit section into the cavity represented by the thinner recess section until the larger radial section of the bit is received in the corresponding larger radial section of the recess such that the amount of surface area contact is expanded. Further as noted above, the geometric configuration of the thinner and more radial thick sections can each be the same or coordinated as to provide two tiers of torque enhancement configurations, or one can be different than the other, as in having a hex, Philips or Torx® shape for each of the radially thinner bit and recess portions, and the present invention's longer/shorter torque enhancement geometry for the more radially extending sections of the bit and recess (or vice versa with the thinner section having the torque enhancement configuration and the more radially bulbous head section provided with a prior art configuration as in a hex configuration).

Also, multiple tier embodiments are inclusive of those that are axially separated, but share a common horizontal border plane, or embodiments that feature multiple tier torque enhancement engagement locations as well as axial spacing there-between; including embodiments having intermediate and or external stage level(s) that are not necessarily torque enhancement or torque in general contact surfaces, but allow for a step-down in size along the Z-axis between two or more torque enhancement or torque in general contact tiers. An example, of such Z-axis spacing between different tiers, can be seen in FIG. 175 of the above noted US Publication 2018/0325776 illustrating two step down stage levels between upper and lower torque enhancement contact tiers (as well as an external sloped stage at top—which can also be considered as an integrated slide positioning component of the upper tier in the noted FIG. 175 context).

Rather than different radius stage level surface axial spacing, there can be provided continuous (e.g., cone) shaped step-downs from one size torque enhancement tier to the next (and associated different sized torque generation) or a common hub or shaft supporting different torque enhancement tiers of different sizes. Such step-down arrangements (e.g., like those that feature staged, generally matching shape but different sized intermediate peripheral stack level(s) in-between (as in the noted FIG. 175 of US Publication 2018/0325776), or a continuous conical exterior surface in-between, or a common hub or shaft supporting different sized torque engagement regions, and any combination of the same) are well suited for fasteners under the present invention in providing for different size driver engagements with different torque levels, but also well suited for other torque generators under the present invention as in gearing (e.g., multi-tier torque enhancement levels in gear contact surfaces that step-down in size, as in bicycle derailleur configurations or windmill turbine drive systems with gearing inclusive of different size gearing on a common hub or shaft).

The radially thinner projection of a multi-tier torque enhancement embodiment (which is often the most distal tier) in the bit (and associated receiving recess) also provides for high performance self-centering in the bit/recess component combination, in that the centering can be initiated upon the radially thinner, preferably more elongated projection being received by the deeper receiving recess. Nonetheless, the one tier configurations under the present invention are also readily self-centerable in that the torque enhancement geometries still provide for self-centering, as in the bulbous shaped driver end being readily received within the conforming shaped recess provided in most embodiments. In an aspect of the invention, one or more tiers can have a tapered configuration as in having the outermost contact walls (one pair or two pairs, for example) having converging Z-axis extending wall surfaces (to opposite sides of intermediate corner concavities) that converge at a desired Z-axis angle as they approach the more distal region of the tool (and preferably as well a similarly converging recess Z-axis wall configuration for receipt thereof) as to facilitate insertion as in Phillips tool general fashion).

A third (or more as in 4, 5, . . . 12 or more) torque geometry tier(s) can also be featured under aspects of the present invention, as in an outer ring with interior socket like torque generator with the radially thinner and bulbous end torque generators noted above positioned radially interior of that outer ring; or a six gear derailleur. The term "tier" as used in the present invention is used in a broad sense (e.g., different rankings or classifications, as being inclusive of a) tool axis spaced apart respective torque contact surfaces (whether sharing a common intermediate border with different sized radially extending contact surfaces, or spaced apart axially with the same or different sized radially extending contact surfaces), b) common tool axis height and radially (or circumferentially) spaced respective contact surfaces, or c) a combination of each of a) and b).

An additional aspect under the present invention includes the addition of holes in one or more of the projections arranged in solid form, as with an exterior surface of a bit having the torque enhancement configuration of the present invention together with one or more holes such as for venting and like in those extensions extending out from the core body of the noted projections (e.g., FIGS. 173 and 174 of the aforementioned, incorporated US Publication 2018/0325776). This can provide a weight reduction as well, and can also be strategically positioned to lessen the potential for wobbling (e.g., added weight balance) in the generally rectangular configured tool, and also can provide a source for fluid release or introduction (e.g., cooling fluid) in an area being addressed. An additional means for providing venting or supply channeling can be seen in the nature of the torque enhancement longer and shorter extensions, as where there is inserted a driver having torque enhancement in a recess receiver that has a not completely matching recess configuration (e.g., a conventional hex recess) whereupon the less radially extending projections of the driver provide added gap space, while the more radially extending projections still can catch upon rotation. Still further, while the holes in the above noted FIGS. 173 and 174 of the US Publication 2018/0325776 are shown as extending parallel to the Z-axis, alternate configurations include having radial holes extending to a central aperture on one or more of the noted projections (preferably in a pair formation to retain bi-symmetry and with the notion of weight balancing relative to the respective mass of the projections). Alternatively, rather than projecting radially only or along the Z-axis only, embodiments of the invention include having a combination as in having a lower opening of a channel (representing the above noted "hole" initiate at the periphery of the projection(s) and then curve upward so as to open out at the upper, exposed region of that same projection mass, again with the benefit of both weight balancing and liquid passageway if such passageway is desired.

The degree of surface contact potential expansion provided by the torque enhancement configuration further provides for a lower profiled head (and associated weight reduction). That is, there is a relationship between depth of the bit within the recess as to the level of surface contact and level of torque that can be generated. Thus, with the enhanced surface contact potential provided by the torque enhancement configuration of the present invention, the profile depth insertion can be lessened while retaining a common torque level potential (the loss in profile depth surface contact is compensated for by the torque enhancement configuration in the periphery of the bit (and/or recess)). Also, since the longer length sections of the bit (and/or recess) provide good strong surface torque contact, there is avoided chipping etc., relative to the "teeth" featured in the torque generation.

The torque enhancement geometries of the present invention are also well suited for receiving a coating (strengthening, scratching resistance, corrosion resistance, etc.) that have become more commonly used in the art. This added coating usage can present problems relative to proper meshing of a bit/recess in the prior art (particularly for "stick" meshing bit and recess arrangements in the prior art), which can be avoided under embodiments of the present invention. The usage of coatings under the present invention is also useful relative to RPM insertion situations as a strengthening coating on either the bit or recess or both can help relative to the rotating contact of the bit being inserted into the recess during full or stepped-back rotation. The rectangular longer/shorter length side wall torque enhancement relationship of the present geometries can also assist in avoiding problems in the prior art that can occur upon adding such coating layers, as on the driver and/or receiving recess. That is, under the toque enhancement configuration of the present invention there are surfaces provided relative to the different wall length torque enhancement configuration wherein meshing is not need to be as tight (e.g., the lower length projection wall surfaces) while still achieving a high torque generation in the remaining surfaces that are not strategically spaced from the receiving recess walls. This potential spacing also provides for insertion and removal capability of fluids, etc. That is, the gaps between the wall surfaces of the recess and the shorter length walls facilitate the receipt and/or removal of cooling fluids, grease, adhesives for permanent fastening, extraction facilitating solvents (e.g., Liquid Wrench® solvent), etc.

Further aspects of the present invention are inclusive of bulbous bit heads, as in in ones having proximal and distal curved surfaces (opposite base surfaces) that extend into a common intermediate peripheral ring having the enhanced torque contour configuration, including the corner concavities that help define the shorter and longer length projections in the described torque enhancement geometry. The bulbous head can include a proximal ring concavity as a demarcation between the bulbous head and a supporting shank section. In some embodiments that shank body includes its own torque generating surface as in the present invention's torque enhancement geometry or some other, as in a hex configuration. In this way a high depth recess can receive the bulbous head in a corresponding deepest region of the recess, while the shank distal end with the noted own torque generating surface, such as the torque enhancement configuration or a hex surface, can also be received at the upper end of the overall receiving recess.

Aspects of the invention are also inclusive of a first illustrative aspect (referenced as "Aspect 1" for convenience) represented by a torque enhancing device, comprising:
  a. a torque contact body having one or more torque driver and/or recessed recipient torque contact surface configurations,
  b. at least one of the one or more torque contact surface configurations having four concave contoured surface portions (with concave being used in a general sense of extension inward relative to the adjacent end points and can be contoured like a hollow circle or have a variety of other shapes both linear and/or curvature and with or without added sub-cavities; noting that when the torque enhancement shape represents the exterior periphery (e.g., the outer periphery of a bolt head) the concave surface thereof will be a recess relative to that peripheral surface; and thus, when the torque enhancement surface is an interior wall, as in a recess in a fastener head, the concave surface portion thereof will be represented by a radially inward extending solid portion of the surrounding fastener head as to define the concave surface portion of the torque enhancement surface's interior ring wall) positioned between respective adjacent ends of a pair of X-axis extending torque contact side walls, that are Y-axis spaced apart for a length L1, and a pair of Y-axis extending torque contact side walls, that are X-axis spaced apart for a length L2, and wherein the X-axis extending torque contact side walls and the Y-axis extending torque contact side walls are arranged such that a ratio of L2/L1 is less than 1 as to provide a torque enhancement contact surface configuration.

Additionally, a version of the torque enhancing device of Aspect 1 is one that features at least two of the one or more torque contact surface configurations as having the torque enhancement contact surface configuration such as where the at least two torque enhancement surface configurations are axially spaced along the Z-axis or are radially separated on a common X-Y axes plane. The axial spacing can result in the torque enhancement contact surface configurations sharing a common X-Y axes border plane or there being an intermediate space there-between, with the intermediate spacing being occupied, for example, by one or more different peripheral step down ledges, conical or tapered continuous wall surfaces, or a common supporting hub or shaft.

An alternate form of Aspect 1 has the body as a fastener head having two different sized regions with respective surface contouring, with the surface contouring of at least one of the two different sized regions defining the torque enhancement surface configuration. For example, an arrangement where the surface contouring of each of the two different sized recess regions has the torque enhancement surface configuration with at least one of the regions being an interior recess region in the fastener head. An alternate example is one wherein one of the two different sized recess regions has a non-torque enhancing configuration (e.g., a hex, Phillips, Torx®, square, etc. configuration) and the other different sized recess region is the torque enhancement surface configuration which preferably has bi-symmetry or essentially bi-symmetry.

An additional configuration under Aspect 1 is one wherein the body is a driver having two axially spaced torque contact surfaces at least one of which defines the torque enhancement surface configuration. For instance, there is considered an arrangement wherein the two axially spaced torque contact surfaces each have the torque enhancement surface configuration. There is additionally considered an arrangement wherein the two axially spaced torque contact surfaces of the driver have different sizes (e.g., different peripheral area dimensions) as in a radial thinner or less area more distal torque contact surface configuration and a wider or greater area less distal torque contact surface configuration. An example includes a more distal tool end torque enhancement configuration having a Z-axis converging pair (or pairs) of side walls with preferably conforming recess reception wall surfaces which end in a pointed, concave (e.g., a reverse silo) or cut-off cone free end.

An additionally considered arrangement relative to the aforementioned driver having the two axially spaced torque contact surfaces is one wherein one of the axially spaced contact surfaces is a bulbous configuration and the second of the two axially spaced torque contact surfaces has a non-bulbous configuration such as one with linear only side walls. Such linear side walls can be those parallel to the Z-axis and/or converging toward distal most end configurations, with the latter also providing for enhanced insertion and removal configurations as in enabling mutual sliding even when Z-axes orientations between the two are not aligned.

Another considered arrangement, relative to the aforementioned driver having the two axially spaced torque contact surfaces, is one wherein one of the two axially spaced torque contact surfaces has a non-torque enhancement surface configuration (e.g., a hex or square configuration) and the second of the two axially spaced torque contact surfaces has the torque enhancement surface configuration preferably with bi-symmetry or essentially bi-symmetry. Also, the two axially spaced torque contact surfaces can be both of the same functioning configuration (e.g., each fastener drivers) or one can be of one function and the other of a different function (e.g., one a gear and the other a fastener driver as can be seen in a drill chuck key design (with bevel gear and pilot extension combination, with the present invention including a modified pilot extension with dual functioning fastener drive tip distal of the bevel gear)).

An aspect of the present inventions also features the aforementioned driver as being a driver having a hand support as in a grip handle (e.g., a generally overall cylindrical handle grip, a T-shaped handle grip, or a common housing with pivoting tooling support(s) (as in a Swiss Knife® housing configuration).

Further aspects of the present invention including providing the contact surface regions of either the male and/or female component with texturing as in grooving or ridges in strategic locations, including adding such material to favor added friction contact in one direction or the other (e.g., weighting the added texturing to a side where rotation is for extraction to better accommodate the noted higher torque requirements often associated with extraction per the discussion above).

Under aspects of the present invention there is also featured an arrangement wherein the driver is elongated with a curving section and two straight end sections with the two end sections having the two axially spaced torque contact surfaces (sharing some similarity with an "Allen" wrench general shape) with the two axially spaced torque contact surfaces either being the same in configuration or different, and with one or both of the two having the torque enhancement surface configuration. In addition, to having respective torque contact surfaces at opposite ends of the L-shaped tool, each or both ends can be provided with multiple-tier driver torque contact surfaces.

Aspects of the present invention are also inclusive of the aforementioned driver being a driver that is elongated with a shank end that is configured for receipt within a chuck of a powered rotating device.

There is also featured an assembly of the present invention having the torque enhancing device with shank end configured for receipt within a chuck of a powered rotating device, as well as the powered rotating device itself.

An additional aspect of the present invention features a multi-tier torque enhancing device, comprising:
 a. a torque contact device having radially or axially separated torque contact surface configurations; and
 b. at least one of the one or more torque contact surface configurations having four concave contoured surface portions positioned between respective adjacent ends of a pair of X-axis extending torque contact side walls, that are Y-axis spaced apart for a length L1, and a pair of Y-axis extending torque contact side walls, that are X-axis spaced apart for a length L2, and wherein the X-axis extending torque contact side walls and the Y-axis extending torque contact side walls are arranged such that a ratio of L2/L1 is less than 1 as to provide a torque enhancement contact surface configuration.

An additional aspect of the present invention features the aforementioned multi-tier torque enhancing device with the torque contact device having a fastener head with the radially or axially separated torque contact surface configurations, at least one of which has the enhanced contact surface configuration.

Alternatively, the aforementioned multi-tier torque enhancing device is a driver device with axially separated torque contact surface configurations of which at least one has the enhanced contact surface configuration. This is inclusive of having the enhanced torque contact surface configuration of the driver device having, on one of the X-axis or Y-axis extending side walls, a Z-axis taper that axially diverges toward, for example, a distal free end of the driver.

A further aspect of the invention includes a method of operating a torque enhancing device comprising rotating and contacting a first fastener head with the multi-tier torque enhancing device driver noted above, and then adjusting that driver device, while still rotating, into contact with a second fastener head.

An additional aspect of the present invention features a multi-tier torque enhancing combination (a combination aspect), comprising:

a. a first torque enhancing device, comprising a driver torque contact body having at least two torque driver torque contact surface configurations with the driver torque contact body having a Z-axis depth or thickness, and at least one of the torque contact surface configurations comprising a pair of X-axis extending torque contact side walls that are spaced apart along a Y-axis for a distance L1, and a pair of Y-axis extending torque contact side walls that are spaced apart along the X-axis for a distance L2, and four concave contoured surface portions positioned between respective adjacent ends of the X-axis extending torque contact side walls and the Y-axis extending torque contact side walls, and wherein there is an L2/L1 ratio of less than 1; and b. a second torque enhancing device, comprising a recessed recipient torque contact body having at least one torque contact surface configuration that comprises a pair of X-axis extending torque contact recess side walls that are spaced apart along a Y-axis for a distance L3, and a pair of Y-axis extending recess torque contact side walls that are spaced apart along the X-axis for a distance L4, as well as four concave contoured surface portions positioned between respective adjacent ends of the X-axis extending torque contact side walls and the Y-axis extending torque contact side walls, and wherein there is an L4/L3 ratio of less than 1, and c. wherein the first and second torque enhancing devices are designed for torque generation mesh engagement at least at the torque enhancement contact surface configurations of the respective first and second contact enhancing devices.

Under the aforementioned combination aspect there is an arrangement that features the driver torque contact body as having two torque driver torque contact surface configurations that are Z-axis axially spaced apart, and wherein the recessed recipient torque contact body has two driver torque contact surface configurations that are Z-axis axially spaced apart, and wherein the two axially spaced apart driver torque contact surface configurations are in respective torque generating contact with the two axially spaced apart torque driver torque contact surface configurations of the recessed recipient torque contact body when the first and second torque enhancing devices are in a torque generation mesh engagement.

An additional aspect of the present invention involves a method of removing or installing a fastener with the fastener representing the second torque enhancing device. The method includes utilizing the first torque enhancing device, which is in the form of a driver, by inserting the first driver torque contact body into the recessed recipient torque contact body of the fastener, which fastener has a fastener head having the two torque driver torque contact surface configurations that are Z-axis axially spaced apart (with a common X-Y axes border wall or with distal-proximal spacing therebetween, as in one or a combination of hub or shaft spacing, step-down ledging, or conical bridging regions), and then rotating the meshed first and second torque enhancing devices to achieve the tightening or loosening (e.g., extraction) of the fastener depending upon the direction of rotation.

Additional features and advantages will be set forth in the detailed description which follows, and in part will be readily apparent to those skilled in the art from that description or recognized by practicing the aspects of the invention described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate various aspects of the present invention, and together with the description serve to explain principles and operation thereof.

BRIEF DESCRIPTION OF THE DRAWINGS

In order to understand the invention and to see how it may be carried out in practice, embodiments will now be described, by way of non-limiting examples only, with reference to the accompanying drawings, in which:

FIG. 9 also shows a bottom plan view of the torque enhancer of FIG. 7, but with a considered "spiral-centrifugal" contact point illustration and with the closed off base illustrated as would be present in a cap nut or the like.

FIG. 27 shows the same combination in engagement as in FIG. 26, but in a vertical orientation.

FIG. 28 shows the driver and fastener of FIG. 27 but in an engagement setting, as would be present either during a fastener insertion or a fastener extraction setting.

FIG. 29 shows a vertical plane cross-sectional view of the combination shown in FIG. 28 taken along cross-section XXIX-XXIX in FIG. 28.

FIG. 34 shows a view similar to that in FIG. 27, but for the depiction of a fastener recipient, which in this view is shown as a conventional hex nut for threading on the bolt, which bolt again is shown as a shorter length bolt as compared to the FIG. 24 counterpart.

FIG. 35 shows a vertical cross-sectional view of that which is shown in FIG. 34.

FIG. 44 shows the same combination in engagement as in FIG. 42, but in a vertical orientation.

FIG. 45 shows the coordinated geometry driver and fastener combination of FIG. 44, but in an engagement setting, as would be present either during a fastener insertion or fastener extraction mode.

FIG. 46 shows the driver and fastener combination of FIG. 45, but from a vertical perspective view.

FIG. 47A shows a full view of a relatively shorter/thicker extended driver projection embodiment similar (but with a distal tier driver portion that is shorter and thicker) than that shown in FIG. 43.

FIG. 47B shows, for comparison purposes, a similar general configuration as shown in the intermediate length and thickness lower tier projection driver embodiment in FIG. 43, but with a thinner and longer in Z-axis extension in its distal driver tier (and thus also thinner and longer than the thicker and shorter FIG. 47A distal driver tier).

FIG. 48 shows the driver in FIG. 47B featuring the more elongated distal projection.

FIG. 58 shows, in vertical orientation, another male driver embodiment of the present invention which features opposite driving heads on a common shank body.

FIG. 59 shows, a first perspective view, of the dual headed male driver embodiment shown in FIG. 58.

FIG. 60 shows, a second perspective view, of the dual headed male driver embodiment shown in FIG. 58.

FIG. 61 shows an end view of the driver of FIG. 58 (the opposite end being the same for the embodiment presented).

FIG. 62 shows still another embodiment of a male/female combination of the present invention also having a torque enhancement relationship which features a dual headed tool with one head shown close to engagement with (or just recently disengaged from) a corresponding female reception cavity of a fastener.

FIG. 63 shows an end view of the female reception cavity of FIG. 62.

FIG. 64 shows a cut-away driver end view of one of the heads of the tool in FIG. 62.

FIG. 65 shows the same combination as shown in FIG. 62 but in a different orientation.

FIG. 66 shows yet another embodiment of a male/female combination of the present invention having a torque enhancement relationship which also features a dual (common) headed tool with a different head configuration as compared to the heads in FIG. 62.

FIG. 67 shows a view of one of the driver head ends of the tool in FIG. 62 in cut-away.

FIG. 68 shows the embodiment of FIG. 66 from a different side view perspective orientation.

FIG. 69 shows the embodiment of FIG. 66 from a different top perspective orientation.

FIG. 70 shows an end view of the reception head of the fastener shown in FIG. 66.

FIG. 97 shows a perspective elevational view of an additional fastener member having two axially separated reception recesses with each having a torque enhancement configuration in this embodiment.

FIG. 98 shows a bi-sectional cross-sectional view of that which is shown in FIG. 97 and illustrating the torque enhancement reception region at the center of the fastener head, and which reception region includes a two tier (axially separated) cavity pair, with an enlarged radius upper end torque enhancement (interior) surface configuration and a smaller radius lower end torque enhancement surface configuration (also interior) extending axially and inwardly converging fashion to form the reception region's base.

FIG. 99 shows a top plan view of that which is shown in FIG. 97.

FIG. 100 shows another perspective view of the fastener in FIG. 97.

FIG. 101 shows still another, different perspective view of that which is shown in FIG. 97.

FIG. 116 shows a perspective bi-sectional cross-sectional view of that which is shown in FIG. 112.

FIGS. 117A and 117B show examples of TORX® drivers, with FIG. 117A showing a TORX T25 ® driver, and FIG. 117B showing a TORX T25 ® driver (in partial cut-away).

FIGS. 117C and 117D show two axial tier examples of torque enhancement drivers under the present invention.

FIG. 117E shows a standard hex configured driver end.

FIG. 118A to 118E show the respective driver shown in FIGS. 117A to 117E in association with an associated fastener.

FIGS. 119A and 119B show examples of TORX® drivers, with FIG. 119A showing a TORX T25 ® driver, and FIG. 119B showing a TORX T25 ® driver (in partial cut-away).

FIGS. 119C and 119D show two axial tier examples of drivers sharing similarities with those in FIGS. 117C and 117D, with their contoured (convex/concave) distal end projections.

FIG. 119E shows a standard hex configured driver end.

FIG. 120 shows a view similar to FIG. 3A but for a torque enhancer having notched walls (both of the long walls having a spaced pair of notches in this embodiment).

FIG. 121 shows another view of the torque enhancer shown in FIG. 120 having a different notch configuration (two notches on one long wall surface and one elongated notch on its other, but otherwise being bi-symmetric).

FIG. 122 shows an additional embodiment of the present invention featuring a two-tier/two-different driver form (gear and torque enhancement driver head) combination.

FIG. 123 shows an additional embodiment of the present invention featuring a T-handle hand grip tool with torque enhancement driver.

Figure 124:
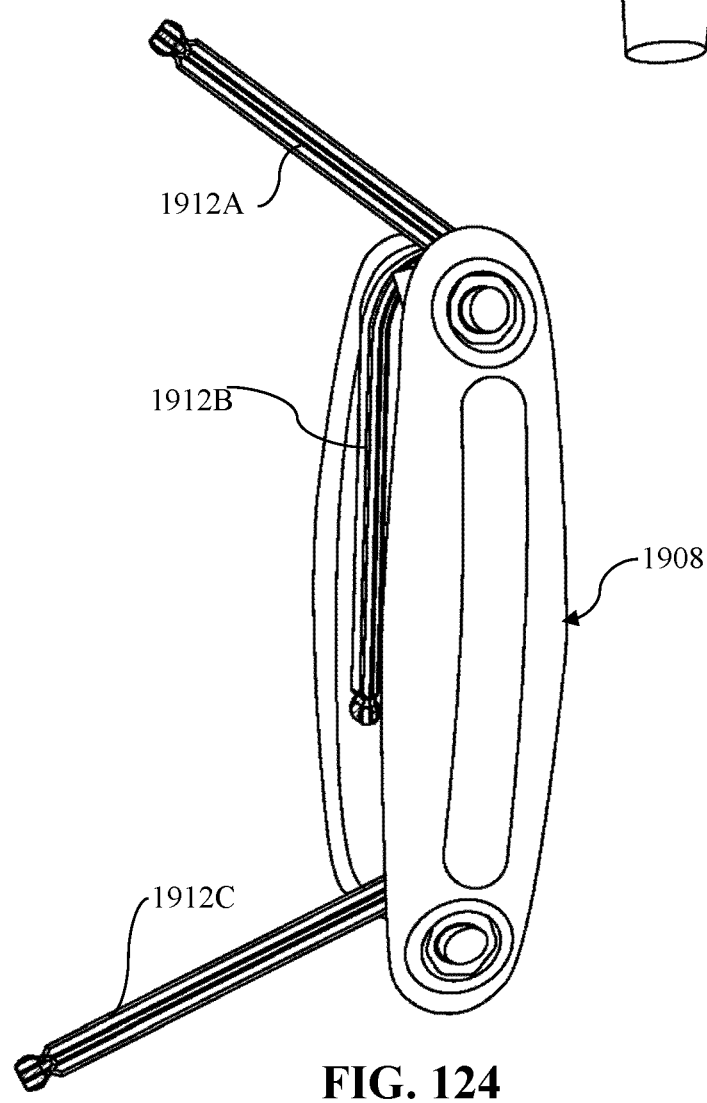

FIG. 124 shows an additional embodiment of the present invention featuring a multi-tool device with a different size torque enhancement tool combination set pivotably supported in a common housing.

FIG. 125 shows a vertical orientation view of another driver embodiment of the present invention.

FIG. 126 shows an early initial insertion state of the driver in FIG. 125 within a receiving recess (or an almost fully withdrawn state).

FIG. 127 shows an initial contact state of the driver in FIG. 125 within a receiving recess (or a partially withdrawn state).

FIG. 128 shows a fully engaged and in meshing relationship state relative to the driver and recessed recipient featured in FIG. 127.

Figure 129:
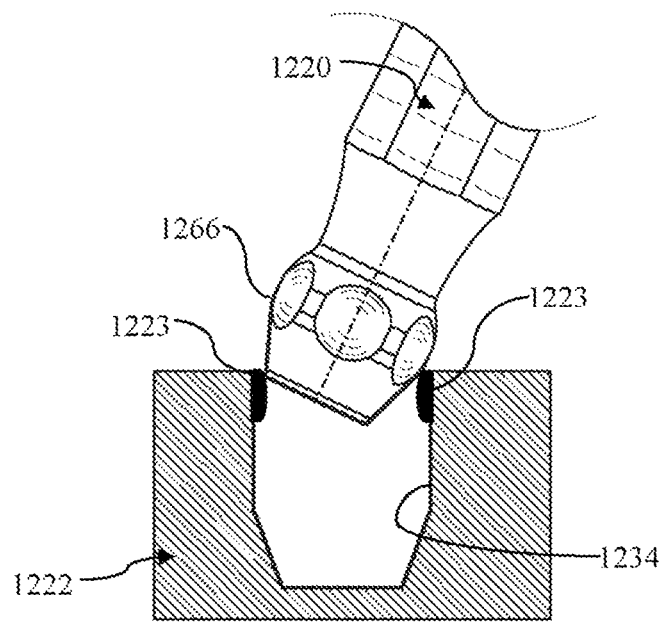

FIG. 129 shows a view similar to that of FIG. 127 but with the recessed recipient having an added, upper capture rim.

Figure 130:
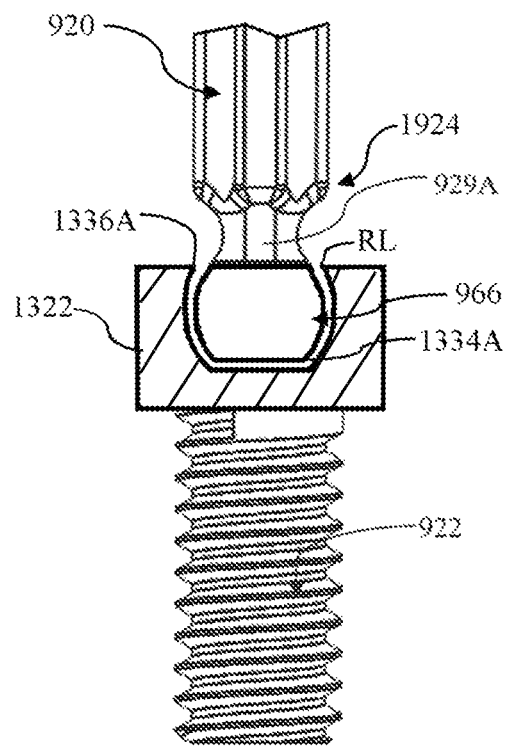

FIG. 130 shows an alternate engagement relationship which is similar to FIG. 128 but with a different driver and recessed recipient having a different capture rim design (with better matching geometries) than that of FIG. 129.

Figure 131:
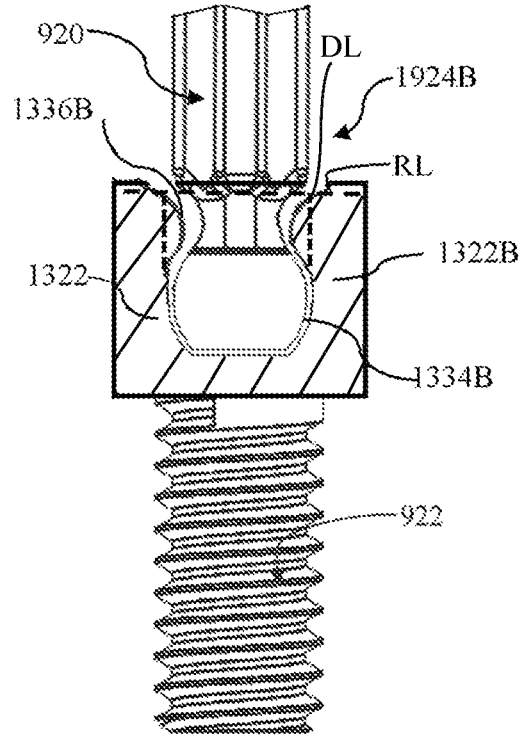

FIG. 131 shows the same driver as in FIG. 130 but with a still different recessed recipient by way of a modified sloped down and less proximal capture rim design that also has a matching geometry relationship.

Figures 132, 133:
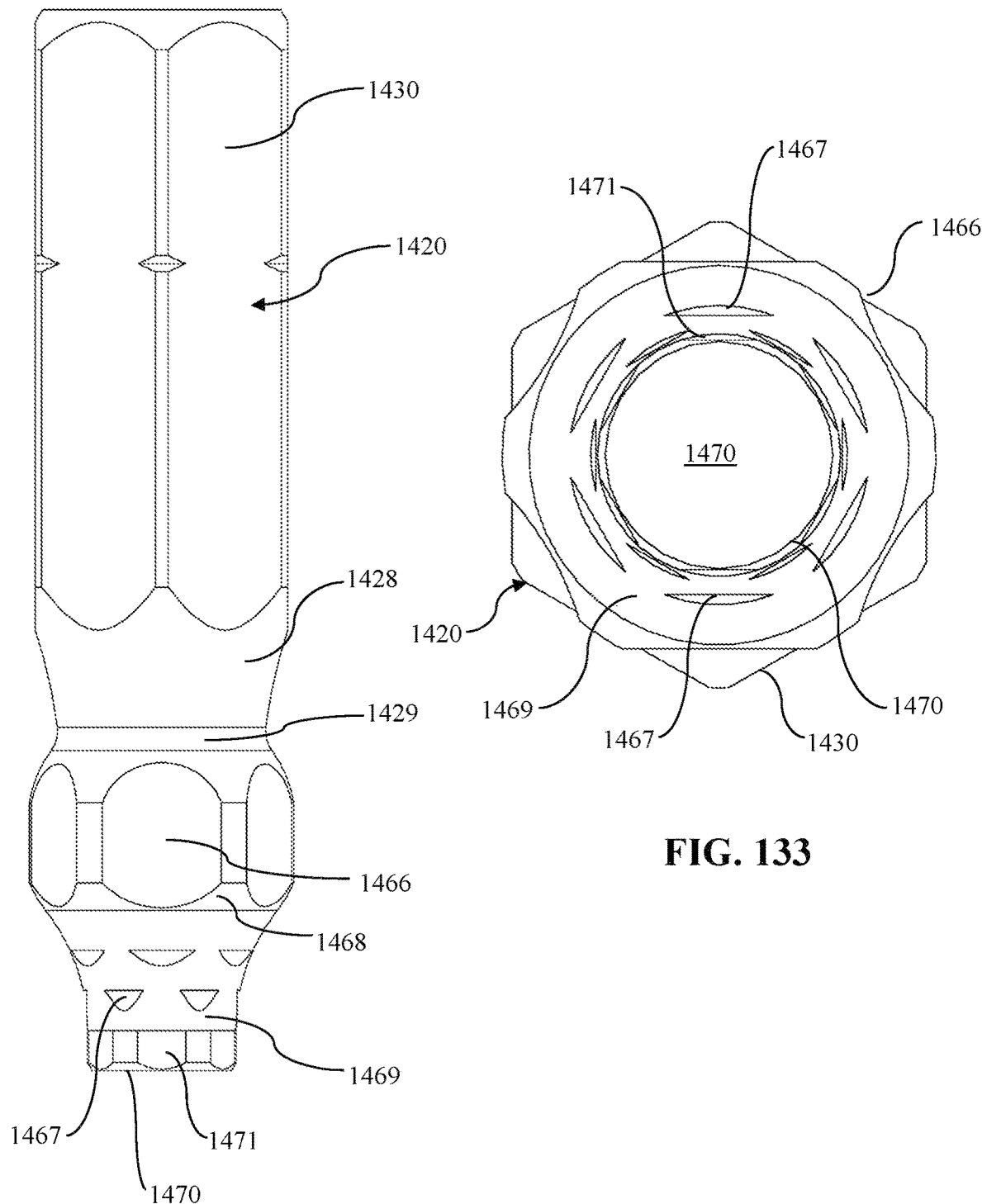

FIG. 132 shows a modified driver embodiment in vertical orientation and having textured surfacing at a distal region of the driver.

FIG. 133 shows a distal driver end plan view of the driver in FIG. 132.

Figures 134, 135:
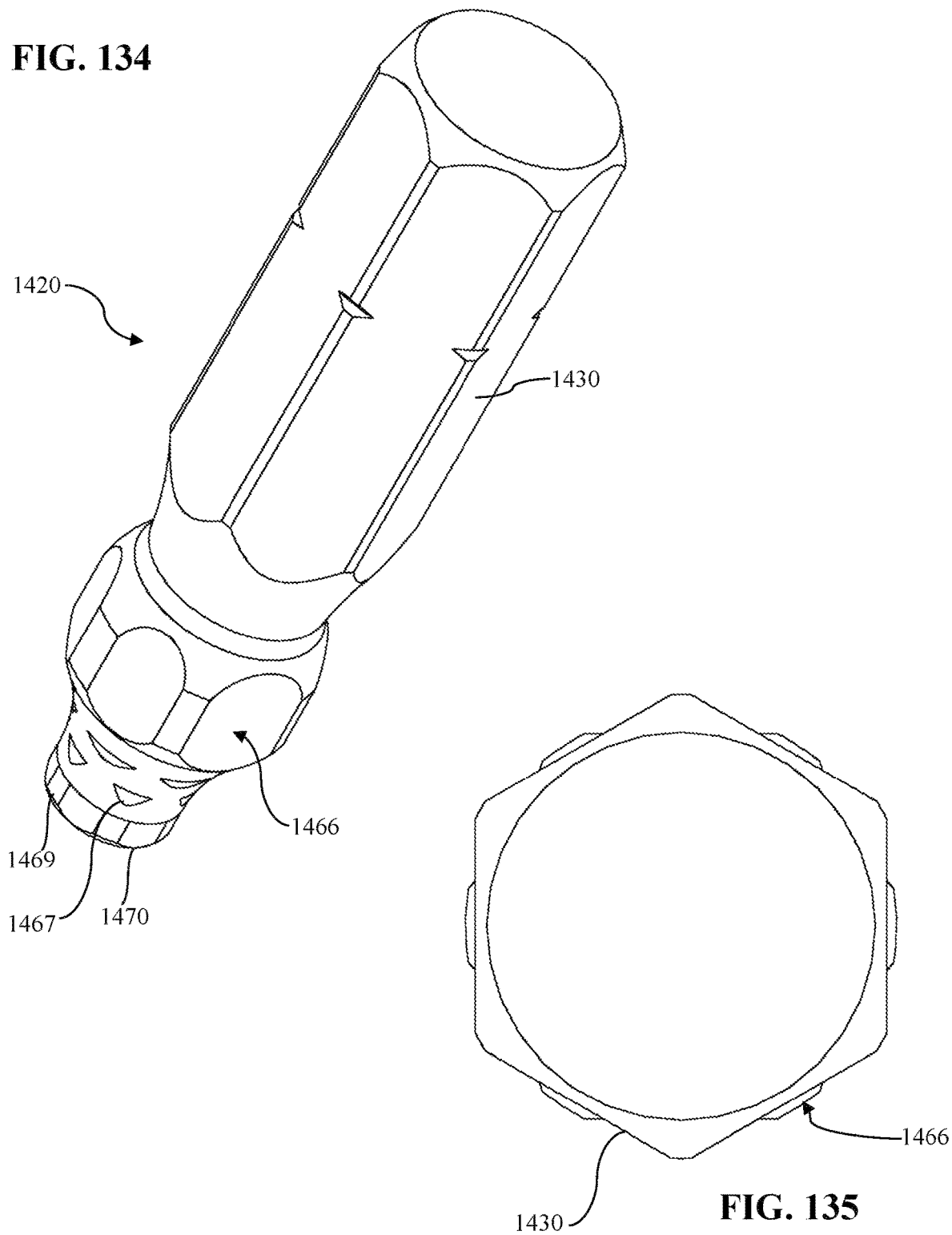

FIG. 134 shows a perspective view of the driver shown in FIG. 132.

FIG. 135 shows a top or proximal plan view of the driver shown in FIG. 132.

Figure 136:
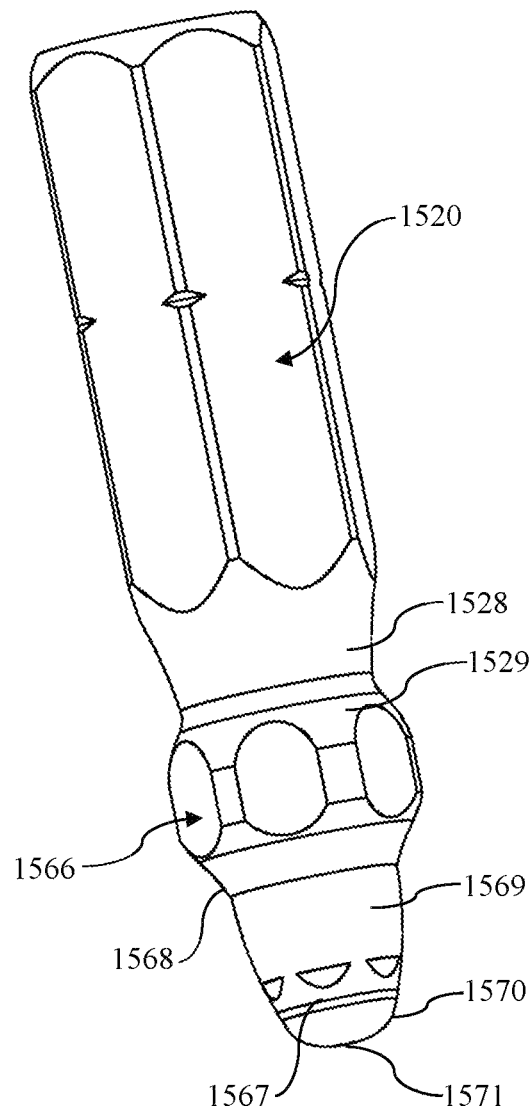

FIG. 136 shows a perspective view of an additional driver example under the present invention that has texturing means.

Figure 137:
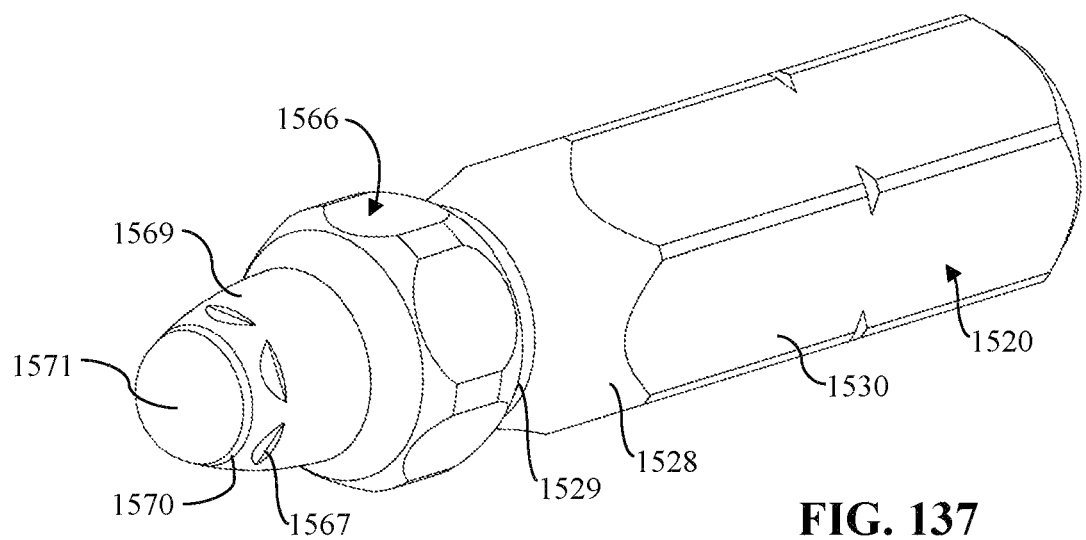

FIG. 137 shows the driver of FIG. 136 in a different perspective view.

Figure 138:
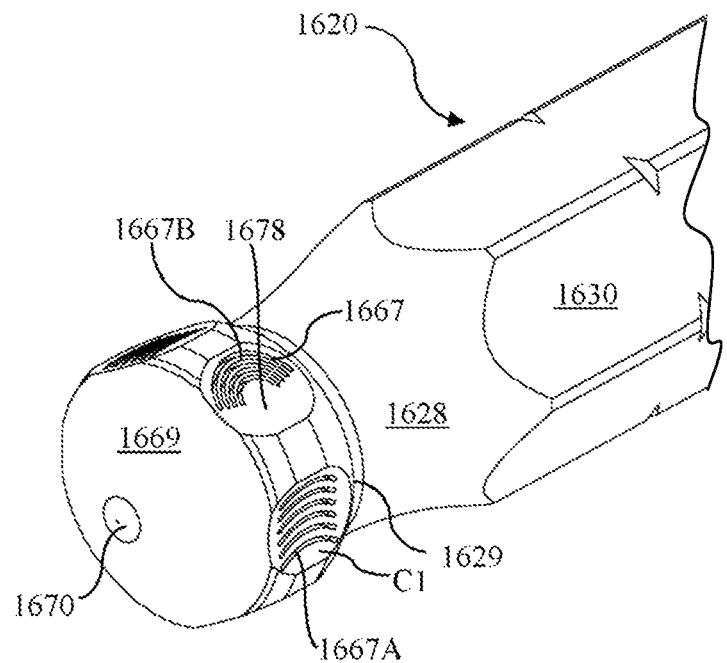

FIG. 138 shows a perspective view of a still further driver example under the present invention that has texturing means.

Figure 139:
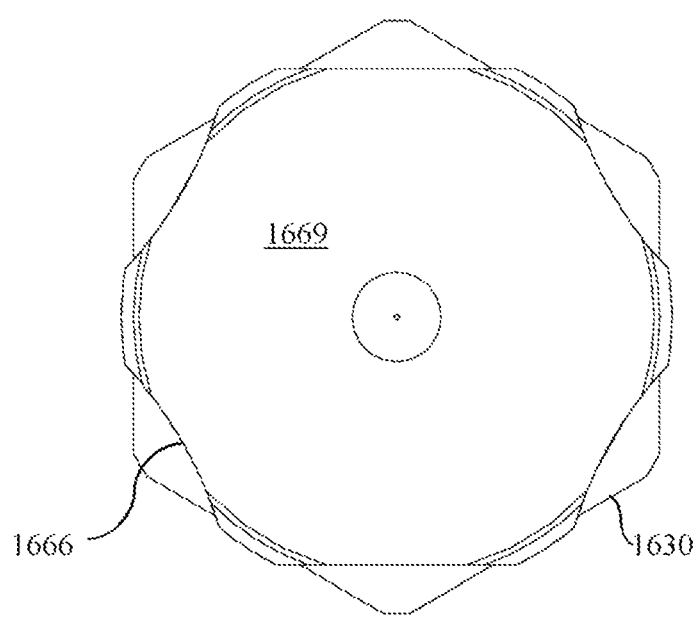

FIG. 139 shows a distal plan view of the driver in FIG. 138.

Figure 120:
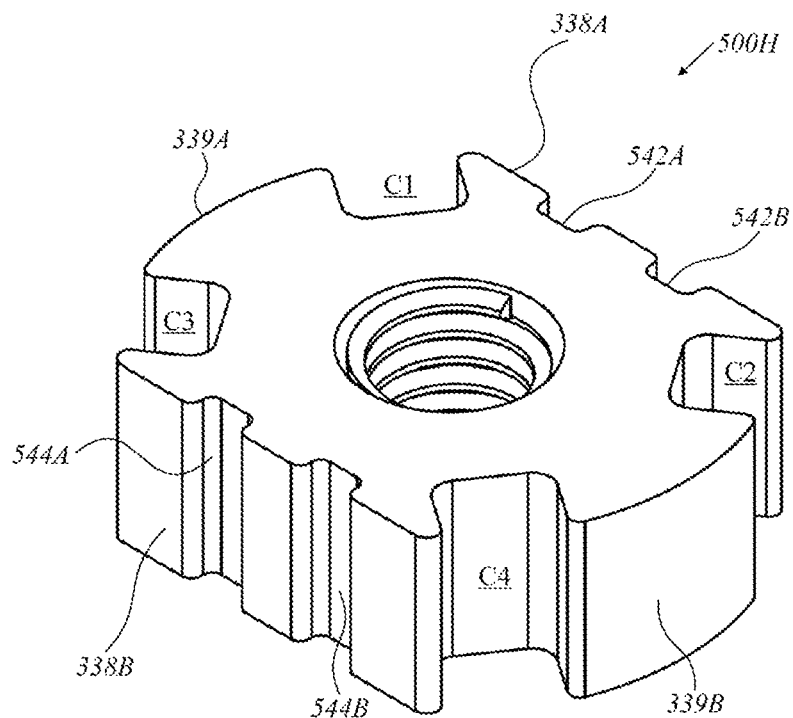
Figure 140:
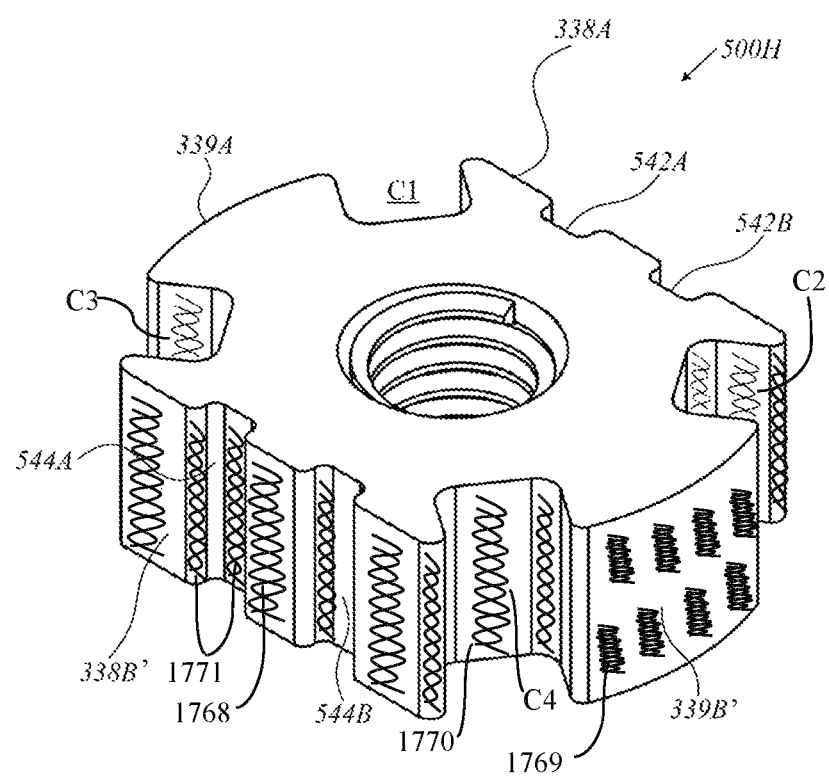

FIG. 140 shows a view similar to FIG. 120 but with textured peripheral surfacing.

DETAILED DESCRIPTION

Figure 1:
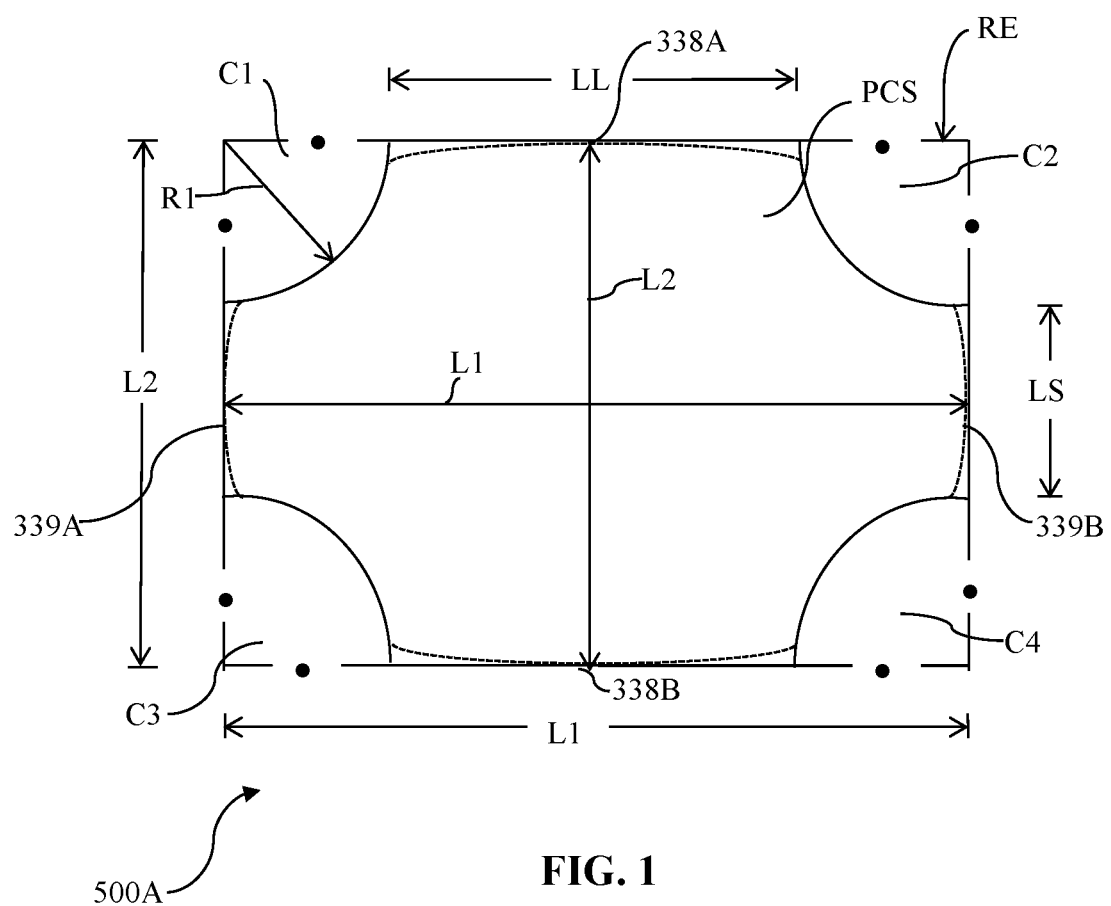
FIG. 1 shows a schematic depiction of a top plan view of a torque enhancement member of the present invention with some of the lengths and corner cut out cavity depths demarcated.

FIG. 1 provides a schematic depiction of a torque enhancement component 500A (also representing a 500A series configuration) under the present invention which is shown as having a solid top end (as might be associated with the head of a fastener; although as seen from the embodiments below the torque enhancement configuration can represent the exterior of an object with a central aperture and/or an internal cavity configuration and thus can take on a variety of forms). The FIG. 1 top plan view of the torque enhancement member features a long length L1 and a width length L2 defining dimensions of a surrounding outer rectangle RE, together with corner cavities or "cut outs" (actually preferably molded in or otherwise formed cavities) C1 to C4 each shown as being concave with a general radius value R1 (with all four concavities C1 to C4 shown in this embodiment as commonly configured and sized for each of the four). The corner concavity open areas C1 to C4 result in projection regions PCS inclusive of projection regions (above and below in FIG. 1) that are radially less extending out from the center and which define longer length contact surface walls (defining parallel or substantially parallel surfaces 338A and 338B, each of peripheral length LL), as well as longer radially extending out from the center projection regions PCS (left and right in FIG. 1) which define shorter length contact surface walls (having surfaces 339A and 339B, each of peripheral length LS). Also, a slight curvature can also be provided in each of the long and/or short sides as demarcated with dashed lines in FIG. 1, with the dot-dash lines reflecting the rectangular configuration, but for the concavities extending inwardly where no material is present (for this embodiment featuring a solid interior body head, or where material is present when the torque enhancement surface configuration is defining surface walls extending about a recess (e.g., a fastener head receiving recess with solid material surrounding the torque enhancement surface configuration defining the receiving recess) with examples provided below). Also, although not shown in FIG. 1, on either the slightly curved or straight walls there can be provided further cavities or notches that extend inwardly toward the center (not shown in FIG. 1).

For some of the intended uses of the present invention FIG. 1 configured torque enhancement device, the length L1 ranges from, for example, 20 to 40 mm (e.g., 30 mm), the length L2 ranges from 10 mm to 30 mm (e.g., 18 mm), resulting in LL ranges from 8 mm to 18 mm (e.g., 13 mm), LS ranges from 4 mm to 10 mm (e.g. 6.5 mm) and radius R1 sufficient to form the desired ratio in the LS and LL lengths, with suitable concave edge-to-edge distancing of 5 to 15 mm as in 8 mm, coupled with a radius of 8 mm to 12 mm as in 10.5 mm. The above referenced dimensions are not intended to be limiting and some additional non-limiting, but illustrative, alternate dimensions are also presented elsewhere in the present application. As will be explained below, the dimensions are relative to intended environments with some of the additional, below described environments and alternate dimensions being described (e.g., micro-screws for surgery usage featuring smaller dimensions, and other environments such as large industrial usages (e.g., bridge repair or large truck equipment) featuring larger dimensions).

Figure 2:
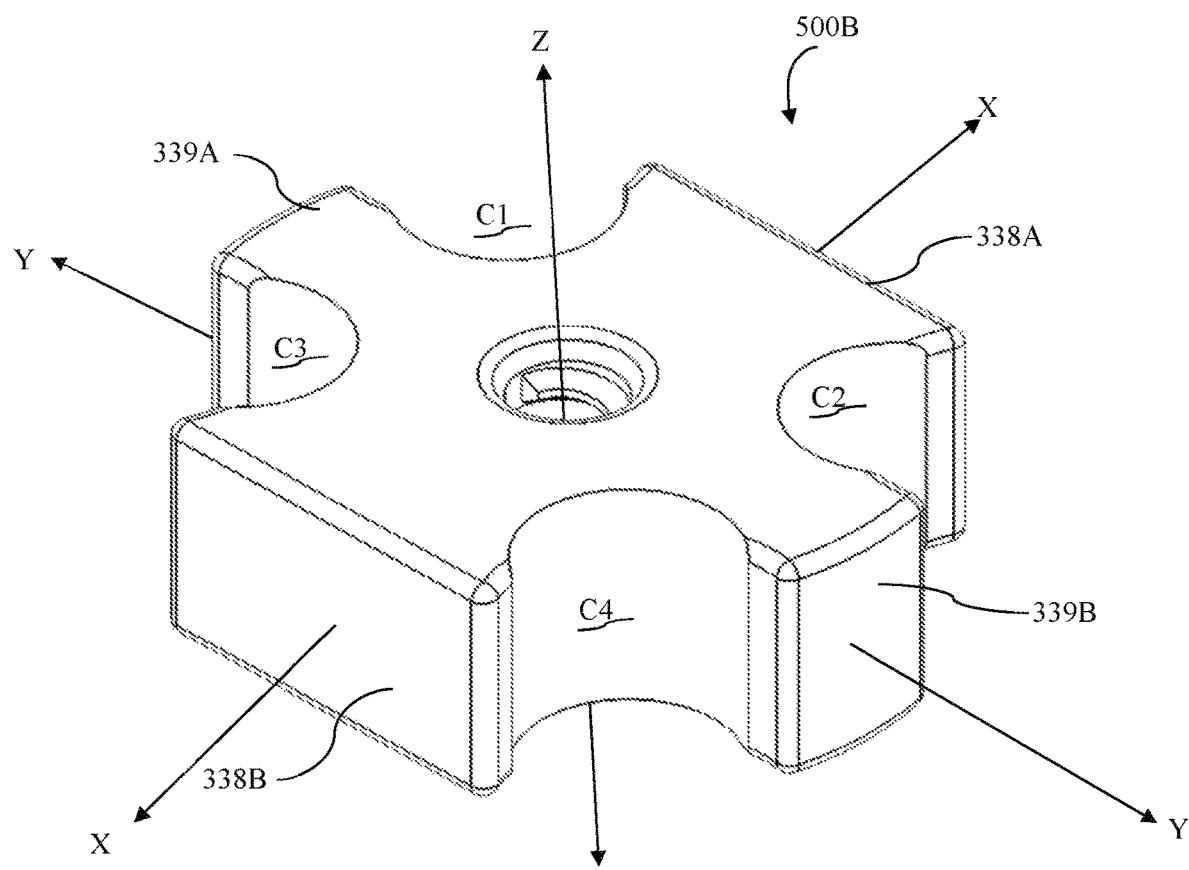
FIG. 2 shows a perspective view of an alternate embodiment of the torque enhancer of the present invention which in this embodiment has the same general bi-symmetry configuration as shown in FIG. 1 and is in the form of a threaded nut (e.g., bolt nut) with the longer length surfaces extending in the Y-axis direction (extending parallel and in a common direction to the center mass Y-axis presentation), the shorter length surfaces extending in the X-axis direction (extending parallel and in a common direction to the center mass X-axis presentation), and the Z-axis extending perpendicular to the horizontal plane defined by the X-Y axes combination.
Figure 3A:
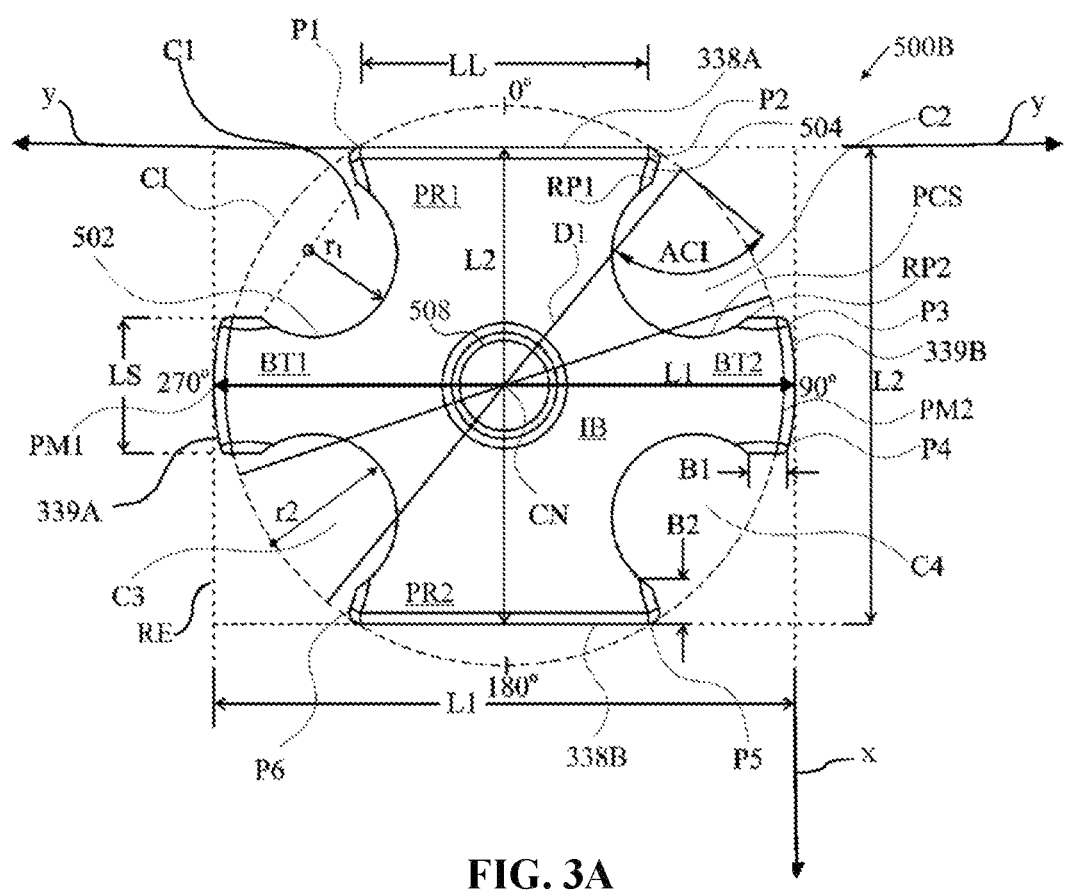
FIG. 3A shows a top plan view of the torque enhancer member shown in FIG. 2.

With reference to FIGS. 2 to 3A, there is further illustrated the non-equal nature of the projection region lengths in another embodiment of the invention. For instance, as shown in FIG. 3A, a circle contacting the outer ends of each of the longer length sides 338A and 338B (at points P1, P2, P5 and P6) extends inward of the maximum extension of the other pair of the associated projection regions' contact wall surfaces 339A and 339B. This relationship provides a geometric form that provides for a multitude of beneficial uses (e.g., torque generation enhancement).

As noted above, while the FIGS. 1, 3A and 3B embodiments illustrate torque enhancement surface contouring defining an exterior peripheral surface of the body shown, alternate embodiments feature the longer and shorter side walls and corner regions defining an interior torque enhancement surface configuration or contouring, as might be present in a recess formed in the center of a fastener head; some examples of which are described below as in that describing the FIG. 96 fastener (inclusive of embodiments having a head with both interior and exterior torque enhancement surface configurations, each having the noted corners C1 to C4).

Figure 3B:
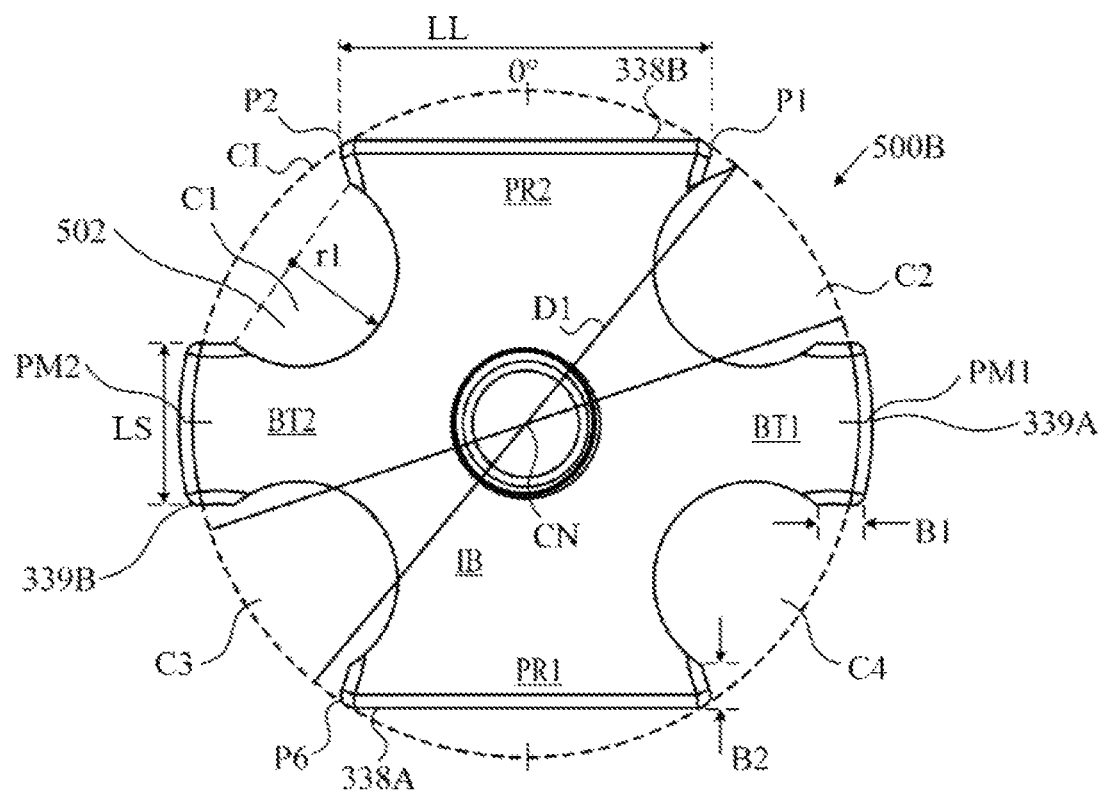
FIG. 3B shows a bottom plan view of the torque enhancer member shown in FIG. 2.

In FIGS. 3A and 3B there is also presented a reference framework which is provided relative to the torque enhancer therein shown (which in this embodiment is represented by an interior threaded nut for a fastener which is depicted in FIG. 2 in perspective, although can also be illustrative of driver head and/or reception recess configurations as discussed above and below). In the discussion to follow, regarding different aspects of the present invention's torque enhancer, there is similarly referenced the long length L1 and width length L2, together with the noted corner "cut outs" C1 to C4. Each of cavities C1 to C4 is shown in FIG. 1 as being concave without side edge extensions at the ends of the concavity, while cavities C1 to C4 in FIG. 3A are shown as having side edge extensions 504 leading to semi-circular regions 502 leading in from the boundary of the concavities with the side walls with side edge extensions 504 and semi-circular regions 502 combining to for the corner recesses C1 to C4. The below discussion also references the corner concavity open areas C1 to C4 that result in projection regions PCS inclusive of radially shorter extending projection regions (defining the longer length surface contact walls 338A and 338B, each of peripheral length LL), as well as the longer radially extending projection regions (defining the shorter length surface contact walls 339A and 339B, each of peripheral length LS). The concave cut-outs can also be formed in other shapes as in the noted added end side walls and/or stepped side walls and/or generally more rectangular than semi-circular configurations.

Also, the below discussion also uses the frame-of-reference rectangular RE shown in FIG. 1 which is in co-linear contact with the straight edge(s) of the 338A and 333B side and extends into tangent contact with the slight curvature sides 339A and 339B (or along straight edge versions of the same). As further described below, the co-linear relationship is made whether there exists or not, intermediate side wall notches between the linear extension ends (see, for example, the side wall notches shown in FIGS. 120 and 121). The same being true relative to each of the shorter and longer long sides which can be notch inclusive or notch-less (e.g., each of the long and short sides as demarcated with dashed lines in FIG. 1 with the dot-dash lines reflecting the concavities where no material is present in the illustrated exterior surface torque enhancement contouring). As seen, length L1 extends to the maximum Y axis direction length (shown as L1 extending between the center points PM1 and PM2 of the slightly curved side walls and thus transverse to those walls, while L2 is also shown in FIG. 3A as extending perpendicular to the respective walls 338A and 338B, which, since free of notches, also is the maximum extension between the Y-axis extending side walls).

Figure 6:
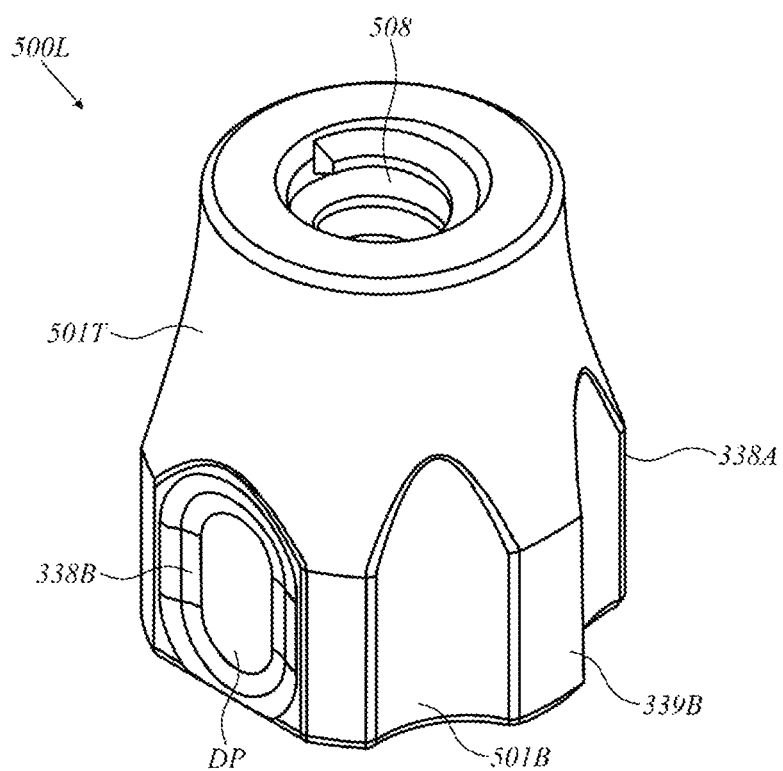
FIG. 6 shows a perspective view of an alternate "tapering" embodiment of the torque enhancer of the present invention and one which is also shown in the form of a base capped threaded nut in that the central, threaded aperture is not a through-hole as in the above embodiment.

Also, side walls 338A and 338B can be perpendicular to the top plane frame of reference in three dimension, or can be sloped inward and/or outward (either in linear or curved or both linear and curved) relative to the top plane, and can also be smooth walled or have one or more recessions in the wall region (with examples of the same being described for other examples of the invention, inclusive of oval shaped centered wall recesses provided on walls such as 338A and 338B which can provide potential compression benefits, potential weight balancing means, and/or a finger reception recess as shown in FIG. 6).

FIGS. 2 and 3A, 3B also show views of torque enhancement device 500B (also representing a 500B series configuration) in the form of a fastener nut as a torque enhancement member (with the shape also being potentially illustrative of various other functioning torque enhancement members such as a gear). As seen for this embodiment, and other embodiments featured in the present application, the torque enhancer has a generally bi-symmetrical configuration (left and right symmetry of the vertical line extending between compass points 0° and 180° as well as above and below symmetry of the horizontal line extending between compass points 90° and 270° in FIG. 3A). Also, since all four concavities C1 to C4 are of a common configuration (each having semi-circle radius r1 concavity portions 502 and end side extensions leading up to side wall points such as point P2 for side edge walls 504) there is also full diametrical symmetry for each set of C1-C4 and C2-C3). The torque enhancement member 500B is shown in the form of a threaded nut (e.g., bolt nut, with the central threaded hole represented by hole 508 having center point CN also representing the center point of the body defining the torque enhancement device) with the longer length surfaces 338A and 338B extending in the (FIG. 1 and FIG. 3A) illustrated Y-axis direction, the shorter length surfaces 339A and 339B extending in the X-axis direction, and the Z-axis extending perpendicular to the horizontal plane defined by the X-Y axes combination).

FIG. 3A shows a top plan view of that shown in FIG. 2, while FIG. 3B shows a bottom plan view thereof. As seen from a comparison of FIGS. 3A and 3B, the side walls of torque enhancement member 500B are generally non-sloped between the area defined by the top plan view and bottom plan view, which views are shown equal in area (although tapering and/or notched matching side wall set(s) are also featured under the present invention as well as the inclusion of the aforementioned finger depressions as well). As noted, FIGS. 120 and 121, discussed below, show examples of notches provided in the side walls (both corresponding notch pairs provided on the long side walls only in the FIG. 120 instance).

FIG. 3A also shows aforementioned overlay reference plane RE like that shown in FIG. 1, as well as an added reference circle CI. As seen in 3A (and 3B) torque enhancer 500B includes two elongated surfaces 338A and 338B (which can be of similar length as the earlier referenced same reference numbers, or of different length, and are preferably of equal length relative to each other relative to a preferred bi-symmetry configuration). Also, like reference numbers and letters used throughout the application relative to the referenced information (e.g., reference plane illustration, reference circle illustration, various lengths, radius values, angles, etc.), can vary in value or attribute from one embodiment to the next despite the commonly used reference number or letter (with a few examples of such potential variety, despite common reference number or letter set, being described below). For example, a corner cut out C1 in FIG. 3A may be referenced again in another figure set as C1 despite having a specific configuration different than that in FIG. 3A.

An aspect of the present invention includes an advantageous geometric form that provides for a multi-purpose torque enhancement device with enhanced torque generation potential. In this regard, reference is made to the reference circle CI shown as extending through the end points (P1 and P2 in FIG. 3A) of the side walls 338A and 338B of projections PR1 and PR2 (each representing a PCS region earlier noted) extending out along the X-axis from interior body portion IB. As also seen in FIG. 3A, the reference circle CI extends radially inward of at least the outer points (PM1 and PM2 relative to the Y-axis extension length L1) of the exterior surfaces 339A and 339B formed at the end of the "bow-tie" projections BT1 and B2T extending in the Y-axis direction out from interior body portion IB. FIG. 3A also shows that, for this embodiment, the entirety of the exterior surfaces 339A and 339B fall outward of reference circle CI. As will be explained in greater detail below, this geometry provides points of leverage extending beyond the reference circle CI and thus is illustrative of a longer torque generating moment arm as to provide increased rotation force (while also avoiding instability due to the differential, as through centrifugal force generation countering control as explained in greater detail below as well). This differential is also represented by the spacing differential between the maximum thickness of the torque enhancement body in the X-axis direction and the maximum thickness of the torque enhancement body in the Y-axis direction (i.e., L2 and L1 are different). With the preferred common sized corner cut-outs there is also a size differential relative to the peripheral length longer walls as in 338A (LL length) and the shorter peripheral length walls as in 339B (LS length).

In the embodiment shown in FIGS. 3A and 3B there is featured solid or uninterrupted (e.g., notch-less) sides 338A and 338B of common length LL, although the illustrated example in FIG. 3A can have one or multiple features varied from that which is depicted (e.g., the inclusion of notched or interrupted side walls 338A and 338B in place of the notch-less side walls 338A and 338B shown).

Torque enhancement member 500B further includes shorter length side walls defining surfaces 339A and 339B (which are also preferably equal in length relative to each other in accordance with the noted bi-symmetry). Walls 339A and 339B are shown having a minor curvature (notchless) with the reference rectangular RE having short side walls extending tangentially from the mid-point or maximum outer curvature points PM1 and PM2 of walls 339A and 339B. In alternate aspects of the invention, the short side walls 339A and 339B can be straight walls as to continue on a common line with the short length reference rectangle RE's walls. Also, as shown in FIGS. 3A (and 3B), there is featured solid or uninterrupted (e.g., notch-less) slightly curved side walls defining surfaces 339A and 339B of length LS, although again the surfaces 339A and 339B can be linear so as to coincide with the corresponding side lines of reference rectangle RE and/or each provided with one more notches (that preferably still satisfy the bi-symmetry noted).

FIGS. 3A and 3B further illustrate that, from a three dimensional perspective, the side walls 339A and 339B are perpendicular to the top plane frame of reference. Alternate embodiments feature long and/or short side oblique (to the top plan view plane) walls that slope inward or outward (either in linear or curved or both linear and curved fashion) relative to that top plane reference plane; and in addition to the embodiment shown in FIG. 2 with all walls 338A, 338B, 339A and 339B being smooth walled sides, embodiments of the invention include having different designs for the side wall pairs, as in having one or more recesses in the internal wall surface region and/or the border region of those side walls (as in, for example, an embodiment having inward sloping long and short side walls of equal or different angle values such that the area on the top surface periphery is larger and the periphery of the bottom surface of the torque enhancer is smaller or vice versa). The slope angle of the short sides 339A and 339B can be the same as those of the long sides 338A and 338B or can be different (e.g., a different slope angle in or out for a wall 338A and 338B can be the same or different as compared to a 339A and 339B), or different recesses can be provided in the interior region of the side walls. Further, as explained in greater detail below any or all or any sub-combination of the side walls can be supplemented with added texture means (a plurality of small depth recesses imparted as to extend inward of the main surface of the wall and/or a plurality of small height ridges or other projection types extending outward of the main surface of the wall).

The ratio of long (L1) versus short (L2) can be varied in accordance with intended needs, as in situations where low stress (e.g., low torque speeds and low torsion stress concerns) can provide for a lower percentage value representing the L2/L1 ratio (less square like configuration) versus situations wherein there is high stress and torsion wherein a higher percentage value (closer to square configuration and preferably with thicker projections) may be desirable (L2/L1 less than 100% but greater than 75%). Under embodiments of the present invention (some of which are shown in this application) L2/L1 ratios are from 60% (farthest removed from reference frame RE being a square) to 99% (closer to reference frame RE being a square), and more preferably 65% to 98% for some considered environment of use under the present invention. Under further embodiments of the present invention the L2/L1 ratio is from 75% to 90%, as in ratios of 76% to 81% which is also suitable for a variety of environments (noting gearing ratios can vary depending on functional torque generation needs).

Under alternate aspects of the present invention, as in those featuring bulbous or ball point headed drivers (as well as distal projections) and suitably corresponding female reception cavities (particularly those intended for motorized or otherwise non-hand tool driven embodiments), the ratio L2/L1 of 75% to 99% and more preferably 80% to 98% is featured. This provides for, in some environments, the ability for the driver to be rotating concurrently with insertion of the driver head into the female reception cavity, as is desirable on, for example, an assembly line operation or a controlled robotic arm application where there is a need for rapid and repeated fastener assembly steps often with a common configured fastener.

Figure 3C:
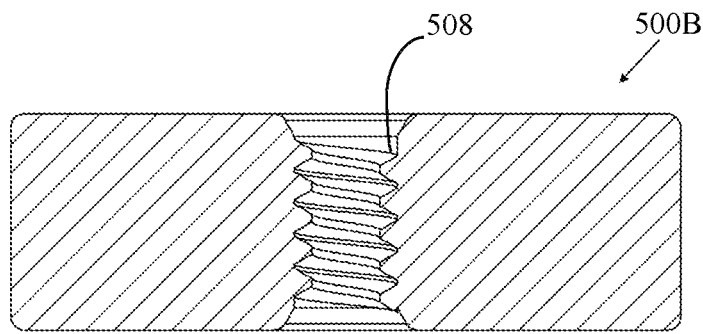
FIG. 3C shows a cross sectional view of the FIG. 3A torque enhancer member (taken along the length line L1) to illustrate the solid nature and central thread aperture.

Also, while not having 360° symmetry, preferred embodiments of the invention feature an opposing symmetry or bi-symmetry configuration with respect to a common X-Y axes plane (e.g., a horizontal top plan plane or horizontal cross-sectional plane), as in a first symmetrical relationship for opposing sides/areas to opposite sides of the X-axis and a second (different than first) symmetry to opposite sides of the Y-axis. Thus, with reference to FIG. 3A there can be seen a first symmetry to opposite sides to a line extending along the X-axis between the 0° and 180° compass points, and a second (different) symmetry to opposite sides to a line extending along the Y axis between the 270° and 90° compass points and thus also through the maximum extension points PM1 and PM2 for the bow-tie projections BT1 and BT2. In FIGS. 3B and 3C there can also be seen Z-axis symmetry (the top FIG. 3B having the same configuration as the bottom shown in FIG. 3B, although variations in configuration are also featured under the present invention as in with converging side walls going in the Z-axis direction which would result in a smaller area on the X-Y axis plane where the side wall taper ends (not shown in this FIG. set, although represented in the FIG. 6 discussion below).

In the fastener nut embodiment featured in FIGS. 2 to 3B there are provided four corner recessed regions C1 to C4 (inward with respect to each of the four corners of reference rectangle RE). The surface portions of torque enhancement member 500B that define the radially interior-most portion of the corner notch regions C1 to C4 are each of the same configuration and length, and are shown as each being a semi-circular surface 502, with each of radius r1 (each being the same in this embodiment although variations in the shape and/or relative size for the interior-most portion are also featured herein). Also, there is shown in FIG. 3A that each of recesses C1 to C4, in addition to the semi-cylindrical portions represented by radius line r1, have less curved and somewhat outwardly tapered sections as represented by length dimensions B1 and B2 for projection sets BT1, BT2 and PR1, PR2, respectively. Accordingly, the full depth for each of corner notches is shown as being generally of radial dimension r2 relative to the reference circle CI, with r2 thus being greater than r1.

Torque enhancer 500B is shown as having a central point CN from which the reference diameter lines D1 for reference circle CI are shown. Aperture 508, formed in inner body IB, is also shown as being centered on point CN. Thus member 500B is well suited for use as a nut (or gear—as in a shaft key in place of the illustrated threaded aperture), and when featured as a nut, can feature (as seen in the cross section depicted in FIG. 3C) threading extending along the Z-axis for the full thickness of the member 500B as to open out at opposite ends, or an aperture can partially extend through the full thickness of the inner body IB (as featured in the below described FIG. 6, for example). Further, the Z axis thickness can be varied to suit the intended function with the FIG. 3C thickness shown being illustrative of an intermediate thickness nut (having a Z-axis thickness TH of about 30% of its maximum L1 length, although other embodiments, as in a washer, would have a lesser TH/L1 ratio of 10% for example; or, in the opposite direction, as in a thick gear element with a 150% TH value relative to the maximum L1 length (e.g., a ratio range of 1/10 to 3/1 for TH/L1 is illustrative of many embodiments of the invention))

Torque enhancer 500B can come in a variety of sizes with preferably relative relationships retained such that the presented view is merely an accurate or zoomed in or zoomed out presentation of that which is shown. Thus, there is no intention to be limited to a particular size as that would be dictated by the intended use. In the torque enhancement member shown in FIG. 2 there is an L2/L1 percentage ratio of 80%. Also, to help illustrate the relative relationships in the different components, the following dimensions are provided (which are generally on a larger size parameter as might be well suited for industrial structures requiring relatively large bolt and nut sizes such as those involved with I-beam girders and the like): L1=75 mm; L2=60 mm; L2/L1=0.8 or 80%; LL=40 mm; LS=18 mm (giving a properly rounded ½ or 50% ratio for the 18/40 ratio); r1=11 mm; B2=6 mm.

Also, the central aperture can also be sized for intended use and in consideration of the overall size of the torque enhancement member, with a suitable range for the FIG. 2 embodiment's aperture diameter being 2 to 26 mm, with 16 mm being a value featured in conjunction with the dimensions described in the paragraph above.

The thickness TH is use dependent as well, with standard nut thickness being applicable depending on the overall nut size and intended use. For example, in micro-screw uses as in the medical field, the lower Z-axis thickness range is reduced to those described above for other uses, as in values (e.g., 1.5 to 5 mm as in 2 mm to 3.5 mm) in micro-screw environments such as might be found in the medical field (e.g., orthodontic surgery, or oral and maxillofacial surgery, etc., often utilizing titanium metal for the screws). Again, here and other areas of the application, it is noted that given dimensions are not intended as being limited, as different environments dictate different sizes (although a similar ratio conversion can be maintained despite the dimension differential). That is, environments such as micro-environments as with circuitry boards and the like can involve Z-axis apertures, thickness lengths, etc. at or below 2 mm, while larger industrial environments might involve well over 26 mm for such dimensions.

Figure 4:
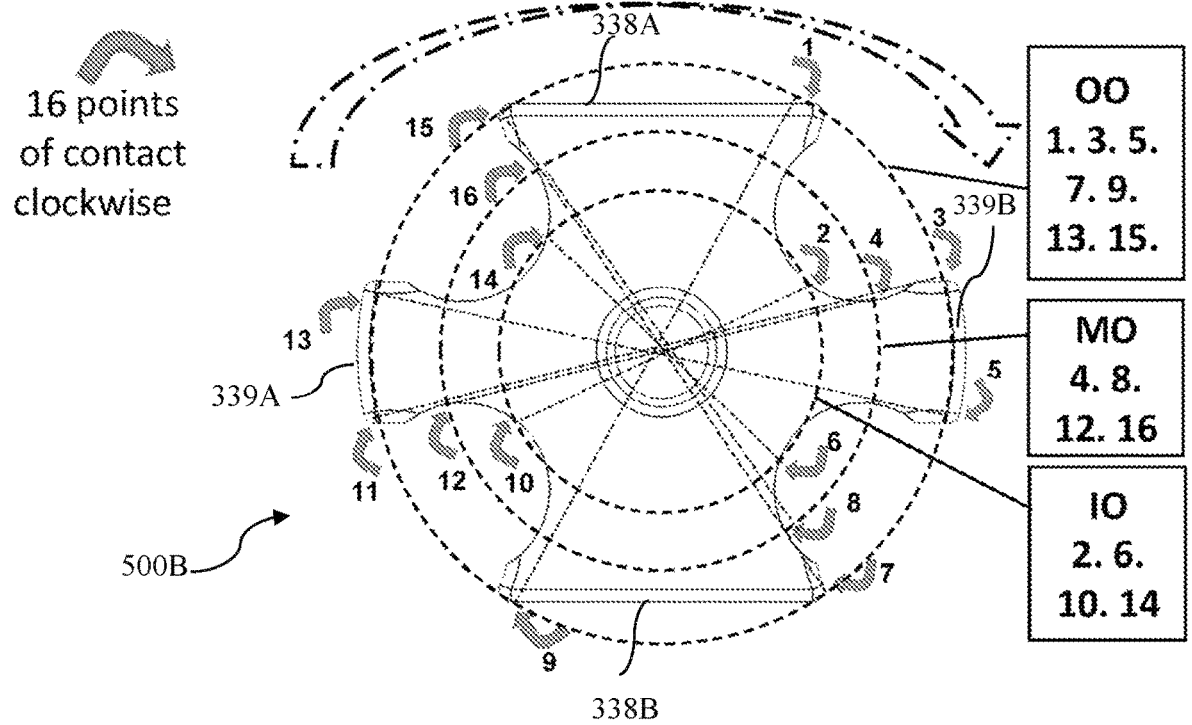
FIG. 4 shows a similar top plan view as that shown in FIG. 3A, but with a considered "mechanical" contact point illustration (without consideration of a centrifugal/centripetal force impact that might arise as with a powered driver at higher RPMs).

With reference to FIG. 4 there is provided the same top plan view as in FIG. 3A, but with an added overlay of initial considered force contact points (without centrifugal/centripetal rotation influence considered, which influence increases with increased RPMs if, for example, a powered driver is used). These considered contact points are representative of the contact points that would arise as when there is utilized a hand wrench having a common configured torque enhancement interior recess designed for insertion around the exterior periphery of the nut shown in FIG. 3A. For purposes of the present invention, this initial contact mode showing (as in a hand wrench) will be referenced here and below as a considered "mechanical contact" mode presentation as to differentiate over the also below described RPM rotation consideration, which involves consideration of centrifugal/centripetal rotation influences as well as tool impact and friction forces that arise on the contact surfaces (wall and corner recesses) etc.

As seen from FIG. 4, the illustrated torque enhancement member 500B features relatively deep corner cut-outs C1 to C4 and therefore is marked as providing for three orbital contact circles relative to, for example, a conforming torque generating tool such as a torque wrench. The three orbitals are denoted as inner orbit IO, middle orbit MO and outer orbit OO in FIG. 4. Further, as shown in FIG. 4, each of the illustrated mechanical contact point presentations is depicted as having a common diameter opposite contact point (differently numbered) on a common orbital. Thus there is shown IO contact point sets 2-10 and 6-14 representing contact points at the base of the corner-cut outs along inner orbit IO in the common side (right side) as the clockwise progression shown for torque tool rotation (an opposite rotation would put the contact points on the opposite side of the common configured surface in similar diametrically opposed relationships). There is further shown in FIG. 4 contact point sets such as 4-12 and 8-16 that fall on middle orbit MO and are shown as falling on the same contact side as the earlier described IO contact points, but at a location farther up so as to land on the upper side portion of the respective cut-out corners.

FIG. 4 still further shows (as an approximation of surface contact points) additional contact points generally pertaining to the OO outer orbital. Shown are projection contact points, both relative to the exposed surface and corners of projections defining straight edges 338A and 338B and the exposed are surface and corners of the bow-tie projections 339A and 339B. Thus, there is shown contact point 1 on the far right upper surface of straight edge 338A and, based on the bi-symmetric configuration for torque enhancer, a far left surface contact point 9 in surface 338B (contact point set 1-9); as well as contact point 3 at the corner cut-out upper (straightened) edging just before formation of the arc surface of 339B and a similar arrangement, but for being on the lower rather than upper side and on the bow-tie projection 339A as to define contact point set 3-11. Contact point set 5-13 is shown as being contact points on the clockwise end of the arc surface defining bow-tie projections 339B and 339A, respectively. Additionally, mechanical contact point set 7-15 are contact points still within the corner cut outs C1 and C3, but on the far ends just before the periphery of torque enhancer goes into the straight side walls 338A and 338B. Thus, as shown in FIG. 4, there are 16 total illustrated mechanical contact points depicted featuring three contact points in each cut-corner zone with the outer most being in the corner region where the corner cut out straightens and just before the torque enhancer periphery extends into the straight wall edges 338A and 338B.

There would also be envisioned 16 mechanical contact points going in the counterclockwise direction (not shown), but they would conform to the bi-symmetry nature of the torque enhancer (e.g. the points 14, 16 and 15 shown all hitting their respective inner, middle and outer orbits would instead by hitting the opposite side of corner cut out C1 (the left side wall of corner cut out C1 shown in FIG. 4)). In similar fashion the outer surface contact points 5 and 13 would shift to the opposite lower/upper side as the side presently shown in FIG. 4. Further, as explained in greater detail below with respect to FIG. 138, such shifting of contact points as during a counterclockwise release of the fastener in FIG. 4, can be supplemented with texturing to that same side of the contact surface in recognition that fastener release is often more difficult than initial insertion due to the aforementioned conditions that can arise after initial insertion.

Figure 5A:
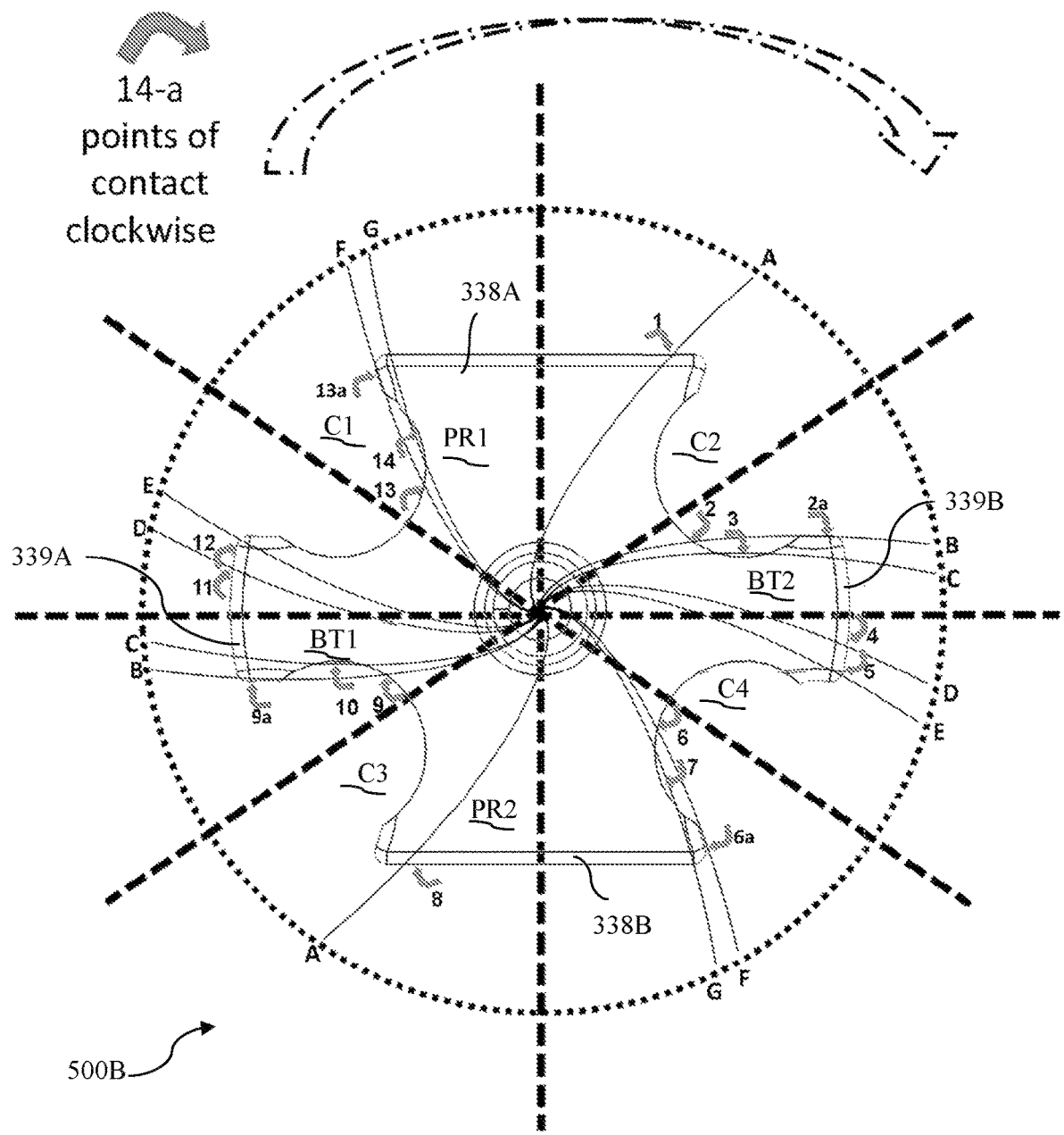
FIG. 5A also shows a top plan view of the torque enhancer of FIG. 2, but with a considered "spiral-centrifugal" contact point illustration (representative of an initial spin rotation status with consideration of initial centrifugal/centripetal force (radially outward/inward) development with the centripetal force counterpart in the inward radial direction; plus friction contact forces that are deemed to develop in the engaging male/female contact surfaces, and that, from an overall friction force standpoint, may or may not extend directly along a radial line).

With reference to FIG. 5A there is shown a presentation of potential contact points relative to the "spiral-centrifugal" mode described above. While not being bound by any theory, it is Applicants' belief that the geometry of the present invention provides the beneficial force interrelationships described above, herein and below, with reference to the contemplated generated force contact points presentations being utilized to help illustrate these concepts. Further, in light of the additional forces that would be generated in a spinning nut (or other torque enhancement device such as a gear), there is utilized curved (spiral segments) to help illustrate what is considered to be the potential contact points on the nut as it is being spun as described. That is, FIG. 5A depicts spiral segments A to G (two sets with one to each side of the vertical line shown in view of the bi-symmetry) relative to the 14 (spiral segments) point contact presentation for this mode (shown with rotation in the clockwise direction with 7 spiral segments to each side of the vertical). Further shown in FIG. 5A is the single or multiple contact points considered present on the respective spiral segments, with the below description directed at the force developments thereat. The centrifugal/centripetal force generation is associated with RPM rotation, which rotation includes levels that can be incurred with, for example, an air (or other pneumatic gas driven), electric motor (e.g., lithium battery powered), support shaft rotation, or alternate driving means for rotating of the driver (as with those having free rotation driver speeds of 10 RPM to 10,000 RPM or other speeds depending on the environment and tooling type involved).

Figure 5B:
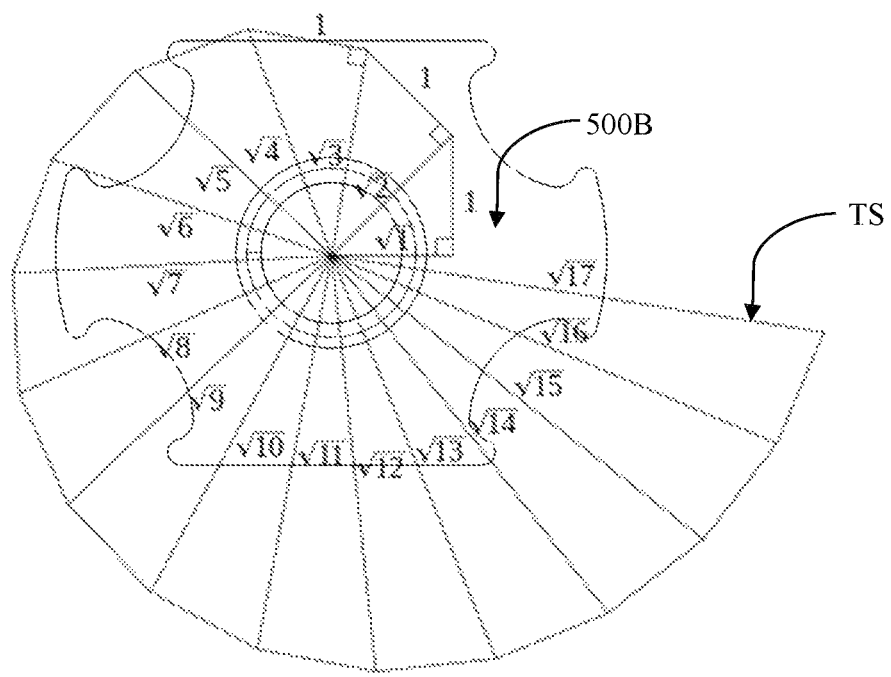
FIGS. 5B and 5C illustrate, respectively, an RPM increase in angular momentum Theodorus spiral development illustration overlaid on a top plan view of a torque enhancement device, and a corresponding overlay of a spiral depiction of centrifugal and centripetal force interplay considered to develop, and with anti-camming and anti-wobbling characteristics considered to arise relative to the torque enhancement configuration with different radial extension projection lengths.

Also with increasing RPM there is considered to be developed, again not being intended to be bound by any particularly theory (both here and in the discussion above and below), differing angular momentum values depending on the relative force contact points associated with the different length siding and corner recesses. That is, the magnitude of the angular momentum of an orbiting object is equal to its linear momentum (product of its mass m and linear velocity v) times the perpendicular distance r from the center of rotation to a line drawn in the direction of its instantaneous motion and passing through the object's center of gravity. Thus, with the additional "r" value allotted with the length differentials, there is considered achieved a higher angular momentum at those contact points further removed from the center of gravity (a greater "r" value) as compared to closer in contact points, and with the associated angular momentum considered to increase in Theodorus spiral like fashion with increasing RPM (see FIG. 5B showing Theodorus spiral square root segments TS overlaid on a generic representation of torque enhancement device 500B). Despite the potential for higher RPMs and the associated increased potential for wobble or cam-out, the configuration of the present invention is considered provide added stability against such actions. For example, it is considered that the longer side walls 338A and 338B (with associated shorter projection length outward from the center (PR1 and PR2) and corner cut-out adjacent regions add stability against such wobble and cam-out as the parallel (or essentially parallel) longer walls 338A and 338B are considered to feature a large frictional advantage and longer energy absorbing contact surfaces that is considered to foster stability. This occurring at the same time the shorter side walls 339A and 339B (provided at the ends of associated longer length projections BT1 and BT2 outward from the center) and associated corner-cut out adjacent regions provide the advantage of added leverage relative to the torque transfer based on the added "fulcrum" advantage.

For example, contact point 1 is found on spiral segment A, and is shown on the right side end region of surface 338A with a contact force out and down on that surface (and with consideration of the associated opposite force presented by the body back in the direction of the driver's contact surface as well as the opposing centripetal and centrifugal forces generated in the driver spun body); contact points 2 and 2a are found on spiral segment B with the more radial outward contact point 2a shown as being both well aligned (essentially parallel with the tangent of the rotation orbit) and relatively far away from the inner body IB center point CN as to represent a strong torque generation point. Contact point 3 is found on spiral segment C and has a generally aligned force direction with that of contact point 2a, but is a bit closer to the center point CN (and thus while having a relatively high tightening (or loosening) force value, is lower than contact point 2a). Point 2 deeper in the corner cut out C2 which not only is lessened in torque generation due to its closer position to the center, but also can be seen as contacting a curved surface tending to generate some force direction back towards the center (again considered to help compensate for the forces developed at contact points such as 2a (higher region of rotation force provided by the longer length projection availability could generate some instability as there is a differential in length in the noted projection sets (PR1, PR2 and BT1, BT2)). However, the overall geometry of the present invention is considered to help avoid such instability brought about by the differential. In this regard, reference is also made to contact points 4 and 5 shown falling on spiral segments D and E, respectively. There can further be seen that, while providing some rotation assistance forces, they also can be seen as being positioned as to generate some radially inward component back toward the center CN (which is considered to provide some outer centrifugal damping aspects). Accordingly, while contact points 4 and 5 are below in torque generation value as that of the two earlier noted contact points of 2a and 3, they are considered to counteract some of the forces generated due to rapid spinning of a not entirely symmetric body as to help avoid instability as might be otherwise generated due to the lack of full symmetry.

Reference is further made to the depicted contact points 6, 6a and 7 falling on segments F and G, respectively, with points 6a and to a lesser extent point 7 considered to present relatively higher torque generation as they are arranged in common with the rotation direction for the most part. Again, with reference to contact point 8 on the left side of side wall 338B, there is considered to be again some force direction directed back toward the center point to help offset any differential developed and centrifugal forces by providing a degree of counteracting driver to body contact forces. Also due to the bi-symmetry, a similar situation is considered to exist relative to the earlier mentioned contact point 1, and the similar (to 6, 6*a* and 7) forces 13, 13*a* and 14 found on segments F and G. In addition, the description presented for contact points 2, 2*a*, 3 and 4, 5 is considered to be applicable to the bi-symmetry contact points 9, 9*a*, 10 and 11,12 working on projection BT1 and falling respectively on spiral segments B to E on the left side.

Figure 5C:
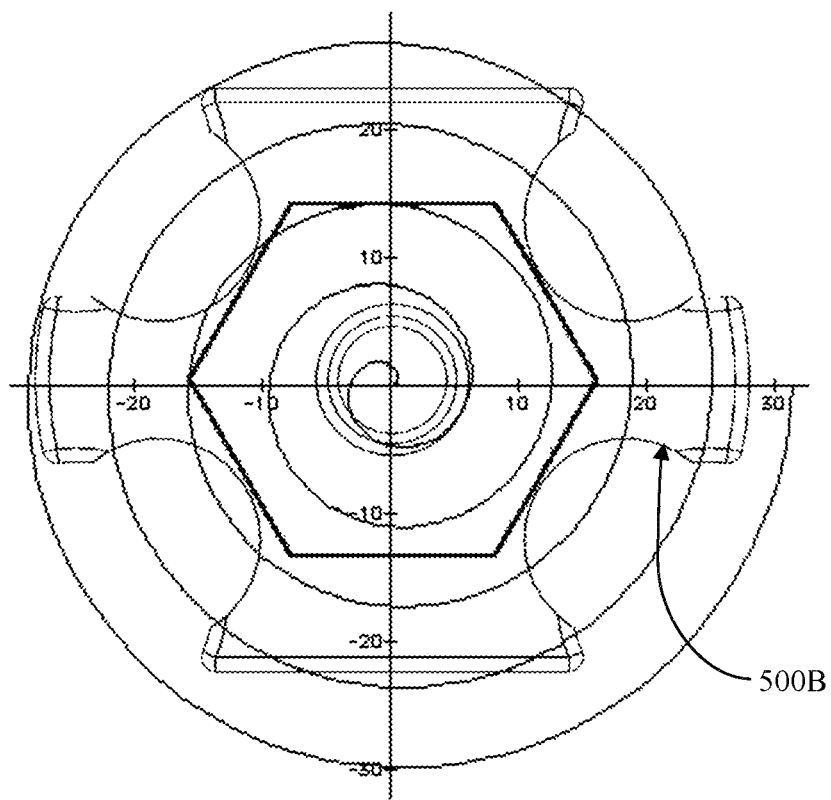

The combination of the various forces and contact positioning that arise under the RPM based contact situation, is believed to present a compact spiral configuration despite higher and higher RPM application, as schematically depicted in FIG. 5C: which also, by way of spiral sections on an overlay of the torque enhancement device, further depicts the L2/L1 ratio differential relative to torque enhancement device 500B. In other words, the spiral depiction of centrifugal and centripetal force interplay in association with the contact surface force development, is believed to promote a torque contact relationship that assists in anti-camming and anti-wobbling functioning relative to the torque enhancement configuration even relative to higher RPM environments of usage.

Figure 7:
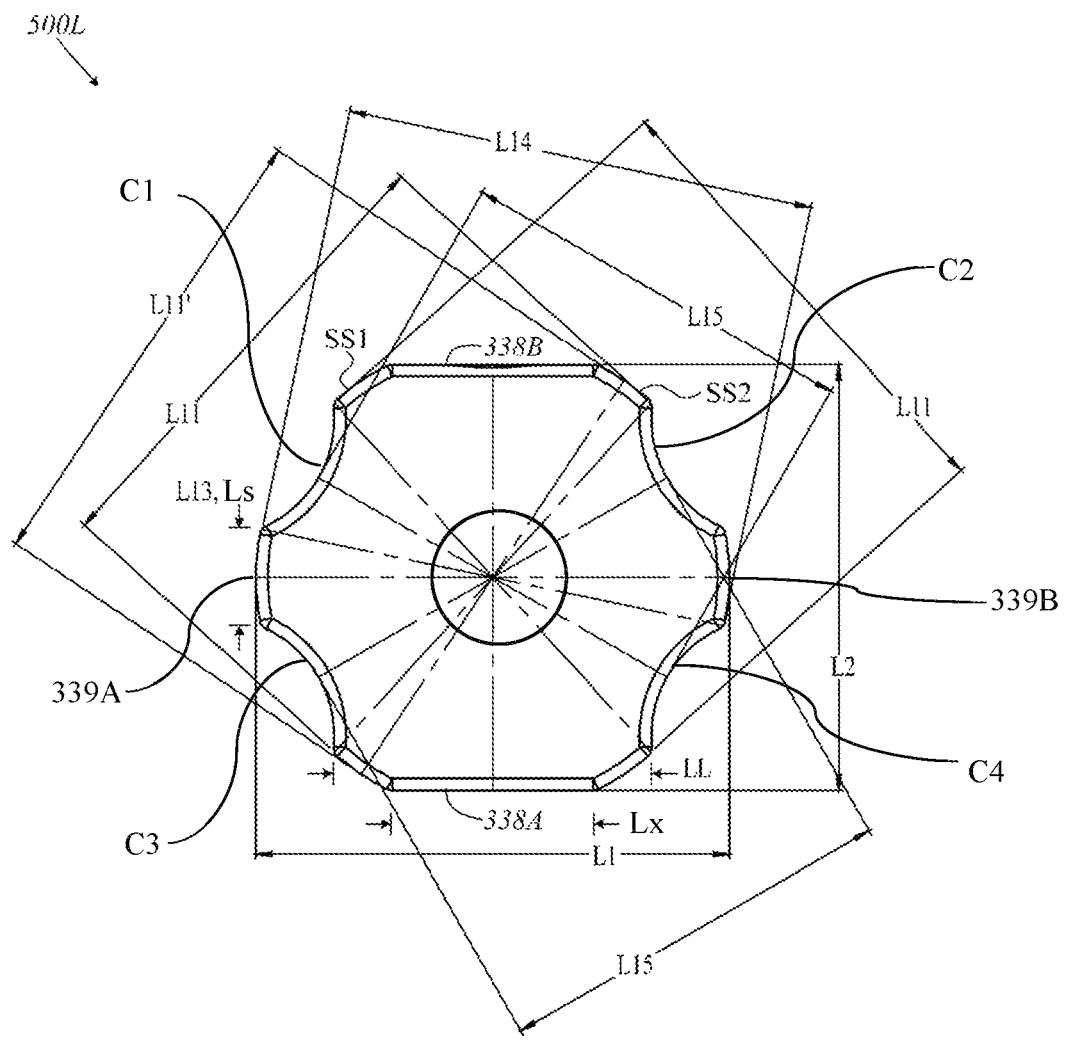
FIG. 7 shows a top plan view of the torque enhancer of FIG. 6.

FIGS. 6 to 10 show an alternate embodiment torque enhancer 500L which is also in a nut configuration as to feature central threads 508 as in the prior embodiments and is also shown to have a different exterior configuration relative to the earlier described nuts, in that it has a conical upper surface 501T extending from its torque enhancement base 501B (with the base presenting the exterior torque enhancement configuration as seen by the top view depicted in FIG. 7). The shape of torque enhancer 500L is thus similar to that earlier described for FIG. 3A of the present application, but has less of a length differential between its parallel sides and thus presents a rectangular RE configuration more closely approximating a square than that shown in FIG. 3. Thus, as described in greater detail below with reference to the driver/recess combinations features of the present invention, the believed torque generating forces and counter balancing forces to prevent instability are better suited in the 500L configuration for higher rotational drive usages.

In the FIG. 6 embodiment there is again featured a nut embodiment of the present invention, with enhancer 500L featuring a threaded interior 508 not extending fully therethrough. In FIG. 6 there is further seen that one of the longer side walls has a bowl shaped minor depression DP (an opposite one preferably on the other side) as to facilitate, for example, finger grasp in collusion with the combination of any one of the cut-outs C1 to C4 and the adjacent edge at the outer border region of that cut-out; and, as explained below, also plays a role in compression deflection stabilization considering the different thicknesses presented in the different length projections PR1, PR2, BT1, BT2) and can also provide added surface contact regions (as with adjustable pin array or projection wrenches) in similar fashion to the below described added notching embodiments of the present invention as well as potentially added fluid reception area.

FIG. 7 shows that there is a different length/width ratio RA as presented in the earlier embodiments. That is, torque enhancer 500L features a closer to square L2/L1 relationship (RA of 90% or more) than the earlier described torque enhancer embodiments. For example, an illustrate ratio range of 50 to 99% (and more preferably 60 to 98%) is featured in the present invention, with the above described enhancer 500B with its 80% L2/L1 value representing an intermediate portion of the range, and the present 500L approaches the higher end of the range with, for example, a 90% plus non-square value. For high speed tooling as in high rpm air or hydraulic drivers, the higher end of the range is preferable (e.g., 75% to 99% is preferred, as in 90 to 98%).

With reference to the bottom plan view in FIG. 7 there can be seen values L1 and L2 with one ratio example being L2=18 mm and L1=20 mm for a ratio L2/L1 value of 18/20 or 90%. Again, these lengths are preferably environment dependent, although a similar ratio retained "zoom-in" for smaller usage environments (as in the noted micro-usages) or a "zoom-out" for larger usage environments (as in the noted larger industrial uses) is featured under embodiments of the present invention.

Figure 10:
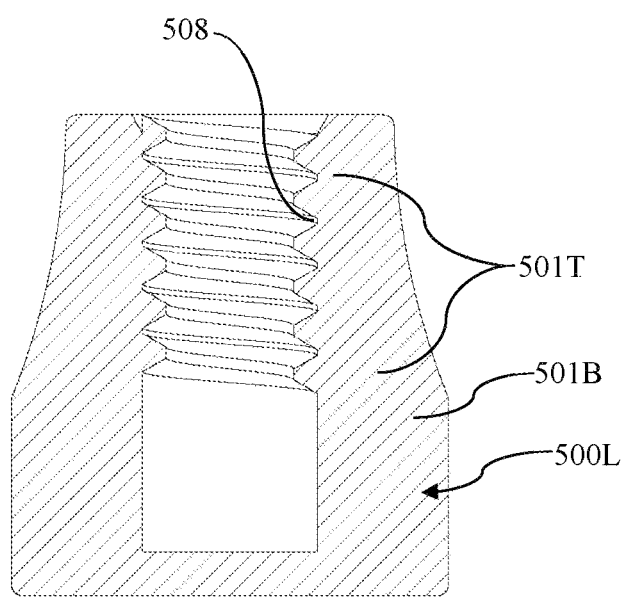
FIG. 10 shows a cross-section view of the torque enhancer of FIG. 6 taken along the elongated axis thereof.

Also, FIG. 7 shows a central aperture 508, but unlike the earlier embodiments is not a through-hole but extends for a majority although not all the way through as depicted in cross-section FIG. 10 (alternate embodiments do feature both threaded and non-threaded through-holes in enhancer 500L as representing, for instance, a hub reception region for when torque enhancer 500L represents a gear).

An additional difference is seen in FIG. 7 in the Y-axis extending oblique (added short base straight wall outer segments SS1 and SS2) provided at opposite ends of the non-oblique, portion of straight side walls 338A, 338B. These added short straight wall segments SS1 and SS2 are optional as the side wall 338A and 338B can extend for the same Y-axis length along an entirely linear line for the same Y-axis length as provided by the illustrated SS1 and SS2 end additions.

Figure 8:
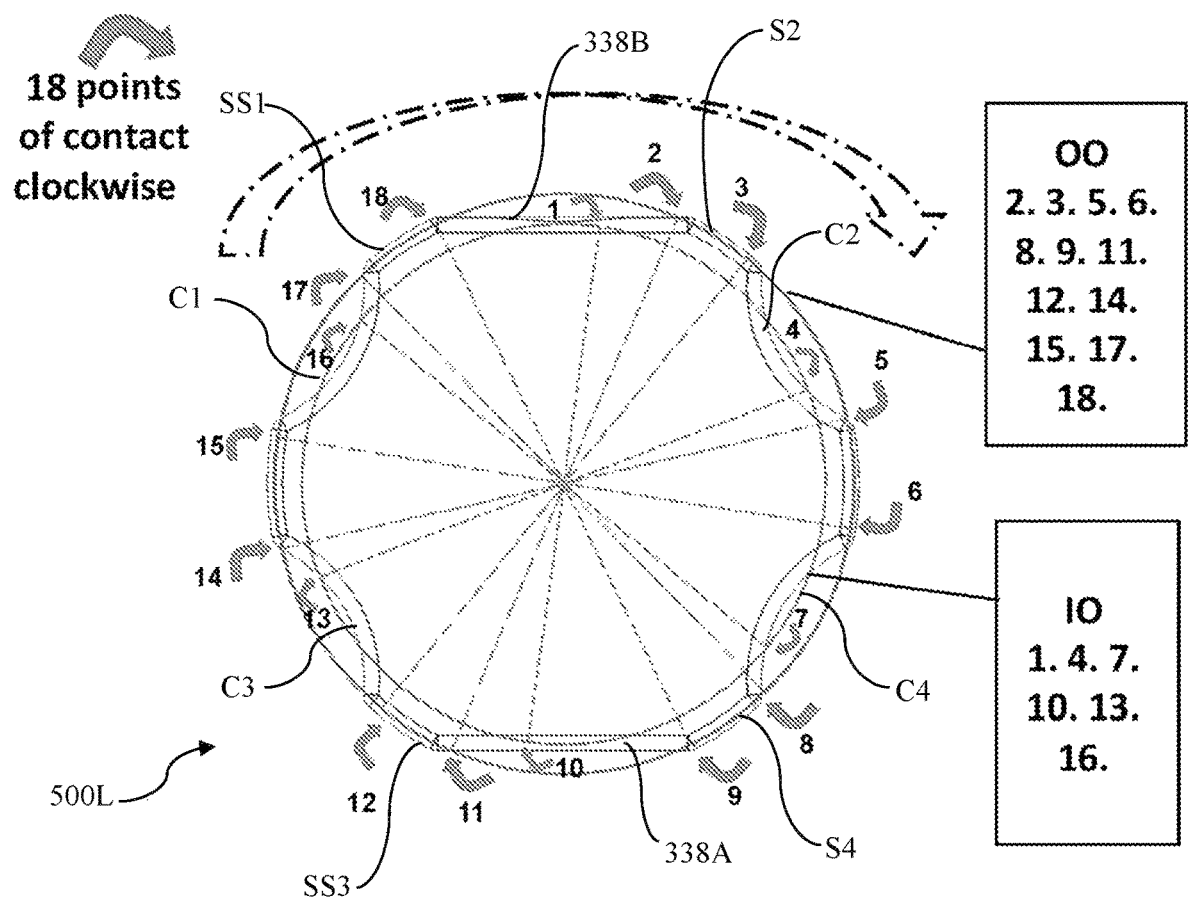
FIG. 8 shows a similar bottom plan view as that shown in FIG. 7, plus a considered "mechanical" contact point illustration.
Figure 9:
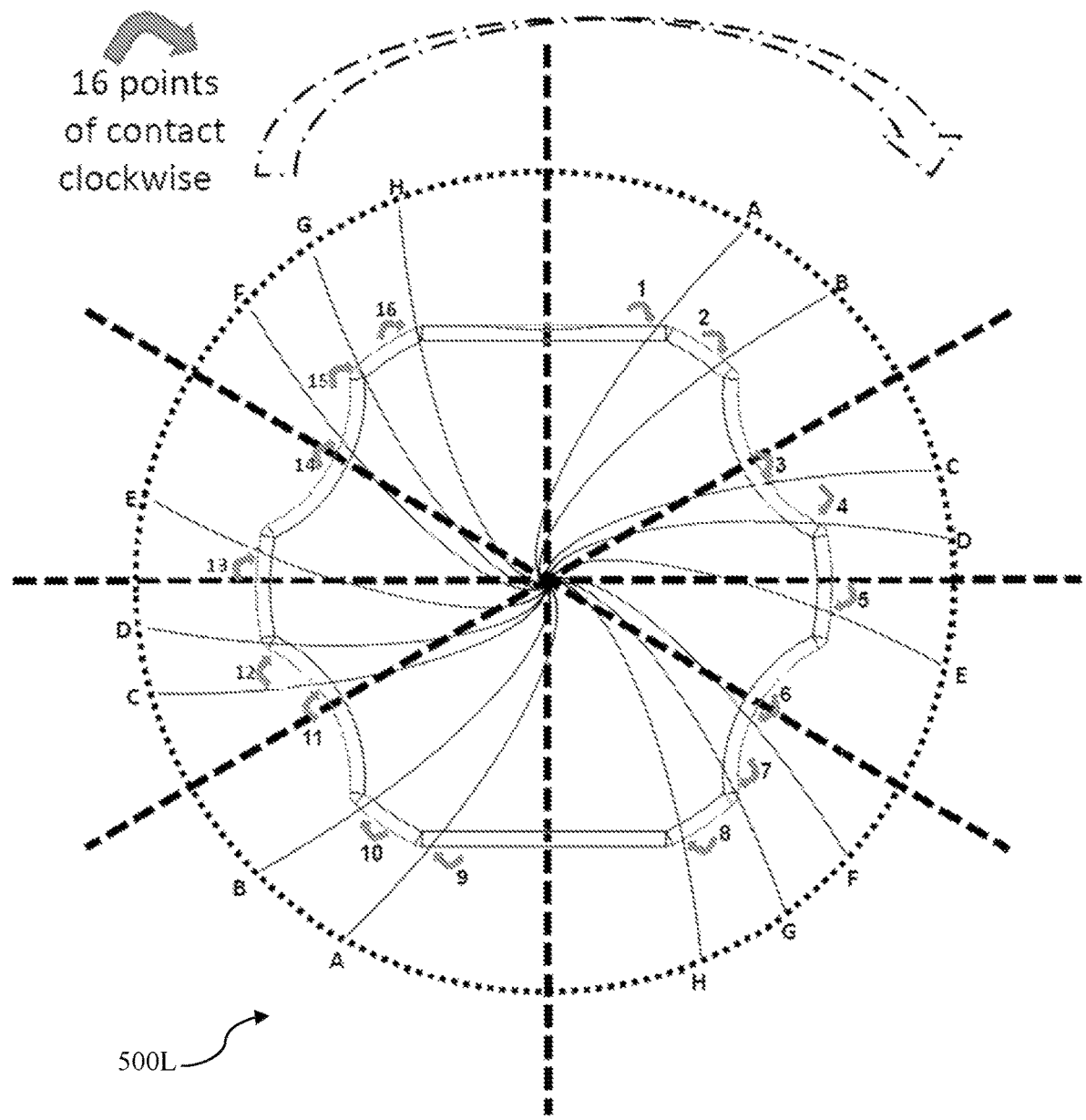

The inclusion of the noted walls SS1 and SS2 does present a variation in both the mechanical and the spiral-centrifugal contact presentments as illustrated in FIGS. 8 and 9. This presented differential is represented by contact points such as contact point 3 on spiral segment C (one of 16 spiral segment presentation shown in FIG. 9) which is shown as having a larger return to center force direction as compared to the situation where the segment did not slope inward and down, but more tangentially to the radial. There can also be seen that there is considered to be a higher percentage of return to center force contact point arrangements (e.g., the very shallow corner cut outs result is a higher percentage of return to center stabilizing forces than is found in the earlier embodiments with a) deeper or less smoothly curving cut outs, and/or b) a closer to square L2/L1 ratio and thus less relative differential in the respective projections (as in PR2 and BT2). The enhancer 500L is considered to present a very stable embodiment, and one that does provide torque enhancement, but not the same torque generation potential (based on fulcrum differential consideration) provided by a lower L2/L1 RA % value as is provided in some of the other embodiments.

Some non-limiting dimensions provided to help appreciate some of the geometrical relationships include (for the L2/L1 smaller embodiment featuring lengths of L2=18 mm and L1=20 mm) are as follows (all in mm): L11=19.9; L11'=20; L15=16.97). A larger scaled up embodiment features (all in mm) L1=72; L2=65; L11=71.5; L11'=72; L15=61; L1=31; LL=48; LS=15 and the maximum depth of the corner cut-outs 4.5. As noted above, however, the usage environment dictates the dimensioning (as in a scale up and scale down potential while retaining the overall ratios represented by the dimensions given above). Thus, for instance, for an orthopedic micro screw the dimensions above might be reduced at a ratio conversion of ⅕ such that the noted 18 mm length is 18 mm/5 or 3.6 mm, with the same ratio applicable to reduced values for the other noted dimensions for the first referenced size set above). As noted above, the dimensions provided in this paragraph are not intended as being limited, as different environments (such as those different environments described above and below) dictate different sizes (although a similar ratio conversion such as that referenced can be maintained despite the dimension differential).

As described above, the torque enhancement configuration of FIG. 7 features a higher level RA % as in 90% plus to below square, which is closer to overall symmetry, but still retains a degree of the beneficial bi-symmetry arrangement with parallel longer wall length along one axis as compared to the set of perpendicular extending walls.

Figure 11:
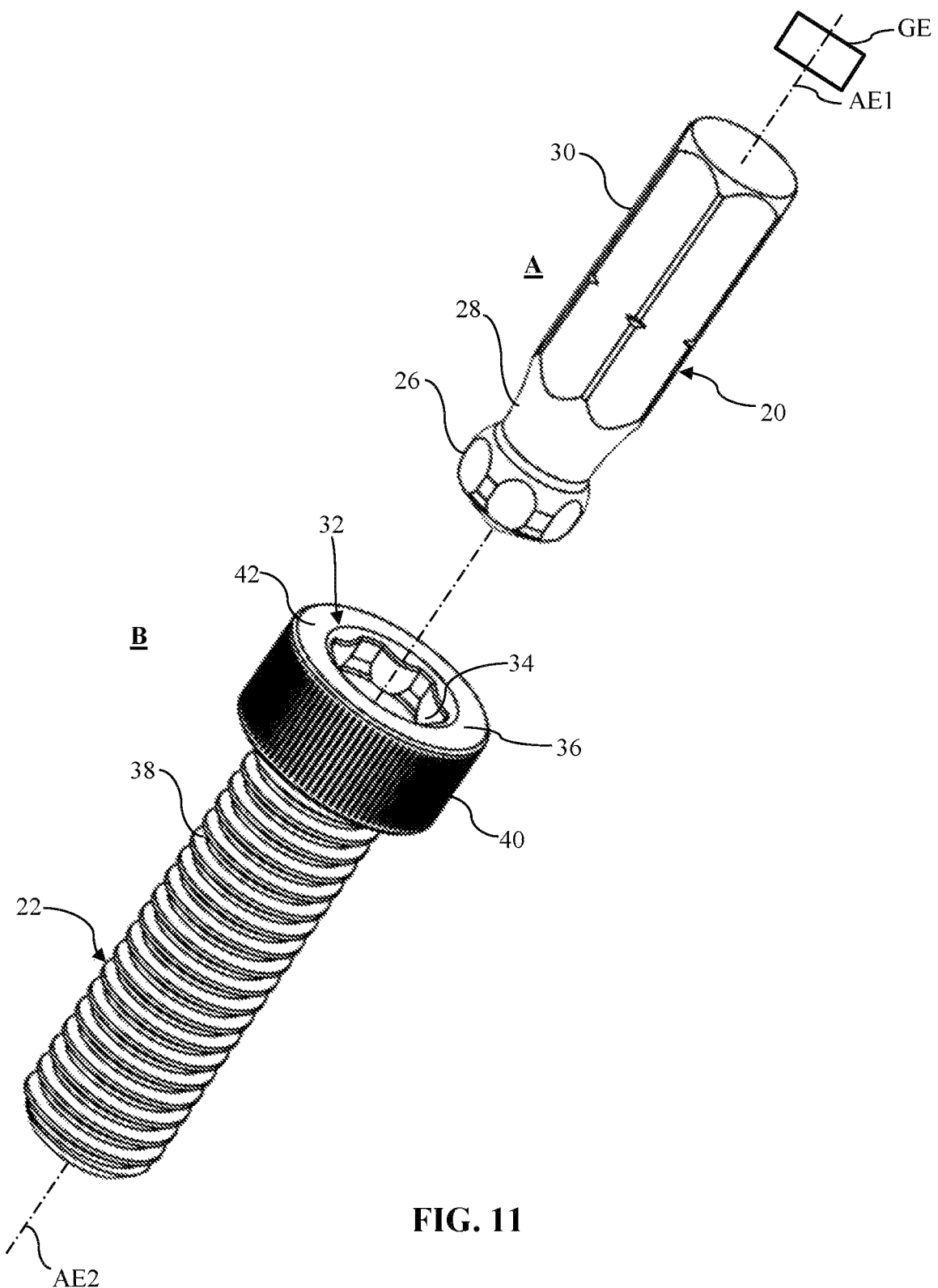
FIG. 11 shows a male/female combination of the present invention featuring a pre-insertion (or just separated), but generally aligned, driver (male member) and recessed recipient in the form of a fastener (female member) having a common or coordinated geometry designed for torque engagement with the driver.

With reference to FIGS. 11 to 20 there is described some additional aspects of the present invention inclusive of each of (i) a male driver component (or "driver" or "bit" as it is presented in the depicted embodiment), (ii) a female reception component (or "recessed recipient", with "fastener" being an example), and (iii) the combination of (i) and (ii). FIG. 11 shows an alignment along common axes of elongations AE1 and AE2 for driver (or bit) 20 and recessed recipient 22, which when in engagement present an engaged male-female combination 24 ((A+B) (see FIG. 20)). Each of (i) and (ii) are shown separated in FIG. 11, although generally commonly aligned along the noted AE1 and AE2 axes which is representative of a pre-insertion state (or a just removed state). The axes AE1 and AE2 common alignment is a preferred insertion alignment, although environmental conditions can require an angling of one axis relative to the other (with the driver and recess recipient of the present invention being well suited for handling such angling while still maintaining adequate installation and extraction forces).

The FIG. 11 depiction features driver 20 as having driver head 26, tapered section 28 and main body shank 30. Recessed recipient 22 is shown as a fastener and features female reception head 32, with centered female reception recess 34 and head body 36 (shown as having a knurled outer surface 40 with annular horizontal upper ring 42 in the illustrated example). Recessed recipient (fastener in this embodiment) 22 is shown in this example as having a threaded fastener shaft 38 extending from the head body 36 (which in the illustrated example is non-tapered, although alternate embodiments can assume tapered forms as when a tapered shank screw is featured).

Driver 20 is shown in this embodiment as a non-hand tool embodiment or adaptable hand tool embodiment with its main body shank 30 being well suited for insertion in either a hand-tool grip slot or a chuck of a revolution generator (e.g., an electric or fluid revolution generator inclusive of those described above—schematically represented by diagram box GE in FIG. 11). The revolution generator GE is configured as to generate revolutions in the main shank of driver or bit 20 (referenced as revolutions-per-minute ("RPM")). The configuration of driver 20 is also well suited, however, for hand tool usage as with the appropriate integrated grasping region rearward or proximal of the illustrated bulbous driver head 26.

Driver 20 shown in FIG. 11 represents an embodiment well suited for being driven at RPMs to provide means for installation of fastener 22 into a fastened setting or as a means to extract fastener 22 from a fastened setting. Higher RPMs are often desirable for many settings as in, for example, initial industrial assembly line settings. Driver 20 (and the geometrically coordinated fastener head 32 in this embodiment) is (are) particularly well suited for achieving higher RPM usage; inclusive of being able to maintain that RPM (or a non-stop portion thereof as in at least 50% of the prior head contact RPM level) in going between a first fastener to a next fastener (e.g., as in an assembly line wherein multiple fasteners are presented for installation or removal in sequence).

The ability of present invention geometries to maintain the RPM level utilized in the fastener installation and/or removal during mating of the driver and fastener, or at least the maintenance of a portion (e.g., at or greater than 50%) of the utilized RPM drive level, enables the avoidance (or at least a lessening) of ramp-up time in the RPM used in the installation/removal operation. This avoidance of ramp-up time and the ability to maintain insertion rotation from one fastener to another in a sequenced fastening (or extraction) operation is highly advantageous and sought after in the noted settings. Moreover, under the present invention, the strategically designed driver and/or fastener head geometries enables an actively rotating driver to be inserted, while still rotating, into the fastener head without rapid degradation of those geometries in the driver and/or reception head (e.g., stripping or chipping of the driver and/or fastener head geometries relative to standard materials used for such drivers and fastener heads). There is thus avoided a prevalent degradation problem commonly associated with prior art geometries. This includes providing the peripheral wall configuration of the torque enhancement device with a tapered and/or curved portion to facilitate initial insertion until sufficient penetration to align the intended full rotation engaging contact surfaces (as in those more proximal and/or less curved if curvature is involved).

Figure 12:
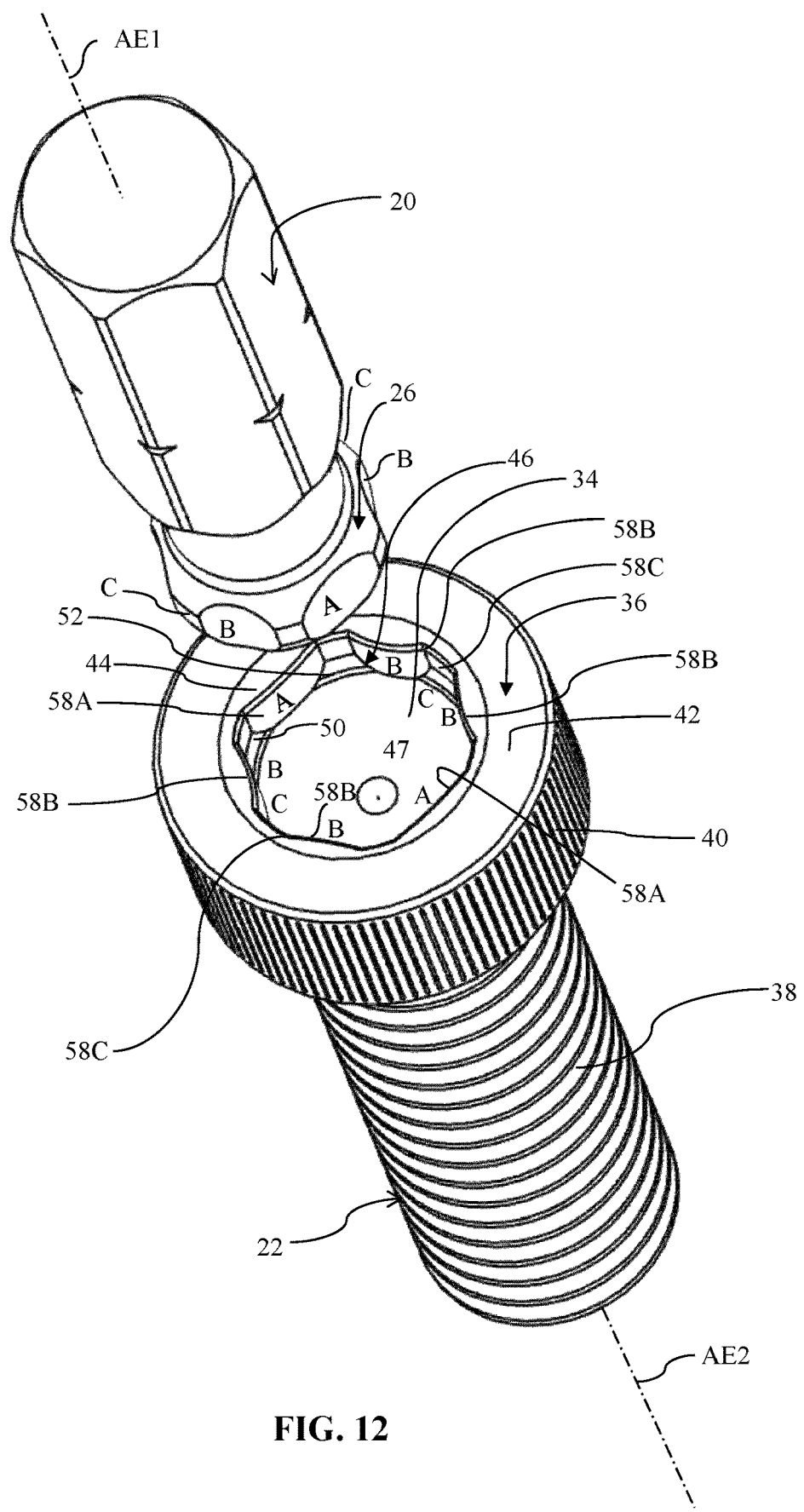
FIG. 12 shows another view (from a different orientation) of the FIG. 11 pre-insertion, but generally aligned, combination of a driver (male member) and fastener.
Figure 17:
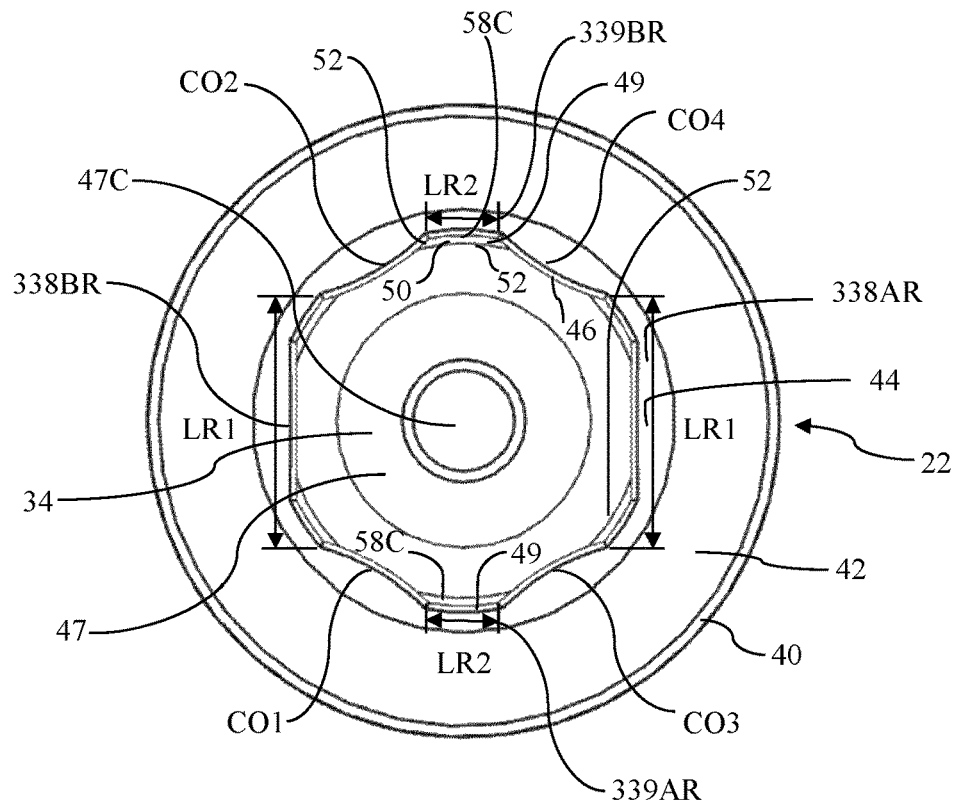
FIG. 17 shows the insertion end view of the female recipient head of the fastener in FIG. 11.

FIG. 12 provides a better view of female reception recess 34, which in this embodiment features a corresponding or coordinated geometry relative to driver head 26. Reference is also made to FIG. 17 which shows the top plan view of recessed recipient 22 as well as female reception recess 34. As seen in FIGS. 12 and 17, head body 36 features outer peripheral surface 40 which in this embodiment is shown as being a knurled surface. Additionally, shown is flat, upper surface 42 extending annularly about female receipt recess 34. Extending radially inward from the inner periphery of upper surface 42 is found tapered flange 44 (e.g. a slope down from a horizontal plane flush on upper surface of 2° to 60° (as in 10° to 30°). Extending down from the inner peripheral edge of tapered flange 44 and circumferentially around recess 34 is geometrically contoured ring 46 that is designed in this embodiment to coordinate with that of the torque enhancement driver geometrical configuration. Geometrically contoured ring 46 has a lower edge that merges into the concave bowl bottom 47 of female reception recess 34. In this embodiment, concave bowl bottom 47 has a closed bottom surface as to generally represent a semi-spherical bottom surface with a flattened central bottom region 47C to further define the bowl shape.

To facilitate the later discussion concerning the meshing of female reception recess 34 with driver 20, there is referenced four convex regions CO1, CO2, CO3 and CO4 formed within contoured ring 46 that are generally designed to correspond with the aforementioned concavities C1, C2, C3, C4 (see FIG. 18 of driver head 26 as well as the similar contoured torque enhancement periphery featured for torque enhancer 500L shown in FIG. 7). Further to facilitate the discussion below as to the driver meshing with female reception recess 34, there is labeled the two longer sides 338AR and 338BR formed in reception recess 34 designed to coordinate with the longer walls 338A and 338B formed in driver head 26 (see FIG. 18 as well as FIG. 7), as well as the shorter reception recess side walls 339RA and 339RB designed to generally conform in geometry for reception purposes with projections 339A and 339B in driver head 26, with projections 339A and 339B also shown in FIG. 7 relative to the torque enhancement discussion for the torque enhancer 500L (as one example well suited for RPM generation situations due to the higher relative percentage values associated with torque enhancer 500L).

Working clockwise from the top of FIG. 17, at the 12 O'clock location of contoured ring 46 features a first radial driver projection reception set 58C-58C (at a common locations as the referenced reception regions 339RA and 339RB designed to receive projections 339A, 339B) with each projection reception set 58C-58C having a generally flat, vertical wall 49 at the reception recess "C" location seen in FIG. 12, that merges at its bottom with a sloped ledge 50 with ledge 50 merging at its bottom with vertical rim 52 that is of a height less than vertical wall 49 and is more steeply sloped than sloped ledge 50. Also, as seen from FIG. 17, vertical wall 49 is essentially flat along its circumferential length or provided with only a slight curvature along its circumferential length. Also, first radial driver projection reception set 58C and 58C are each designed to receive, respectively, the shorter length set (339A and 339B) (driver "C" location match) of the above referenced straight or essentially straight walls of the geometrical configuration for the driver with the above noted torque enhancement ratio feature.

With reference to FIGS. 12 and 17, there can be further seen that the adjacent individual members of the first radial driver projection reception set 58C and 58C (two total), border convex (radially inward extending) wall regions 58B (four total). The referenced four wall regions 58B corresponding as well to one of the aforementioned four convex regions CO1, CO2, CO3 and CO4) and at reception recess matching "B" mesh engagement locations, which correspond with the matching driver "B" mesh engagement locations corresponding with the curved surfaces C1 to C4 in the driver).

Figure 18:
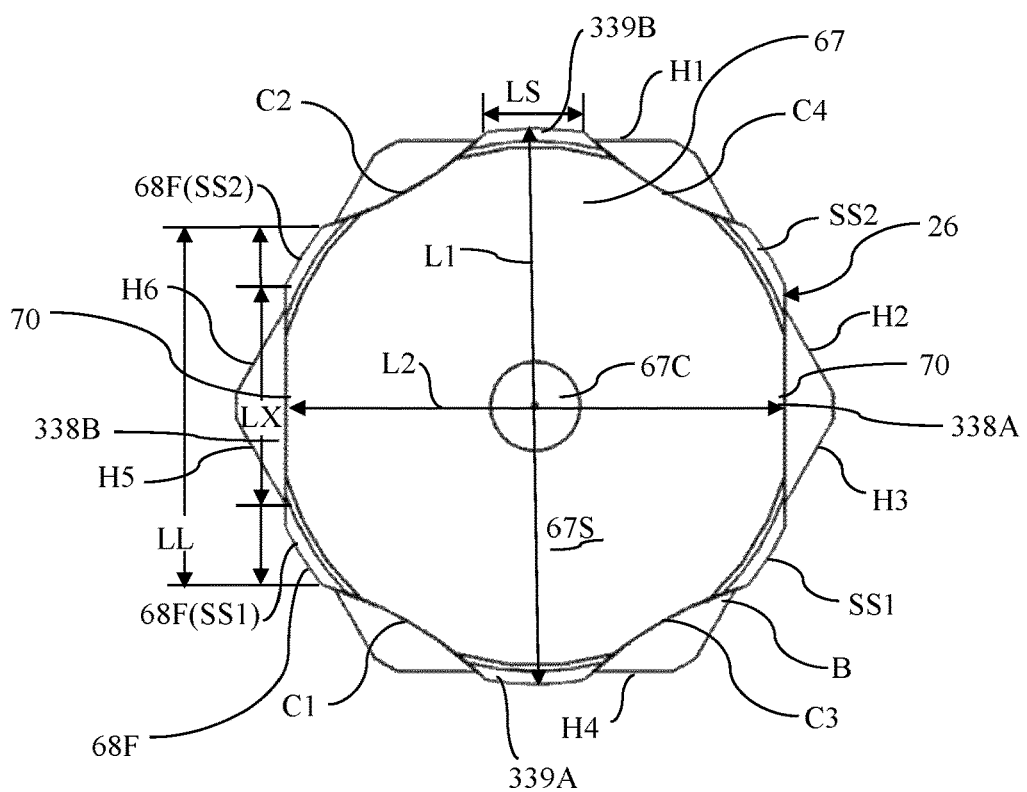
FIG. 18 shows the insertion end view of the male driver shown in FIG. 11.

With further reference to FIGS. 12, 17 and 18, and to help illustrate the alignment involved relative to the bi-symmetrical arrangement of the driver and reception recess that are meshed for torque engagement, there is referenced the longer reception recess walls 58A (two in total having a flat intermediate area and two shorter oblique wing extensions) and each of length LR1, and designed to mesh with the corresponding longer driver walls of driver head 26 also designated with an "A". Still further, and as noted above, each of the convex regions 58B (comprised of CO1 to CO4) of the reception recess is labeled "B", while the corresponding concave regions C1 to C4 of driver head 26 are also labeled B. Thus, between the adjacent most convex walls B in the reception recess there is situated the shorter reception wall regions 58C (a diametrically opposed set) that are situated to mesh with the shorter projection walls in driver head 26 (which are noted with the corresponding "C" alignment letter in FIG. 12); and, as shown in FIG. 17, have length LR2.

Thus, at the time of desired torque engagement, the driver head is arranged to align with the reception recess such that pairs of A-A and B-B and C-C are sufficiently aligned as to enable appropriate torque meshing. The four convex wall region CO1 to CO4 of reception recess 34 at the B locations are each shown as extending vertically the entire height of the geometrically contoured ring 46 such that it too extends down from lower interior edge of tapered flange 44 and up from the uppermost edge of concave bowl bottom 47.

The axial length of the driver head walls are generally the same as the meshing reception recesses of aligned pairs A-A; B-B and C-C, although as noted above other embodiments feature the reception recess axial wall length being longer than that of the driver's such that there can be axial adjustment of the meshed walls (e.g., see the discussion below as to the further incorporation of a second tier meshing arrangement as in a shank hex configuration following an intermediate-to-deep driver head insertion, with an example in FIG. 52 discussed below).

Figures 13, 14:
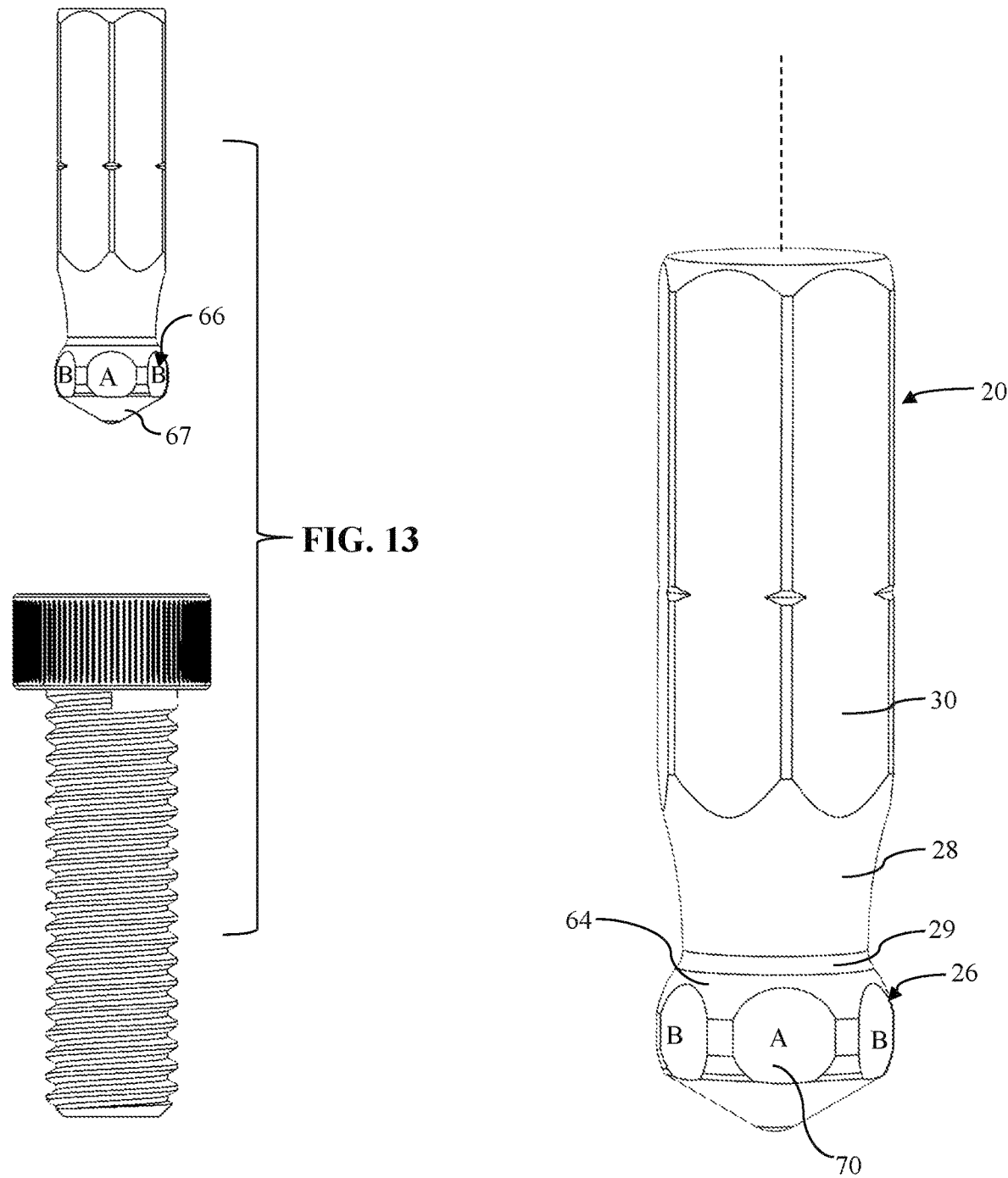
FIG. 13 shows the same combination as in FIG. 12, but from a vertical alignment viewpoint.
FIG. 14 shows the driver or bit of FIG. 11 alone and in a vertical orientation.
Figure 15:
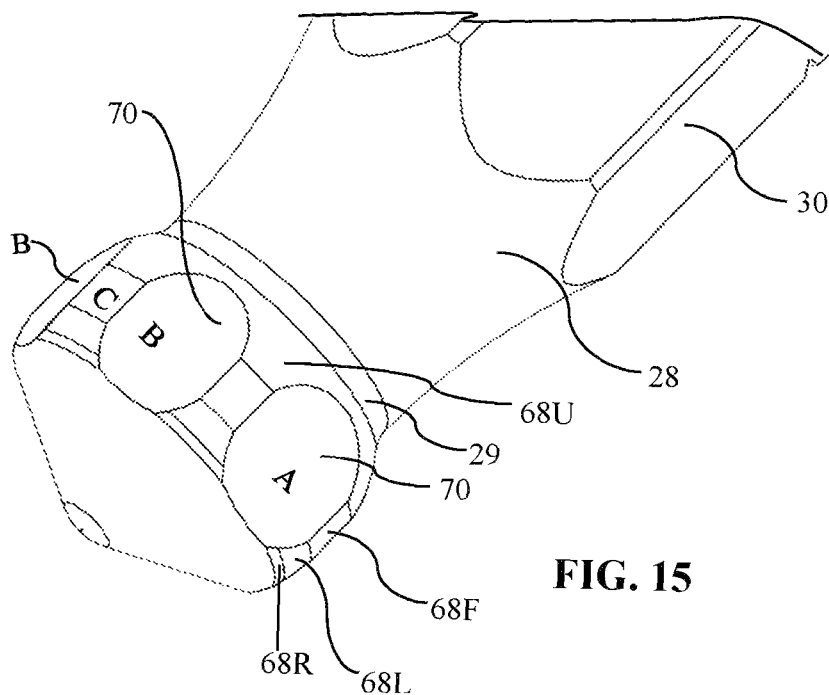
FIG. 15 shows, in cut-away perspective, a closer up view of the driver (male member) shown in FIG. 11.
Figure 16:
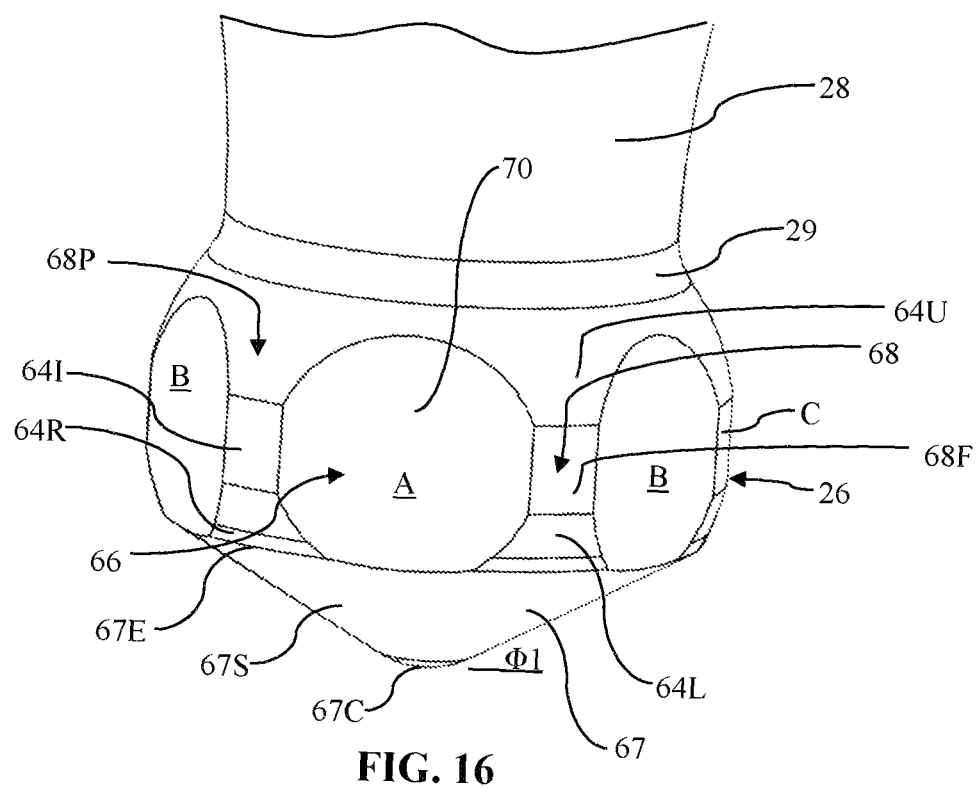
FIG. 16 shows a still closer up view of the driving end of the driver shown in FIG. 14.

With reference in particular to FIGS. 14 to 16 as well as FIG. 18, there is provided additional detail as to the driver head 26 for driver (or bit in this embodiment) 20. Although intended to be a variety of potential geometrical configurations under the present invention, FIGS. 14-16 and 18 illustrate an embodiment wherein main body shank 30 has a hexagonal cross section with each side wall referenced as H1 to H6 in FIG. 18. This provides for a highly universal configuration in that many chuck or cavity receptors (not shown) for RPM drivers or hand held handle adaptors (not shown) have the same hexagonal configuration. In this way, embodiments of the present invention provide a torque enhancer driver head 26 that is readily received by pre-existing RPM drivers or hand held tool chucks or bit reception cavities. As another common chuck engagement shape, rather than a hexagonal configuration body shank 30 can have a square configuration for chuck or hollow handle reception.

Tapered section or neck 28 is shown in FIGS. 14-16 and has a contour and axial length that provides sufficient clearance as to facilitate meshing despite non-aligned AE1 and AE2 axes (FIG. 20), provides added visualization potential as to the driver head 26 reception with respect to female reception recess 34, and avoids main body shank 30 contact with the female reception head 32. As described below, there are some embodiments where the axial length of tapered section 28 is shortened such that the distal end of the main shank can also function in some settings as a driver within a female reception recess (e.g., see FIG. 38 described below). At the border region between tapered section 28 and driver head 26 there is provided an annular concave recess 29 that facilitates and angled insertion or extraction of driver head 26 as it provides for edge reception as well as driver head and fastener edge manipulation (e.g., sliding or rotation relative to each other).

Driver head 26, in the example shown in FIG. 16, features an upper ring 64U that has an outer curved contour as to present a smooth outer curvature in the axial direction that forms an upper region of the bulbous, ballpoint end in driver head 26 of driver 20. Driver head 26 further includes a generally corresponding lower ring 64L that has an outer curved contour that also presents a smooth outer surface in the axial direction and forms a lower region of the bulbous, ballpoint end in driver head 26 of driver 20 (and is well designed for full driver insertion contact with ledge 50 of recess 34). At the lower extremity of lower ring 64L is presented rim band 64R shown in this embodiment as a flat, relatively shortened in height band that extends about the bottom region of the bulbous, ballpoint end in driver head 26 of driver 20 (and is well designed for full driver insertion contact with ridge 52 of recess 34). Thus, as shown in this embodiment upper ring 64U has a longer axial height than lower ring 64L, but each ring has a smooth contoured outer surface which provides meshing/removal as well as self-centering benefits as described in greater detail below relative to the engaged or meshing male-female driver and fastener meshing combination 24. Between upper and lower rings 64U and 64L there is flat walled ring 64I (made up of individual surfaces 68F of the below described individual projections, which provide vertical torque generating edging). The axial length of ring 64I is lower than the upper ring 64U and greater than that of lower ring 64L.

Provided in driver head 26 is depression-projection ring set 66 that includes, in the circumferential direction, a plurality of projection sets 68 that are designed to mesh with respective counterparts in the aforementioned mesh projection reception sets 58A, 58B and 58C forming part of the reception recess 34 in female reception head 32. To provide a conforming projection-mesh projection/reception interface, each projection set 68 features flatter wall projection 68F (individual members of intermediate ring 641 and defining wing surfaces SS1 and SS2) that extends (preferably presenting a vertical planar face) down from its interface region with the lower edging of upper ring 64U. Extending off from the lower edging of each flatter wall projection 68F is a portion of lower ring 64L and thus each projection set has a generally curved in profile extension projection 68P (representing uninterrupted parts of lower ring 64L, upper ring 64U, rim band 64R positioned between periphery interrupting surfaces 70 of the longer peripheral walls shown, which walls 70 also have an axial length greater than the adjacent circumferentially inclined surfaces and also represent portions of the "A" meshing contact regions relative to the corresponding mesh "A" counterparts in the reception recess).

Depression-projection ring set 66 further includes a plurality of concave depressions of meshing "B" locations and generally corresponding to the concavities C1 to C4 noted for the torque enhancer 500L of FIG. 7 (which in turn generally corresponds with the meshing location "B" concavities which are referenced the same in FIG. 1). The concavities in depression-projection ring set 66 are shown in their mesh match locations "B" for receipt by the "B" locations in the reception recess 34.

FIG. 18 further illustrate the commonly configured, generally linearly extended planar wall regions 68F and 70 of driver head 26 (generally corresponding to walls 338A and 338B in FIG. 7 relative to torque enhancer 500L inclusive of the wing extensions shown as SS1 and SS2). There is provided in FIG. 18 peripheral length values LX for wall regions 70 with the full length of the combination of regions 68F and 70 having length LL. Projection set 66 is further inclusive of projections designated as well by 339A and 339B which references are also found in the torque enhancer 500L depiction in FIG. 7, are of length LS, and are provided in meshing "C" locations.

Figures 19, 20, 21:
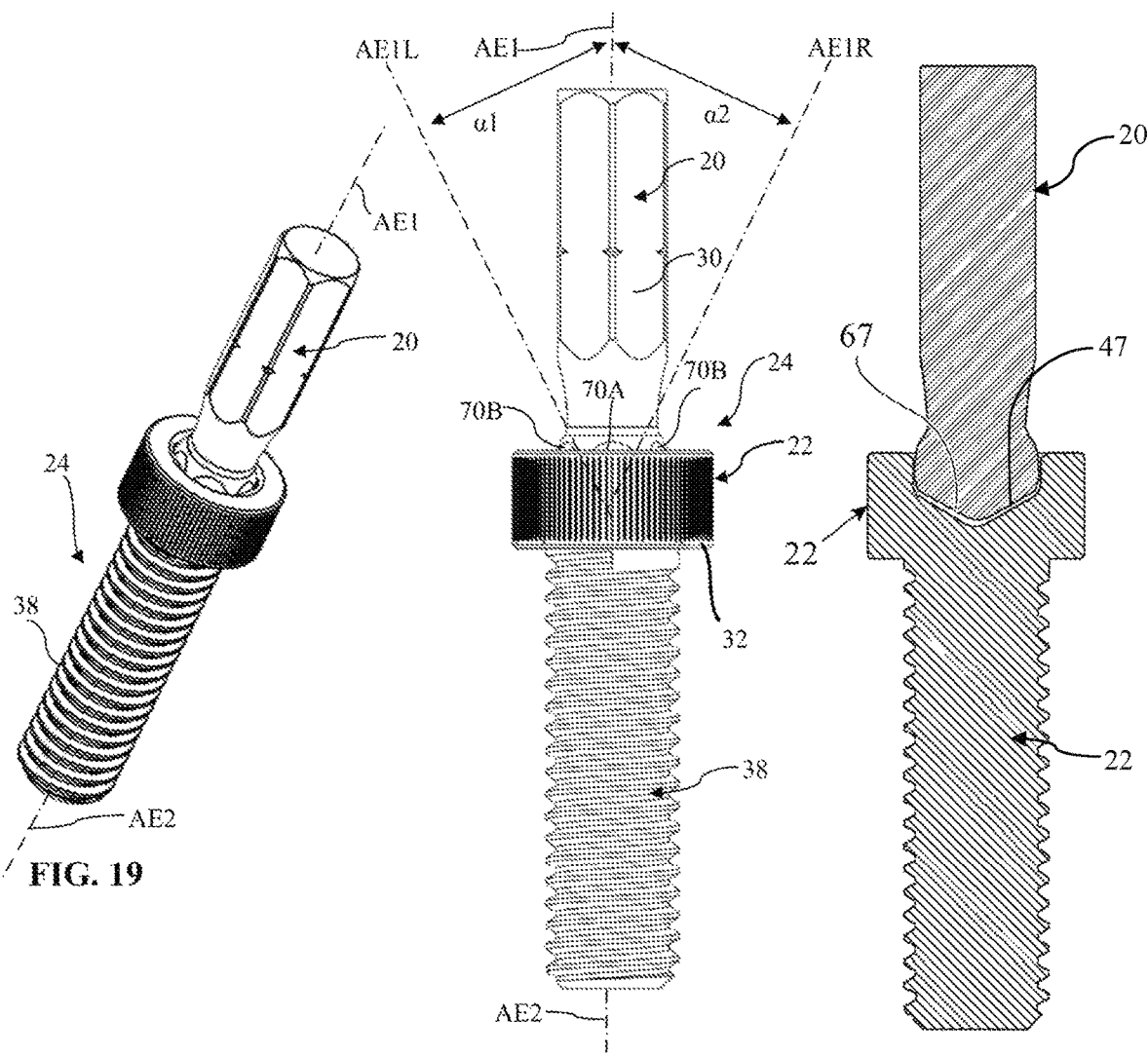
FIG. 19 shows the driver and fastener combination of FIG. 11 in an engagement setting as would be present either during a fastener insertion or fastener extraction setting.
FIG. 20 shows the same combination in engagement as in FIG. 19, but in a vertical orientation.
FIG. 21 shows a vertical plane cross-sectional view of the combination shown in FIG. 20.

On the underside of driver head 26 (that is below band 64R) is provided a convex bottom projection 67 that has a flattened conical configuration and is designed for meshing/contact with concave bowl bottom 47 of female reception recess 34. As further shown in FIG. 16, there is radial curved tip region 67C (as in a rotating top curved end point) at the center of convex bottom projection 67 that is configured to mate with the similarly contoured central bottom region 47C of concave bowl bottom 47 in female reception recess 34. FIG. 16 further references angle Φ1 which is the slope of side wall 67S extending up to the upper edge of 67E of convex bottom projection 67. An illustrative range value for angle Φ1 includes 20° to 60° (as in 30° to) 45°. Side wall 67S, in an aspect of the invention, has a slope that corresponds with that of concave bowl bottom 47 of female reception recess 34 as to achieve a large surface contact meshing relationship as illustrated in FIG. 21. As seen from the below discussion of FIG. 38 there can also be provided additional clearance as by different angling to provide for fluid insertion and, preferably, desired fluid retention.

With reference to FIGS. 17 and 18 there is seen the two pairs (four total) of concavities C1 to C4 in FIG. 7 (with FIG. 17 showing a 90° rotation as compared to FIG. 7). These concavities are configured to receive correspondingly contoured convex projections CO1 to CO4 shown in FIG. 17 as projecting radially inward toward the central region of reception recess 34. In addition, the side walls represented by longer driver walls 338A, 338B (68F (or SS1, SS2) and 70)) and shorter walls 339A, 339B are designed for mesh contact with similarly configured side walls 338AR, 338BR (with SS1R, SS2R), 339AR, and 339BR, respectively. In view of the interplay between difficulties in inserting the driver head 26 into contoured ring 46 of female reception recess 34; versus having too much looseness relative to engaging surfaces in the engaged male-female combination 24, there is preferably provided some gap tolerance (e.g., LR2 of the recess is greater than length LS of the driver (LR2>LS) to provide suitable torque meshing but insertion receiving gap spacing). The relative gap spacing can be made with the understanding that the longer/shorter length differential feature in the noted torque enhancer configuration provides some added leeway with providing a larger gap (relative to the less outward extending projections preferably and the adjacent recess wall), while still ensuring good torque engagement, as the longer length projection portion makes robust surface contact upon rotation even when there is a larger gap on the shorter projection wall side than might exist in the prior art due to the noted differential. This added gap can be relative to only a portion of the axial length driver surface, as in a more easily inserted distal end having a common shape as the ultimate torque generation ring, but provided with a taper or the like in the deeper part of the receiving recess. This tapered (different angle than the receiving recess wall) shaping can also provide for accommodation of inserted fluids as well as other situations as in burrs or poor tolerance manufacturing in the receiving side walls. Alternatively, the relative gap spacing can be retained both axially and peripherally constant as by having the recess and driver with the same shape configurations with the driver head being made slightly smaller relative to common long/short side wall alignments and insertion configurations to achieve a predetermined gap spacing about the entire torque contact surface periphery of the driver head that is preferably for the full axial length of the relative torque contacting surfaces as well.

With reference to FIGS. 19 to 21 there is seen a fully meshed or engaged driver (bit shown) 20 within recessed recipient 22 as to provide the noted engaged male-female torque meshing combination 24. There can be seen that in such an engaged state (see particularly the cross-sectional view of FIG. 21) that convex bottom projection 67 of the driver has its side wall 67S (FIG. 16) in conforming friction contact with concave bowl bottom 47. Additionally, the respective contoured tip regions 47C of the reception recess 34 and surface 67C for convex projection 67 of the bulbous driver head 26 and concave bowl bottom 47, respectively, are also in conforming friction contact within the limited radial tip region of each. Also, there is generated the enhanced torque relationship based on the relative surface contacts in the meshing surfaces featured in meshing sets A-A; B-B and C-C in the respective driver and recess combination.

As further seen from FIGS. 20 and 21, each of the wall surfaces 70 and the concavities like C1 extend partially axially out in an exposed manner when there is a fully meshing (full contact) of the convex bottom projection 67 and the receiving concave bowl bottom. With the aforementioned angle Φ1 for the convex bottom projection wall 67S as in 30°+/−10°, there is featured a fairly shallow reception arrangement which facilitates rapid insertion (even preferably of a still rotating driver head 26) while still achieving high level torque engagement (noting that the prior art requires a deeper engagement as it lacks the same level of torque enhancement provided by the more radially outward extending portion of the driver head and enhanced momentum provided by that relationship). Still further, the aforementioned outer curvature geometry for driver head 26 and particularly the shallow sloped wall 67S provides for rapid insertion and self-centering even when the relative axes AE1 and AE2 are not aligned (e.g., see the offset AE1 axis in FIG. 20 with each of AEL1 and AER1 having offset angles α1 and α2 to the left and right of AE1 (with exemplary maximum offset angles for α1 and α2 being, for example, from 20° to 40° and more preferably not more than 30° as the maximum angle of deviation, which is well suited for assembly line usage for different product needs). A direct axes AE1 and AE2 co-linear relationship is typically preferred for engagement and disengagement, although there are numerous situations where such co-linear alignment is not available, as when there is an obstruction above the fastener head body 36. Despite this offset represented by the angles α1 and α2 (which are equal and can be seen as opposite angles of a cone shaped region for which insertion is possible despite an overhead component blocking a direct common axis meshing) the nature of the contoured walls of the ball point end of driver head 26 provides for sufficient edging contact to carry out insertion or removal of fastener 22 despite the off center insertion relationship represented by angles α1 and α2 (which still potential engagement is facilitated by having the axial length of the meshing surfaces such as surface 70 greater than the depth of the recess as to provide the FIG. 20 illustrated exposed regions 70A and 70B in the fully inserted driver ring 66).

Furthermore, the interplay between sloped wall 67S (and/or tip 67C) of driver 20 and tapered flange 44 provides for rapid insertion into a mesh engagement like that shown in FIG. 20. Also, since there are no obstructive surfaces until after the driver is sufficiently received below the lower edge of flange 44 and engages the interior geometrically contoured ring 46 of the fastener 22, a currently RPM active driver 20 can be inserted while rotating. The sloped wall of driver engagement with tapered flange 44 also helps facilitate self-centering of convex bottom projection 67 within the corresponding concave bowl bottom 47 (FIG. 17) of fastener 22 during a mesh insertion. Curved upper ring 64U of driver 20 also allows for rapid disengagement in that upon sufficient uplift together with sufficient rotation of axes AE1 and AE2 out away from each other, the smooth, curved upper ring 64U can ride back out along the tapered flange 44 and flat, upper surface 42.

The relative angles that axes AE1 and AE2 can assume during an insertion toward ultimate mesh engagement includes a plus or minus (from coinciding axes AE1 and AE2 at 0°) of, for example, 1 to 30° over a whole 360° range (cone range) where the environment allows (noting there can be a larger deviation angle potential when less RPMs involved and a lesser deviation angle range when higher RPMs are involved). This tilt range is shown in FIG. 20 relative to the fastener having a vertical axis and the driver deviating, although the orientation can be any orientation with the deviation being relative to one reference axis, as of the recessed item wherever positioned. The tilt angle is made available both by the driver head configuration and the ability of the driver head configuration with the torque enhancement offset lengths to more readily be received with the receiving recess (which is sized to receive the maximum length of the longer torque walls, but in view of the shorter length presence provides some looseness or gap formation). This gap formation further facilitates the ability to provide a coating layer on the driver head that will be less likely to be scraped off or cause blockage due to lack of gap formation when initially inserted into the receiving recess. In other words, there is not a need for a perfect match between the driver head and receiving fastener recess under embodiments of the invention; and yet, upon relative rotation of at least one of the driver head and fastener to the other, there is a strong torque catch relationship upon the longer length portion of the driver head contacting with any counterpart contact portion of the receiving recess.

Figure 22:
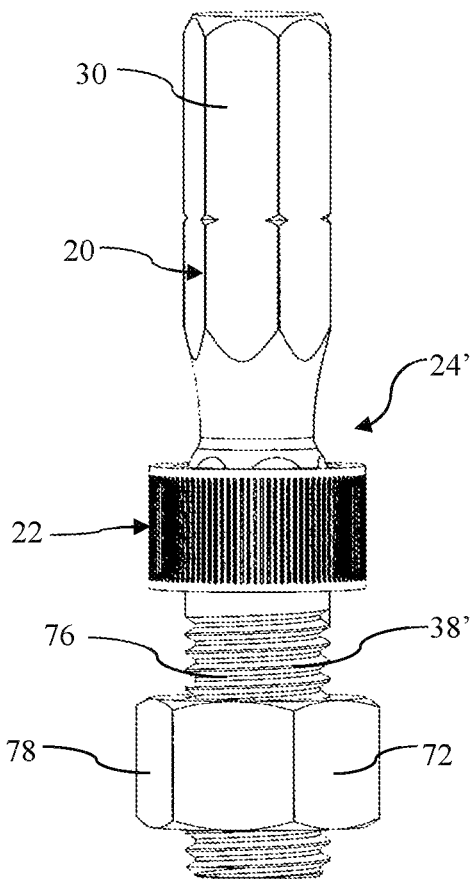
FIGS. 22 and 23 show similar views as in FIGS. 20 and 21, but for the depiction of a fastener recipient combination having an added conventional hex nut received on its threaded bolt, which is of shorter length than that in FIG. 20.
Figure 23:
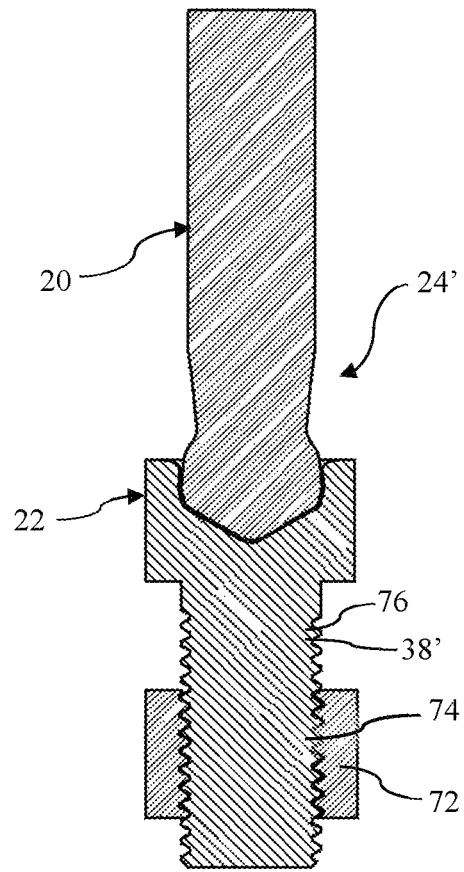
Figure 24:
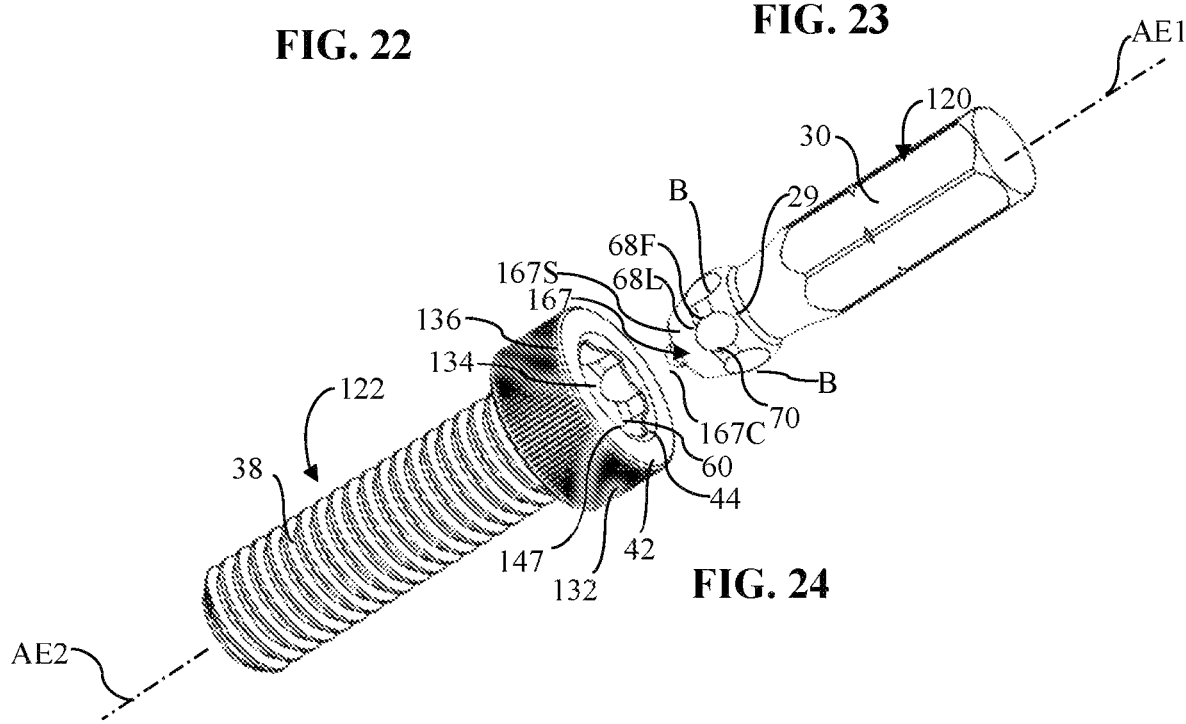
FIG. 24 show a view similar to FIG. 11 but for another inventive male/female combination.
Figure 25:
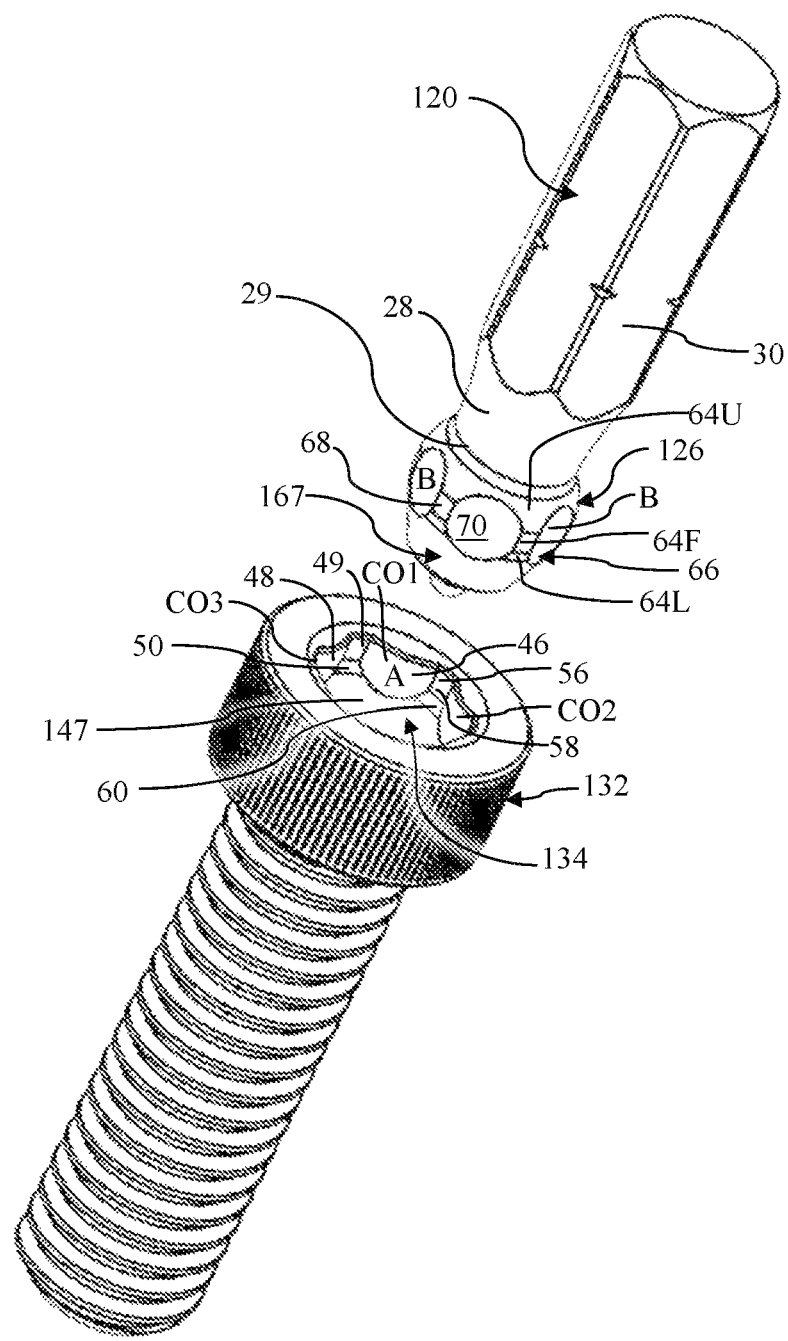
FIG. 25 shows the combination shown in FIG. 24 from a different perspective prior to engagement of the male member with the female member (or just after disengagement as is true of other similarly situated driver/recess combinations).

FIGS. 22 and 23 illustrate engaged male-female combination 24', which is similar to engaged male-female combination 24, but with the addition of nut 72 as well as the presence of a relatively shorter axial length threaded fastener shaft 38' (e.g., a reduction in axial length as compared to threaded fastener shaft 38 while having a common fastener head size). Nut 72 is shown as having interior threading 74 in threaded engagement with threads 76 of threaded fastener shaft 38'. Additionally, in this embodiment nut 72 is shown as having a hexagonal outer periphery shape 78 (a similar configuration as the illustrated hex-configured main body shank 30), although alternate embodiments include nuts having torque enhancement configurations such as those described herein (e.g., 500B and 500L torque enhancers). Also, as noted above the elongated male-female combination 24' can range in size from, for example, the mini (or micro)-screws (bolts) and nuts (or large or macro sizes as in large industrial settings such as that used on heavy machinery, buildings, bridges, etc.). Various diameter, lengths, thread pitch, head sizes, etc. (where applicable) can be utilized in the present invention torque enhancement devices such as those well established in the standard metric and imperial bolt dimensions' charts used in the art.

An additional embodiment of the present invention is featured in FIGS. 24 to 31 which is similar in all respects to the driver 20 and recessed recipient 22 (e.g., a threaded bolt fastener with central recessed head) featured in FIGS. 11 to 21, but for the below noted differences (and thus common reference numbers are featured, but for distinctions between the two embodiments or in some instances a hundred value is added). Thus, as seen in the FIGS. 24 to 31 set there is featured driver 120 (shown also in bit form in this embodiment) having a similar configuration as that of driver 20, but for a modified driver head 126 having the same upper and intermediate configuration as that of driver 20, but a modified bottom projection 167. In view of the modified bottom projection 167, there is featured a modified female reception head 132 (relative to this embodiment featuring coordinated driver and female reception head, although as noted embodiments of the invention feature one or the other of a driver and a female reception head only having features of torque enhancement under the present invention).

Figure 26:
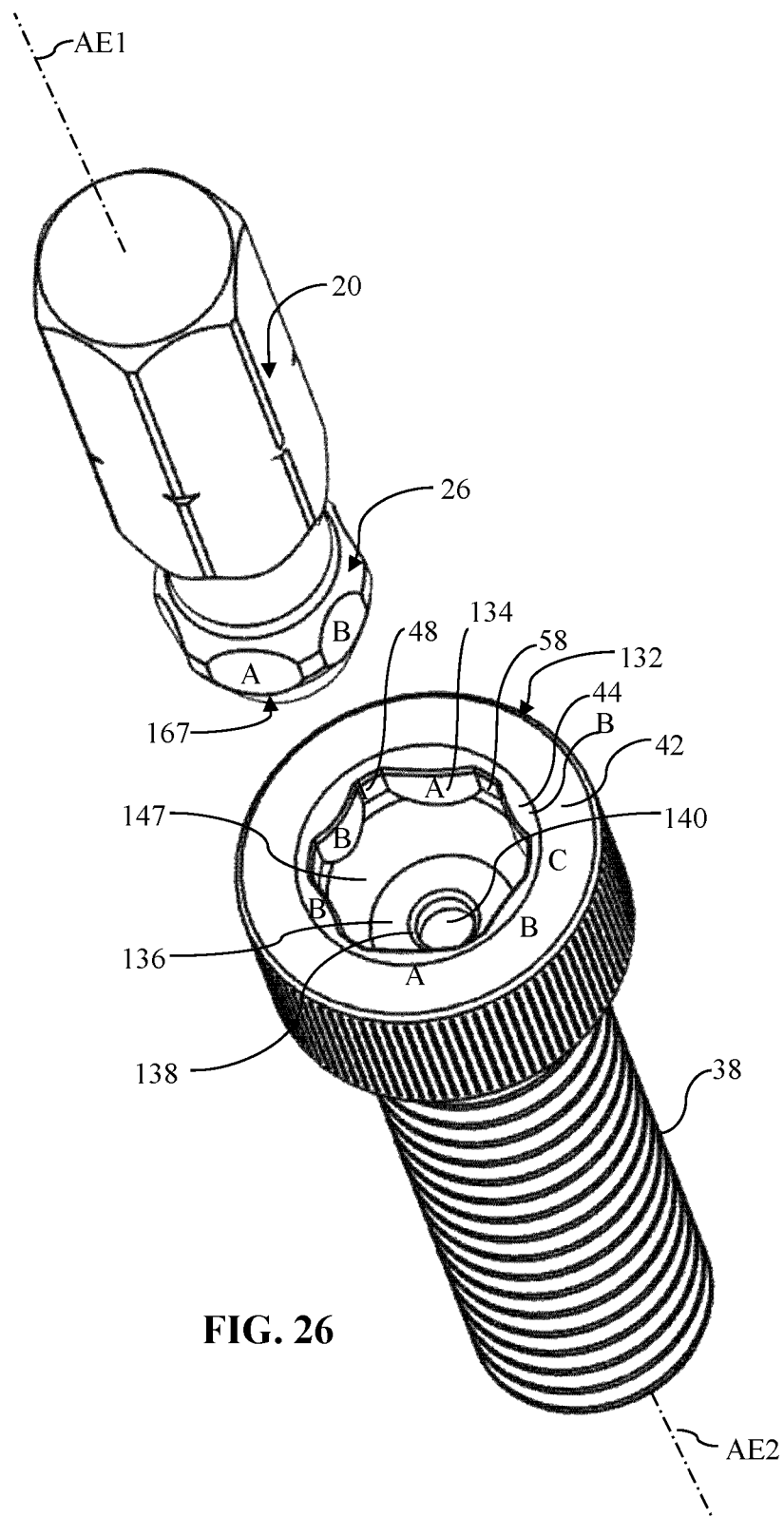
FIG. 26 shows the combination shown in FIG. 24 from still a different perspective.
Figure 30:
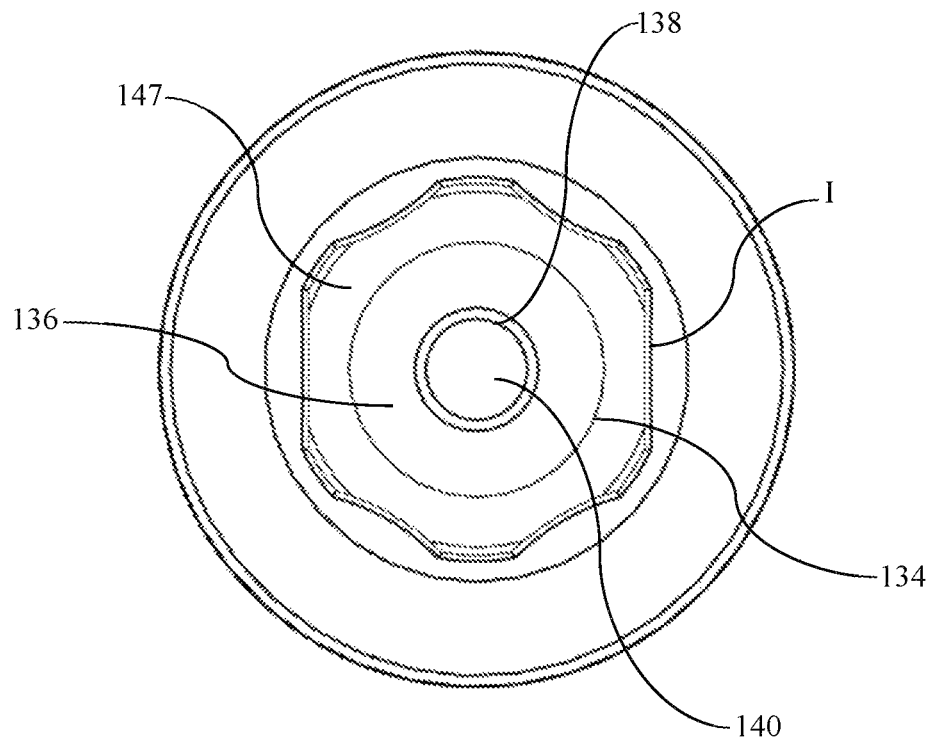
FIG. 30 shows the insertion or receiving end view of the female recipient head of the fastener in FIG. 24.

FIGS. 26, 29 and 30 provide a view of modified female reception head 132 with its corresponding modified centered female reception recess 134 configured to properly conform to the driver 126. Female reception recess 134 is shown as having an upper concave bowl wall surface 147 generally conforming to the upper region of the aforementioned concave bowl bottom 47 of the first embodiment. However, to accommodate the alternate driver head 126 (discussed further below) there is featured a flatter (flatter than the concave bowl bottom 47 as in horizontal, or perpendicular to axis AE1, as shown in FIG. 29) abutment surface 136 that forms an annular ring around a centralized tapered edge 138 that, in turn, forms an annular ring around a centralized cavity 140 extending deeper into the threaded fastener body 142 (FIG. 29) and thus has a central axis of elongation that extends along axis AE2 into fastener body 142 such that its lowest, base end is below the bottom of the fastener head 132. Tapered edge 138 provides an added self-centering featured relative to driver insertion into position within female reception recess 134. Centralized cavity 140, as shown in FIG. 29, features a reverse silo configuration featuring a cylindrical upper part 144 leading to a concave lowest positioned region 146. Thus, for this embodiment, there is a smooth surface interface between centralized cavity 140 and corresponding reverse silo-shaped extension 148 of driver 126.

Figure 32:
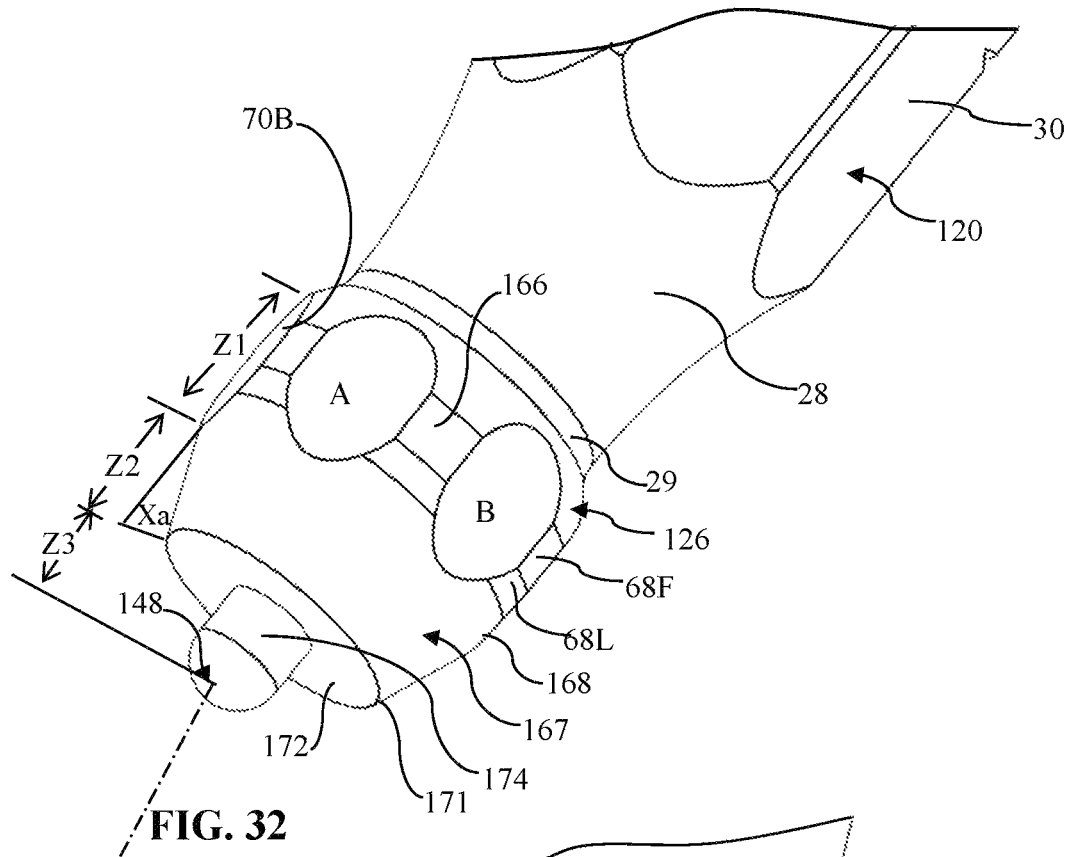
FIG. 32 shows, in cut-away perspective, a closer up view of the driver (male member) shown in FIG. 24.
Figure 33:
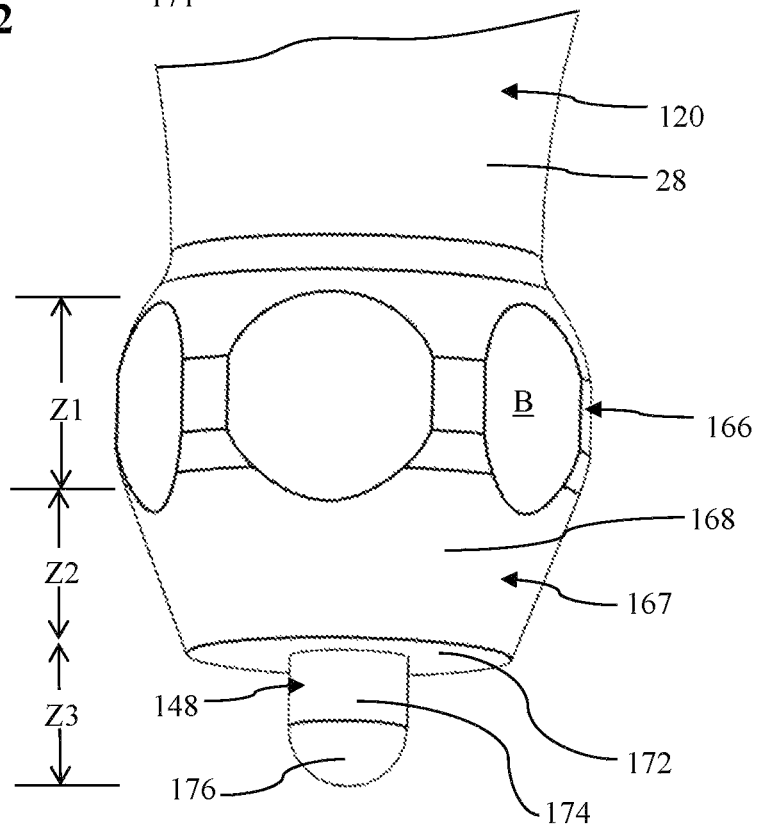
FIG. 33 shows a vertical orientation view of the driving end of the driver shown in FIG. 32.
Figure 36:
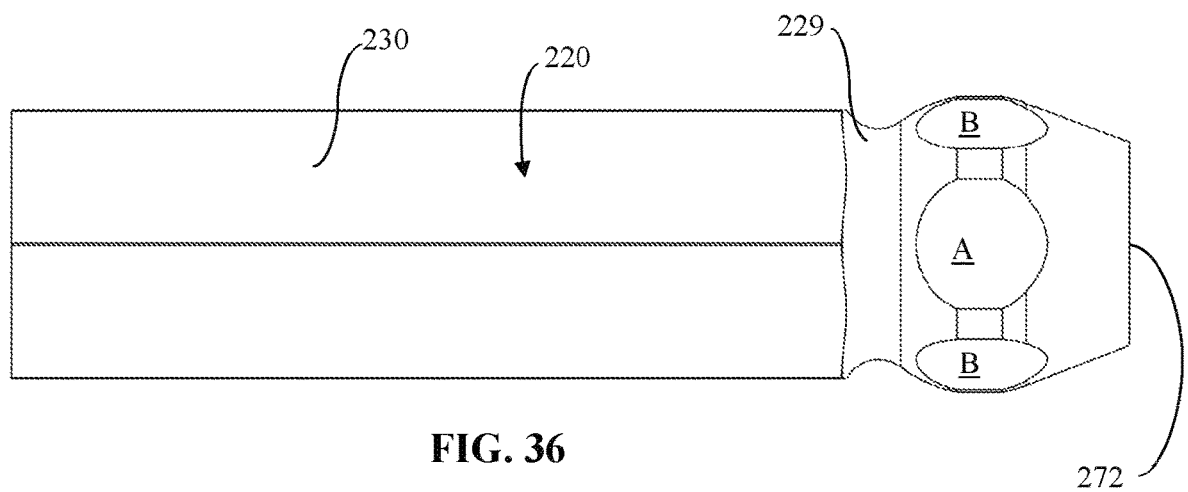
FIG. 36 shows another driver (male member) representing another embodiment driver which includes a flat, distal end.

With reference to FIGS. 32 and 33 there can be seen driver 120 having driver head 126 with bottom projection 167. Bottom projection 167 is shown as including a frusto-conical extension surface 168 that extends down from the distal ends of surfaces 68L ("A" meshing area) and con-cavities C1-C4 ("B" meshing area) and the lower edge of lower ring 68L. On the underside of driver head 126 (that is below ring 68L), frusto-conical extension surface 168 is designed for meshing/contact with female reception recess 134. As further shown in FIG. 32, frusto-conical extension surface 167 tapers inward in a distal direction as to form angle Xa relative to a vertical extension that is flush with flattened ring surface 68F and parallel to axis AE2). Angle Xa is of, for example, 15° to 30° and more preferably 20° to 23°. From the distal-most edge 171 of extension surface 167 there is provided annular shelf region 172 that extends radially inward from edge 171 as to preferably form a horizontal step-in surface that defines a plane extending perpendicular to axis AE1. Step-in shelf region 172 is designed to have a radial length suitably configured for sliding receipt on the flat, annular ring 136 in the female reception recess 134.

From a central region of annular shelf region 172 extends the reverse silo-shaped distal extension 148. Extension 148 is configured for (preferably flush) slide reception within centralized cavity 140 and thus features cylindrical extension 174 with lower semi-spherical extension 176 defining the distal-most end of extension 148 and configured (preferably) for slight frictional contact with the deepest part of centralized cavity 140 when annular shelf region 172 is in flush engagement with abutment surface 136 of female reception recess 134.

FIG. 33 further shows driver head 126 as having projection member 167 and distal extension 148 extending down from shelf region 172 and featuring cylindrical extension 174 with lower semi-spherical extension 176. Distal extension 148 is shown as extending for a longitudinal distance (i.e., an extension along axis AE1) that is shorter than the axial distance of extension for the portion of driver head extending between annular concave recess 29 and shelf-region 172, and in this embodiment is also shorter in longitudinal length than the longitudinal length extension of frusto-conical extension surface 167. Hence, the embodiment shown in FIG. 33 represent a "stubbier" (and not designed for rotation torque engagement) version of an extension extending distally away from shelf-region 172 of driver 126 as compared to some alternate embodiments such as those described below featuring a distal (e.g., distal-most) torque engaging projection.

Figure 31:
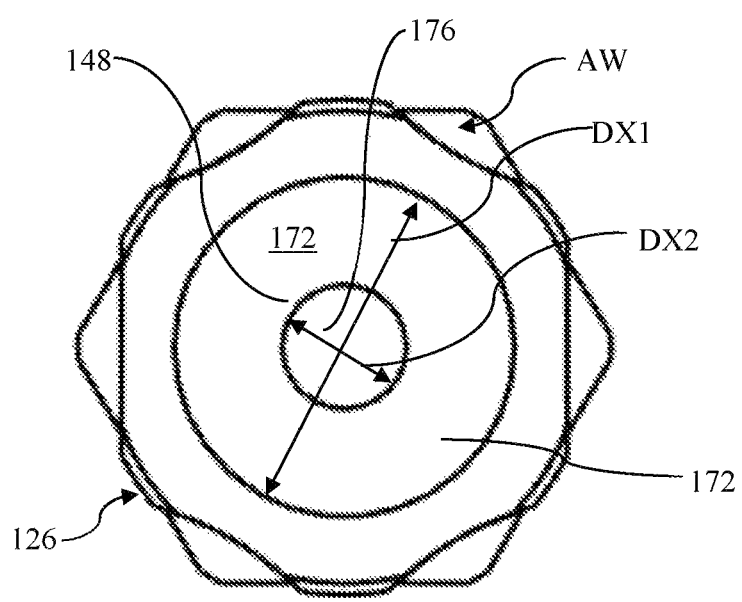
FIG. 31 shows the insertion end view of the male driver shown in FIG. 24.

FIG. 31 provides an end view of driver 126 and thus there can further be seen that in this embodiment extension 148 (with its smooth cylindrical outer surface) is designed for non-torque generation contact relative to its receiving cavity 140, although in conformance with its self-centering and retention of centering (AE1 and AE2 co-aligned) arrangement, is preferably generally in frictional contact or a small tolerance gap. This thus leaves a torque generation zone (or potential torque generation zone depending on how much of the driving ring of the driver extends out of the fastener head) like that illustrated in FIG. 29 which shows Z1 representing a degree of interfacing (torque meshing) of the geometrically contoured recess ring 46 and depression-projection ring set 166 of driver head 126. Also, shelf-region 172 is shown in FIG. 31 as having diameter DX1 while distal projection 148 is shown as having diameter DX2 with the relationship of DX1/DX2 being preferably in the range of 5/1 to 1.5/1 as in 2/1 to 4/1. Further, with a preferred slight contact or low percentage gap between distal projection 148 and distal recess 140 this embodiment involves more of a common axes AE1 and AE2 alignment, at least when distal projection is sufficiently received in distal recess 140. The rounded end 176 does, however, allow for tilted insertion and sliding into the final alignment position within distal recess 140.

FIGS. 28 and 29 show a meshed or torque-engagement setting as to provide engaged male-female combination 124 featuring a similar torque engagement relationship as described for male-female combination 24 shown in FIGS. 19 to 21. There is provided the difference of a more elongated (along the common axial axes AE1 and AE2) telescoping relationship between the driver and fastener in the combination 124 as compared to the combination 24 made possible by the additional percentage of depth from rim 42 down to the bottom most surface of the receiving recess of the fastener. This meshing relationship also features the designed to be lesser torque generating engagement arrangement defined as zone Z2 (FIG. 29) extending between the portion of the driver head 126 below the lower end of concave meshing regions B of driver ring 166, along the region of tapered wall 167 down to annular shelf region 172. For example, with the smooth wall contour, the nature of torque engagement is unlike the contacting wall surface torque generation of driver ring 166 and associated torque enhancement reception recess contact region, although the flush surface engagement between the bowl shaped surfaces (particularly when there is the typical compression arrangement along the common axes of extension via the driver and fastener relationship which compression level can be altered with relative differences in taper wall contact) could impart some degree or torque generation potential. FIG. 29 further shows third zone Z3 represented by the extension length of reverse silo-shaped extension 148 of driver 126, which in view of the preferred axially extending smooth cylindrical wall surfaces in slight or gap spacing is generally deemed not a torque generation region or a less of one than the other zones Z2 and Z1.

FIGS. 32 and 33 further shows zones Z2 and Z3 as to the driver 126 (with Zone Z1 being shown but can be varied based on the desired axial length of mesh engagement and thus the degree of exposure of driver concavities in ring 166 above upper surface 42 of the fastener (preferably less than 25% as in 0% to 15% (with 0% being where there is not any exposure, as full and beyond depth insertion is possible as well—noting that the depth of featured insertion can play a role in insertion flexibility and time from mesh-to-mesh movement if different fastener heads are to be driven (tightened or removed depending on rotation direction)).

FIGS. 34 and 35 are similar views as that in FIGS. 22 and 23 but showing an added hexagonal nut 72 received on fastener shaft 138' which is shorter than fastener shaft 138 featured in FIG. 27 and thus illustrative of a variety of different fastener types for which the present invention is applicable including different length fasteners of a common head diameter as well as different head diameters inclusive of sizing up and sizing down. Reference is also made to the different size discussion for the description describing the embodiment shown in FIGS. 22 and 23 (which discussion as to sizing is additional applicable here).

FIGS. 36 to 41 illustrate an additional driver embodiment of the present invention, with the illustrated driver 220 in FIGS. 36 to 41 sharing many of the same features as driver 120, but for some visible differences, inclusive of an extended main shank 230 in driver 220 resulting in a limited length neck region 229 (as compared to tapered region 28 in the prior embodiment). The extended shank (or shorter neck region), puts the hex (in this embodiment) distal end of shank 230 closer to the projection ring 266 with meshing surfaces of meshing regions A, B and C. An addition difference lies in shoulder-region 272 extending entirely across the undersurface of driver 220 and sharing a fully exposed surface region of a diameter either conforming to that of the lower edge of tapered (frusto-conical) surface 167 shown as having the earlier referenced taper angle Xa of, for example, 15° to 30°, or can be made as to catch within the depth of the recess as to leave a gap therebelow when fully inserted.

Driver 220, with its extended shank 230, provides, in coordinated driver/reception recess embodiments, the potential for a pair of axially separated (two-tier) torque generation locations. That is, with an appropriate configured recessed recipient, as in the FIG. 38 illustrated recessed recipient 222, there can be achieved a two-tier torque generation relationship (with proximal and distal respective locations of the two tiers axially separated by way of neck 229 as not to share a proximal/distal common boundary—although embodiments of the invention include a two tier "axially separated" relationship that involves two different radial area torque engagement surface tiers sharing a proximal/distal boundary, in the sense that the torque engagement surfaces are axially separated despite the common proximal/distal boundary therebetween).

Figure 38:
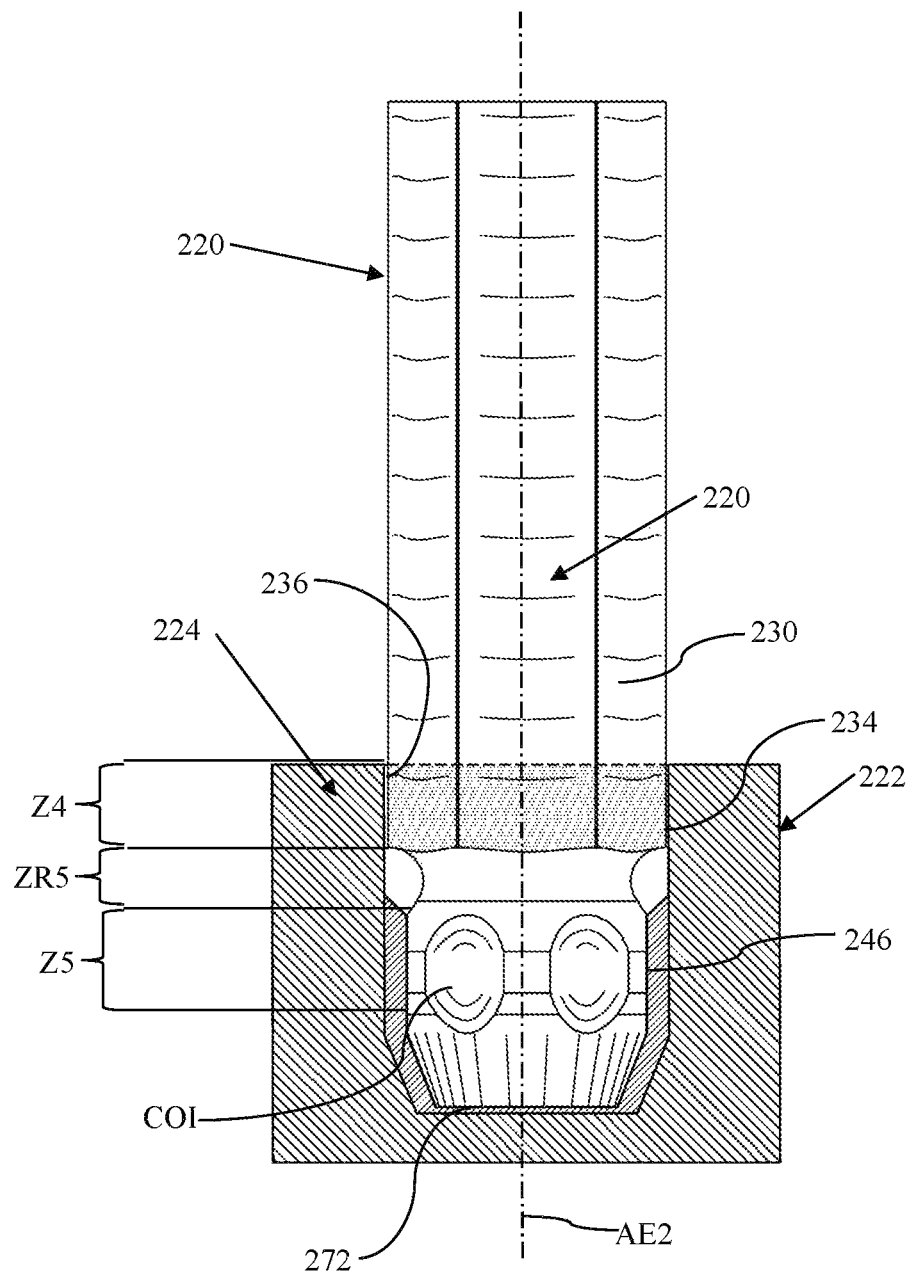
FIG. 38 shows an engagement mode of the driver in FIG. 37 within a female reception cavity as well as a second axial tier shank body reception in the coordinated female reception cavity.
Figure 39:
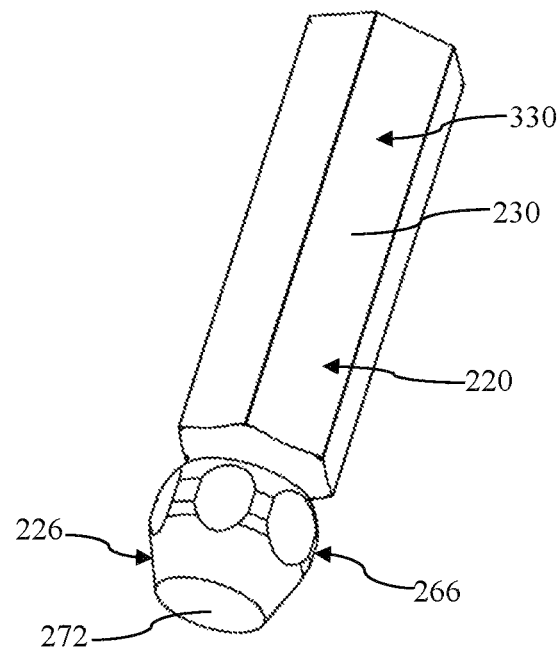
FIG. 39 shows a perspective view of the driver shown in FIG. 38.
Figure 40:
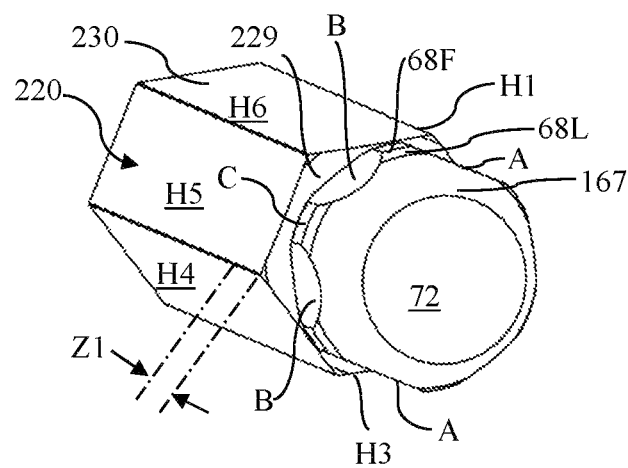
FIG. 40 shows that which is shown in FIG. 39, but from a different orientation and with a torque generation zone demarcated.

FIG. 38 illustrated the two tier torque generation locations featuring a deeper or distal mesh relationship at zone Z5 (relative to the torque enhancement bulbous driver head 266 and associated torque enhancement configured recess 246 which has at least the longer length projections in driving contact, with spacing potential relative to the less radially extending projection of the ring and/or less than full convex insertion into the driver concavities C1 to C4 for fluid reception. FIG. 38 also shows the cross-sectioned less extending projections which results in the illustrated gap within which fluid such as described above can be inserted and retained if desired. An addition example of gap providing can be seen in the below described FIG. 55 with reception recess contouring designed to form an intermediate area in the axial direction where there is not direct driver to reception recess contact.

Alternatively, the reception recess can be made to have a more peripherally conforming drive contact configuration for both sets of contact surface wall pairs and all four associated concavities as to have limited gap spacing about its full periphery. FIG. 38 further shows a more proximal mesh relationship represented by contact surface zone Z4 with meshing shank surface and upper region of recess 234. Thus, in FIG. 38, there is shown for the engaged male-female combination 224, two torque generation zones Z4 and Z5 separated by non-drive contact zone ZR5 corresponding with neck 229 axial spacing. In the illustrated embodiment main shank 230 is shown with a hexagonal outer configuration 233 which is also seen in the end view of driver 220 shown in FIG. 41 (with the hexagonal surface walls H1 to H6 also labeled for reference). Driver 220 has driver head 226 with the same bulbous driver head configuration as driver head 126 shown in FIG. 33, but for the removed reversed-silo extension 148 (although embodiments are also inclusive of the same driver head 126 provided on the modified extended shank main body as in this FIG. 38 embodiment). Further, reception recess 222 is shown as have a body surrounding the recess which can take on a variety for forms as in the aforementioned head or body of a fastener (e.g., threads on the exterior of the body shown in FIG. 38 and free of a threaded shaft) or any of a variety of torque reception means as in a pulley, gear, turbine blade shaft hub, etc.

Zone Z4 is represented by a degree of extension of main shank 230 into female reception recess 234, which in this embodiment is a hexagonally configured (at least in the upper portion of the recess shown as in at least zone Z4) to match the interior hex-configured surface 236. The relative spacing of the hexagonal surface 233 of driver 220 and the receiving surface of recessed reception recess 234 within zone Z4 is similar to that described above as in a sliding friction fit or a small gap tolerance that is suitable for torque generation without edge degradation upon rotation. Thus the meshing contact in zone Z4 is an example of a non-torque enhanced meshing contact surface relationship, while the more distal (separated by the illustrated axially extending neck region ZR5 zone) features a torque enhanced meshing contact between the ring 266 and corresponding configured receiving recesses with matching A, B, C regions within the torque enhancement recess region within zone Z5.

Thus, zone Z5 represents a second, more distal (e.g., lower most) tier torque engagement zone featuring a similar torque enhancement depression-projection ring set (driver head 226) engagement with mesh engagement between depression-projection ring set 266 of driver 226 and similarly torque enhancement contoured ring 246 of recessed reception recess 234 (for at least zone Z5 or at least the portion not represented by conventional zone Z4 (with the same relative geometries as that earlier described for ring set 166 and geometrically contoured ring 146 shown in FIG. 35, for example).

Figure 41:
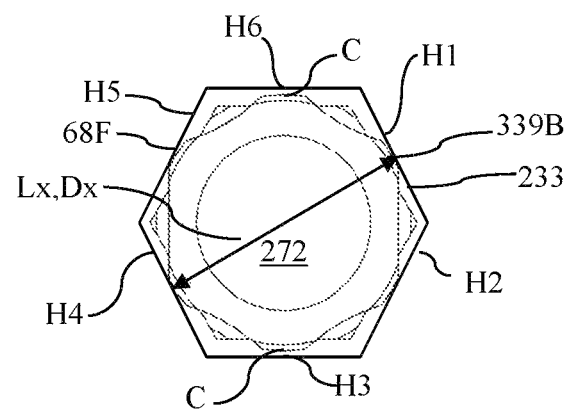
FIG. 41 shows a distal end view of the driver of FIG. 40.
Figure 42:
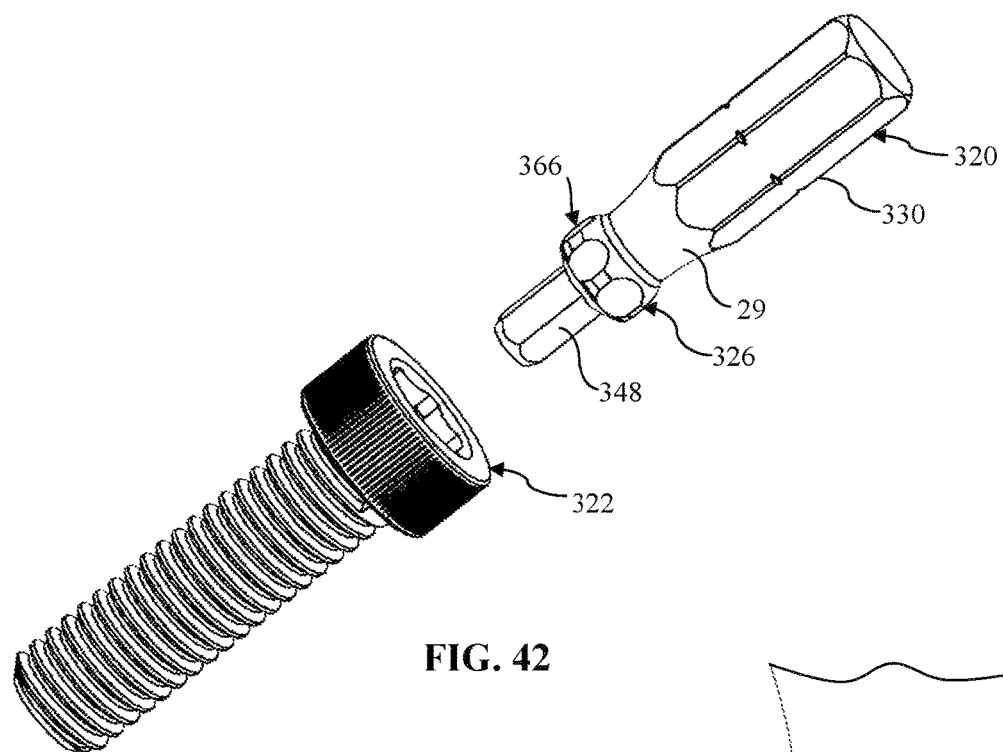
FIG. 42 shows a pre-insertion or initial withdrawal view similar to FIG. 11, but for another inventive male/female combination, and which is shown as having a two-tier (axial) driver configuration (with the fastener recess having a conforming geometry as that of the driver in this embodiment).

FIG. 41 further illustrates an additional benefit of the torque enhancement configuration (such as that of torque enhancer 500L); wherein in this embodiment the torque enhancement configuration is represented by the second, more distal tier mesh engagement between depression-projection ring set 266 of driver 226 and geometrically contoured ring 246 of recessed reception recess 234, and the more proximal torque contact surface is a conventional one (hexagonal in this instance) as to provide greater flexibility.

Moreover, the arrangement represented in FIG. 41 also provides for the benefit of enabling only a partially inserted driver 220 within recess 234 to be still functional. That is, in FIG. 41, the exterior surface 233 of shank 230 has a mid-point to mid-point on opposing hexagonal side walls distance Lx (shown between walls H1 and H4) that corresponds to the separation distance Dx from end point to end point of projection walls 339A and 339B in mesh zone C of driver head 226. In other words, the maximum spacing of the torque enhancement components represented by side walls 339A and 339B (C mesh locations) as well as the exterior walls 68F of the A mesh zone) of the driver head can fit within the same recess that receives the hexagonal configured shank extension shown engaged in zone Z4, and there is further assured that the edging at the end of side walls 339A and 339B are configured for contact with any portion of the recess 234 including the upper region with conventional hex-shaped recess configuration. For example, an arrangement can be that the bulbous head is only partially inserted for an initial tightening of a fastener wherein the torque levels need not be as high as a final tightening level. After the initial tightening involving the torque enhancement configured bulbous head portion of the driver can be later fully inserted as for a final clamp down wherein the lower head is in engagement with a common torque enhanced configured reception portion of the recess in zone Z5 and the upper zone with hex-shaped shank reception region Z4 is also in engagement as to provide for a strong torque generation configuration well suited for higher torque levels associated with a final clamping of a fastener as opposed to an initial insertion mode (the same being true in reverse in that the strongest torque generation mode with both zones in torque generation operation being used to initially loosen a fastener followed up after (including a return well after a series of initial loosening of a plurality of fasteners) to fully remove the earlier loosened fasteners).

Alternatively, the driver 220 can be as described above, but the reception recess can be made conventional for its full length (as in, from a proximal end to a distal end, an axially continuous hexagonal configuration as the reception recess). Thus, with the driver still having the torque enhancement driver configuration as described above at its distal end (with the retained conventional more proximal hex engagement surface), and the reception recess being free of a torque enhancement configuration (as in a full depth hexagonal configuration) there is still the option of a partial depth insertion with just the bulbous head to drive the recess recipient, or a situation where the bulbous head is placed sufficiently deep until the hex contact region Z4 of the driver is received by the upper region of the hex shaped recess (i.e., Z4 and Z5 regions both involved). In this way (with reference to the Dx and Lx above) there can still be achieved an engaging relationship between a conventional recessed surface and the bulbous torque enhanced ring configuration, where the full axial length of the reception recess 234 in FIG. 38 is hexagonal and of a dimension to properly engage hexagonal walls H1 to H6 of the shank 230, since projection walls 339A and 339B, when rotated around, engage an adjacent wall edge as to catch in a torque enhancement contact relationship. This further illustrates the flexibility of driver 220 in that it is operational on a variety of reception recesses as to make it advantageously more universal in usage.

As an additional alternative, rather than the shank region (shown in FIG. 40 as zone Z1) having a conventional design, it too can have a torque enhancement configuration of either the same radial area configuration (in which case recess 234 can be formed of a common torque enhancement configuration and area over its full length or can also be conventional and receiving the two axially separated torque enhancement zones) or one where the shank at zone Z1 has a larger radial area, and the reception recess has an enlarged proximal recess portion receiving the torque enhancement configured larger area shank in zone Z4, and a smaller area distal reception recess portion in zone Z5 for torque enhancement meshing with the bulbous, torque enhancement configured portion 226 of driver 220.

Under the above described example of both of zones Z4 and Z5 being torque enhancement meshing zones, and preferably the recess having conforming torque enhancement reception recessing) there can be seen that FIG. 38 can also be considered representative of a full depth engagement of the two torque enhanced contact zones Z4 and Z5. Under this scenario there is provided the potential of particularly high torque force engagement, as there is both the enhanced torque generation of the more distal zone, and the enhanced torque generation of the more proximal zone. This combined torque enhancement drive relationship at both the proximal and distal zones is particularly adept at removing fasteners and the like that have become frozen together or otherwise deteriorated and hence made difficult to remove if not impossible with only a hexagonal type engagement, this being especially true if both zones Z4 and Z5 are utilized.

If instead there is desired less than the full enhanced torque generation at both zones, there can be utilized less than a full insertion of driver 220 into reception recess 234 as to avoid the mesh engagement of zone Z4; and, as represented by an alternately positioned bulbous region of the driver (raised up or not as deep a zone contact) in FIG. 38, there can be provided only the more distal bulbous head drive meshing relationship (that is a Z5 type engagement but shifted axially up). This one meshing zone engagement arrangement presents less of a potential torque generation setting than the dual zone (Z4 and Z5) meshing shown in FIG. 38, but one that can be more easily reached due to the insertion location (less of an insertion relative to the relationship shown in the hard line FIG. 38 relationship, which is the deepest possible insertion and has potentially both torque generation zones in simultaneous use). As an example, during a programmed driver operation by a robotic arm or the like, there can be utilized only the more distal bulbous driver portion meshing at a partial insertion location (Z5 zone shifted up from that which is shown in FIG. 38 and Z4 non-applicable as it is lifted out of the recess 234) as for programmed situations featuring initial fastener insertion prior to full torque down; or for programmed situations involving both zone application for initial release of a fastener during extraction, followed by the bulbous portion only driving for final loosening or removal of the fastener (with the two zone meshing being suited for the more difficult fastener initial loosening to enable extraction). Thus, the two tier meshing like that showing in FIG. 38 can be utilized for the above noted full torque down by the robotic arm or other driver attachment following initial partial torque down installation either with the robot arm in a common station position or a return from a different station application (and again, a reverse two stage operation, as by the robotic arm involved in a disassembly operation, can feature a first full (both zones Z4 and Z5 in operation) to initially loosen a fastener, followed by a later only zone Z5 type engagement for the easier subsequent unthreading and again with the robot arm either retaining a common station setting or shifting stations).

Also, in view of the higher depth associated between the telescoping engagement of driver 226 and recessed recipient 222, the flat surface represented by 272 and corresponding base of recess 234 is suitable in most environments and thus the feature of the reverse-silo configured extension 148 can be avoided for some environments of usage.

FIGS. 42 to 47A illustrate an additional embodiment of the present invention, both with respect to driver 320 and recessed recipient 322; which, when engaged together, there is provided engaged male-female combination 324 (FIGS. 45 and 46). FIGS. 42 to 47A illustrate driver 320 as being similar to driver 120 in FIGS. 24 to 31, but for some illustrated differences inclusive of those described below. That is, rather than the non-torque engagement distal projection 148 of driver 120, driver 320 includes a distal (second-tier or two-level) torque engagement distal projection 348 in its driver head 326. Distal projection 348 also extends out from an underlying convex surface 367 extending below the depression-projection ring set 366 (convex surface 367 being different than the planar, horizontal shelf-region 172 of driver 120, although distal projection 348 can also extend out from a flat facing).

Figure 43:
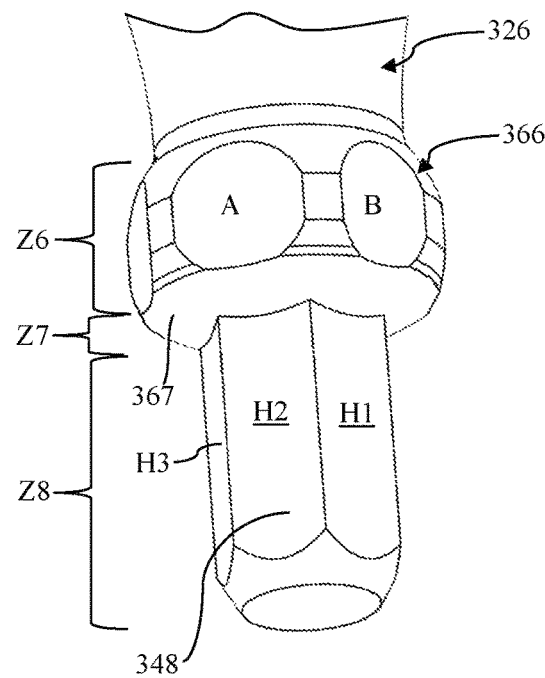
FIG. 43 shows the insertion end view of the male driver shown in FIG. 42 with an extended engagement projection.
Figure 49:
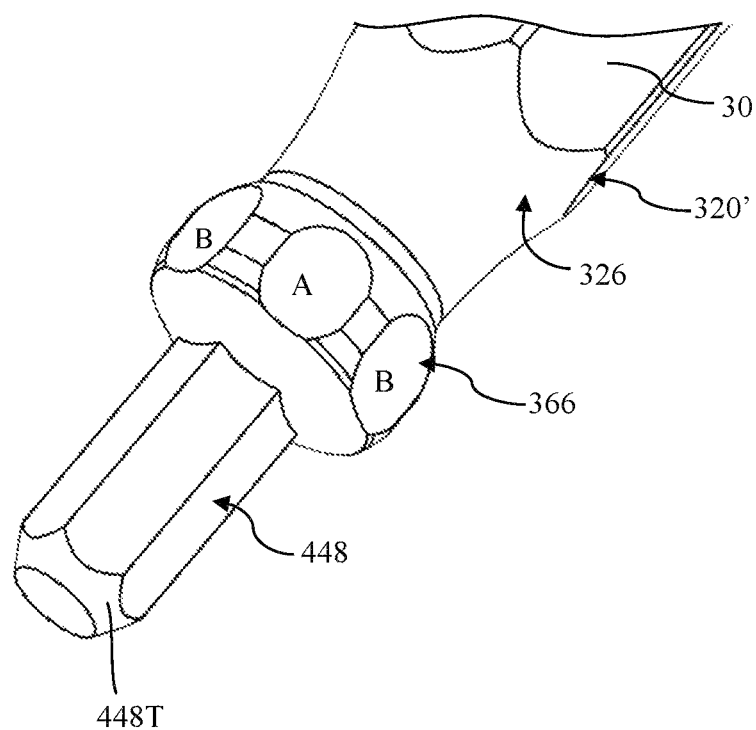
FIG. 49 shows the (elongated) extended projection driver of FIG. 48 from a different perspective view.

As seen in FIG. 43, the exterior peripheral configuration 366 of driver head 326 corresponds with the aforementioned depression-projection ring set 166 for driver 120. The noted distal projection 348 is shown in this embodiment as having a hexagonal conventional configuration (a non-torque enhancement configuration), although other conventional configurations as well as torque enhancement configurations under the present invention are featured (e.g., distal projection 348 having a smaller sized peripheral geometry, but one that generally conforms in configuration to that of the torque enhancement depression-projection ring set 366).

Driver 320 is further shown to have zones Z6, Z7 and Z8, with zone Z6 representing the torque enhancement section provided by depression-projection ring set 366, zone Z7 representing an axially extending transition section provided by tapered, conical surface 367, and zone Z8 representing the torque generation surface provided by distal projection 348.

Using a conventional configuration for distal projection 348, as in the illustrated hex-configuration with six walls (e.g. H1, H2, H3 . . . ), provides for enhanced versatility. That is, in addition to driver 320 being able to work with coordinated torque enhancement female reception heads (featuring a common mesh geometry between a contoured ring (such as contoured ring 46 (FIG. 25) in meshed male/female engagement 124)), the same driver 320 via its distal projection can be used with non-torque enhanced coordinated meshing arrangements. For example, with limited insertion, projection 348 can be received within a hex-configured recess in a fastener having only that type of reception recess. When driver 320 is used with a coordinated mesh arrangement at both axially separated tier levels, there is provided the additional advantage of presenting a strong torque generation suited for problem extraction or when one tier is degraded but the other tier is still functional. Also, with a suitable environment, featuring a sufficiently long enough projection 348 relative to the reception recess such that the end of the projection 348 can be received by a corresponding configured distal recess in the fastener, while the torque enhancement depression-projection ring set 366 is sufficiently external to the reception recess of the reception body as not to be in torque engagement, there is the potential for use of just the distal end of projection 348 for torque application (as during an initial fastener tightening or a post initial release fastener further loosening) and using both tiers upon deeper insertion of the driver 326 into that fastener head (as when subjecting the fastener to a final tightening stage as after an initial strain release following initial clamp down or in the breaking of bonds in an initial removal stage of the fastener, which removal can be more difficult for reasons set out earlier).

Figure 52:
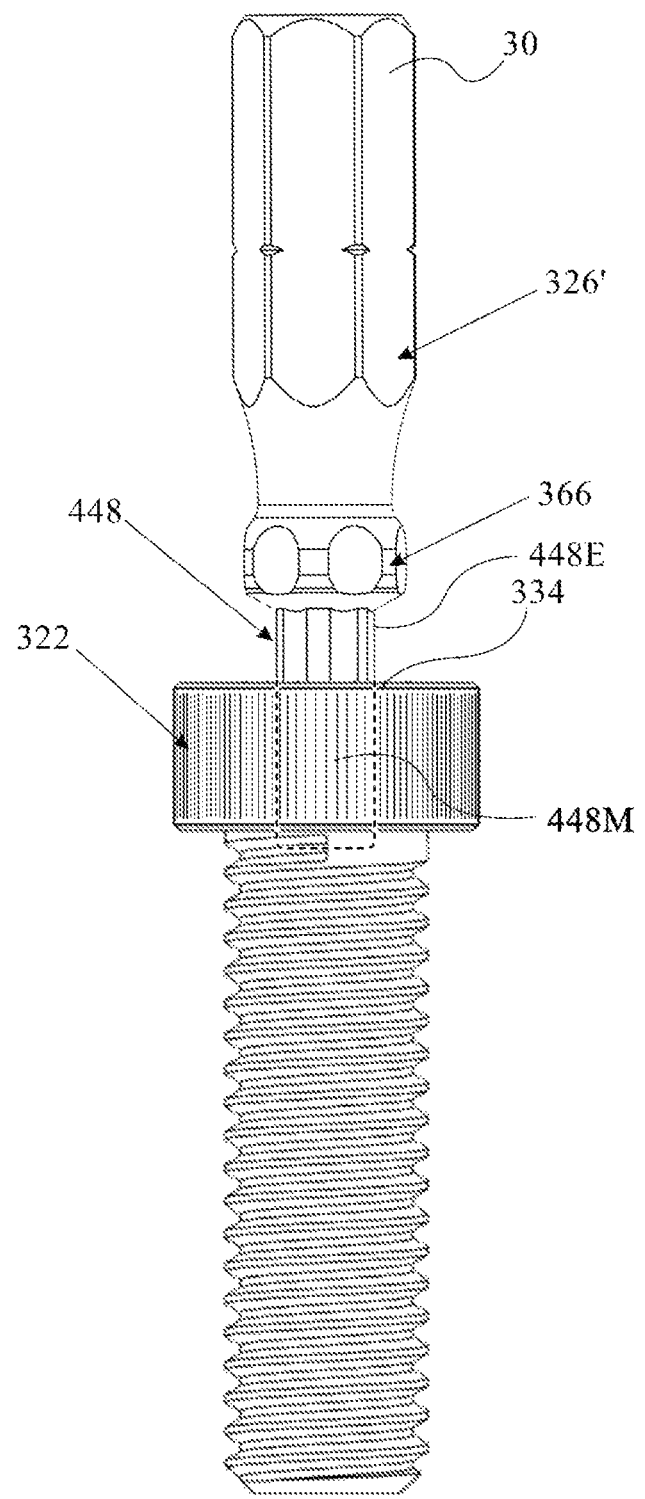
FIG. 52 shows the same combination as shown in FIG. 51 (with ghost lines to illustrate the interior depth of driver penetration), and with the driver received in non-full-depth fashion within the radially smaller female reception cavity of the fastener, as to present an additional combination embodiment of the present invention featuring receipt of the distal lower tier (lower torque generation portion of the two tier driver) in engagement with a corresponding geometry recess provided in the fastener, and with the larger torque, more distal bulbous portion of the driver not engaged or engageable.

FIG. 44 shows driver 320 aligned for insertion into fastener 322. FIGS. 45 and 46 show driver 320 and fastener 322 being in meshed engagement 324 (in this case a full meshed engagement, wherein both torque tiers are engaged as the driver 320 is maximally inserted into the reception recessing of fastener 322). The FIGS. 45 and 46 illustrated meshed engagement 324 follows insertion of driver head 326 fully into female reception recess 334 which involves insertion of distal projection 348 into the conforming, deepest portion 340 of female reception recess 334 until contoured ring 346 of recessed recipient 322 fully meshes with depression-projection ring set 366 of driver 326. In other words, FIGS. 45 and 46 show a fully inserted driver 320 relative to recessed recipient 322 (e.g., a fastener as shown), which full mesh arrangement presents a two-tier torque engagement setting that provides for maximum torque application and also can provide back up as when one or the other tiers becomes inoperative (e.g., stripping of one and not the other). Again, upon partial withdrawal and with a suitably configured head body 336 and sufficiently elongated driver projection 348, there can be a partial retraction of driver 320 out of recess 334 until the upper, depression-projection ring set 366 disengages from a meshed torque arrangement with the fastener, but a distal region of projection 348 remains in torque engagement with an upper region of the deepest portion 340 of female reception recess 334 (or the reverse sequence of initial insertion of the distal projection 348 until only it is received in the reception recess). Again, the use of just one tier during one stage can be helpful as where the first stage is an initial tightening but not full tightening and the full torque availability of both meshing torques is not yet required (and this first stage only requires a quicker, partial insertion within the reception recess—and with a similar potential in the two stages of fastener removal discussed above). An illustrated example of use of only one of two torque engagement tiers based on a partial insertion of a two tier driver within accommodating recessing of a fastener is seen in FIG. 52 and discussed below for a similar, but somewhat longer distal projection 448 in driver head 326'.

Relative to potential variations in the longitudinal length and/or relative thickness of distal projection from what is preferably a more radially outward extending and more proximal driver ring 366, reference is made to the figure sets of FIGS. 47A and 47B. That is, a comparison of FIGS. 47A and 47B reveals that FIG. 47A shows a relatively axially shorter extended distal driver projection (distal driver end 348 of axial distal length PL1) embodiment; while FIG. 47B shows an axially more elongated version of the driver (a more elongated distal driver end 448 of axial distance PL2). Thus, PL2 is greater than PL1 when comparing FIGS. 47A and 47B. This additional extension preferably includes all or a portion of the illustrated torque engagement surface or can be attributed to all or a portion of added extension relative to the tapered region at the distal most end of the distal driver ends (as in 348T being shorter than 448T to make up some or all of the difference in relative length difference).

Additionally, seen in a comparison of these two figures, is that distal end 348 has a thicker configuration (maximum cross-sectional length) compared to distal end 448 of FIG. 47B; or TW1 is greater than TW2. As further seen from a comparison of these two figures, all components but for the different configured distal ends 338 (348T) and 448 (448T) can be of a common configuration.

Therefore, the variations in distal end size (length and/or width) can be representative of a set (e.g., in similar fashion as a varied size socket set) that can have common sized torque enhancing rings or depression-projection ring sets 366 while having different projection 348 configurations and/or a set of varying size driver rings with common or different sized projections (e.g., with larger in size rings such as 366 there can be larger lengths and/or thickness projections 348 associated in the set).

The differential between length and thickness can also be varied to alter the surface area contact ratio and hence torque generation levels (e.g., the two different distal projections 348 and 448 can be made to have equal overall surface areas due to the increase in length in one and the increase in transverse thickness for the shorter axial length one; or they can be rendered different in contact surface area to suit a desired environment).

While the relative distal projection length and width differential in the two embodiment sets shown in FIGS. 47A and 47B, there can also be seen the potential for using the same main shank and first tier mesh arrangement (closest to shank) configuration with different distal projection configurations.

Thus, in such potential modifications, there can be provided drivers having lengths PL1 and thickness TW2 or length PL2 and thickness TW1 as but a few potential combinations which are representative of some of the different kit potentials for providing different tooling size sets.

Figure 50:
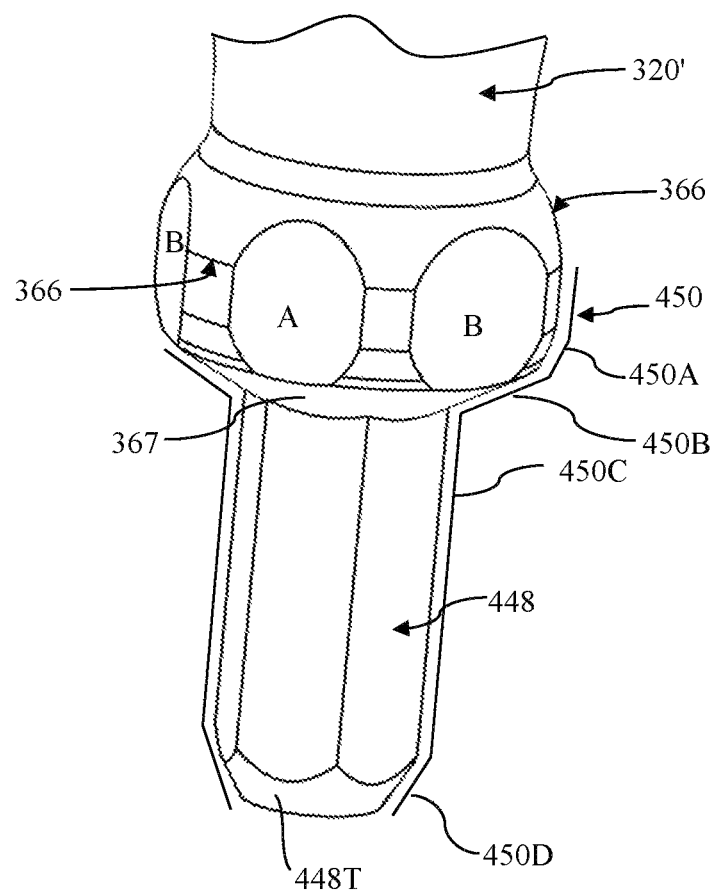
FIG. 50 shows the (elongated) extended projection driver of FIG. 48 from still a different perspective view.

Thus, with reference to FIGS. 48 to 52, there can be seen driver 320' shown in FIG. 47B as being a relatively thinner, longer axial length driver that is well suited for one or two mesh arrangements when in usage with a conforming recess recipient 322. For example, FIG. 50 shows added reference contour lining 450 wherein there is seen the generally axially extending convex configuration 450A associated with depression-projection ring set 366 of driver 320', followed by contour portion 450B for frusto-conical interface 367, with the latter being adjustable in axial length as well to provide for different embodiments and different degrees of axial extensions between the distal, free end of the projection and the other tier represented by toque enhancement depression-projection ring set 366 (occupying contour lining section 450A). Contour lining 450B is shown extending to the level of the supported base of distal projection 448. Distal projection 448 is also shown as being represented by linear contour section 450C leading to the proximal end of distal most end 448T with the latter having an inward tapering, frusto-conical segment occupying contour lining section 450D (which taper facilitates insertion and removal functioning).

Figure 51:
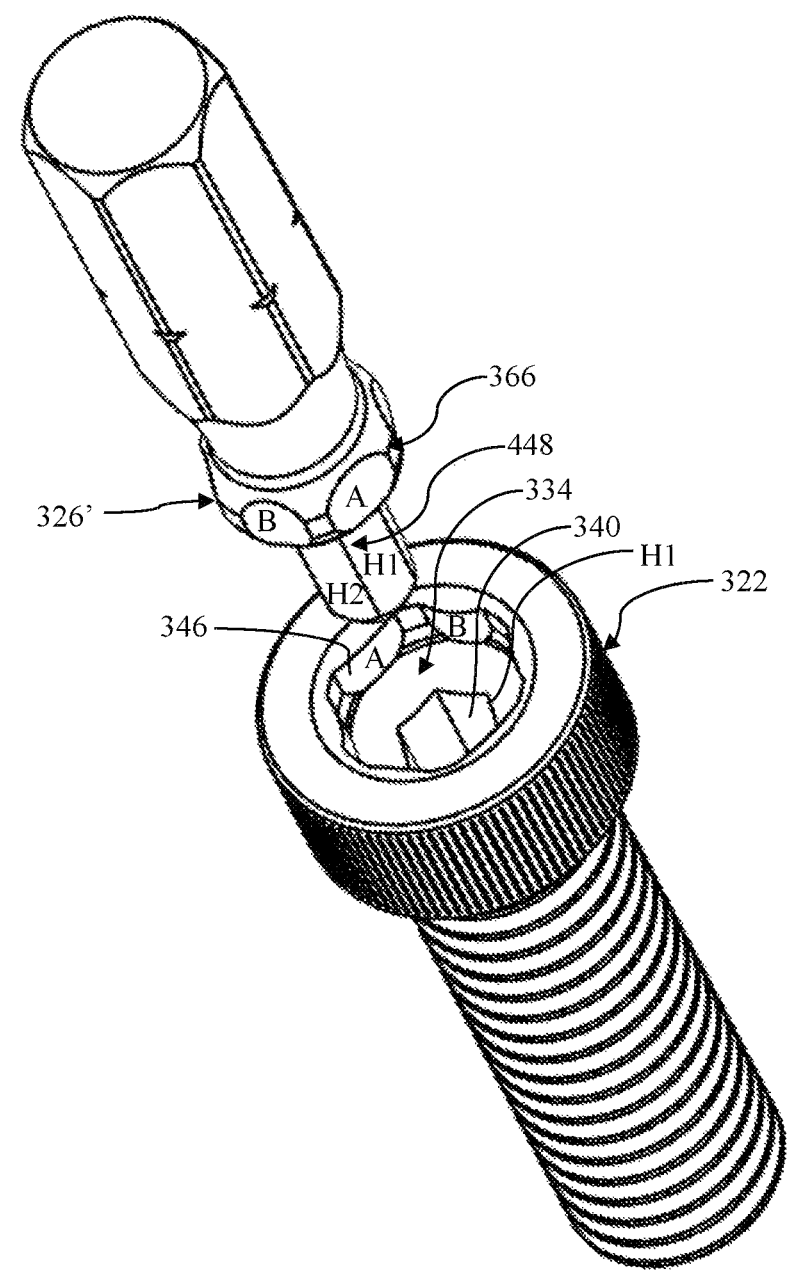
FIG. 51 shows a combination similar to that shown in FIG. 42 prior to engagement of the male member with the female member (or just after disengagement as is true of other similarly situated driver/recess combinations) but with the more elongated distal projection shown in FIG. 50.

FIG. 51 shows the (elongated) extended projection driver 326' of FIG. 48 just before receipt within (corresponding geometry) fastener's female reception cavity 334 having distal recess 340 specifically designed for torque meshing engagement with distal projection 448 once either partially inserted (as in depression-projection ring set 366 not yet engaged and distal projection only partially inserted (see the FIG. 52 discussed below) or fully inserted such that both axially separated tiers are in meshing engagement. There can also be seen how the A concavities of depression-projection ring set 366 are designed for engagement with the corresponding A convex projections of contoured ring 346 of recessed recipient 322.

FIG. 52 illustrates an example of the above discussed intermediate mesh arrangement optional setting, wherein only one of the two torque engagement tiers is in mesh engagement (in this case the non-torque enhancement driver portion 448 is engaged and the more proximal torque enhancement driver portion not). As shown in FIG. 52 depression-projection ring set 366 is not in meshed engagement and is thus exposed without recessed recipient 322 contact. Distal projection 448, on the other hand, is in mesh engagement with an intermediate recess portion 340 of female reception recess 334. Recessed portion can have a geometry such as the torque enhancement geometries described herein (e.g., one of the same contours as that represented by the torque enhancement geometry of depression-projection ring set 366). However, in many contemplated usages, having a different configuration for one of the other tiers in beneficial, as in having a conventional geometry for the distal most of the two tiers when the two tiers are axially separated tiers. For example, FIG. 52 shows a conventional geometry example with its hexagonal geometry with wall surfaces H1 to H6 shown earlier. As such, there is provided a one of two tier engagement well-suited, for instance, for initial fastener tightening during an assembly line application or a multi-assembly fastening for a product having multiple common fasteners requiring assembly. Further, there is shown in FIG. 52 that distal projection 448 has sufficient length as to enable different mesh engagement percentages along its length which accommodates the notion that the deeper the mesh the more surface contact torque generation potential, while the deeper the insertion the more time consuming in an assembly line scenario in going from one fastener to the next. Relative to promoting insertion and removal there is further shown in FIG. 49 conical distal most free end taper configuration 448T in distal projection 448 (similar to distal free end taper 348T for distal projection 348).

Figures 53, 54, 55, 56, 57:
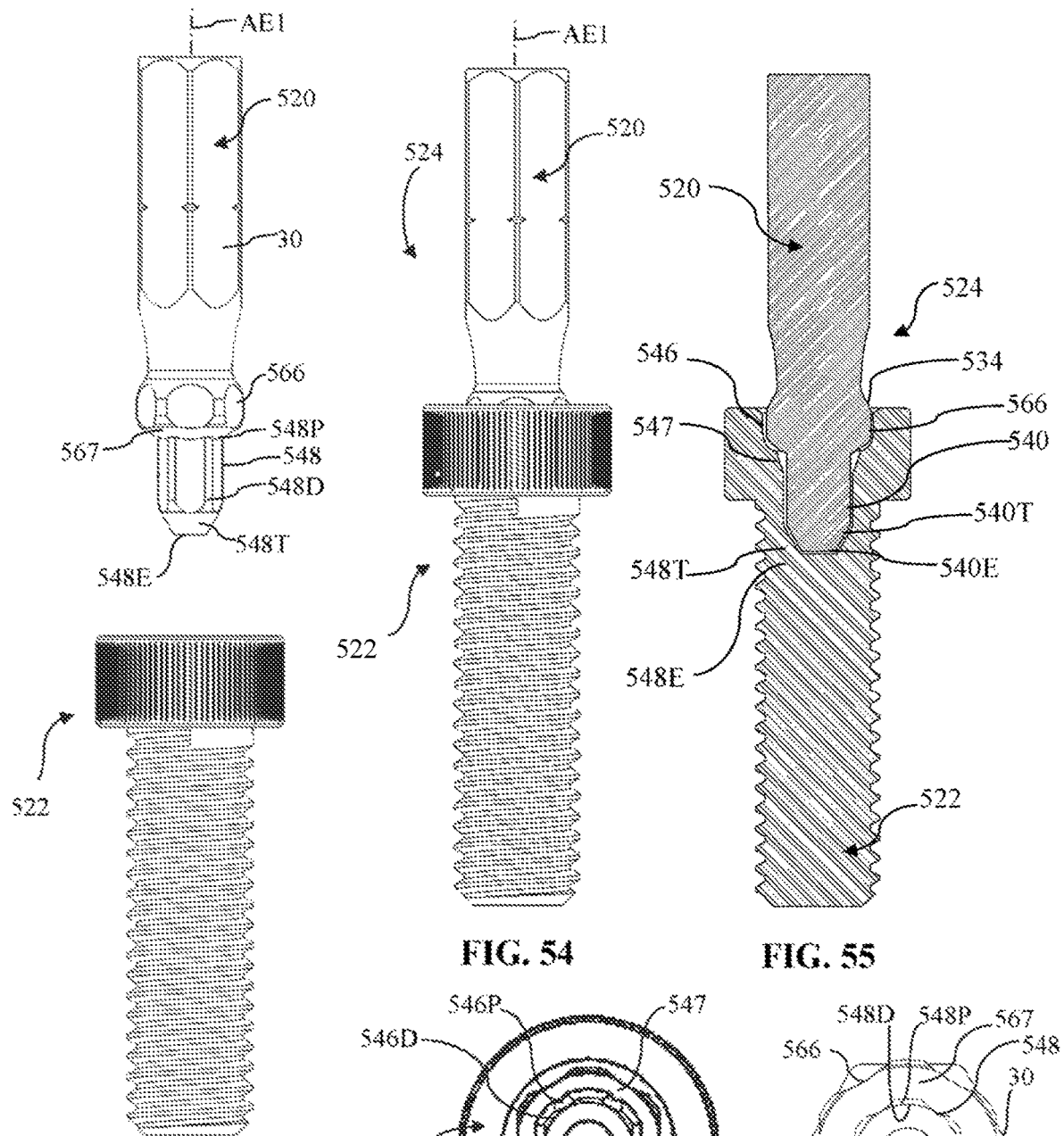
FIG. 53 shows, in a vertical orientation, an additional, alternate male/female combination embodiment of the present invention.
FIG. 54 shows the driver and fastener of FIG. 53, but in an engagement setting, as would be present either during a fastener insertion or fastener extraction mode.
FIG. 55 shows a vertical plane cross-sectional view of the combination shown in FIG. 54.
FIG. 56 shows an end view of the female reception cavity of the fastener component of the combination shown in FIG. 53.
FIG. 57 shows a distal end view of the driver of FIG. 53.
Figure 71:
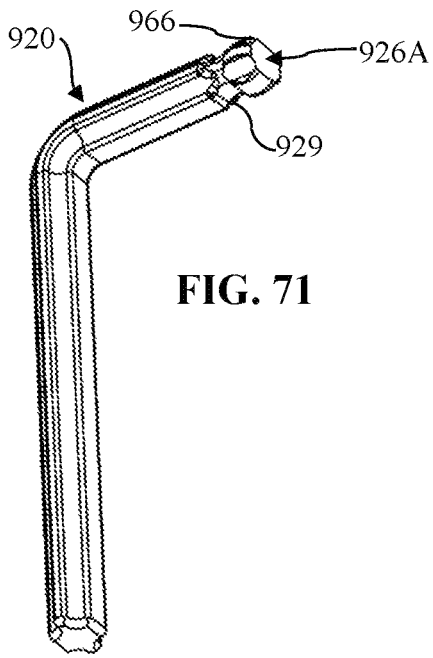
FIG. 71 shows a first perspective view of an additional tool embodiment of the present invention with torque enhancement features.
Figure 72:
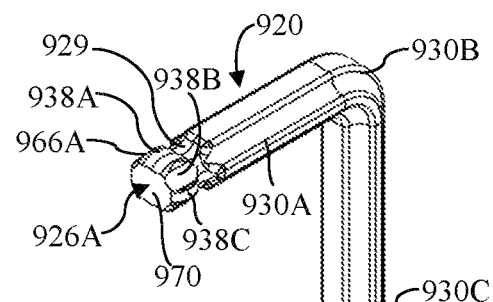
FIG. 72 shows a second perspective view of the additional tool embodiment shown in FIG. 71.
Figure 73:
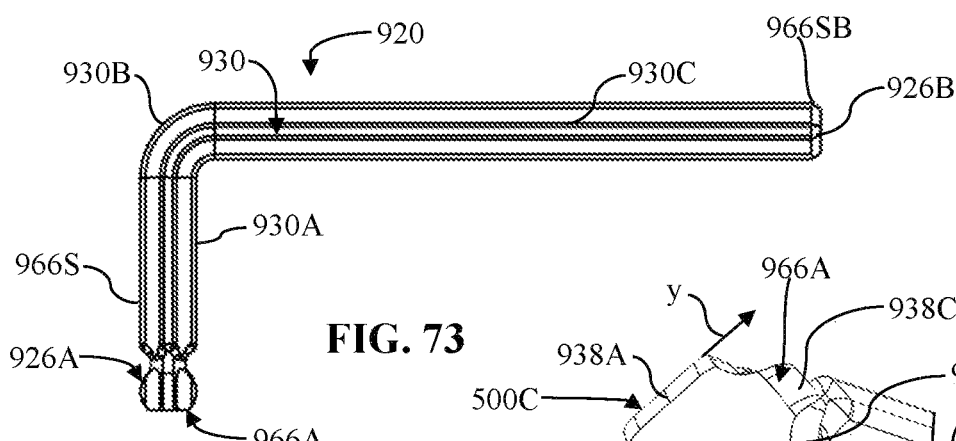
FIG. 73 shows a side view of the additional tool embodiment shown in FIG. 71.

Reference is made to FIGS. 53 to 57 illustrating an additional example of the present invention. FIG. 53 shows a pre-mesh relationship between alternate driver 520 having the same main shank body 30 and depression-projection ring set 366 and interface region 367 as earlier embodiments, but a modified distal projection 548. FIG. 53 shows driver 520, with its modified distal projection 548, just prior to insertion into fastener 522 (or just after removal). Modified distal projection 548 represents an example of the above described option wherein each of the two axially separated tiers features a torque enhancement configuration at each tier level (rather than one with a conventional configuration and one with the torque enhancement configuration) with the torque enhancement configuration being any of the aforementioned torque enhancement configuration examples featuring the noted ratio L2/L1 that is below the value of one, as in close to a square presentation (with a ratio at or greater than 90% and less than 100% being an example of a close to a square presentation), but with the noted differential as to provide the above described torque enhancement feature. Further, the general torque enhancement configuration (e.g., 500 series type configuration) can be the same or different relative to the two different axially separated torque enhancement driver sections 566 and 548 (and in this case there is two of the same general torque enhancement configurations as seen by the end view in FIG. 57 showing the radially outer and inner driving torque enhancement configurations of different size, but generally similar contouring).

FIG. 53 illustrates a pre-engagement (or a point just after disengagement) relationship, while FIGS. 54 and 55 provide illustrations of full meshing such that each of the axially separated tiers is in a meshing, torque generation potential state. As with earlier described embodiments featuring distal projections with side-walls extending longitudinally in parallel with axis AE1, distal projection 548 features non-tapered side walls initiating at a proximal end with conical support wall 367 and continuing down to the proximal end of the frusto-conical distal tip 548T shown as extending to a distal-most flat surface 548E at the end of the continuous taper shown. Alternate embodiments of the above described distal projections include ones with more of a tapered configuration as wherein the side walls slope inward to a more pointed end as with those having all walls tapering in starting with the border location 548P or initiating somewhat earlier than that shown in FIG. 53 as to provide a more tapered end then shown (generally akin to a Phillips point) instead of a flattened end such as shown in FIG. 53.

FIGS. 53 to 57 illustrate driver 520 with a torque enhancement geometry as featured, for example, in torque enhancer configuration 500L in each of its axially separated torque enhancer driver sections 566 and 548). Alternately, as noted, the type of torque enhancement configuration can vary between the distal and more proximal locations, or the tapered distal projection 548 can be of an alternate geometry as in a tapered square or hexagonal driver. A reverse situation (here and in the other different two tier embodiments) is also featured as where, in place of the first tier (more proximal) torque enhanced depression-projection ring set 566, there is provided a conventional geometry (e.g. hex, star, square) that is thus not torque enhanced as in a manner of the present invention, with a distal projection (inward tapered or not) preferably having a torque enhancement geometry. Additional aspects of the invention include having more than two tiers as in 3, 4, 5, 6, 7 or more, as in with a mix of torque enhancement/not torque enhancement combinations. Also, instead of the various fasteners described herein, aspects of the invention include, alternate torque generators and methods of using the same. For instance, aspects of the invention include turbines, gears, centrifugal devices (as in pumps), blade involved (e.g., windmill) torque generation devices (e.g., gears and/or blade hubs) and other enhanced torque generating means having the torque enhancement feature of the present invention.

With further reference to FIGS. 53 to 57 there can be seen that distal end 548D of distal projection 548 leads to frusto-conical extension 548T having a lower edge commensurate with distal most flat bottom end 548E. Flat bottom end 548E is designed, preferably, for contact with base or closed end 540E of lowest tier cavity 540 for recessed retainer 522. Lowest tier cavity 540 is designed for coordinated geometry torque meshing with the distal end 548D of driver 520 with its torque enhancer driver section 548. Female reception recess 534 further includes frusto-conical shelf 540T for mesh engagement with distal end 548T. Reception recess 534 further includes geometrically contoured ring 546 which is configured for enhanced torque meshing with the bulbous drive ring 566 of driver 520.

FIGS. 54 and 55 show a maximum insertion setting for driver 520 relative to fastener 522, which has coordinated torque enhancement contouring for reach of its torque engagement levels, as represented by the less deep surface ring portion 546 having a torque enhancement geometry coordinating with that of depression-projection ring set 566 of driver 520, and deepest portion 540 of female reception recess 534 having a torque enhancement geometry coordinating with that represented by the exterior torque enhancement surface of distal projection 548.

Accordingly, with the insertion of distal projection 548 only partially within reception recess 534 to achieve mesh engagement with the upper region of deepest portion 540 (but not sufficiently inserted to achieve meshed engagement of the bulbous ring set 566 of driver 520), there is enabled the potential for a narrower, less powerful torque application (as compared to the upper tier torque potential or both tiers meshing). This less torque generation tier only meshing can be utilized for initial fastening or initial application of a driving torque. In alternate embodiments the proximal-to-distal length of projection 548 can be shorter and designed only for commensurate enhanced torque drive meshing with ring 566 also in a mesh state. In other words, the tool 530 can be designed for only simultaneous dual torque enhancement meshing which, although losing the lower-torque/higher-torque meshing options described above, provides for a rapid positioning into a single, full torque meshing relationship following minimal insertion length which can be beneficial in some environments.

Under either scenario noted in the paragraph above, if one of the protrusions or receivers is stripped, switching to an alternate geometry is still possible. Further, even if the fastener is totally stripped relative to conventional drivers, there is still the potential for the edging of the more elongated projection of the torque enhancement configuration still catching and turning. As an additional example of such stripped scenarios not readily remedied with conventional designs, there is the potential for the insertion into the cavity with a smaller than usual driver size as that involved with a standard driver configuration, but, once inserted, the rectangular form of the torque enhanced driver will catch on the diagonal corners in accordance with the torque enhancement configuration under the present invention. Alternatively, if the recess is multi-tiered, there can be used the wider, shallower tier which will give more torque (leverage) in a recess that has not yet been stripped.

Another advantage of the two level or multi-leveled differing geometric forms can be seen in the quality of an anti-vibration feature. That is, under conventional designs there is the potential for the circular attachment of the matching male/female bit/receiver relationships to spin off, when responding to normal or excessive usage vibration. The arrangement of the present invention with the two axially separated and different radially dimensioned tiers is considered to help avoid such a spin off tendency.

FIGS. 56 and 57 Illustrate end views of recessed recipient 522 and driver 520, respectively, which have corresponding or coordinated geometries. Hence, driver 520 is shown with distal projection 548 as having a proximal edge 548P that borders and is supported by the distal end of the tapered surface 567 extending distally from the distal end of torque enhanced depression-projection ring set 566. Further, reception recess 534 is shown in FIG. 56 to have distal recess region 546D and proximal recess region 546P designed for depth alignment, respectively, with distal end 548D and proximal edge 548P of distal projection 548. FIG. 55 further shows that in region 547 of the recess the angles can be different than that of the driver as to provide a gap and also which angle can facilitate initial assertion due to its Z-axis converging depth.

FIGS. 58 to 61 illustrate an additional variation of a driver. In this variation, driver 620 is an opposite, dual headed driver tool with torque enhancement (bulbous) heads 626A and 626B. In the illustrated embodiment, driver 620 features common opposite configured driver ends (same size and shape in this embodiment although alternate embodiments such as those with different configured ends are featured in the present invention). The opposite ended embodiment depicted provides an advantage of extended use as with providing a replacement for a degraded (e.g., stripped) one end with the opposite end still being available at sufficient torque engagement.

FIG. 58 provides a side view and shows (as an example of a conventional shank configuration) hexagonal exterior configuration 666H in main body shank 630. FIG. 58 also shows non-elongated tapered neck region 629 that, like shown in FIG. 38, can provide for a two tier engagement with the first tier mesh being based on the periphery 666H of the main shank body 630 and the second tier having a similar torque enhancement bulbous head drive mesh with a corresponding geometry in a female reception recess (not shown, but of similar type as the receiving head shown in FIG. 38 (inclusive of ones with a stepped in region for accommodating the below described radial differential where the hex surface is circumferentially larger than the driver ring 666A or 666B) and thus there is featured some common reference numbering, but with "A" and "B" added to show first end/second end (e.g., 626 to 626A and 626B)). Alternatively, main shank body 630 with its torque generating periphery can be that which is inserted into a chuck of a rotation generator or the chuck of a handle connector (not shown) and the female reception recess can be designed for mesh engagement only with one tier (either of 626A or 626B), with each end shown as having a flat distal most surface 672.

Unlike driver 220 in FIG. 38 featuring a common maximum radial sized periphery in main shank periphery 266S and depression-projection ring set 266 in driver head 226, FIGS. 59 and 61 show the periphery 666H of main shank body 630 as being radially larger than each of depression-projection ring sets 666A and 666B. That is, as shown in FIG. 61, the radial reaching out to either a corner (R3) or flat surface (R2) of hexagonal shank periphery 666H is greater than the radial length of the driver heads most radially extending projection (R1) in depression-projection ring sets 666A and 666B. In this way, at each end of driver (tool) 620 there is a two-tier option, as with the bulbous driver head being in a first mesh zone (a deeper, radially inward recess designed for meshed engagement with either of driver heads 626A and 626B) and the enlarged (conventional hex configuration zone shown) being engaged with an enlarged surface recess (that conforms to the hexagonal periphery 666H). This could involve (as with the limited neck region embodiment shown) having the option of both zones always being in mesh engagement as to facilitate rapid insertion (removal) and rapid torque generation (release). Depending on the relative Z-axis length of the driver head and neck, the radially interior female recess designed for meshing with driver ring 666A or 666B can be provided with a sufficient axial length and common configuration depth as to provide for initial contact without hex periphery 666H contact and then, if desired, the hex shape contact of periphery 666H with a corresponding recess configuration in the fastener following a deeper extension of the applicable head 626A or 626B. The axial length of either of head 626A(B) can be extended and/or the female reception region to better enable an option of usage of either the distal most tier or both tiers (as per the FIG. 52 and FIG. 38 examples). Alternatively, as described above, the distal head and neck can be designed for always having simultaneous meshing of the distal end and bulbous portion whenever the driver is engaged with the reception recess.

In FIGS. 62 to 65 there is shown an L-shaped driver 720 with working torque generating opposite ends 726A and 726B and (potentially) a torque generating main shank 730. In this example each of torque generating driver heads 726A and 726B feature a torque enhancement geometry, but different head configurations. In FIG. 62, driver head 726B features a similar torque enhancement of that as a driver head 266 in FIG. 39 (as well as with a small length neck which can provide (depending upon recessed recipient configuration) with a handle engagement option (e.g., a corresponding torque enhancement configuration in the shank that matches the configuration and circumference of driver ring 766; thus providing an extra tier engagement option like in FIG. 38). This additional tier potential provided by the shank exterior, thus presents two potential different axially positioned torque enhancement tiers at end 726B and three potential torque generation tiers at the opposite end 726A (preferably with at least one of a torque enhancement type at this end as well). That is, at end 726A there is (i) an axially distal projection 748 (e.g., hex) potential option; (ii) an intermediate ring 766A (e.g., a torque enhancement configuration) option that is separated from the distal projection by way of smooth surface conical extension 767; and (iii) shank surface 730A (torque enhancement that in this case is the same as that of ring 766A) separated by smooth surface neck 729. In other words, end 726B can have two tiers of the same torque enhancement configuration provided by the shaped shank surface at the distal end 730C and the driver ring 766B (preferably also having a torque enhancement configuration) separated by a smooth neck, while end 726A has the three tier potential, featuring ring 766A, distal extension 748, and with a conforming recess of a sufficient depth the distal end portion of shank end 730A can be received in torque driving contact with the upper end of that recess.

FIGS. 64 and 65 show driver head 726A at the shorter leg 730A of main shank body 730, while FIG. 63 shows a view of female reception recess 734 having a coordinated geometry that matches in a male/female relationship with driver head 726A (as well as driver head 726B under the illustrated embodiment). That is, in this embodiment female reception recess 734 is universal relative to both ends of tool 720 in this embodiment in that it has a recess designed for reception of each of the tiers at end 726A (as in having a distal deeper recess region that meshes with distal extension 748 of driver end 726A, which deeper recess portion is not in play at the opposite end 726B, although the torque enhancement configuration of both ring 766A and 766B are received by a corresponding recess ring as well as preferably the common shank wall driver portion via an upper receiving recess portion—although alternate embodiments can feature the recess configured for only one of the two ends (e.g., a recess without the deeper distal extension receiving portion would preclude usage of end 726A but allow for end 726B meshing). Also, female reception recess 734, while being universal for insertion of either head end, is specially adapted for at least two tier optional usage with its extended recess 740 designed for torque enhancement engagement with distal projection 748 of head 726A. Thus, FIG. 64 shows distal projection 748 extending off from conical extension surface 767 which merges into depression-projection ring set 766 for the ball-point configured driver head 726. With suitable conforming recess configuration revisions, it can also be the case that recess head 726 is designed to receive all three potential tiers at end 730A of driver 720 (e.g., the reception recess being designed for distal projection 748 receipt, bulbous drive ring 766 receipt as well as shank driver region receipt).

FIG. 65 further illustrates main shank body 730 with its torque enhancement configuration via torque enhancement exterior depression-projection ring set 766S extending along the entire length of main body shank 730. In this embodiment, depression-projection ring set 766S has the same geometrical configuration and size as depression-projection ring set 766A and 766B for driver heads 726A and 726B. In this way there is provided similar added depth and multi-tier torqueing capabilities as described above for the FIG. 38 embodiment (at both ends of driver 720) and/or an improved torque relationship with a handle extension conforming to the shank (not shown). As noted, for shank 766S potential engagement there can be provided added axial depth in the conforming reception recess designed for bulbous head ring 726A contact in fastener 722 (that added depth is not shown in the FIG. 65 embodiment) such that pushing down deeper provides for shank 766S contact in addition to bulbous head ring 726A (or 726B). The shank shape also provides for open wrench or the like engagement particularly relative to the longer length shank portion 730C while head 726B is engaged in a fastener reception recess.

FIGS. 66 to 70 show an additional aspect of the present invention featuring an alternate driver/recipient combination 824 (not yet engaged or just recently separated) comprised of driver 820 and recessed recipient 822 (shown as a threaded bolt fastener with associated nut in this embodiment). Driver 820 is similar to driver 720 described above including a common main shank 830 configuration, but features a common configured driver head at each end. That is, FIG. 66 shows driver 820 having driver heads 826A and 826B which has the same geometrical configuration as driver head 126 described in FIG. 25. Thus, driver heads 826A and 826B each feature depression-rejection ring set 866, leading to frusto-conical extension surface 868, which has a lower edge representing the outer peripheral exterior of annular shelf region 872. From shelf region 872 there extends the distal-most reverse silo-shaped extension 848. Extension 848 is configured for flush reception within centralized cavity 840 and thus features cylindrical extension 874 with lower semi-spherical extension 876 defining the distal most end of extension 848 and configured for light frictional contact with the deepest part of centralized cavity 840 when annular shelf region 872 is in flush engagement with abutment surface 836 of female reception recess 834 of recessed recipient 822. (See FIG. 70).

In the illustrated embodiment of FIG. 66 there can be seen that each of heads 826A and 826B have the same geometrical configuration and size. As noted above, however, aspects of the present invention include different geometrical configurations (inclusive of one end having a conventional design) and/or different sized heads as in larger or smaller common geometries, extended distal projections as a few examples). Further the exterior surface configuration 866S for shank 830, while preferably having the aforementioned torque enhancement configuration similar to that provided for each of heads 826A and 826B, can also have a different configuration inclusive of a conventional configuration as in a hex-shaped or square-shaped configuration, or no torque generation surfacing as in a circular handle. The opposite is also true from the standpoint that the exterior surface configuration can be of a torque enhancement configuration while the driver heads are of conventional designs such as any of those described above.

An additional feature of driver 820 is the usage of a stubby leg (830A) in the overall L-shaped configuration for shank 830 comprised of stubby leg 830A, intermediate curved region 830B and elongated section 830C, with essentially the neck region 829A starting at the end of the intermediate curve region.

FIGS. 71 to 78 illustrate an additional driver (tool) and recessed recipient combination 924 (FIG. 77) featuring driver 920, which is also in an L-shape configuration as in driver 820, but with a more elongated first section 930A in the main shank body 930 of driver 920. Combination 924 also features recessed recipient 922, again having a corresponding torque enhancement geometry relative to driver 920. At the free end of first section 930A is provided driver head 926A sharing similarities with the aforementioned driver head 226 in FIG. 37, but for a different 500 series configuration (500C in FIG. 71 as compared to a 500L series in FIG. 37). Driver head 926A, like driver head 226, is shown as including depression-projection ring set 966A together with a flat distal most surface 970 that can be received by the deepest part of a receiving reception recess such as recess 934 in recessed recipient 922 shown in FIG. 76. At the opposite end of driver 920 is provided driver head 926B (which is represented by the free end of the longer section 930C of main shaft 930—with both the shank and distal end of the shank having a continuous driver ring torque enhancement configuration (966S equals 966B)).

Figure 74:
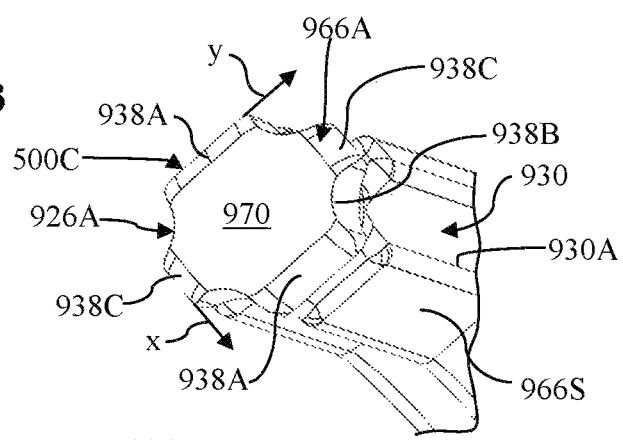
FIG. 74 shows an enlarged view of the bulbous (as provided, due in part, to a radial expansion away from the thinner, adjacent neck recess of the supporting main shank) driver head side of the tool shown in FIG. 71.
Figure 75:
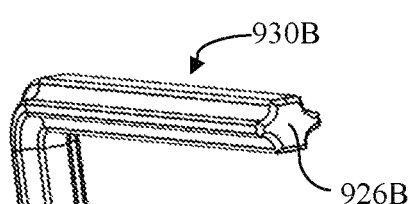
FIG. 75 shows another view of the tool in FIG. 71 with an end of the non-bulbous, torque enhancement end of the tool shown.

FIG. 74 provides a close up view of driver head 926A formed at the free end of first section 930A which forms the shorter leg of the overall L-shaped main shank 930 which also includes curved intermediate section 930B and elongated section 930C. Driver head 926A extends distally from neck cavity 929 that borders driver head 926A and the end of first shank section 930A. Also, in this embodiment there is provided a single-tier or multi-tier configuration at the one end 926A, depending on the shape of the conforming reception recess. For instance, with reference to FIG. 80 there can be seen a reception recess that is shallow (quick insertion and meshing potential) receiving only the bulbous portion of driver head 926A having torque enhancing depression-projection ring set 966A. In an alternate embodiment, reception recess 934 can be altered as to have a sufficient depth to receive both the projection ring set 966A and the portion of shank section 930A (also having a correspondingly sized and configured torque enhancing depression-projection ring set 966S). Also, as seen by relative short/long wall relationship L2/L1 and associated concavities this embodiment features a 500C shape configuration for its torque enhancement configuration. In this regard reference is made to the to the discussion below relative to FIG. 93 of the present application as well as the incorporated US Publication 2018/0325776 which provides as well an illustration and discussion as to the noted 500C configuration.

Figure 79:
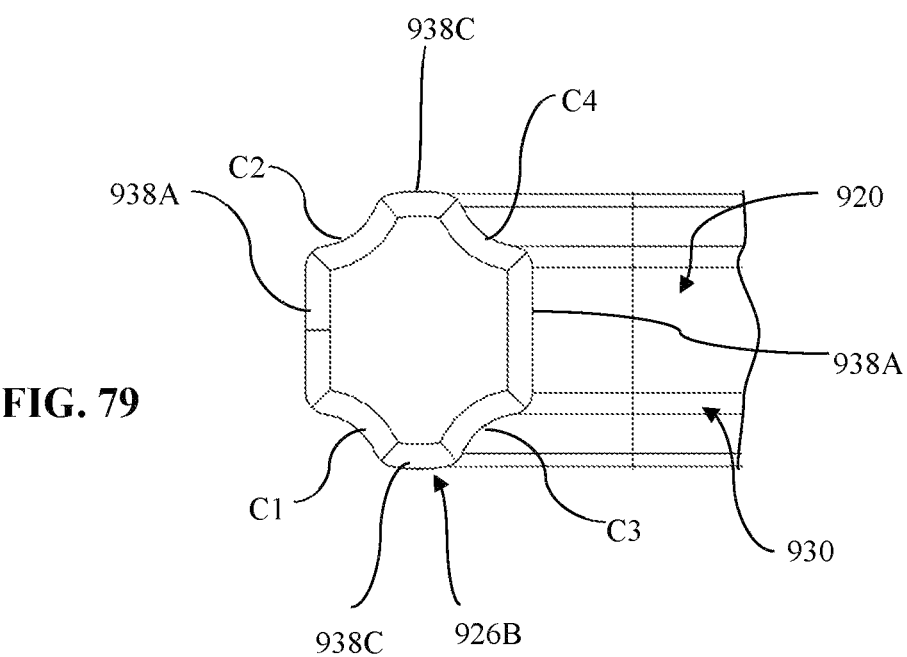
FIG. 79 shows the end view of the driver of FIG. 71 that features the non-bulbous male driver end.
Figure 81:
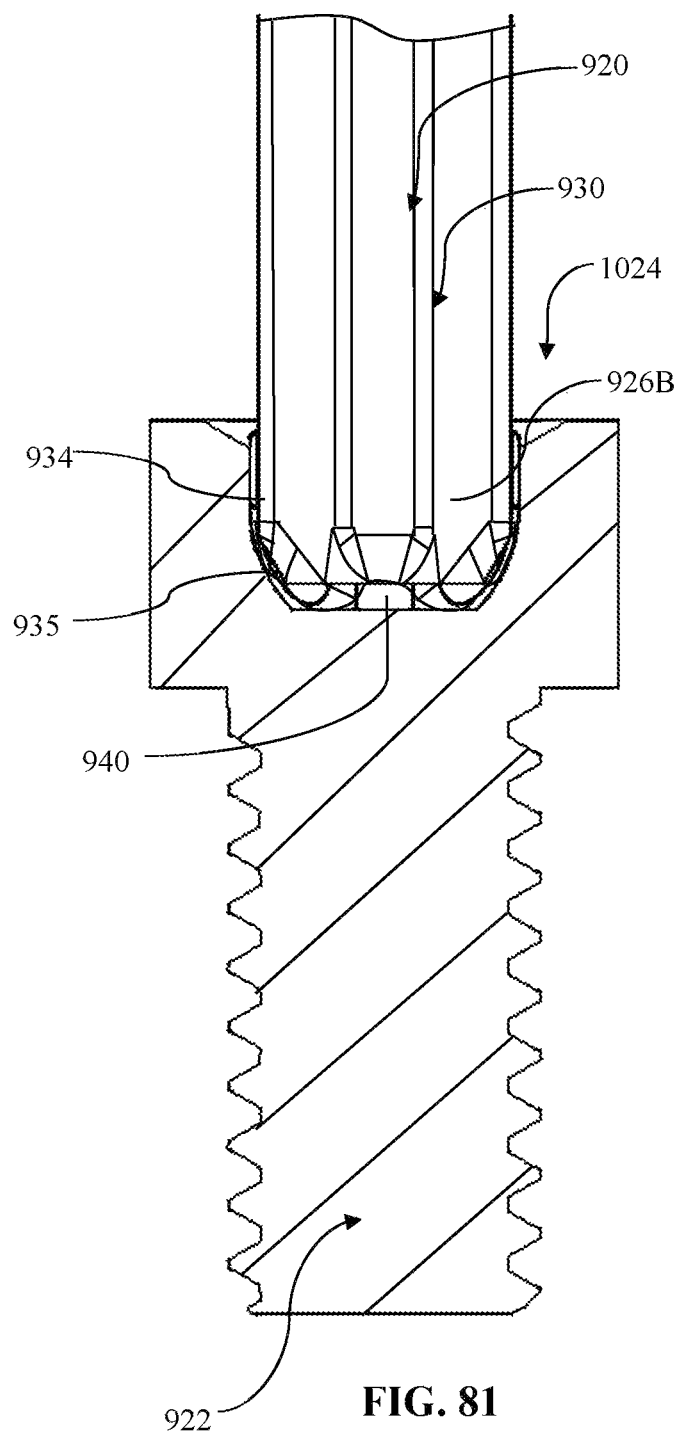
FIG. 81 shows a cut-away view similar to FIG. 80 but showing the opposite non-bulbous end of a tool received in the female component shown in FIG. 77 (and as well in FIG. 79).

As further seen from FIGS. 74, 79 and 81, there is a torque enhancement configuration at the opposite end 926B for engagement in the same reception recess that receives end 926A such that the tool provides a multi-tier (axially separated) torque enhancement combination based on the tools opposite end capability, which can be further expanded upon with appropriate reception recess configuring as to provide for each of ring-sets 966A, 966S and 966SB (at end 926B) engagement each having a common or different torque engagement configuration, as with each having smaller value L2/L1 percentage based on a larger longer length/shorter length ratio than that of the referenced more square type configuration 500L (as in the one depicted in this figure set having a L2/L1 ratio similar to that in torque enhancer 500C).

As further illustrated, main shank 930C shows the noted projection ring set 966S extending over the full length of main shank, although alternate embodiments include only a zone region (such as of a length represented by zone Z4 in FIG. 38 (or relative percentage) that borders the border neck region 929 and a similar length zone provided at the opposite, free end of driver 920). Reference is also made to FIGS. 191A and 191B in US Publication 2018/0325776 which is incorporated herein by reference in its entirety and which figures show a suitable main shank for which the driver head 926 as presented in the FIG. 74 embodiment shown in the present application can be supported. Also, driver head 926A is also well suited for alternate tool supports such as the handle support featured in FIG. 192A of the same US Publication 2018/0325776. An additional feature illustrated in FIG. 74 of the present application is that the radial projection ends (opposite narrow width-longest radially outward extending wall set (938C) and longer width-less radially outward extending wall set (e.g., 938A, 938A)— have an axially external convex curvature as to facilitate a rapid slide into recess capability while still retaining the aforementioned torque enhancement capability once placed in mesh engagement. The slope (e.g., 10 to 30 degrees down and out from the flat plane flush with surface 970) results in the outer edge extremity aligning with the outer edge extremity of the correspondingly geometrically (peripheral) conforming outed peripheral edge of the main shank periphery (966S periphery corresponds with that represented by the outermost edging of depression-projection ring set 966A (and 966B)).

As best seen in FIG. 79, driver head 926B has a set of equal sized and commonly configured corner surface concavities 938B (corresponding with the noted cut-outs C1 to C4). As in the other torque enhancement configurations, between the cut-outs is provided the different length side walls (longer radial projection length—less widthwise peripheral surface length set 938C-938C (shown as spaced apart and running parallel or essentially parallel to each other) as well as shorter radial projection length-longer peripheral surface length set 938A-938A (also spaced apart and extending parallel or essentially parallel to each other). Thus, FIG. 79 illustrates a torque enhancement configuration (such as that of enhancer 500C).

Figure 76:
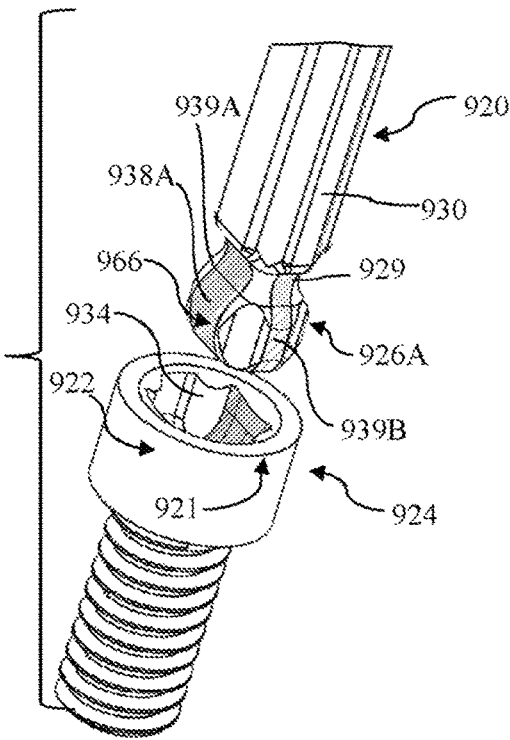
FIG. 76 shows a closer view of the bulbous head end of the driver in FIG. 71 shown just prior (or just after) male/female combination insertion.
Figure 78:
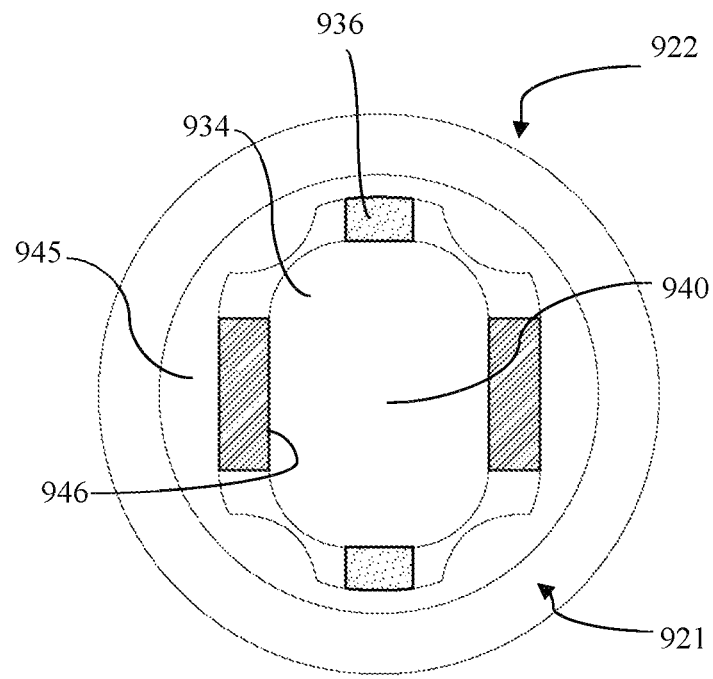
FIG. 78 shows the end view of the female reception cavity of the fastener head of the fastener in the combination shown in FIG. 76.

As best seen in FIG. 76 (showing combination 924 featuring driver 920 just prior (or just after) mesh engagement with recessed recipient 922) driver 920 features the aforementioned smooth contoured bulbous head 926A wherein, for example, the longer peripheral length side wall set 938A and 938A have a smooth curving exterior contour that presents a convex region extending down from a concave side wall formed as neck 929 and which slide enhancement convex region can also be a region provided with surface coating and/or texturing for enhanced abrasion strength and/or improved insertion control. The opposing wall set 938C and 938C are shown as being more linear with a sloped upper region leading from the bottom of neck region 929 into a flat wall extending down to another sloped wall region leading to the flat distal most bottom of driver head 926A. The gently curving neck region and associated longer wall region 938A and 938A provide an insertion and retraction facilitator in that the side wall will smoothly flow into the corresponding configured recessed reception region of recessed retainer (fastener shown) 922 of combination 924. This is true especially when there is featured sloped annular rim region 945 leading into central recess 940 of fastener head 921 (FIG. 78). The slope is designed to facilitate the slide to center positioning of an inserted end 926A and thus can include only a few degrees to achieve this directional nature (e.g., a 3° to 10° incline down and radially inward or greater as in up to 30° if a greater downward convergence is desired). In addition to the downward and radially inward slope of annular rim region 945 there can further be provided a circumferential (in addition to radial) sloped surface configuration to promote a rapid positioning of a spinning driver head into meshed engagement with fastener head 921. In this regard, reference is made to U.S. Pat. No. 7,255,522 having an example of such a circumferential ramp surface arrangement, but with a different driver configuration. Once driver head 926A achieves a full mesh engagement within reception device 922, there is enabled the high torque interfacing as described in the earlier embodiments in combination with the smooth insertion and extraction ease provided by the driver head configuration and/or ramping surface of the reception device 922.

Figure 77:
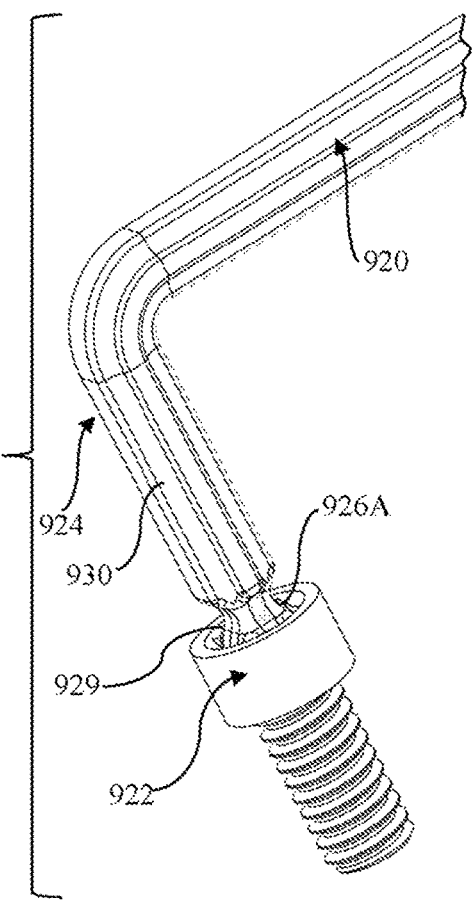
FIG. 77 shows the combination of FIG. 76 but in an engagement relationship.
Figure 80:
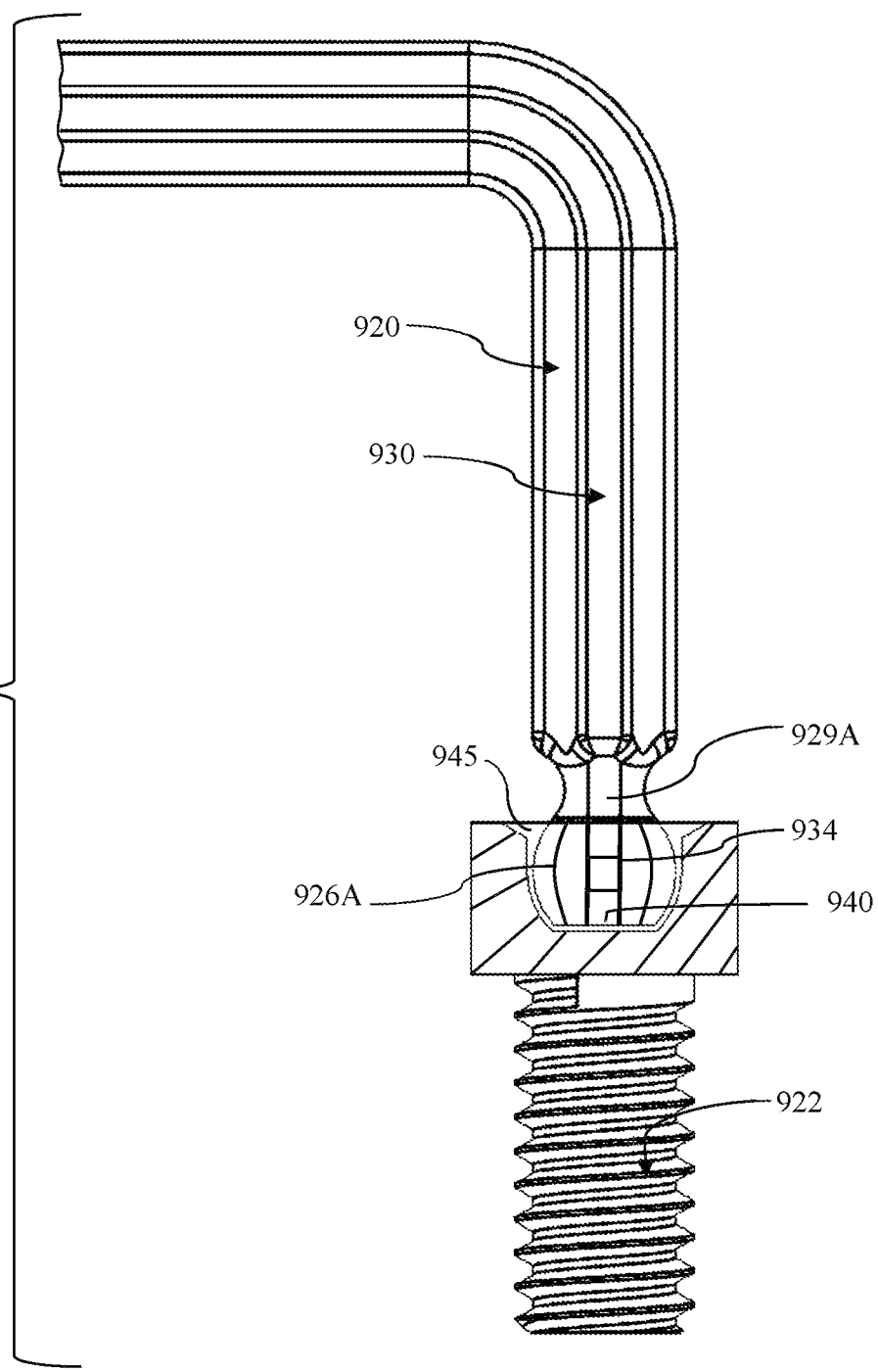
FIG. 80 shows a partial cut-away view of each of the male and female components of the same full engagement combination shown in FIG. 77.

FIG. 80 shows a cut-away view of the combination 924 shown in FIG. 77 with the upper sloped region of the bulbous head 926A essentially level with the upper surface of the annular rim region 945 as to leave exposed neck surface 929A of driver head 926A which is in full meshed contact with the base formed at the end of the recess 940.

FIG. 81 shows an alternate combination 1024 featuring the same recessed retainer 922 shown in FIG. 80 but with the opposite free end 926B (non-bulbous free end) of driver 920 again received within recess 934 of fastener 922. Thus, since there is preferably provided the torque-enhancement configuration all the way from the free end driver 926B, along main shank 930 until the smooth contoured neck cavity 929A, and then again for the bulbous driver head 926A (and all of the same size) either end can be inserted into the fastener 922 depending on environment and torque generation levels required (e.g., a greater moment provided when the hand can push on the longer shank section 930C, while the shorter leg 930A has its bulbous end in mesh engagement).

There can be further seen that the very distal edge of driver head 926B has an annular grouping of sloped walls 935 sourced from the wall sets (938A, 938B and 938C); preferably having tapering of 10 to 30° inward from the vertically oriented side wall of driver head 926B in FIG. 81. Also, the degree of slope can either provide for direct contact between the respective flat end of driver head 926A and the floor of cavity 940 in recessed retainer 922 or there can be provided a gap as seen in FIG. 81 therebetween (which gap can be useful to help maintain the correct meshed side wall depression-projection ring section 966B engaged with the "catching" geometry in the side wall of recess 934, even when debris such as grease or dirt is present). As the slanted distal edging in driver head 926B is intended for facilitating insertion only it preferably represents less than 20% of the overall depth of the receiving recess 934. FIGS. 80 and 81 thus show the versatility in utilizing either driver head design 926A or 926B depending upon the environment and torque needs.

FIGS. 82 to 86 show a few different variations on another driving tool of the present invention which, like the embodiment above, is presented in the context of an L-shaped driving tool 1020, although alternate driving tool means is also contemplated as in those others described herein.

Driving tool 1020 is shown as an L-shaped tool that has a general "Allen" wrench design, but has a torque enhancement cross-section configuration 1066S at least at one free end and preferably at both of the free ends of the shank 1030 of the L-shaped driver tool 1020, as well as potentially along its entire shank body (that is a torque enhancement contour 1066S continuous from one free end to the other of the driving tool 1020).

Driving tool 1020 is shown as sharing many similarities as that of the above mentioned driving tool 920 but, rather than a bulbous end and a non-bulbous end, features two non-bulbous ends each having the same general characteristics as described above for driver head 926B.

An additional difference in driver 1020 relative to driver 920 is that there is added the addition of slanted section 1021 which tapers inwardly from its proximal end down to the edge defining flat surface 1023 in driving head 1026B. A similar slant surface is not present in the other free end of tool 1020, although in alternate embodiments there can be added such a feature as well. Slanted section 1021 is thus in addition to distal most sloped walls 1035 (having similar characteristics to sloped walls 935 described above). Slanted section 1021 is shown as converging inward and being distally deepest (radially smallest) at the border region with flat distal end 1023; and at its more proximal end (more radially outward) it merges with (in the FIGS. 82 and 86 embodiment) one of the longer length peripheral side walls of wall set 1038A. An angle of 10° to 20° from the vertical is contemplated as in one that has less steep an incline than the angle to the vertical of walls 1035 but has a longer Z-axis length. In addition, slanted section 1021 extends longitudinally for a longer length than sloped walls 1035 as in 1.5 to 3 times longer in Z-axis length than that of sloped distal walls 1035.

Figure 82:
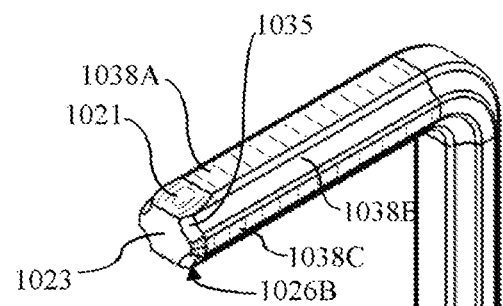
FIG. 82 shows a perspective view of still another tool embodiment of the present invention with torque enhancement feature and which includes two non-bulbous heads with one having a distally inward tapering wall or sloped section.
Figure 83:
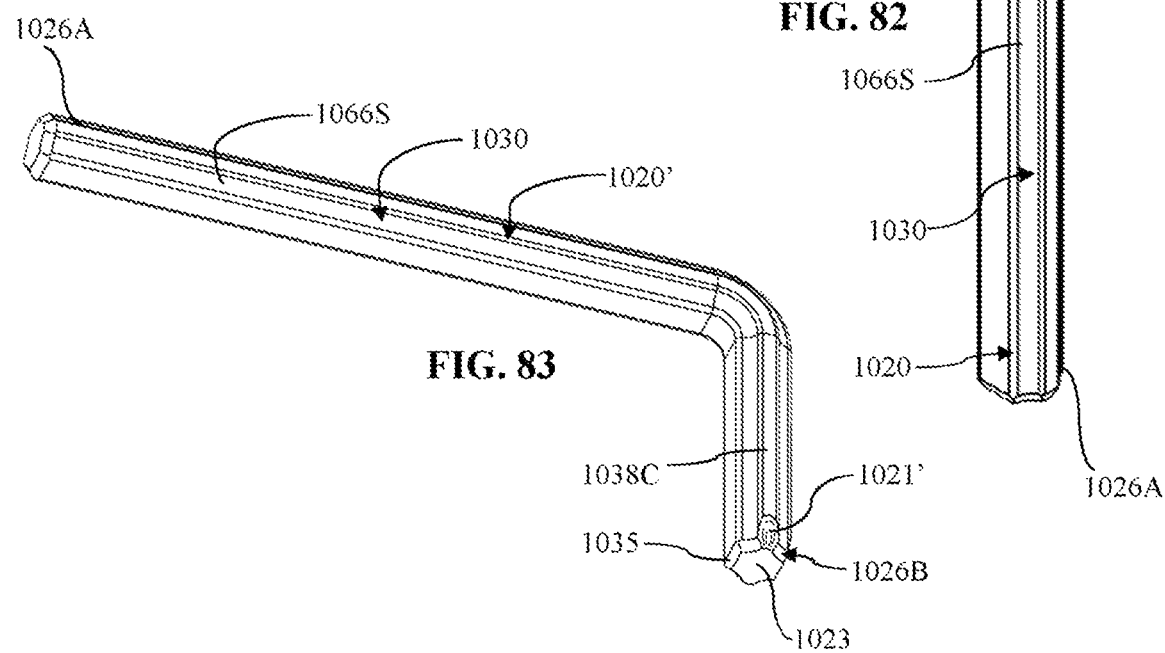
FIG. 83 shows a perspective view of that which is shown in FIG. 82 but with the tapered side wall formed on the shorter length side wall of the torque enhancement configuration.
Figure 84:
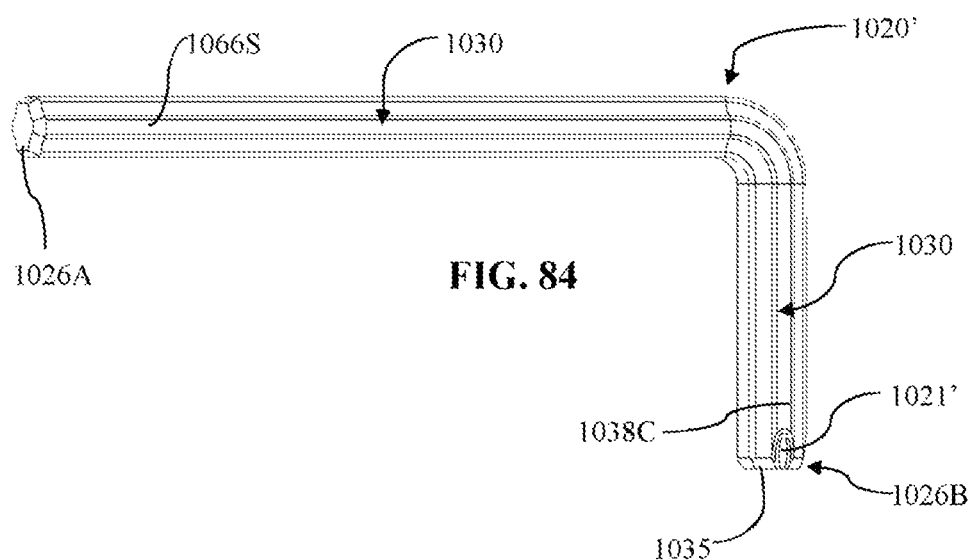
FIG. 84 shows another perspective view of that which is shown in FIG. 83.
Figure 85:
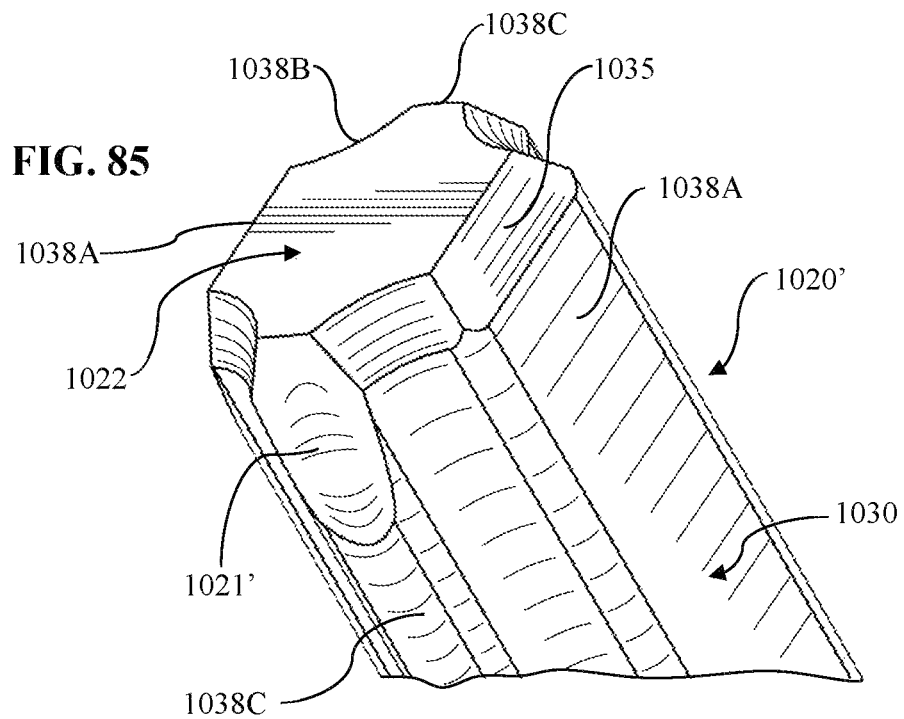
FIG. 85 shows a cut-away, enlarged view of the inward tapered end of the tool of FIG. 83.
Figure 86:
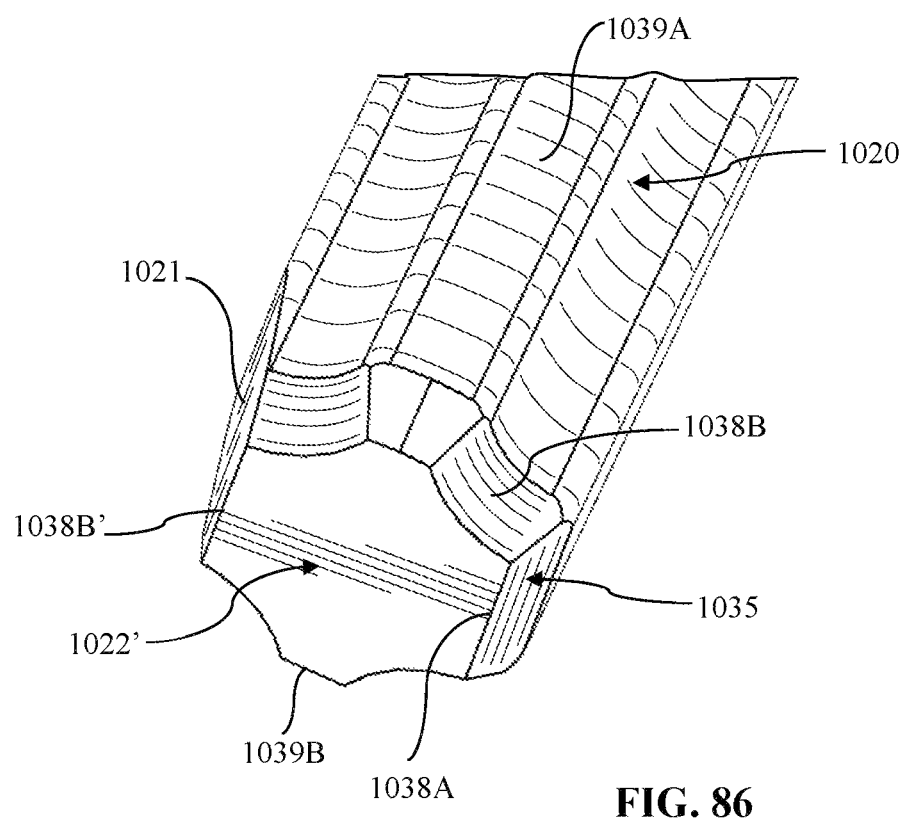
FIG. 86 shows another close up view from a different perspective of the same end as shown in FIG. 82 with the elongated taper provided on one of the longer length torque enhancement walls.
Figure 87:
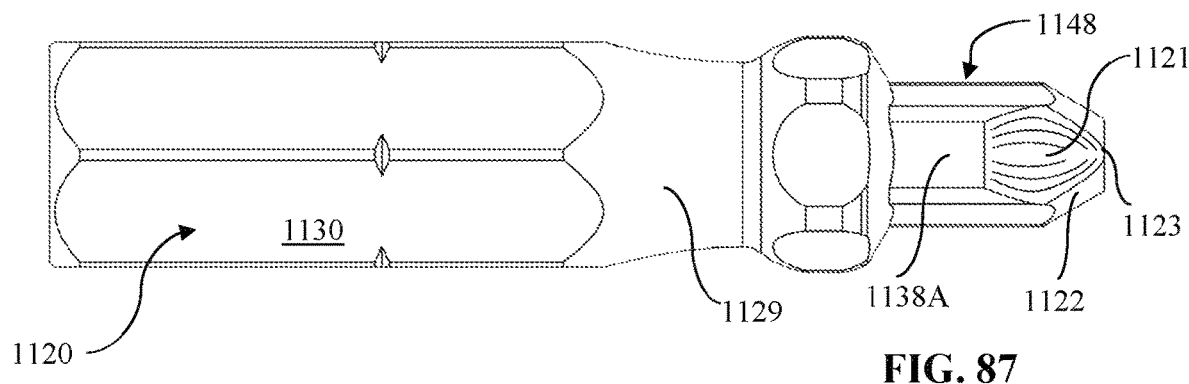
FIG. 87 shows another tapered distal end tool embodiment having the torque enhancement feature of the present invention and which includes, in addition to the bulbous or ball-point configured male driver, an elongated projection with tapered (or sloped section) distal wall surface.
Figure 88:
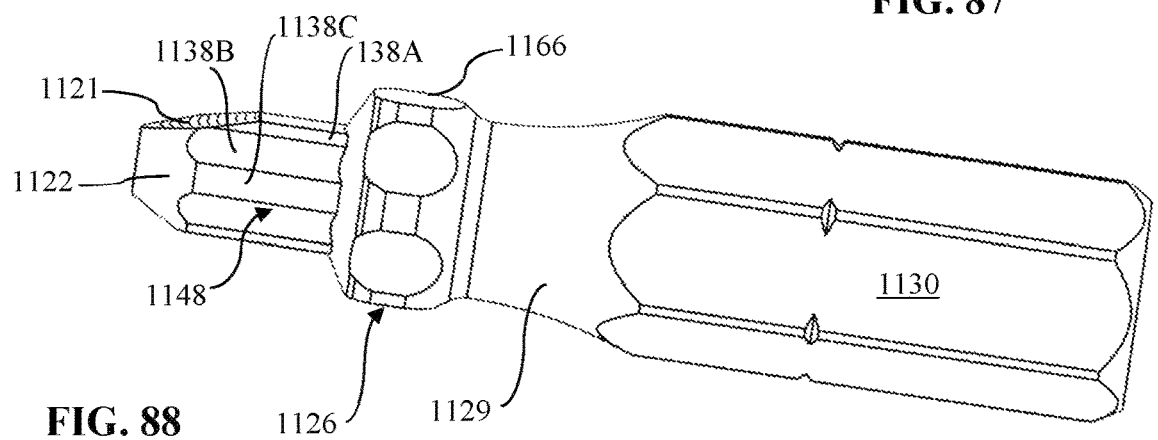
FIG. 88 shows a different perspective view of that which is shown in FIG. 87.
Figure 89:
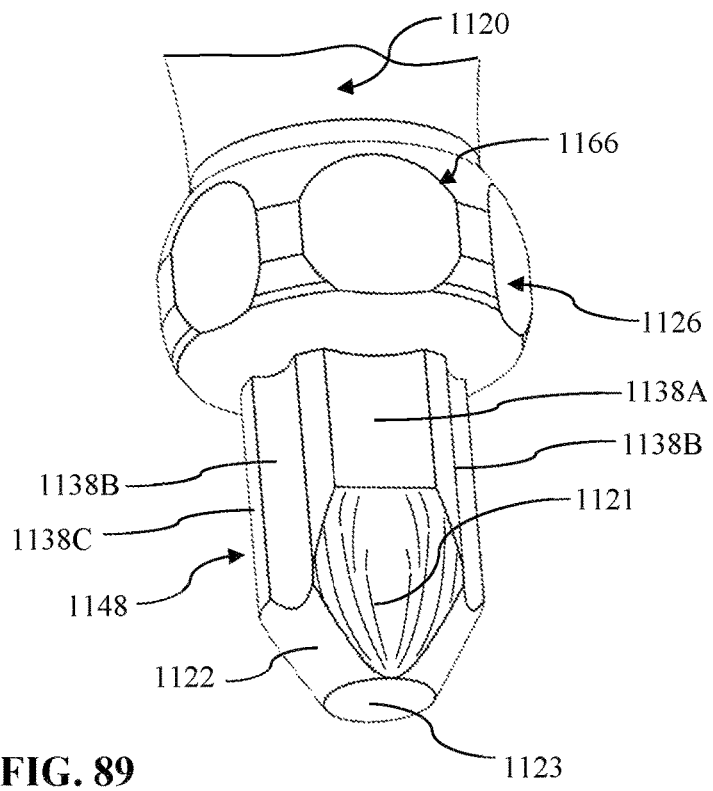
FIG. 89 shows a close up view of the tapered distal end wall surface of the tool in FIG. 87.
Figure 90:
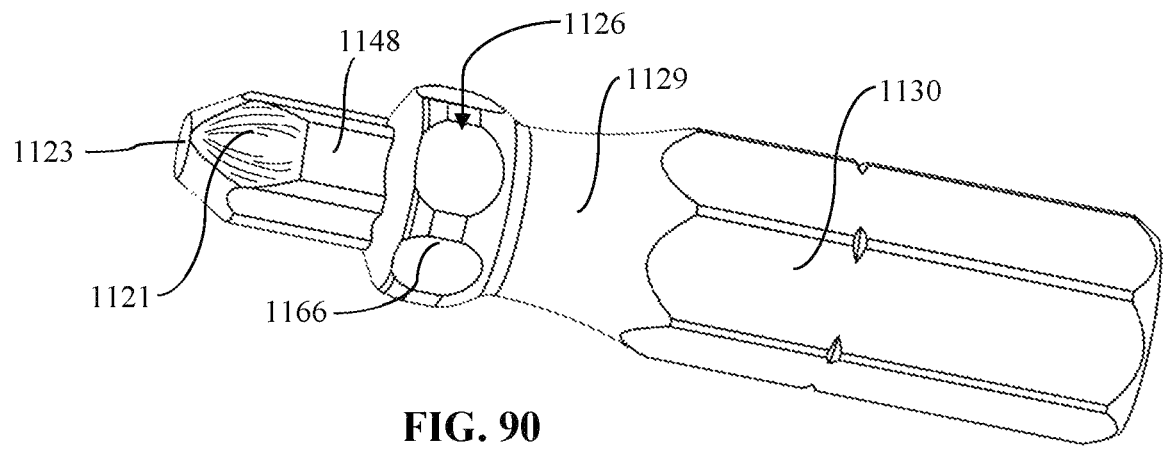
FIG. 90 shows a similar perspective view of the driver in FIG. 88 but rotated 90 degrees for a better appreciation of the tapered distal end wall surface.
Figure 91:
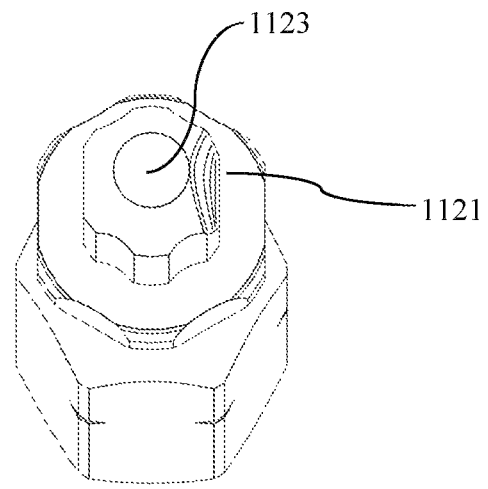
FIG. 91 shows an additional perspective view of the driver in FIG. 88 with an end view focus.
Figure 92:
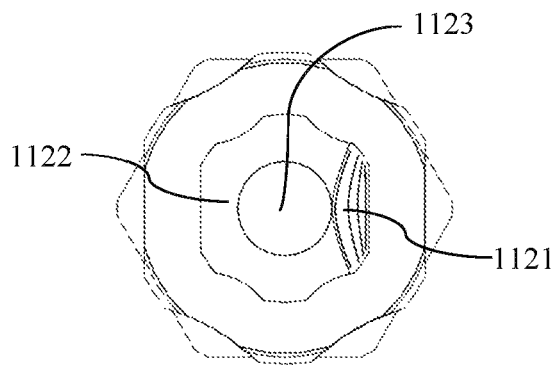
FIG. 92 shows a direct end view of the driving head shown in FIG. 87.

FIGS. 83, 84, and 85 show a view similar to FIG. 82 but with slanted section 1021' being provided on one of the shorter peripheral length side walls of wall set 1038C. Additional slanted sections like 1021 and 1021' can be provided in one or more additional walls making up the torque enhancer configured driver head 1026B, although for many usages only the one slanted section 1021 or 1021' is required. That is, slanted section 1021 (and/or 1021') provide an added clearance region without a degrading imposition on the torque enhancement edging. This gap is well suited to enable the insertion of the driver head despite obstructions such as a burr, bent edge of the receiving recess edging or adhered debris in the recess side wall, that slanted section 1021 or 1021' can accommodate and thus enable removal of what would otherwise be a difficult (and time consuming) component to remove.

FIGS. 87 to 92 illustrate an additional aspect of the present invention featuring slanted section 1121 on distal projection 1148 of driver 1120 which shares many similarities with driver 520 featured in FIG. 53, but with a few differences that include slanted section 1121 as well as a more axially extended frusto-conical distal ring surface 1122 extending up from flat surface 1123 (as does slanted section 1121) until reaching the torque enhancement edging in distal driver projection 1148. In the FIG. 89 embodiment, there is provided, more proximally, a bulbous torque enhancement component 1166 which is supported on handle (shank) 1130 and is bordered by concave neck region 1129 leading up to a grip surface of the illustrated tool (hand grip or mechanical grip as in a hex or square shank chuck reception surface).

As with the earlier described embodiments, the inclusion of slanted section 1121 allows for more universal usage in that tool 1120 can be used in a greater variety of recessed reception (fastener) situations including those with burrs or regions that are degraded as due to fastener edge deflection or degradation. Also as with the earlier embodiment, rather than the longer peripheral length wall 1138A shown, or in addition thereto, an alternate one of the torque enhancement walls in distal projection 1148 may be relied upon as the support region for the slanted section inclusive of shorter peripheral length (longer radial projection length) walls such as wall 1138C.

As noted above, driving tool 1020 can be a hand manipulated driving tool, although additional embodiments include similar shaft driving head combinations that can be used on standard driving power source devices as in air guns, etc. For example, in an alternate embodiment of driver 1020 (not shown), the same tool has the same driving head but a back end that is contoured (e.g., four sided) and thus well suited for insertion into a square sided chuck or the like, inclusive of a chuck for an electric or fluid driven tool driver, as in a drill with a multi-prong chuck head designed to expand and collapse as to receive and fix (or release) torque enhancement tool 1120 with an RPM chuck reception proximal end (not shown).

Figure 93:
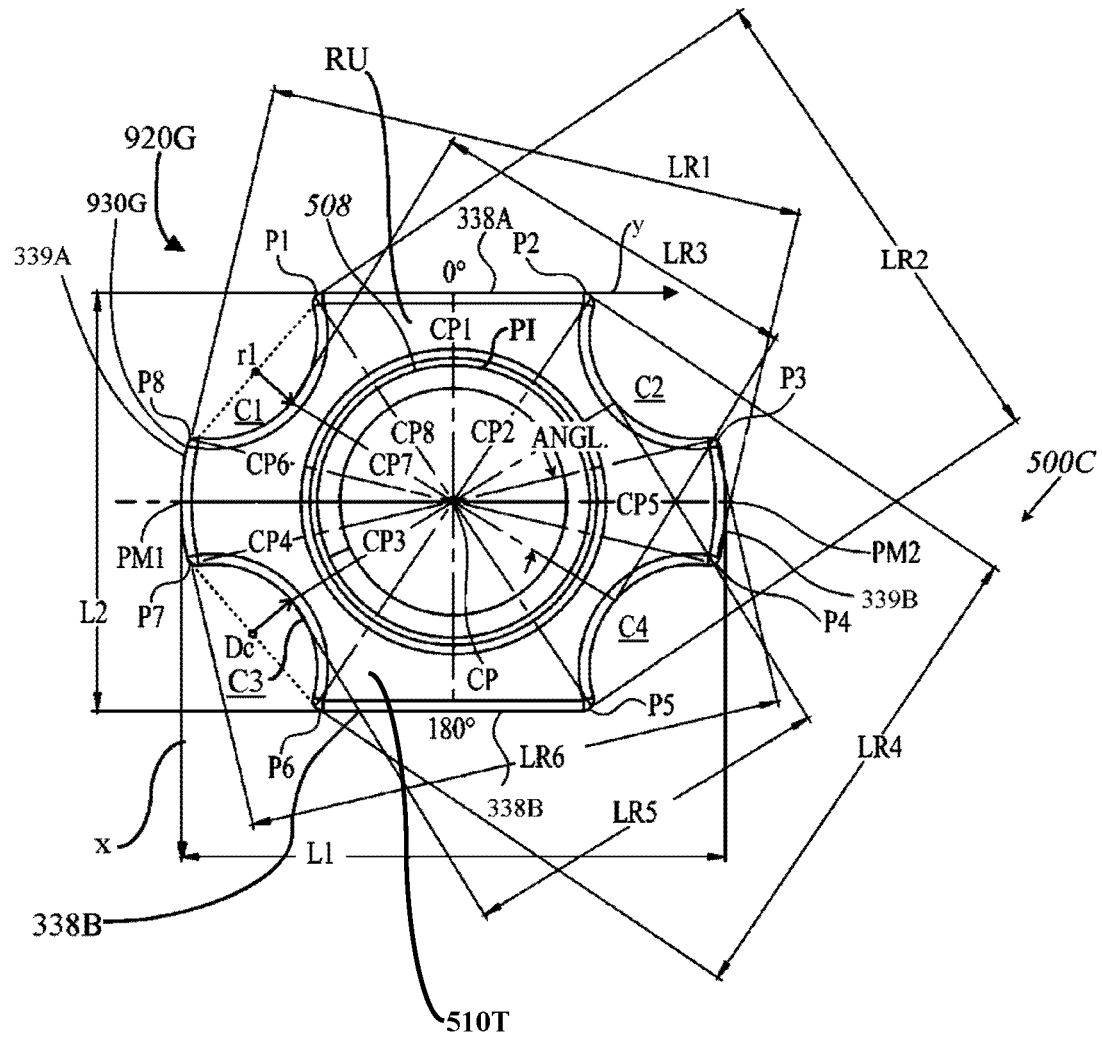
FIG. 93 shows an end view similar to FIG. 7, but for a torque enhancer configuration that is less square or presents a torque enhancer configuration with a greater disparity in the L2 and L1 lengths (as well as in the longer torque surface versus the shorter torque surface—in similar fashion to the bulbous driver end in FIG. 74).

FIG. 93 is illustrative of a torque enhancement configuration that has an external periphery corresponding with, for example, shank 930 of the aforementioned driving tool 920. That is, FIG. 93 shows an end view of driving tool 920G featuring a torque enhancer gripping shank surface 930G.

FIG. 93 further shows tool 920G with exterior gripping surface material RU (preferably formed of a suitable elastomeric material used for tool grips as in thermoplastic elastomers (TPEs) that is bonded and/or mechanically connected to a central support post PI (shown as a hollow metal pipe in this embodiment although solid rods are also featured)). The gripping surface RU is formed as to have a torque enhancement shape as in enhancer configuration 500C (described above). As with the other torque enhancement 500 series embodiments, the FIG. 93 driver configuration, rather than a hand grip configuration for a driver handle, can also be used on a variety of other driver or recipient configurations, such as those found in a distal driver end, threaded nut (e.g., bolt nut), gear, centrifugal device, or other torque enhancement means, preferably having the above described bi-symmetry (or essential bi-symmetry) with longer and shorter length characteristics. This lower percentage L2/L1 ratio embodiment is well suited for hand manipulation tools under the present invention, particularly when formed of an elastomeric (or other compression partially collapsible material); and, also, due to it being farther removed from a true square depiction, depending on the circumstances it might be less desirable in high RPM usages. However, it does provide for even further enhanced torque leveraging due to the lower L2/L1 ratio.

With reference to FIG. 93 for driving tool 920G there can be seen that length L1 corresponds to the long length between the outermost points PM1 and PM2 in the respective short sides 339A and 339B. That is, rather than reliance on reference rectangle RE, a different reference approach is taken in this figure set to depict the long length which is carried out through use of length depiction L1 free of an overlying reference rectangle. In FIG. 93 there is illustrated compass point diameters (CP1, CP2, . . . CP8) all passing through center point CP (which is also the center point for the noted central post PI (or can represent an aperture such as a thread ring 508 formed in the interior of a nut body 510 (or the center point of an extending threaded shaft or gear hub in an alternate embodiment)). If the embodiment features threads 508 those can take on any suitable form for a bolt, shaft, nut or other locking member as the present invention works well with a variety of binding means (e.g., threads, key slots (e.g., a key slot relationship such as those used suited for shaft or hub retention with or without a compression fix), expansion mechanisms, etc.).

As shown in FIG. 93 (with the axes X and Y featured for added frame of referencing):

compass point diameter CP1 runs between the center point of the long wall side set 338A, which in this embodiment is represented by compass point diameter running from 0 degree to 180 degrees and which is also a suitable length L2 representation as no notch is shown formed in the wall set 338A and 338B at this location;

compass point diameter CP2 runs between opposite end points P2 and P6 of long side wall set 338A, 338B;

compass point diameter CP3 runs between opposite end points representing the deepest concavity points of the surfaces 502 of corner notch regions C2 and C3;

compass point diameter CP4 runs between opposite end points P3 and P7 of short wall side set 339A and 339B;

compass point diameter CP5 runs between the center point of the short wall side set 339A and 339B, which in this embodiment is represented by compass point diameter running from 90° to 270°. As such, CP5 also runs between the maximum points PM1 and PM2 of the illustrated slight curvatures as to define length L1 (also in view of no notch formation on walls 339A and 339B, which if formed in the middle could make an adjacent region informative of the maximum length L1);

compass point diameter CP6 runs between opposite end points P4 and P8 of short side wall set 339A and 339B;

compass point diameter CP7 runs between opposite end points representing the deepest concavity points of the surfaces 502 of corner notch regions C1 and C4; and compass point diameter CP8 runs between opposite end points P1 and P5 of long side wall set 338A. 338B.

The aforementioned contact points thus illustrate potential contact points of an appropriately configured (meshing) device as in a rotating socket driver or chain drive or some other driving means, with the aforementioned compressible material RU being one potential type material, with higher strength (e.g., steel or other strong metal) optionally being utilized as when used for different environments (e.g., sprockets) requiring additional strength or less compressible material.

As also seen from FIG. 93, the end walls represented by short side wall set 339A and 339B, while slightly curved, are also smooth in surface configuration. Torque enhancer configuration 500C for driving tool 920G is also shown as having a top planar surface 510T; although, at least in an embodiment with a bolt form of torque enhancer, the reference to top is for references purposes only as the final orientation of the torque enhancing device (e.g., nut) 500C is controlled by the threaded component to which it is threaded. There is also the potential (not shown), for side walls 338A and/or 338B (and/or wall set 339A and 339B), there can be provided therein side wall contouring as in an oval depression OA featured in FIG. 6 with smooth sloping inwardly walls.

With further reference to FIG. 93, there is seen additional reference length values LR1 to LR5 (in addition to the aforementioned shorter length L2 and long reference rectangle length L1). LR1 is directed at the length of CP6 running between points P4 and P8; LR2 represents the length of CP8 running between P1 and P7. LR3 represents the length of CP7 running between the maximum depression points in respective surface portions 502 of corner-notch regions C1 and C4; LR4 represents the length of CP2 running between P2 and P6; LR5 represents the length of CP3 running between the maximum depression points in respective surface portions 502 of corner-notch regions C2 and C3; LR6 is directed at the length of CP4 running between points P3 and P7; LR2 represents the length of CP8 running between P1 and P7.

Length L1 is longer than length L2, with an example of suitable ratio "RA" values for the L2(shorter)/L1(longer) ratios being as described above for the various 500 series inclusive of the FIG. 93 embodiment 500C.

For instance, in the embodiment shown in FIG. 93 there can be provided a long length L1 of 26 mm and a short length of 20 mm, leading to a L2/L1 ratio RA of 0.76. With such dimensions suitable LR1 to LR6 values are 25.74 mm; 23.64 mm; 18.11 mm; 23.64 mm; 18.11 mm; 25.74 mm, respectively, with the matching values showing the bi-symmetry nature of the present invention as described above. Again, this is not intended to be limiting but only one example of many possible size and ratio arrangements depending on the intended environments (with some of those potential usage environments discussed above).

Figure 94:
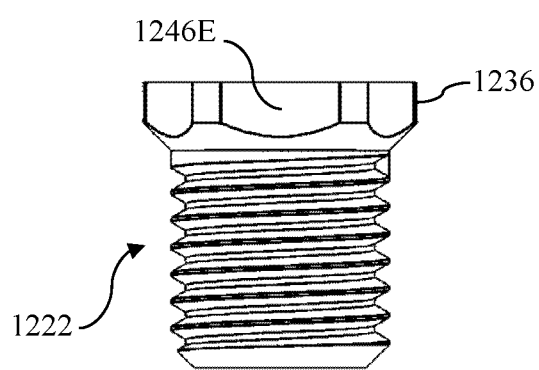
FIG. 94 shows an elevational view of a multi-tier fastener member having a torque enhancement female reception region at its center and an external torque enhancement exterior fastener head geometry suited for receipt in a female type driver as in a socket (i.e., a fastener member featuring radially or circumferentially separated torque enhancement surface configurations on a common plane (exterior—interior in this case)).
Figure 96:
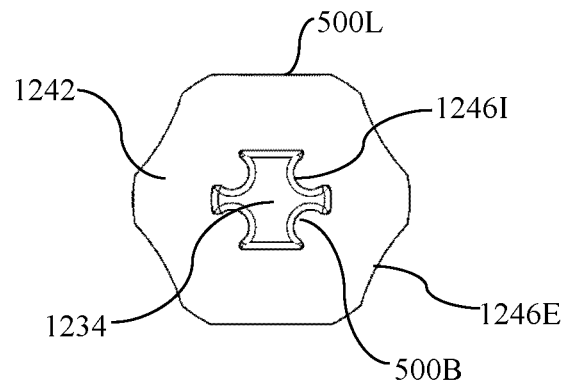
FIG. 96 shows a top plan view of that which is shown in FIG. 94.
Figure 102:
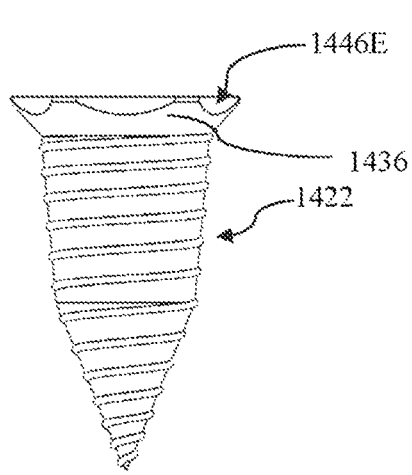
FIG. 102 shows an elevational view of another fastener member (tapered screw) having a torque enhancement female reception region at its center and an external torque enhancement exterior fastener head geometry suited for receipt in a female type driver, as in a socket; and thus providing a common horizontal plane (radially spaced) two tier torque enhancement fastener embodiment.
Figure 103:
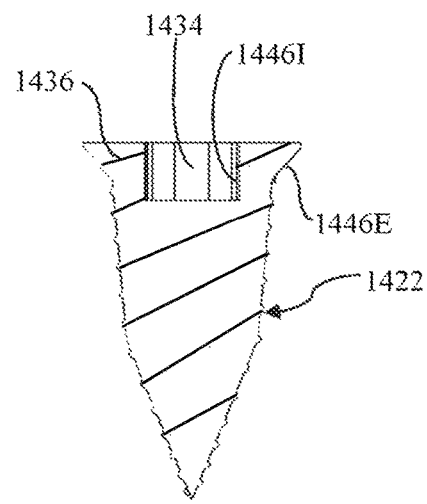
FIG. 103 shows a bi-sectional cross-sectional view of that which is shown in FIG. 102.
Figure 104:
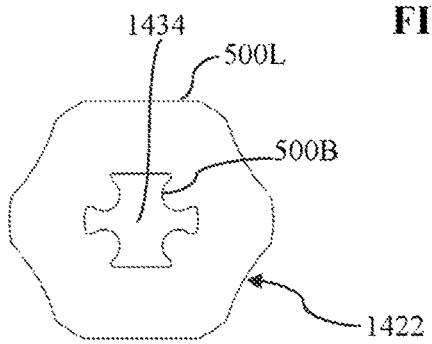
FIG. 104 shows a top plan view of that which is shown in FIG. 102.
Figure 105:
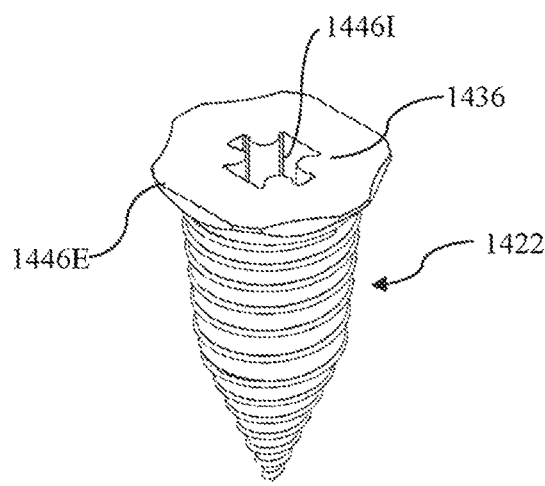
FIG. 105 shows a perspective view of that which is shown in FIG. 102.
Figure 106:
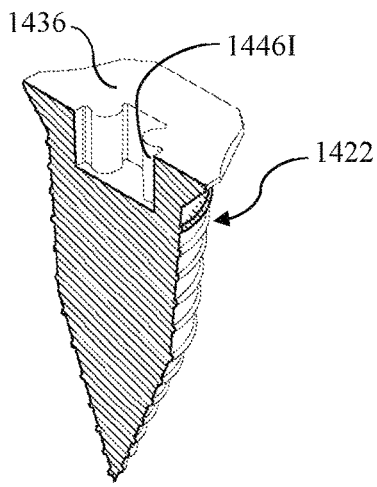
FIG. 106 shows perspective bi-sectional cross-sectional view of that which is shown in FIG. 102.
Figure 107:
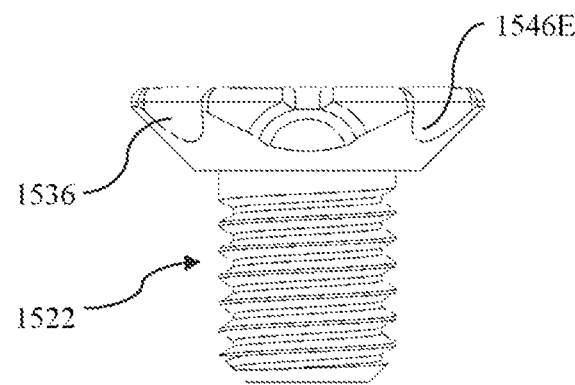
FIG. 107 shows an elevational view of another fastener member (bolt with countersinking head) having a torque enhancement female reception region at its center and an external torque enhancement exterior fastener head geometry suited for receipt in a female type driver as in a socket so as to provide another embodiment of a common horizontal plane two tier torque enhancement fastener embodiment.
Figure 108:
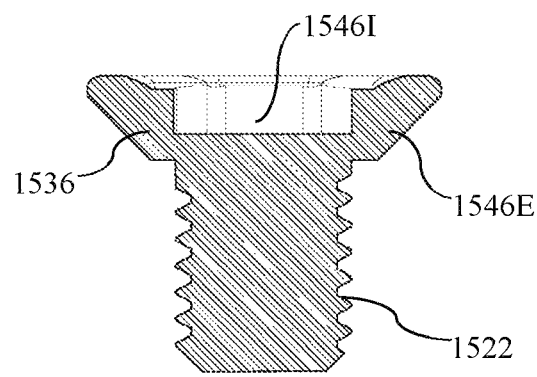
FIG. 108 shows a bi-sectional cross-sectional view of that which is shown in FIG. 107.
Figure 109:
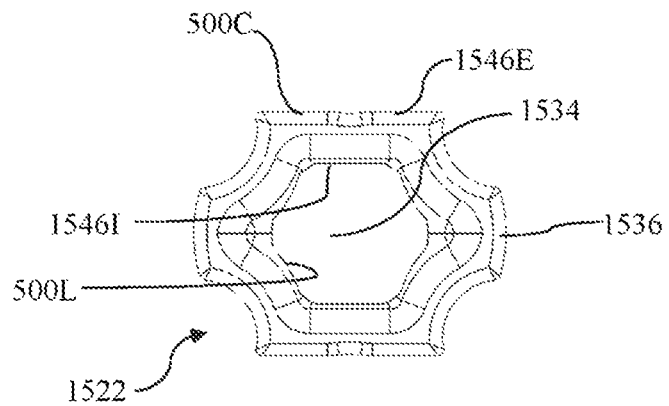
FIG. 109 shows a top plan view of that which is shown in FIG. 107.
Figure 110:
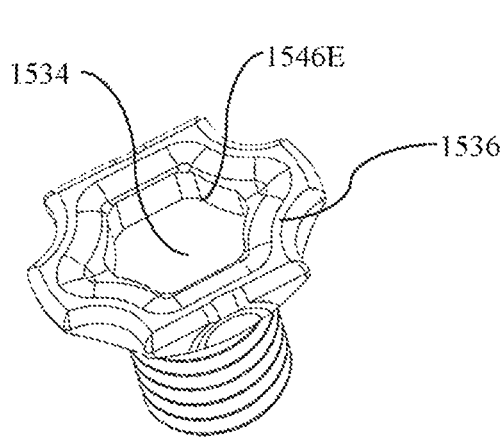
FIG. 110 shows a perspective view of that which is shown in FIG. 107.
Figure 111:
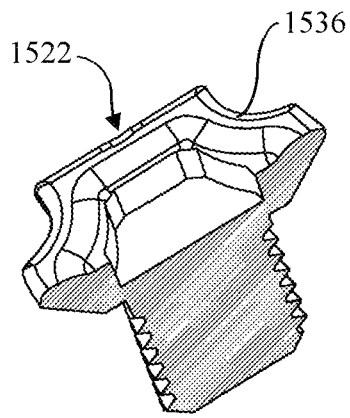
FIG. 111 shows a perspective bi-sectional cross-sectional view of that which is shown in FIG. 107.
Figure 112:
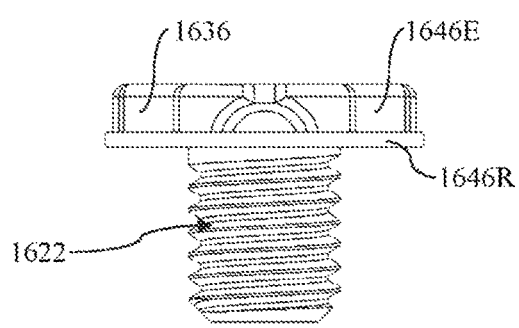
FIG. 112 shows an elevational view of another fastener member (bolt with post inclusion recessed head) having a torque enhancement female reception region in an interior region surrounding a central post, and an external torque enhancement exterior fastener head geometry suited for receipt in a female type driver as in a socket so as to provide another embodiment of a common horizontal plane two tier torque enhancement fastener embodiment.
Figure 113:
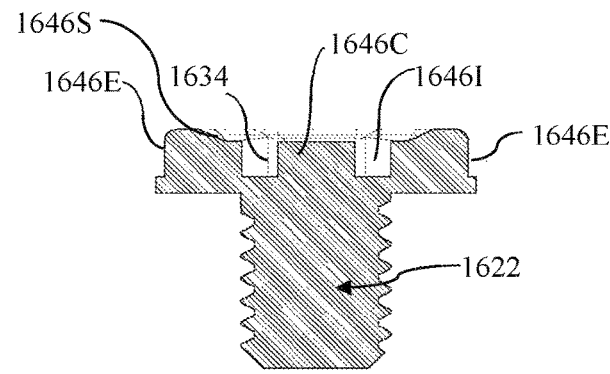
FIG. 113 shows a bi-sectional cross-sectional view of that which is shown in FIG. 112.
Figure 114:
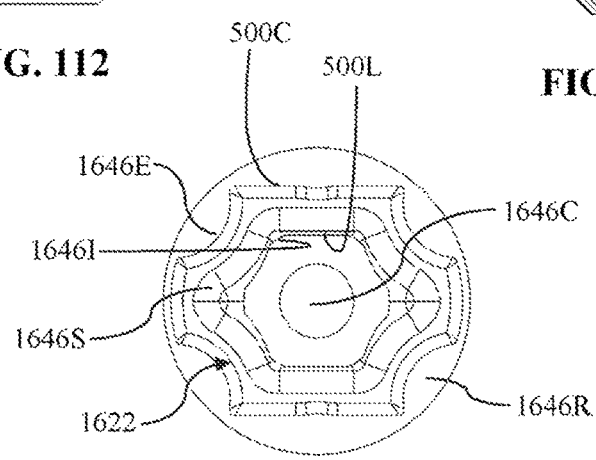
FIG. 114 shows a top plan view of that which is shown in FIG. 112.
Figure 115:
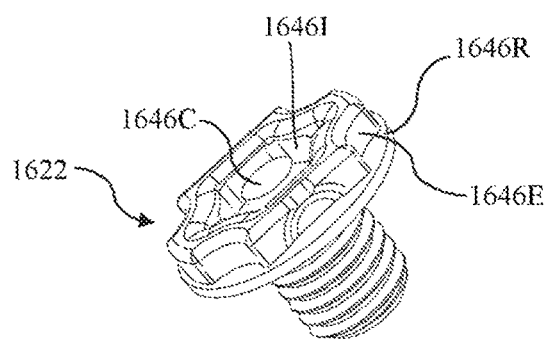
FIG. 115 shows a perspective view of that which is shown in FIG. 112.
Figure 116:
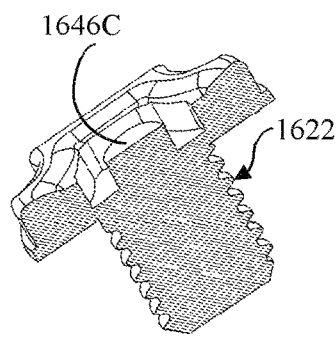

FIGS. 94 and 96 illustrate an additional embodiment of a recessed retainer 1222, which in this embodiment features both an interior geometrically contoured ring 1246I formed within female reception recess 1234 and an exterior contoured ring 1246E formed in the peripheral exterior of head body 1236 of the fastener representing recessed retainer 1222. Thus, FIGS. 94 and 96 show an additional example of a multi-tier (two tier in this embodiment) that features two different and independent torque generating surfaces 1246I and 1246E, which in this embodiment fall on a common X-Y axes plane, but can also be Z-axis separated as in having the exterior configuration present not at the top of the fastener shown, but in an intermediate region (e.g., wherein the threaded region can be placed below that intermediate location and a smooth shank surface above and leading to an upper head member having torque enhancement recess surface 1246I).

Figure 95:
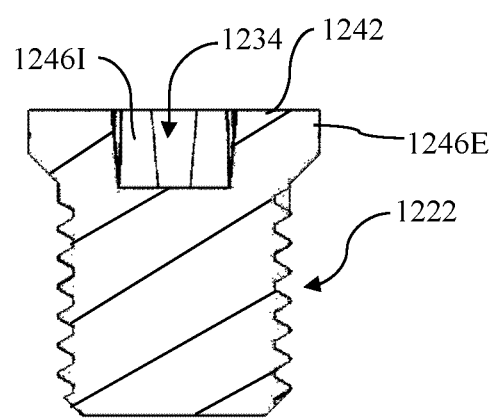
FIG. 95 shows a bi-sectional cross-sectional view of that which is shown in FIG. 94.

In FIG. 95, head body 1236 is shown in the vertical cut away view to include upper surface 1242 (with its peripheral outer edge having the torque enhancement configuration assumed by the exterior contour ring 1246E). In the embodiment featured in FIGS. 94 to 96 there can be seen that there is featured both of the interior and exterior geometrically contoured rings 1246I and 1246E having a torque enhancement configuration (with the exterior radially or circumferentially larger than the interior). As shown in this FIG. 96 embodiment the inside/outside multi-tier embodiment has two different torque enhancement geometries, with one (the interior one in this instance) having a first torque enhancement configuration (e.g., 500C) and a second one (the exterior one in this instance) another (e.g., 500L). Alternatively, one of the two of the interior/exterior geometries can be of a conventional configuration like that described above such as a hex shape, and the other of a torque enhancement configuration (as in any one of the torque enhancement configurations described herein in as in one of 500L or 500C configurations. to name a few).

In the illustrated embodiment of FIG. 94 each of the interior and exterior geometrically contoured rings 1264I and 1246E is suited for engagement with a suitably configured, respective, individual driver, or a single driver with two driver engagement means as in a torque enhancement male driver depression-projection ring set relative to interior and exterior rings 1246I and 1246E. An example of an exterior only driver includes a suitably configured driver with its own female contoured ring designed for mesh engagement with exterior ring 1246E of fastener 1222 (inclusive of, for example, open wrench or socket like arrangements), while an interior only driver can be a male-projection such as the above described distal projections (e.g., 548, FIG. 53) designed for insertion into recess 1234. In this way, there can be achieved different torque generation levels as in the interior ring 1246I being not able to generate as much torque as a driver meshed with exterior ring 1246E, but with a male driver insertion into interior ring 1246I being more rapidly possible as with an assembly line initial fastening of fastener 1222. As an example of a single, common driver (not shown but potentially having, in combination, an exterior socket like wall and an interior driver head type driver having a shape similar to distal driver 548, for example, can be utilized). Still further, in the embodiment shown in FIG. 95, both the interior and exterior rings have peripheral sidewalls that extend parallel to the longitudinal axis of the extended threaded fastener extension 1223 illustrated. Alternate embodiments include providing non-parallel walls (e.g., the interior recess 1246I or ring 1246E having tapering sidewalls, etc.).

In this regard, reference is made to FIGS. 97 to 100 showing an additional multi-tier recessed retainer 1322 (with a pair of axially spaced, independent torque enhancement surface configurations). As seen, recessed retainer 1322 is shown again in the form of a threaded fastener, although the alternate torque enhancement devices are also featured as in the noted gears (e.g., removal of threaded portion with retention of the upper body as in a pulley roller with recessed body exterior and the same 1346 reception recess shown, etc.). Fastener 1322 features head 1336 with interior ring 1346 of torque enhancement configuration, which is formed with two different axially spaced torque meshing geometries inclusive of a deeper, narrower stage 1346L which opens up into upper section 1346U. Each of the upper and lower stages 1346U and 1346L is shown having a different taper configuration with the upper one having minor or generally vertically (or no taper) extending side walls, and the lower one with a more tapering (converging inward down) side wall configuration, although alternate embodiments feature each having non-tapered walls or one of each of stages 1346U and 1346L having inwardly/downwardly converging tapered walls (e.g., those having a taper to preferably coincide with a tapered driver of torque enhancement design or an alternate design as in "Phillips" configuration with a taper of an acute angle relative to the vertical section for each (or just one of the two axially separated regions 1346U and 1346L); with the other being a different acute angle within the noted range or 0 degrees for a vertical wall)). The above fastener thus features an abutting shelf 1346S well suited for proper placement of a correspondingly configured driver, wherein the driver distal tip is properly placed in a lower compression setting at the base 1346B of fastener 1322. This embodiment thus features two sets of tiers including a two axially separated tier (both internal recesses) 1346 arrangement, although it is also possible to feature a conventional (non-torque enhancement) and torque enhancement mix, as in having the deeper recess with a hexagonal, Phillips™, Torx®, etc. configuration, and the less deep recess a torque enhancement configuration or the reverse as in having the deepest with a torque enhancing configuration and having a conventional configuration like that noted above.

FIGS. 102 to 106 illustrate an additional embodiment of an inside/outside ring recessed retainer 1422 which is in the form of a tapered screw that features an upper head 1436 having interior contoured ring 1446I and exterior contoured ring 1446E. Interior contoured ring 1446I has a vertical walled cavity 1436 that includes the torque enhancement configuration as in torque enhancer 500B contouring (with, for example, a L2/L1 ratio such as that described above for the 500B series). Additionally, exterior contoured ring 1446E is also shown with a torque enhancement configuration (shown as different 500 series configuration 500L, but optionally matching that of the interior). The FIG. 104 arrangement illustrated features torque enhancement surface 1446E having a 500 series configuration that has a closer to a square configuration than that of the interior 1446I torque enhancement surface configuration described above; although, as in the earlier embodiments, either one of the interior and exterior rings can have a common torque enhancement contour configuration, or various combinations amongst the potential 500 series options are available as in the higher (closer to square) RA ratio value can be internal and the lower RA ratio value external, or one of the two can be a conventional configuration like those described above).

Also, in the illustrated embodiment head 1436, with its exterior contour ring 1446E, has a sloping exterior wall configuration (as in a screw head taper better suited for flush (e.g., wood penetration) surface insertion). The fastener 1422 is also shown to be a tapered thread screw illustrating the versatility of the present invention.

FIGS. 107 to 111 illustrate an additional embodiment of multi-tier (inside/outside rings or torque enhancement surface configurations) recessed retainer 1522 which is in the form of a bolt that features an upper head 1536 having interior contoured ring 1546I and exterior contoured ring 1546E. Interior contoured ring 1546I has a vertical walled cavity 1534 that includes the torque enhancement configuration as in torque enhancer 500L contouring. Additionally exterior contoured ring 1546E also has a torque enhancement configuration such as the noted torque enhancement 500C configuration (i.e., as illustrated both tiers are shown with different respective contour rings of 500L and 500C; although, like the earlier described interior/exterior embodiments each of the interior and exterior rings can have a common (different circumferentially sized) torque contour configuration or one of the two can be a conventional configuration like those described above or the relative RA ratio values can be switched as in 500L external and 500C internal). Also, in the illustrated embodiment head 1536 with its exterior contour ring 1546E has a sloping peripheral wall configuration (as in a bolt head taper better suited for flush surface insertion as when a nut fastener is tightened down on an intermediate object so the head 1536 digs in on the taper while also providing a degree of locking provided by concavities and edging in exterior ring 1546E). This digging into a surface of the exterior contour ring with the torque enhancement configuration is considered to represent an addition advantage associated with the torque enhancement feature, in that the different ratio side walls will hold better (better anti-torque rotation bite into the material) against vibrations and the like.

FIGS. 112 to 116 illustrate an additional embodiment of a multi-tier (inside/outside ring) recessed retainer 1622 which is in the form of a bolt that features an upper head 1636 having interior contoured ring 1646I and exterior contoured ring 1646E. Contoured ring 1646I has a vertical walled cavity 1634 that includes the torque enhancement configuration as in torque enhancer 500L contouring, while the exterior one has a lower ratio contour ring such as a 500B or 500C series (less square presentment) configuration, although different ring ratio combinations, like the options described above, inclusive of common L2/L1 ratios in each of the interior and exterior torque enhancement surfaces shown are available). Moreover, interior contoured ring 1646I surrounds central post (cylindrical with circular diameter in this embodiment). The smooth cylinder post facilitates central axial alignment of a correspondingly designed received driver while the meshed torque enhanced engagement is utilized.

As noted, relative to interior ring 1646I, exterior contoured ring 1646E has a less square or smaller L2/L1 ratio (as well as a smaller LS/LL ratio) in its torque enhancement configuration, and thus provides a large torque potential particularly for removal as when the lower ring skirt 1646R bonds with an underlying connection surface (e.g., a rust or adhesive bonding) all while being properly stabilized and having added interior torque generation made available by the central post and torque enhancement interior ring 1646I (and like the earlier embodiment either one of the interior and exterior rings each can have a common contour configuration or one of the two can be a conventional configuration like those described above or there can be a reverse L2/L1 ratio torque enhancement configuration arrangement). Also, in the illustrated embodiment head 1636 features ledging with an inwardly tapering step-down 1646S that bridges the exterior of head 1636 and the shown vertically aligned interior torque enhancement configured mesh geometry 1646I. This stepped down ledge or bridge region helps in aligning a driver with the central axis of post 1646C when there is initiated driver initial engagement. Suitable socket configurations (not shown) can also provide for simultaneous engagement of both the interior and exterior configurations which makes available even higher potential torque applications. The noted socket (not shown) can also include a recess designed for centering with the post 1646C.

Figures 117A, 117B, 117C:
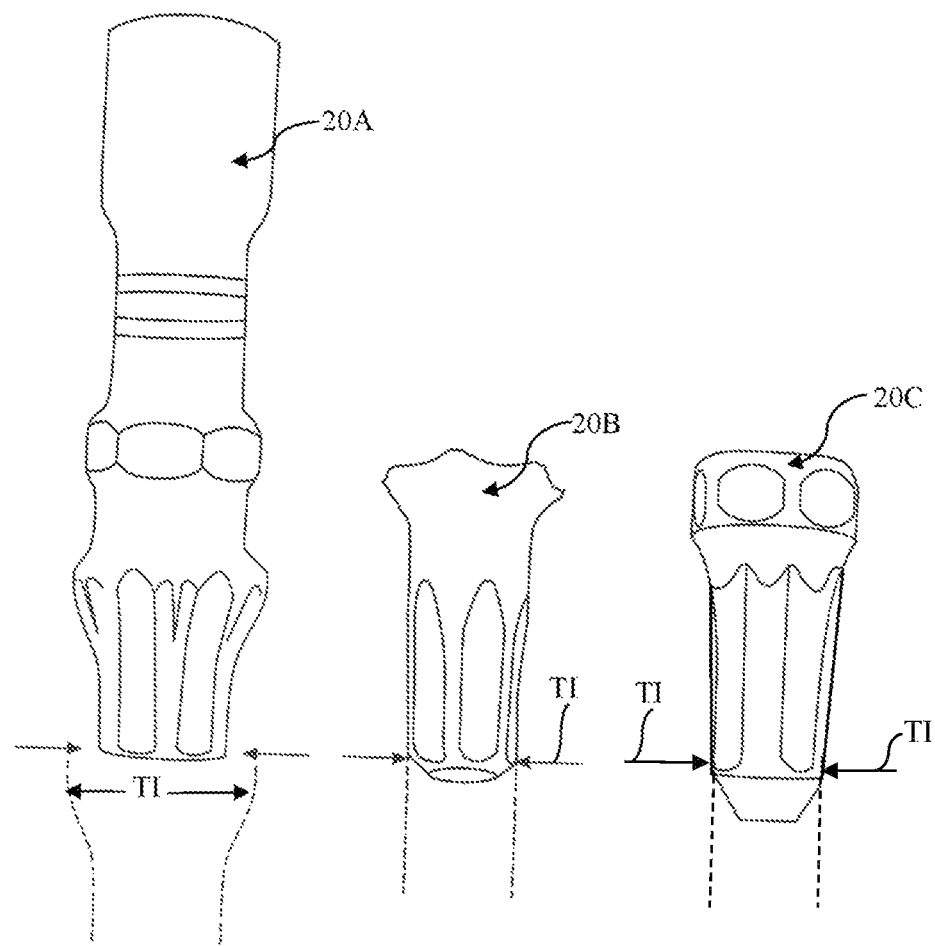
Figures 117D, 117E:
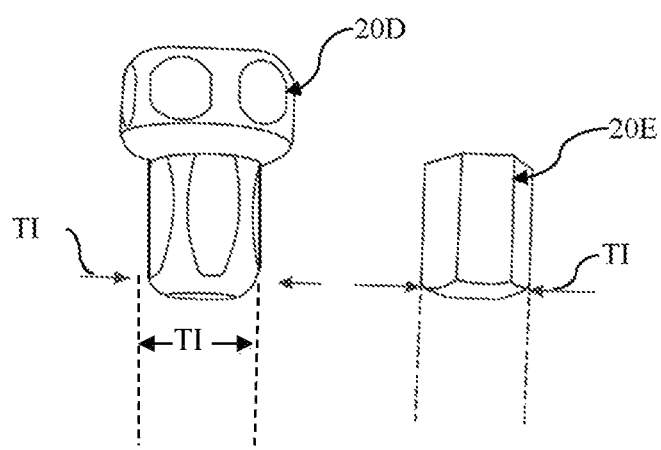

FIGS. 117A to 117E present a side-by-side view of both conventional and present invention embodiments. As seen FIGS. 117A and 117B show examples of TORX® drivers (20A and 20B) with FIG. 117A showing a TORX T25® driver, and FIG. 117B showing a TORX T25® driver (in partial cut-away). FIGS. 117C and 117D show two axial tier examples of drivers under the present invention (20C and 20D), while FIG. 117E shows a standard hex ended driver (20E).

To help in the comparison consideration, there is demarcated the maximum thickness TI of the driver portion of each driver by way of the dashed lines in FIGS. 117A to 117E, which are all similar but with the present invention embodiments having the below noted differences.

That is, if the value X is the standard maximum thickness TI for each embodiment, the longer length wall region of the torque enhancer is provided with X while the shorter side region has a length less than X based on the desired ratio of L2/L1 (e.g., see FIG. 1). For instance, if X is 4 mm, and the desired offset ratio under the present invention is 94%, then TI can be 4 mm while the shorter length wall region can be 3.78 mm to provide the desired offset. Further, as the 4 mm setting is often provided with a degree of gap tolerance, under the present invention the longer length region can exceed the 4 mm value (or equivalent TI value) in accordance with that gap tolerance. As an example, rather than 4 mm the longer length side region of the torque enhancer can be 4.02 mm and still fit and also provide even a more advanced potential for catching when there is a stripping in the receiving female recipient recess, inclusive of a conventional design that can receive the shape of the present invention such as those described herein (e.g., a hex cavity device).

Figures 118A, 118B, 118C, 118D, 118E:
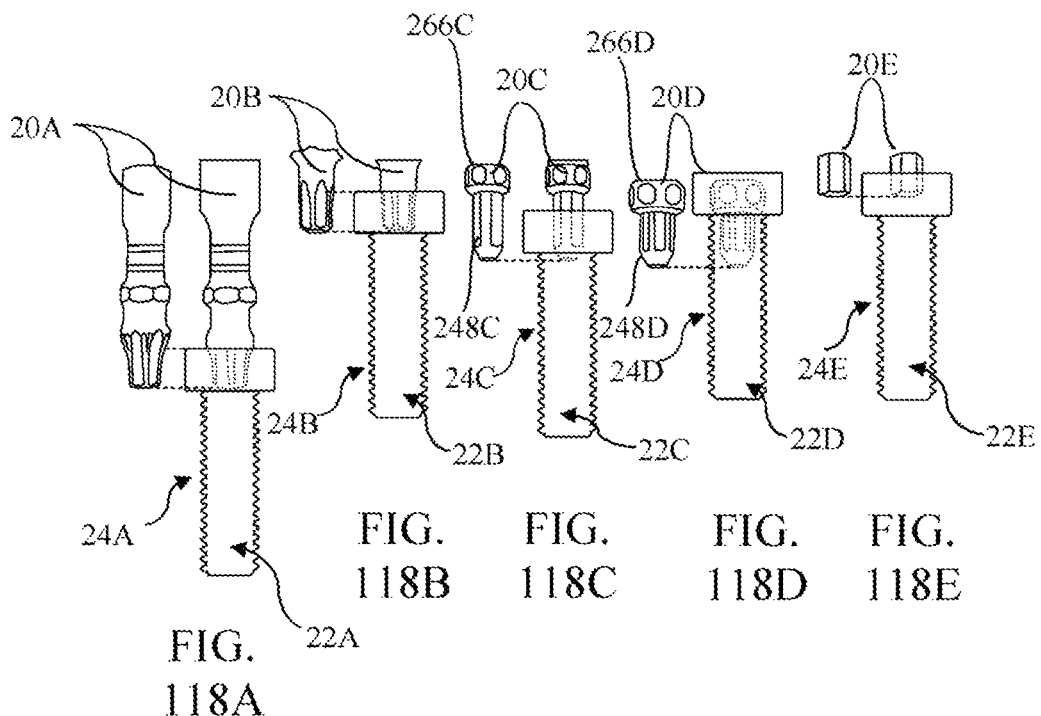

FIGS. 118A to 118E show the same drivers as featured in FIG. 117A to 117E, respectively but in combination form (24A to 24E) with a receiving recessed recipient (represented by 22A to 22E, respectively, and having geometries coordinated with the driver type to be inserted. Thus, FIGS. 118A to 118E illustrate a variety of different driver/fastener combinations as representing by the corresponding combinations 24A to 24E. FIGS. 118A, 118B and 118E also show some of the typical depths relationships featured in the prior art as well as two examples (FIGS. 118C and 118D) for the present invention. As seen in FIG. 118C there is featured a two tier driver 20C having an elongated distal projection 248C of the longer version that is shown in one potential use with only the one tier (the distal one) being utilized per the design of the fastener head of retainer 22C. Thus, in FIG. 118C there is shown an example of one tier operation with the fastener head designed for receipt of only the distal projection. However, with the appropriate depth fastener head recess there can be utilized both of a two axial tier driver with an example shown in FIG. 118D relative to a shorter distally extended elongated projection 248D shown meshed together with the circumferentially larger torque engagement ring 266D (noting ring 266C also being a potential engager with appropriate recessed head).

That is, FIG. 118D shows two tier driver 20D having both of its torque enhancement tiers in simultaneous engagement as made available by the relative dimensions of the driver (e.g., distal projection 248D being of a shorter or stubbier version as compared to distal projection 248C in driver 20C, while the bulbous torque enhancement section 266C is also in meshing engagement with a correspondingly configured reception recess (extending within both the head region and partially within the threaded shaft portion of the fastener shown).

FIGS. 119A to 119E show a similar comparison with that shown in FIGS. 117A to 117E but for variations illustrated for the present invention two tier (axial separation) torque enhancer drivers 20CZ and 20DZ. That is, all features of drivers 20CZ and 20DZ correspond with respective counterpart drivers 20C and 20D, but for there being curved contouring in the side walls of the distal projection portion in each. That is, in FIG. 119C the driver 20CZ features a beveled inward wall in its distal projection portion 248CZ such that there is an annular concave taper in the side walls of the exterior periphery of distal projection 248DZ with the beveled nature provided by such concave contouring providing a narrowing peripheral cross-section with thickness TI being at the narrower end (noting also there is the distal most tapered regions in FIGS. 119C and 119D that can be replaced with a distal most flat section instead (not shown in this figure set)). Also, the drivers shown in FIGS. 119C and 119D (like there 117C and 117D counterparts) are shown in cut-away fashion with the more proximal portions of each not shown (as in a hand grip or mechanical engagement shaft like those described above), although in alternate embodiment of the invention, the depictions featured in FIGS. 117C, 117D and 119C and 119D can be representative of the complete driver component, as in an adapter having a proximal most portion provided with a recess or the exterior contouring itself for receipt of a male driver of female socket extension or the like (not shown) or in the case of FIGS. 117C and 117D a socket suited for the proximal tier with projection set 226C can be placed thereover for driving of the distal projection 248CZ, for example. The adapter 20D can be used to bridge two different driving configurations as in having the distal end 248D being a torque enhancement configuration (as well as bulbous ring 266D) and a receiving recess provided in the adapter top head (not shown) being a conventional configuration as in one of the above noted conventional configurations. The reverse is also an example under the present invention wherein the distal end can be conventional and the recess (not shown) a torque enhancement configuration for receipt of a torque enhancement driver such as one of the ones described herein. Similarly, component 20C can represent an adapter like that described in this paragraph with similar features and alternate embodiment potentials as described for 20D.

Figures 119A, 119B, 119C, 119D, 119E:
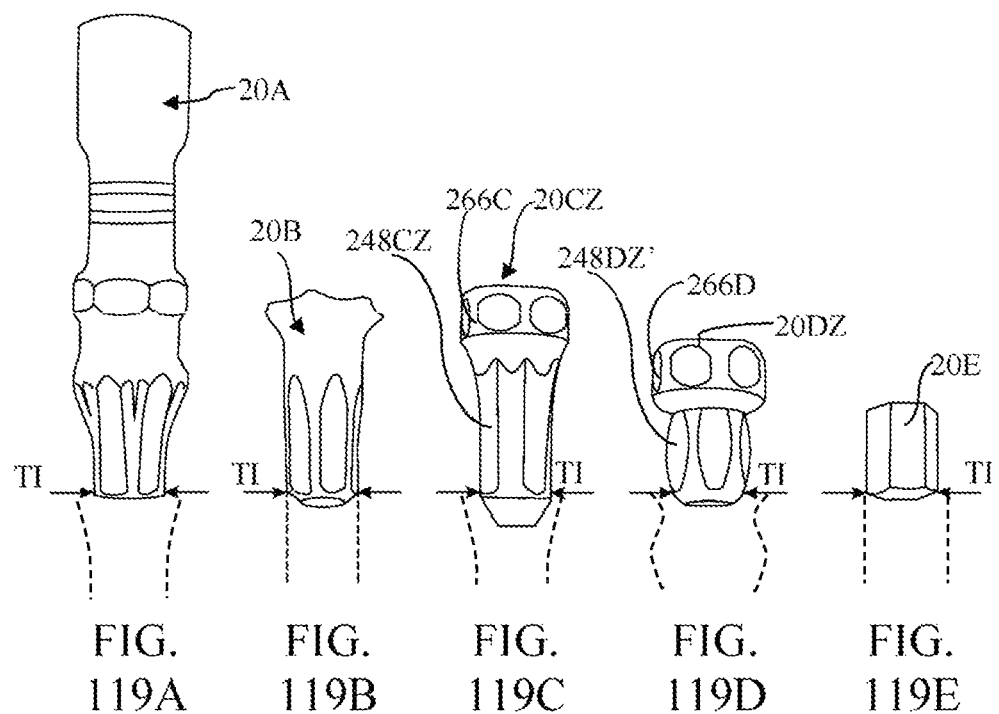

The contouring in FIG. 119D is opposite to that of 119C in that rather than an exterior concave or beveled narrowing there is an annular convex contour or a slight bulbous intermediate portion provided, which can represent the maximum thickness TI value as in the aforementioned 4.02 mm comparison to TI values of 4.0 mm for the standard driver heads (and with the smaller 3.78 being applicable to the shorter range walls providing the aforementioned L2/L1 ratio).

The discussion above describes various embodiments with, for instance, 500 series L2/L1 ratio values that are illustrative of some of the torque enhancement values featured under the present invention. For instance, FIGS. 1-5 are shown with 500B contouring; FIGS. 6-70 and 87-92 are inclusive of 500L contouring; FIGS. 71 to 86 and 93 500C contouring; while FIGS. 94 to 116 include 500 series contour combinations (as in 500B and 500L combinations). These 500 series are illustrative of preferred 500 series values for the noted torque enhancement devices, although the present invention includes variations of such surface contouring relative to the different drivers and recess recipient described and illustrated, including a switch out of any of the various 500 series torque enhancement configurations amongst that shown and described to suit an environment envisioned and preferably having the L2/L1 ranges noted.

FIG. 120 shows an alternate embodiment torque enhancement member 500H that is similar to that featured in FIG. 3A, but for the inclusions of notches in its side walls. Thus, commonly situated features are similarly referenced, but for the added referencing of the pair of notches 542A and 542B provided on one of the longer walls and shown equally spaced in from the corner recesses C1 and C2 (and closer to the center of the long walls than respective closest-to-corner recess ends of the long walls). With the bi-symmetry there can be seen similarly situated notches 544A and 544B on the opposite long wall. While not shown, one or more notches can be provided on the short walls as to have notches on all four walls, or, alternatively one or more notches can be provided on only the shorter wall set (not shown) or all side walls can be free of notches. The inclusion of notches does provide, when present, alternate force configurations and can facilitate having tight spiral force arrangements even during higher RPM usage as described above relative to FIGS. 5B and 5C in that there is provided altered centripetal-centrifugal and surface friction and compression contact points with some having greater tangential catch force vectoring as when a side wall of a notch is engaged with a driver.

Figure 121:
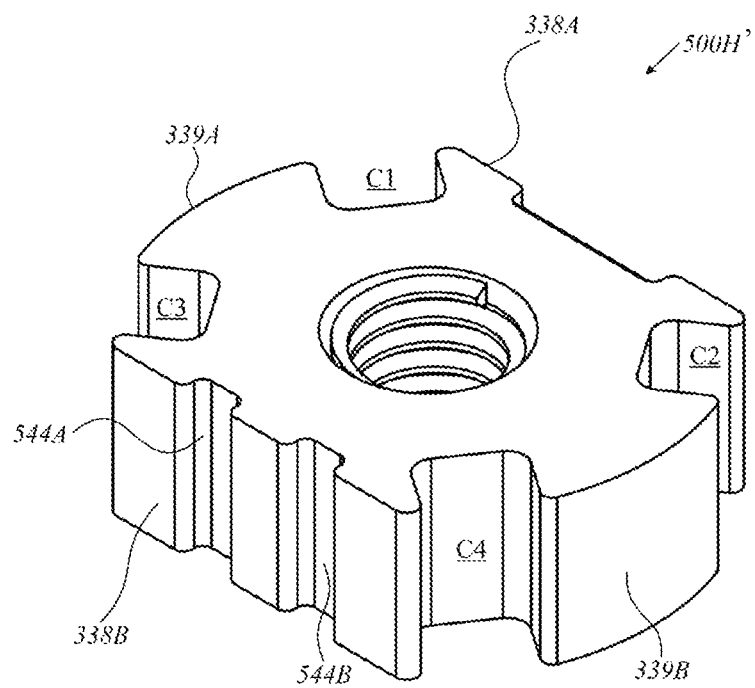

Alternatively, the torque enhancement device (500H') can have one of a pair of the long side walls with different notching than that in FIG. 120, as in a pair similar to that shown in FIG. 120 on one of the two long side walls, but on the opposite side a single, longer length notch extending along the central region of the long side wall. Suitable driver meshing configurations (or reception recess if FIG. 121 is representative of a driver rather than a reception recess device) can also be provided such that the point of contact of a meshing driver can be increased and such that if an end point of one of the longer walls gets sheared off, a notch mesh can still provide for rotation in a desired direction (with the points of contact reduced relative to a singular central notch as opposed to an opposite pair of notches). In addition, or alternatively, there can be different notch relationships on the short side (one central notch on one short side and two spaced notches on the other short side). The providing of different respective notch configurations can be utilized in precision torque/rotation relationships where a location of a different configured notch can be monitored, as by a visual sensor as to facilitate achieving a desired torque level before disengagement of the combination of driver and recipient.

Figures 122, 123:
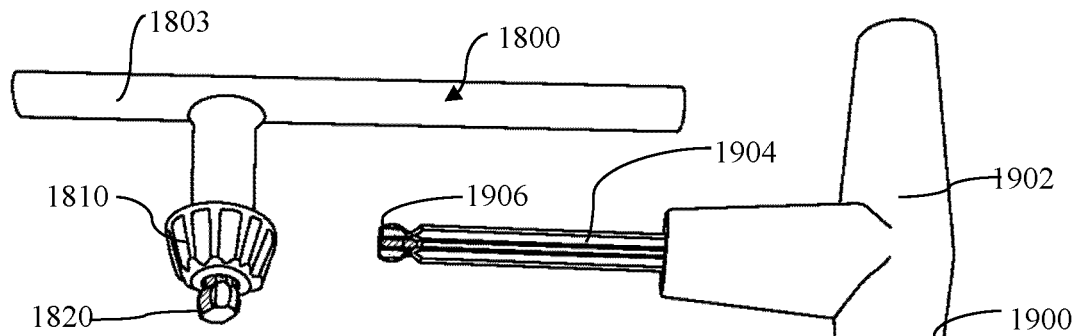

FIG. 122 shows an additional embodiment of the present invention featuring a two-tier/two-different driver form (gear and torque enhancement fastener driver head) combination. That is, FIG. 122 shows a "collapsible chuck" tightening tool or key such as used with a drill driver (e.g., hand drill or drill press) that is an example of a two tier torque engagement tool (with the tiers falling into two different function categories as well (gear/insertable driver head)) with the bevel gear 1810 shown suited for collapsible chuck ring tightening (gear meshing with a circumferential gear to expand and collapse a set of chuck prongs) and supported on support 1830, together with an added torque enhancement bulbous end 1820 at the end of gear post 1840 and suited for torque generation in an associated reception recess (and yet can also function as a post for receipt within the pilot hole of the drill chuck as the bevel gear works to either open or close the collapsible prongs used to engage an inserted shank of drill bit or the like).

An aspect of the present inventions also features the aforementioned driver configurations as being a driver having a hand support as in a grip handle (e.g., a generally overall cylindrical handle grip, a T-shaped handle grip, or a common housing with pivoting tooling support(s) (as in a Swiss Knife® housing configuration). FIG. 123 shows an example of a T-shaped handle tool 1900 with T-shaped handle 1902 and associated torque enhancement bulbous head 1906 and support shank 1904 (also shown with a common torque enhancement configuration as the bulbous head). Further, FIG. 124 shows an example of a multi-tool device 1908 with housing 1910 that is shown receiving in different end pivot point fashion a plurality of individual drivers 1912A, 1912B and 1912C (each having a common general configuration as the above shank and bulbous head shown in the T-shaped handle tool 1900 (but preferably of different sizes to provide a versatile multi-tool set)).

Figure 37:
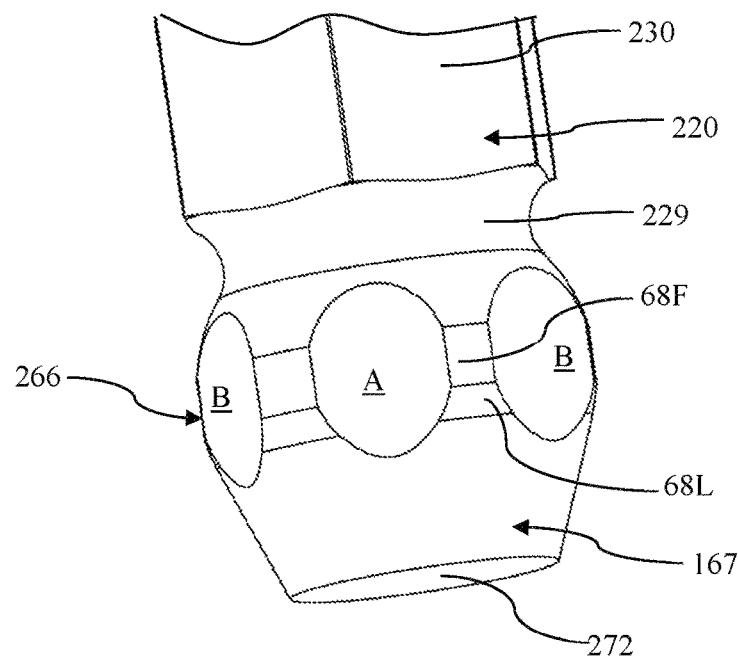
FIG. 37 shows a close up view of the distal end of the driver of FIG. 36.

With reference to FIG. 125 to FIG. 128 there can be seen a driver and combination similar to that shown in FIGS. 37 and 38 respectively, but for a "long neck" variation of the driver. That is, as seen in FIG. 125, driver 1220 has a similarly peripherally shaped shank (for hand or higher RPM driving means) as the FIG. 37 embodiment, but longer neck 1228 leading down to the rounded section 1229 bordering the bulbous driver head portion 1266 (having the same torque enhancement configuration as described relative to FIG. 37).

FIG. 126 shows an early initial insertion state (or an almost fully withdrawn state) of the driver 1220 within a receiving recess 234 of a similar reception recess 222 as that featured in FIG. 38.

FIG. 127 shows an initial contact state of driver 1220 within the receiving recess 234 of reception recess 222 (having the same attributes as reception recess in FIG. 38 although optionally having a cylindrical smooth recess or textured (see below further texture discussion) across zones Z4 and ZR5, with zone Z5 retained for torque enhancement drive meshing with bulbous driver 1226 of driver 1220. In this initial contact state there can further be seen tapered frusto-conical section 1268 helping in making initial and alignment adjustments (less vertical AE2 orientation to a more vertical AE2 orientation) during this stage of insertion (or removal). This reorientation of driver central axis AE1 from a state of being less vertical or less aligned with the central recess axis AE2, to one more vertical or more aligned therewith is seen in a comparison of FIGS. 126 and 127. As further seen in the comparison of FIGS. 126 and 127, the long neck facilitates the insertion viewing as well as the realignment involved when a driver head is not perfectly aligned at the time of initial assertion or when the driver is being pulled away (by hand or relative to a driver tool including a robotic support arm driver attachment, or other driving means).

FIG. 128 shows a fully engaged and in meshing relationship state relative to the driver 1220 and recessed recipient 222. Thus, bulbous driver head with its torque enhancement configuration is in mesh engagement with (a preferably similarly configured torque enhancement configuration) recess 234 surface configuration 246 in the engagement zone Z5 shown. Also with the full engagement relationship shown in FIG. 128, there can be further seen an alignment of axes AE1 (driver) and AE2 (central axis of the recess 234 of recess recipient 222). Further, recess level line RL shown in FIG. 128 for the combination 1224 and the driver alone in FIG. 125 illustrates the smooth concave curvature above the bulbous driver head which is heavily involved in the initial contact with the recess recipient during, for example, the noted initial stage of insertion or during various stages of removal.

FIG. 129 shows a similar initial combination view like that in FIG. 126 for the same driver but with a modified reception recess which has an upper (upper most in this instance) capture rim 1223 which extends entirely around the proximal top of recess 1234 (or can be a set of protrusions forming a similar annular ring, but with spacing between the protrusions, with the protrusions preferably representing a greater area than the in-between cavities). Capture rim 1223 can be a portion of a monolithic reception recess as to have the same material or an integrated rim as in one of lesser friction coefficient for easier sliding as in a low friction material. Rim 1223 is further shown in this embodiment as having a convex configuration extending inward of the recess and preferably defines an interior circle with a diameter less than the maximum circumference associated with the outermost wall periphery of ring 1266. Preferably the diameter differential is minimal to achieve the desired axial capture engagement, but not make it too difficult for tilted insertion or removal. Thus, absent added features such as the diametrically opposite less rim thickness described below, there is required some degree of angling during initial insertion (or final removal) wherein one side of the bulbous driver head drops below (or raises above during removal) the recess level RL (FIG. 128) as to enable the contoured bulbous head to have its opposite side drop in upon reorientation to a less angled state (or fully release). The L2/L1 ratio differential can also facilitate the relative insertion despite the capture diameter dynamics. Moreover, to facilitate that initial assertion the capture ring can be provided with less radial inward extending portion(s) as in one or more pairs of diametrically opposed, less radial inward extending portions that are designed to receive the L1 spaced torque enhancement driver surfaces in key like fashion prior to the final depth meshing with the C-mesh locations in the zone Z5 that are preferably key-like circumferentially offset from the noted less radially extending portions.

Once dropped into the cavity, the bulbous head can be captured due to the noted outer driver and inner capture ring sizing. This facilitates retaining the driver during driving states inclusive of hand manipulation or higher RPM driving, in that there is avoided a complete disengagement during such a time period to facilitate any reinsertion that might be needed as with difficult access locations where it is difficult to maintain drive engagement (and where in the prior art magnetic attraction may be attempted as a solution), camming out or driver head inadvertent adjustment, inadvertent pull up and separation which can be common particularly in hand driver working, etc. This capture ring capturing of the driver head under the present invention can take the place of prior art magnetic driver connection retention means which magnetic usage can be problematic in some uses where magnetic fields are not desirable in the area as in some electronic environments.

FIG. 130 shows an alternate combination 1924 sharing many similarities with that shown in FIG. 80 (including a common driver 920) but features a different reception recess 1322 that has (instead of the tapered down proximal rim region 945) a proximal capture ring or edge 1336A which is shown formed by having a generally similar concave contoured cross-section extending inward at level RL of the recess to an extent that defines a capture rim that has a smaller diameter than the maximum diameter of the bulbous driver head 966 of driver 920. Thus, the capture rim is shown as generally having a sharp edge. Also, although driver 1924 is shown as a portion of the FIG. 80 "Allan" like configured driver, it can instead have some other driver configuration as in a shank like that in FIG. 125 rendering it RPM driver engage-able (e.g., chuck engaged) or still hand tool engage-able. As with the above embodiments, instead of a full circumference capture ring and minimum diameter differential as to enable a tilt insertion, the capture ring shown can be a representation of the maximum radially inward extending diameter area of the capture ring, with less radially inward extending regions at other location(s) as to facilitate such initial assertion followed preferably by the noted key C-mesh circumferential shift by the time of full torque drive meshing contact.

FIG. 131 shows still another alternate combination 1924B sharing many similarities with that shown in FIG. 80 and FIG. 130 (including a common driver 920), but features a different reception recess 1322B that has (instead of the only tapered down proximal rim region 945 or the sharp edge proximal capture ring 1336A) a combination smooth contoured convex rim 1336B that has a proximal downward and inward sloping section, an intermediate rim limit defining portion, and a distal downward and outward sloping section. Also, the capture rim is shown as having its intermediate capture rim limit defining portion below RA of the reception recess 1322B. Also, the relative capture relationship between the bulbous head 966 in the noted limiting intermediate portion is present here as in the above embodiments (involving a tilt insertion and removal which is facilitated by the proximal and distal portions of the convex rim shape). Also, although shown as a portion of the FIG. 80 "Allan" like configured driver, the driver can have other configuration as in shank like that in FIG. 125 rendering the driver in FIG. 131 RPM driver (e.g., chuck) engage-able or still hand tool engage-able. Further, the key slot provisions in the capture rim described above are also featured for this embodiment (e.g., see the dashed lines DL in FIG. 131 illustrating possible diametrically opposed gaps in the capture rim).

The above described capture rims embodiments share similarities with, for example, those presented in FIGS. 189A to 189C in the incorporated US Publication 2018/0235776, in the mutual providing of a means for axial blockage of a driver relative to the recipient of that driver, although in the above capture rim there is the potential for blockage in both a push and pull axial direction as opposed to the push only axial blockage (one from both sides potentially) featured in the FIGS. 189A to 189C noted embodiments.

FIG. 132 shows a modified driver embodiment in vertical orientation and having textured surfacing at a distal region of the driver. That is, in FIG. 132 there is shown driver 1420 which is similar to those drivers such as driver 20 shown in FIG. 14, but for a modified distal portion that extends away from the contoured, bulbous torque enhancement driver ring 1466. Thus, driver 1420 has shank 1430, intermediate axial extending neck 1428, ring 1429, the noted torque enhancement driver ring 1466, distal smooth taper portion 1468 which leads to curved or frusto-conical further tapering surface 1469; and, at the distal most end, multi-sided distal surfacing 1471 (approximating a circle but showing individual peripheral straight walls) and flat bottom 1470.

Additionally, within the tapering surface 1469 there is shown texture means which can be in the form of rises or recesses. In the FIG. 132 embodiment there is a series of semi-circle shaped recesses or grooves which have more generally straight sides more proximal and the more generally curved portion extending both distally and radially deeper inward. In this way there is provided edge surfaces that provide a degree of slide abutment upon adjustment of the noted contact surface. Various other recess shaped are contemplated (scallop, crescent, polygonal, etc.) with preferred shapes having a most proximal portion with a horizontal edge configuration or extension (straight line or elongated wavy line, etc.). Further, the number and location of such texturing means can be varied along the preferred tapered distal portion acceptance region of the driver, with the design being associated with a preferred gripping or grabbing the reception recess surface (e.g., on a rim edge such as the capture rims described above) during insertion and removal sequences as to facilitate proper orientation engagement and timing without undue disruption (the texture is designed to control, but not preclude relative sliding of the driver relative to the reception recess, as in slowing down a smooth surface insertion or withdrawal). Moreover, the noted texturing can increase the friction level relative to a receiving wall of a reception recess as to facilitate grabbing together with the one or more associated torque enhancement engagement regions of the combination.

FIG. 133 shows a distal driver end plan view of the driver in FIG. 132 with the above described texture means 1467 and nature of the distal region of the driver 1430 further illustrated therein.

Also, as with the above embodiments, the reception recess (not shown) receiving driver 1420 would be designed for proper driving engagement and proper depth insertion allowance to align the noted torque enhancement and distal end region capture in the noted reception recess.

FIG. 134 shows a perspective view of the same driver shown in FIG. 132, while FIG. 135 shows a top or proximal plan view of the driver shown in FIG. 132, wherein there can be seen the hexagonal shank surface and contoured ring 1466 peripheral surface relationship.

FIGS. 136 and 137 show two different perspective views of an additional driver example under the present invention. That is, FIGS. 136 and 137 show driver 1520 which shares many attributes with driver 1420. Thus, driver 1520 has shank 1530, intermediate axial length neck 1528, ring 1529, torque enhancement contoured contact surfaces (bulbous) driver ring 1566, distal smooth taper portion 1568 which leads to externally curved or frusto-conical further tapering surface 1569. As seen by a comparison of FIGS. 134 and 136, tapering surface in 1469 has a generally (slight radially inward) concave surface configuration, while tapering surface 1569 has a generally (slight radial outward) convex shaped configuration. An additional difference is found in the distal most end of driver which features semi-spherical cap 1571 which is entirely smooth and extends distally from concave border ring 1570. Also, while having generally similarly shaped texture providing means 1567 (semi-circular recesses as in above), there is less in number and a focus on providing that texture means only at the distal end of the tapered surface 1569 and equally circumferentially spaced around the full periphery adjacent border ring 1570.

FIG. 138 shows a perspective view of a still further driver example under the present invention. That is, FIG. 138 shows driver 1620 which shares many attributes with driver 1520. Thus, driver 1620 has shank 1630, intermediate axial extending neck region 1628, ring 1629, torque enhancement (bulbous) driver ring 1666. A difference is found, however, in the distal end portion of driver 1620 which features shallow rounding 1669 having small diameter flat cap 1670 at its center. Thus, driver 1620 represents a driver that has an axial configuration that is shallow and thus can fit and drive a receiving reception recess that is also relatively shallow (not shown; but as with the above combinations of driver and reception recess the recess is configured to coordinate with the driver both with respect to torque generation and meshing axial receipt).

An additional difference is that texture means 1667 is formed not in the distal tapered end portion as in the earlier described embodiments, but rather is located at the torque enhancement 1666 region (or at both locations although not shown). For example, in FIG. 138 there is represented a set of linear (axially extending) and concave conforming radially ridges or grooves 1667A that are provided within most of the area of the concave recess C1 depicted. Similar friction enhancing grooving or ridging for providing texture means can also be provided in the other concave recess (C2 to C4—not fully shown in FIG. 138). In addition, or alternatively, alternate texture means 1667B is provided on one or more of the bulbous driver ring peripheral wall surfaces. For example, in FIG. 138 there can be seen a plurality of semi-circular lines in a pavilion row pattern on one side of the engagement surface 1678 (representing a driver "A" meshing location driver surface). The illustrated (left side only or one side region) texture means 1667B positioning can be strategically located, as where the surface portion of the mesh driver A section of the driver ring is on the side used for fastener/reception recess disengagement where higher and more assured torque engagement is often required to break the aforementioned adhesion, cold weld, rust bonds, etc., that can develop over time, as with a fastener facing the elements. Alternatively, there can be a fully dispersed pattern on the noted friction contact surfaces such as the torque enhancement ring's A and C mesh contact surface either in addition to or instead of the mesh B concave texture means shown. Also, embodiments can include all of the A, B, and C driver ring mesh surfaces being provided with the noted texturing means, or only some sub-combination thereof (e.g., only A surface pairs; or only C mesh surface pairs or both pairs with or without added B mesh surface texture means). The same ridge or recess or both configurations for the texture means can be strategically applied (as in grooves on the exterior contact surface and ridges in the concave cavities shown). Further, the same groove (recess) or ridge or both features for the texture means is also applicable to the texture means described for drivers 1420 and 1520 above (noting that the recesses are less likely to be scraped worn but can be more easily subjected to clogging).

FIG. 139 shows a distal plan view of the driver in FIG. 138 and thus the shank and driver head peripheral surface interrelationship.

FIG. 140 shows a view similar to FIG. 120 but with textured peripheral surfacing. That is, FIG. 140 shows meshing surface regions A, B and C (or in the notches as on side(s) and/or base) for the illustrated fastener nut with added texture means 1768, 1769, 1770 (1771) respectively, which can have the forms such as those featured in FIG. 132 (semi-circular recesses or raised ridges for example) or FIG. 138 (linear or wavy grooves or ridges). In addition to the above described ridge/recess/or both variations noted above, additional variations contemplated as to the nature of the texture means configuration (e.g., opting for the semicircular line grooves or ridges such as shown in the A and B mesh surfaces of FIG. 138 and either over all or a portion of the respective mesh surface as in the strategic one half side arrangement shown in texture means 1667B in FIG. 138, as well as on all or any one or sub-combination of the mesh surfaces associated with mesh regions A, B and C (and notches) like above. Also, while shown on the fastener featured in FIG. 120, the texture means of the present invention can also be provided on any one of the driver or reception regions (or both) where the inclusion of added texture means is desirable.

Still further, relative to the above described embodiments, the reception recess can be provided with texture means like that described above, either to supplement those of the driver or as an alternative to having them on the driver.

All ranges set forth in the above disclosure are considered to encompass each component within the specified range at units that are customary or at least equal to the range end points (e.g., a degree range of 10 to 30 degrees is inclusive of values of 11, 12, 13 . . . etc.) or a range of ratio values such as 65 to 96 is inclusive of the common unit intermediaries as in 66, 67, 68 . . . .

Although the present invention has been described with reference to preferred embodiments, it is not limited thereto and may be modified in various ways. In particular, the aforementioned embodiments according to the invention for the torque enhancement driver, recessed recipient and meshing combinations of the same may be combined with one another and, in particular, individual features thereof may be combined or considered individually when so conveyed.

The invention claimed is:

1. A torque enhancing device, comprising:
a torque contact body having one or more torque driver and/or recessed recipient torque contact surface configurations,
the body having a Z-axis depth or thickness, and
at least one of the one or more torque contact surface configurations comprising a pair of X-axis extending torque contact side walls on the body that are spaced apart by L1 along a Y-axis, and a pair of Y-axis extending torque contact side walls on the body that are spaced apart by L2 along the X-axis, as well as four concave contoured surface portions in the body that are positioned between respective adjacent ends of the X-axis extending torque contact side walls and the Y-axis extending torque contact side walls, and the enhanced torque contact surface having an L2/L1 ratio that is less than 1 as to provide a torque enhancement contact surface configuration, and wherein the torque enhancement contact surface configuration is configured to be operated by a torque generation tool or is configured to operate as a torque generation tool and wherein, on an X-Y axes plane that extends through a most radially outward positioned portion of each of the pair of X-axis extending torque contact side walls of the body, the L2/L1 ratio is at or greater than 60% to less than 100%.

2. The torque enhancing device of claim 1, wherein at least two of the one or more torque contact surface configurations has the torque enhancement contact surface configuration.

3. The torque enhancing device of claim 2, wherein the at least two torque enhancement surface configurations are axially spaced along the Z-axis.

4. The torque enhancing device of claim 2, wherein the at least two torque enhancement surface configurations are radially separated.

5. The torque enhancing device of claim 1, wherein the body is a fastener head having two different sized regions with respective surface contouring, with the surface contouring of at least one of the two different sized regions defining the torque enhancement surface configuration.

6. The torque enhancing device of claim 5, wherein the surface contouring of each of the two different sized regions has the torque enhancement surface configuration and at least one of the regions is an interior recess region in the fastener head.

7. The torque enhancing device of claim 5, wherein one of the two different sized regions has a non-torque enhancement surface configuration and the other has the torque enhancement surface configuration.

8. The torque enhancing device of claim 1, wherein, relative to the X-Y axes plane that extends through each of the X-axis and Y-axis extending torque contact walls, a maximum radial extension amongst the four concave contoured surface portions on that X-Y axes plane is less than at least one of the Y-axis and X-axis extension lengths on that X-Y axes plane.

9. The multi tier torque enhancing device of claim 8, wherein the maximum radial extension amongst the four concave contoured surface portions on the X-Y axes plane is less than each of the Y-axis and X-axis extension lengths on that X-Y axes plane.

10. A multi-tier torque enhancing combination, comprising:
as a first torque enhancing device the torque enhancing device of claim 1, wherein the first torque enhancing device comprises a driver torque contact body having at least two torque driver torque contact surface configurations, with the driver torque contact body having a Z-axis depth or thickness, and wherein at least one of the two torque driver contact surface configurations comprises a pair of X-axis extending torque contact side walls that are spaced apart by L1 along a Y-axis, and a pair of Y-axis extending torque contact side walls that are spaced apart by L2 along the X-axis, as well as four concave contoured surface portions positioned between respective adjacent ends of the X-axis extending torque contact side walls and the Y-axis extending torque contact side walls, and wherein the L2/L1 ratio is less than 1, and
a second torque enhancing device, comprising a recessed recipient torque contact body having at least two torque contact surface configurations with the recessed recipient torque contact body having a Z-axis depth or thickness, and at least one of the two torque contact surface configurations having a torque enhancement surface configuration comprising a pair of X-axis extending torque contact side walls that are spaced apart by L1 along a Y-axis, and a pair of Y-axis extending torque contact side walls that are spaced apart by L2 along the X-axis, as well as four concave contoured surface portions positioned between respective adjacent ends of the X-axis extending torque contact side walls and the Y-axis extending torque contact side walls of the recessed recipient, and the torque enhancement surface configuration has an L2/L1 ratio that is less than 1, and wherein
the first and second torque enhancing devices are configured for torque generation mesh engagement at least at the torque enhancement contact surface configurations of the respective first and second torque enhancing devices.

11. The multi-tier torque enhancing of claim 10, wherein the driver torque contact body has two torque driver torque contact surface configurations that are Z-axis axially spaced apart, and wherein the recessed recipient torque contact body has two torque driver torque contact surface configurations that are Z-axis axially spaced apart, and wherein the two axially spaced apart torque driver torque contact surface configurations are in respective torque generating contact with the two axially spaced apart torque driver torque contact surface configurations of the recessed recipient torque contact body when the first and second torque enhancing devices are in a maximum torque generation mesh engagement state.

12. The multi-tier torque enhancing of claim 11, wherein a more distal one of the two torque driver torque contact surface configurations is configured for mesh engagement with the recessed recipient torque contact body in a first state that is prior to the maximum torque generation mesh engagement state and is where a less distal one of the two torque driver torque contact surface configurations is in a non-mesh state with the recessed recipient torque contact body.

13. A method of removing or installing a fastener, comprising utilizing the driver torque contact body of claim 11 by engaging the driver torque contact body with the recessed recipient torque contact body, which has a fastener head having the two torque driver torque contact surface configurations that are Z-axis axially spaced apart, and rotating the driver torque contact body while engaged with the recessed recipient torque contact body.

14. The torque enhancing device of claim 1, wherein the body is a driver having two axially spaced torque contact surfaces at least one of which defines the torque enhancement surface configuration.

15. The torque enhancing device of claim 14 wherein the two axially spaced torque contact surfaces each have the torque enhancement surface configuration.

16. The torque enhancing device of claim 14 wherein the two axially spaced torque contact surfaces have different sizes.

17. The torque enhancing device of claim 14 wherein one of the two axially spaced torque contact surfaces has a bulbous configuration and the second of the two axially spaced torque contact surfaces has a non-bulbous configuration with linear only side walls.

18. The torque enhancing device of claim 14 wherein one of the two axially spaced torque contact surfaces has a non-torque enhancement configuration and the second of the two axially spaced torque contact surfaces has the torque enhancement surface configuration with bi-symmetry or essentially bi-symmetry.

19. The torque enhancing device of claim 14, wherein the driver has a torque enhancement surface configuration grip handle.

20. The torque enhancing device of claim 14, wherein the driver is elongated with a curving section and two straight end sections with the two end sections each having a respective one of the two axially spaced torque contact surfaces.

21. The torque enhancing device of claim 14, wherein the driver is elongated with a shank end for receipt within a powered rotating device.

22. A rotating torque enhancing assembly comprising the torque enhancing device of claim 21 and the powered rotating device, with the torque enhancing device having an L2/L1 ratio at or greater than 90% and less than 100%, and with the powered rotating device having an operating range that includes 10,000 RPM.

23. A multi-tier torque enhancing device, comprising:
a torque contact device having radially or axially, or both radially and axially, separated torque contact surface configurations, wherein
at least one of the one or more torque contact surface configurations provides an enhanced torque contact surface configuration comprising a pair of X-axis extending torque contact side walls, of an X-axis extension length, that are spaced apart by L1 along a Y-axis, and a pair of Y-axis extending torque contact side walls, of a Y-axis extension length, that are spaced apart by L2 along an X-axis, as well as four concave contoured surface portions positioned between respective adjacent ends of the X-axis extending torque contact side walls and the Y-axis extending torque contact side walls, and the enhanced torque contact surface having an L2/L1 ratio that is less than 1, and wherein the enhanced torque contact surface configuration is configured to be operated by a torque generation tool or is configured to operate as a torque generation tool,
wherein, relative to an X-Y axes plane that extends through each of the X-axis and Y-axis extending torque contact walls and at a Z-axis location where the X-axis extending torque contact side walls are radially most removed from the Z-axis, a maximum radial extension amongst the four concave contoured surface portions on that X-Y axes plane, that is defined by a radial extension from a circumference falling on end points of one of the Y-axis extending walls to a point on an adjacent-most concave contoured surface portion closest to the Z-axis, is less than at least one of said Y-axis and X-axis extension lengths on that X-Y axes plane,
wherein the concave contoured surface portions span and directly interconnect the respective adjacent ends of the X-axis and Y-axis extending side walls between which the respective concave contoured surface portions extend,
wherein said Y-axis extension length is longer than said X-axis extension length, and
wherein all, or at least a majority, of each Y-axis extending torque contact side wall extends along a straight, or substantially straight, line, and said line extends perpendicular or substantially perpendicular to L2 when L2 intersects with the Z-axis.

24. The multi-tier torque enhancing device of claim 23 wherein the torque enhancing device has a fastener head comprising the radially and/or axially separated torque contact surface configurations at least one of which has the enhanced torque contact surface configuration.

25. The multi-tier torque enhancing device of claim 23, wherein the maximum radial extension of the four concave contoured surface portions on the X-Y axes plane is less than each of the Y-axis and X-axis extension lengths on that X-Y axes plane.

26. The multi-tier torque enhancing device combination of claim 23, wherein, on an X-Y axes plane that extends through a most radially outward positioned portion of each of the pair of X-axis extending torque contact walls of the body, the L2/L1 ratio is at or greater than 60% to less than 100%.

27. A multi-tier torque enhancing combination, comprising the torque enhancement device of claim 23 and a motorized power rotation device.

28. The multi-tier torque enhancing device of claim 23 wherein the torque enhancing device is a driver device having axially separated torque contact surface configurations of which at least one has the enhanced torque contact surface configuration.

29. The multi-tier torque enhancing device of claim 28 wherein the enhanced torque contact surface configuration of the driver device has, on at least one of the X-axis or Y-axis extending side walls, a Z-axis taper that axially converges toward a distal free end of the driver.

30. A method of operating a torque enhancing device comprising rotating and contacting a first fastener head with the driver device of claim 28 and then adjusting the driver device, while still rotating, into contact with a second fastener head.

* * * * *